US007723265B2

(12) United States Patent
Xu et al.

(10) Patent No.: US 7,723,265 B2
(45) Date of Patent: *May 25, 2010

(54) PESTICIDE COMPOSITIONS CONTAINING OXALIC ACID

(75) Inventors: Xiaodong C. Xu, Valley Park, MO (US); Ronald J. Brinker, Ellisville, MO (US); Tracey L. Reynolds, Ballwin, MO (US); William Abraham, Wildwood, MO (US); Jeffrey A. Graham, Wildwood, MO (US)

(73) Assignee: Monsanto Technology, St. Louis, MO (US)

( * ) Notice: Subject to any disclaimer, the term of this patent is extended or adjusted under 35 U.S.C. 154(b) by 451 days.

This patent is subject to a terminal disclaimer.

(21) Appl. No.: 11/205,978

(22) Filed: Aug. 17, 2005

(65) Prior Publication Data

US 2006/0019830 A1 Jan. 26, 2006

Related U.S. Application Data

(63) Continuation of application No. 09/988,353, filed on Nov. 19, 2001, now Pat. No. 6,992,045, which is a continuation-in-part of application No. 09/926,521, filed as application No. PCT/US01/16550 on May 21, 2001, now Pat. No. 7,049,270.

(60) Provisional application No. 60/206,628, filed on May 24, 2000, provisional application No. 60/205,524, filed on May 19, 2000, provisional application No. 60/273,234, filed on Mar. 2, 2001, provisional application No. 60/274,368, filed on Mar. 8, 2001.

(51) Int. Cl.
*A01N 57/00* (2006.01)
*A01N 57/18* (2006.01)
(52) U.S. Cl. .................................. 504/127; 504/206
(58) Field of Classification Search .................. 504/127, 504/206
See application file for complete search history.

(56) References Cited

U.S. PATENT DOCUMENTS

| | | | |
|---|---|---|---|
| 2,764,602 A | 9/1956 | Ahlbrecht | |
| 2,764,603 A | 9/1956 | Ahlbrecht | |
| 2,803,656 A | 8/1957 | Ahlbrecht et al. | |
| 3,147,064 A | 9/1964 | Brown et al. | |
| 3,255,131 A | 6/1966 | Ahlbrecht et al. | |
| 3,450,755 A | 6/1969 | Ahlbrecht | |
| 3,505,377 A | 4/1970 | Morehouse | |
| 3,799,758 A | 3/1974 | Franz | |
| 3,853,530 A | 12/1974 | Franz | |
| 3,977,860 A | 8/1976 | Franz | |
| 4,042,522 A | 8/1977 | Falk | |
| 4,069,158 A | 1/1978 | Bertocchio et al. | |
| 4,069,244 A | 1/1978 | Mueller | |
| 4,090,967 A | 5/1978 | Falk | |
| 4,140,513 A | 2/1979 | Prill | |
| 4,159,901 A | 7/1979 | Beestman et al. | |
| 4,161,590 A | 7/1979 | Mueller | |
| 4,161,602 A | 7/1979 | Mueller | |
| 4,315,765 A | 2/1982 | Large | |
| 4,405,531 A | 9/1983 | Franz | |
| 4,431,765 A | 2/1984 | Doshak et al. | |
| 4,481,026 A | 11/1984 | Prisbylla | |
| 4,507,250 A | 3/1985 | Bakel | |
| 4,936,901 A | 6/1990 | Surgant, Sr. et al. | |
| 5,118,444 A | 6/1992 | Nguyen | |
| 5,317,003 A | 5/1994 | Kassebaum et al. | |
| 5,389,598 A | 2/1995 | Berk et al. | |
| 5,436,220 A | 7/1995 | Hickey | |
| 5,464,807 A | 11/1995 | Claude et al. | |
| 5,525,576 A | 6/1996 | Medina-Vega et al. | |
| 5,563,111 A | 10/1996 | Hioki et al. | |
| 5,622,911 A | 4/1997 | Hasebe et al. | |
| 5,668,085 A | 9/1997 | Forbes et al. | |
| 5,683,958 A | 11/1997 | Berger et al. | |
| 5,703,015 A | 12/1997 | Berger et al. | |
| 5,750,468 A | 5/1998 | Wright et al. | |
| 5,795,847 A | 8/1998 | Nielsen et al. | |
| 5,849,663 A | 12/1998 | Hasebe et al. | |
| 5,863,863 A | 1/1999 | Hasebe et al. | |
| 5,863,909 A | 1/1999 | Kurita et al. | |
| 5,877,112 A | 3/1999 | Roberts et al. | |
| 5,948,421 A | 9/1999 | Okano et al. | |
| 5,985,794 A | 11/1999 | Hasebe et al. | |
| 5,985,798 A | 11/1999 | Crudden | |
| 6,008,158 A | 12/1999 | Hasebe et al. | |

(Continued)

FOREIGN PATENT DOCUMENTS

DE 4019362 A1 1/1991

(Continued)

OTHER PUBLICATIONS

RD 153034 (ABS), Jan. 1977, Anon.*
Hayes, Sandra A., The Herbicidal Activity of Various Organic Acids on the Growth of Elodea Canadensis, Proceedings of the Twentieth Annual Meeting of the Southern Weed Conference, Jan. 1967, pp. 294.
Research Disclosure Publication No. RDI 15334, Industrial Opportunities Ltd. Homewell; Jan. 1977.

(Continued)

*Primary Examiner*—Alton N Pryor
(74) *Attorney, Agent, or Firm*—Senniger Powers LLP; Joseph A. Schaper

(57) ABSTRACT

Pesticidal concentrate and spray compositions are described which exhibit enhanced efficacy due to the addition thereto of a compound which increases cell membrane permeability, suppresses oxidative burst, or increases expression of hydroxyproline-rich glycoproteins.

25 Claims, No Drawings

U.S. PATENT DOCUMENTS

| | | |
|---|---|---|
| 6,030,923 A | 2/2000 | Okano et al. |
| 6,063,733 A | 5/2000 | Berger et al. |
| 6,083,875 A | 7/2000 | Sato et al. |
| 6,093,679 A | 7/2000 | Azuma et al. |
| 6,117,820 A | 9/2000 | Cutler et al. |
| 6,121,199 A | 9/2000 | Berger et al. |
| 6,180,566 B1 | 1/2001 | Nielsen et al. |
| 6,184,182 B1 | 2/2001 | Gillespie et al. |
| 6,218,336 B1 | 4/2001 | Coleman |
| 6,245,713 B1 | 6/2001 | Brinker et al. |
| 6,667,276 B1 | 12/2003 | Maier et al. |
| 7,141,532 B2 * | 11/2006 | Graham et al. .............. 504/206 |
| 2004/0097372 A1 * | 5/2004 | Abraham et al. ............ 504/127 |
| 2005/0261130 A1 * | 11/2005 | Lennon et al. .............. 504/206 |

FOREIGN PATENT DOCUMENTS

| | | |
|---|---|---|
| DE | 197 52 552 A1 | 6/1999 |
| EP | 0 274 369 B1 | 9/1990 |
| EP | 0 290 416 B1 | 6/1993 |
| EP | 0 617 894 A1 | 10/1994 |
| EP | 0 472 310 B1 | 12/1996 |
| EP | 1 064 844 A1 | 1/2001 |
| GB | 1 306 647 | 6/1971 |
| GB | 1 588 079 | 5/1978 |
| GB | 1 566 770 | 5/1980 |
| GB | 2 267 825 A | 12/2001 |
| HU | 165654 A | 10/1974 |
| HU | P9800751 A | 8/1998 |
| HU | P0302482 A | 11/2003 |
| WO | 92/12637 | 8/1992 |
| WO | 95/16352 | 6/1995 |
| WO | 95/33379 | 12/1995 |
| WO | 97/16969 | 5/1997 |
| WO | 97/32476 | 9/1997 |
| WO | 97/36494 | 10/1997 |
| WO | 98/17109 | 4/1998 |
| WO | 98/17113 A | 4/1998 |
| WO | 98/33384 | 8/1998 |
| WO | 98/33385 | 8/1998 |
| WO | 00/08927 | 2/2000 |
| WO | 00/15037 | 3/2000 |
| WO | WO 00/15037 | 3/2000 |
| WO | 00/41567 | 7/2000 |
| WO | WO 00/59302 | 10/2000 |
| WO | WO 01/10210 | 2/2001 |
| WO | WO 01/11957 | 2/2001 |
| WO | WO 01/20987 A1 | 3/2001 |
| WO | WO 02/26036 A1 | 4/2002 |

OTHER PUBLICATIONS

Wyrill, III, J.B. and Burnside, O.C., Glyphosate Toxicity to Common Milkweed and Hemp Dogbane as Influenced by Surfactants, Weed Science, May 1977, pp. 275.

Turner, D.J. and Loader, M.P.C., Complexing Agents as Herbicide Additives, Weed Research, Nov. 10, 1977, pp. 199.

Turner, D.J., The Herbicide Glyphosate, 1985, pp. 229.

International Search Report for PCT/US 02/06709 dated Aug. 21, 2002.

International Search Report for PCT/US 02/15977 dated Oct. 2, 2003.

Wyrill, III, J.B. and Burnside, O.C., Glyphosate Toxicity to Common Milkweed and Hemp Dogbane as Influenced by Surfactants, Weed Science, May 1977, pp. 275-287, vol. 25, Issue 3.

Research Disclosure Publication No. RDI 15334, Industrial Opportunities Ltd. Homewell-Havant-Hampshire PO91EF, Jan. 1977, United Kingdom.

International Search Report for PCT/US 01/16550 dated Mar. 5, 2003.

International Search Report for PCT/US 02/15977 dated Oct. 2, 2003.

* cited by examiner

PESTICIDE COMPOSITIONS CONTAINING OXALIC ACID

REFERENCE TO RELATED APPLICATIONS

This application is a continuation of U.S. application Ser. No. 09/988,353, filed Nov. 19, 2001, which was a continuation-in-part of U.S. application Ser. No. 09/926,521, filed Nov. 14, 2001, which was the National Stage of International Application No. PCT/US01/16550, filed May 21, 2001, which claims the benefit of U.S. Provisional Application No. 60/206,628, filed May 24, 2000, U.S. Provisional Application No. 60/205,524, filed May 19, 2000, U.S. Provisional Application No. 60/273,234, filed Mar. 2, 2001, and U.S. Provisional Application No. 60/274,368, filed Mar. 8, 2001.

BACKGROUND OF THE INVENTION

The present invention relates to a method for enhancing glyphosate herbicidal efficacy with organic acids. More particularly, the present invention relates to a method of enhancing the herbicidal effectiveness of potassium glyphosate concentrate and tank mix formulations containing one or more surfactants through the addition of a polycarboxylic acid component or another component which increases cell membrane permeability or suppresses oxidative burst.

Glyphosate is well known in the art as an effective post-emergent foliar-applied herbicide. In its acid form, glyphosate has a structure represented by formula (1):

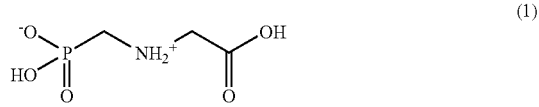

and is relatively insoluble in water (1.16% by weight at 25° C.). For this reason it is typically formulated as a water-soluble salt.

Monobasic, dibasic and tribasic salts of glyphosate can be made. However, it is generally preferred to formulate glyphosate and apply glyphosate to plants in the form of a monobasic salt. The most widely used salt of glyphosate is the mono (isopropylammonium), often abbreviated to IPA, salt. Commercial herbicides of Monsanto Company having the IPA salt of glyphosate as active ingredient include Roundup®, Roundup® Ultra, Roundup® UltraMax, Roundup® Xtra and Rodeo® herbicides. All of these are aqueous solution concentrate (SL) formulations and are generally diluted in water by the user prior to application to plant foliage. Another glyphosate salt which have been commercially formulated as SL formulations include the mono(trimethylsulfonium), often abbreviated to TMS salt, used for example in Touchdown® herbicide of Syngenta. Various salts of glyphosate, methods for preparing salts of glyphosate, formulations of glyphosate or its salts and methods of use of glyphosate or its salts for killing and controlling weeds and other plants are disclosed in U.S. Pat. No. 4,507,250 to Bakel, U.S. Pat. No. 4,481,026 to Prisbylla, U.S. Pat. No. 4,405,531 to Franz, U.S. Pat. No. 4,315,765 to Large, U.S. Pat. No. 4,140,513 to Prill, U.S. Pat. No. 3,977,860 to Franz, U.S. Pat. No. 3,853,530 to Franz, and U.S. Pat. No. 3,799,758 to Franz. The aforementioned patents are incorporated herein in their entirety by reference.

Among the water soluble salts of glyphosate known in the literature, but not known to be used commercially, is the potassium salt, having a structure represented by formula (2):

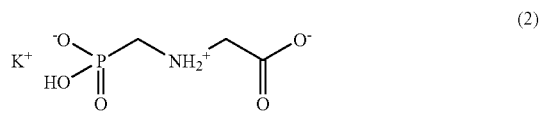

in the ionic form predominantly present in aqueous solution at a pH of about 4. This salt is disclosed, for example, by Franz in U.S. Pat. No. 4,405,531 cited above, as one of the "alkali metal" salts of glyphosate useful as herbicides, with potassium being specifically disclosed as one of the alkali metals, along with lithium, sodium, cesium and rubidium. Example C discloses the preparation of the monopotassium salt by reacting the specified amounts of glyphosate acid and potassium carbonate in an aqueous medium.

Very few herbicides have been commercialized as their potassium salts. The Pesticide Manual, 11th Edition, 1997, lists as potassium salts the auxin type herbicides 2,4-DB ((2,4-dichlorophenoxy)butanoic acid), dicamba (3,6-dichloro-2-methoxybenzoic acid), dichlorprop (2-(2,4-dichlorophenoxy)propanoic acid), MCPA ((4-chloro-2-methylphenoxy)acetic acid), and picloram (4-amino-3,5,6-trichloro-2-pyridinecarboxylic acid), the active ingredient of certain herbicide products sold by DowElanco under the trademark Tordon.

The solubility of glyphosate potassium salt in water is recorded in pending application Ser. No. 09/444,766, filed Nov. 22, 1999, the entire disclosure of which is incorporated herein by reference. As disclosed therein, glyphosate potassium salt has a solubility in pure water at 20° C. of about 54% by weight, that is, about 44% glyphosate acid equivalent (a.e.) by weight. This is very similar to the solubility of the IPA salt. Concentrations expressed as percent by weight herein relate to parts by weight of salt or acid equivalent per 100 parts by weight of solution. Thus a simple aqueous solution concentrate of glyphosate potassium salt can readily be provided at a concentration of, for example, 44% a.e. by weight, comparable to that commercially obtainable with glyphosate IPA salt, as in the aqueous solution concentrate available from Monsanto Company under the name D-Pak. Somewhat higher concentrations can be obtained by slight over neutralization, 5 to 10% for example, of an aqueous solution of glyphosate potassium salt with potassium hydroxide.

Polycarboxylic acid have been used as chelators to enhance glyphosate efficacy in tank mix compositions. For example, D. J. Turner reported in Butterworths (1985), at pages 229-230, that 2% concentrations of polycarboxylic acids in glyphosate (Roundup®) tank mixes gave efficacy enhancement. Further, Research Disclosure publication number RD15334, Industrial Opportunities Ltd., Homewell-Havant-Hampshire P09 1EF, United Kingdom (January 1977), disclosed that glyphosate tank mixes formulated with water containing calcium and/or magnesium ions in concentrations greater than 200 ppm (hard water) had diminished herbicidal activity. Herbicidal activity was restored by adding oxalic acid to the tank mix in weight ratios to glyphosate of between about 1:10 to about 10:1.

U.S. Pat. No. 5,863,863 to Hasabe et al. teaches tank mix formulations comprising about 0.08 wt % a.i. IPA glyphosate (as Roundup®) and about 0.001 moles/l of dipotassium, disodium, diammonium, diethanolamine or dimethylamine oxalate, and an ethoxylated tertiary amine or quaternary ammonium surfactant. Concentrates containing about 41 wt % a.i. IPA glyphosate, 0.21 mols/kg of dipotassium, disodium, diammonium, diethanolamine or dimethylamine oxalate are also described.

U.S. Pat. No. 5,525,576 to Medina-Vega et al. discloses a process for preparing a seed hull extract containing a mixture of polycarboxylic acids for use as a herbicide assimilation agent. 0.25% of the extract was added to tank mixes containing the trimethylsulfonium (TMS) salt of glyphosate (sold commercially as Touchdown®) or the isopropylamine (IPA) salt of glyphosate (sold commercially as Roundup®). U.S. Pat. No. 5,436,220 to Hickey teaches an efficacy enhancing formulation comprising a seed hull extract containing tricarboxylic acids and Roundup® herbicide, with glyphosate application rates of 64 to 191 g/ha in combination with 82 g/ha of a seed hull extract containing about 5 wt % tricarboxylic acid.

U.S. Pat. Nos. 5,849,663 and 6,008,158 to Hasabe et al. disclose tank mix formulations containing Roundup® herbicide at 0.08 wt % a.i. or TMS glyphosate, polycarboxylic acid salt chelating agents including oxalate salts at 0.02 wt %, and ethoxylated tertiary amine and quaternary ammonium surfactants. Hasabe reports polycarboxylic acid to surfactant weight ratios between about 1:2 and about 1:9 with efficacy enhancement resulting from complexation of metal ions.

U.S. Pat. No. 6,093,679 to Azuma et al. discloses tank mixes containing 0.38 wt % glyphosate TMS (Touchdown®), 0.53 wt % hydroxycarboxylic acid-based chelating agents, including potassium oxalate, and a quaternary ammonium surfactant having an alkoxylated carboxy alkyl anion.

U.S. Pat. No. 6,218,336 to Coleman discloses tank mixes containing up to 1.25 wt % Roundup®) Ultra IPA glyphosate and 2.5 wt % of succinic, tartaric or malic acids or their ammonium salts. Sylgard 309® (ethoxylated organosilicone) and Emsorb 6900® (polyoxyethylenated sorbitol ester) surfactants may be added to the tank mixes.

U.S. Pat. No. 5,948,421 to Okano et al. describes aqueous concentrate formulations containing 42 and 51 wt %, respectively of the diammonium or isopropylamine salts of glyphosate, dicarboxylic acid chelating agents including potassium oxalate at 8 wt %, and an ethoxylated quaternary ammonium surfactant.

Polycarboxylic acids have not been reported to be effective in potassium glyphosate formulations. Perhaps this is because commercial applications of potassium herbicide formulations have been limited, and the action of polycarboxylic acids on the numerous surfactants used in the herbicide formulation industry is varied and unpredictable.

The choice of a surfactant has a major bearing on herbicidal performance. For example, in an extensive study reported in Weed Science, 1977, volume 25, pages 275-287, Wyrill and Burnside found wide variation among surfactants in their ability to enhance the herbicidal efficacy of glyphosate, applied as the IPA salt. Suitable surfactants for potassium glyphosate formulations are disclosed in pending application Ser. No. 09/926,521, filed Nov. 14, 2001, (the national stage of International Application No. PCT/US01/16550, filed May 21, 2001), the entire disclosure of which is incorporated by reference. Surfactants tending to give the most useful enhancement of glyphosate herbicidal effectiveness are generally, but not exclusively, cationic surfactants, including surfactants which form cations in aqueous solution or dispersion at pH levels of around 4-5 characteristic of SL formulations of monobasic salts of glyphosate.

Beyond some broad generalizations, the relative ability of different surfactants to enhance the herbicidal effectiveness of glyphosate is highly unpredictable.

Surfactants tending to give the most useful enhancement of glyphosate herbicidal effectiveness are generally but not exclusively cationic surfactants, including surfactants which form cations in aqueous solution or dispersion at pH levels of around 4-5 characteristic of SL formulations of monobasic salts of glyphosate. Examples are long-chain (typically $C_{12}$ to $C_{18}$) tertiary alkylamine surfactants and quaternary alkylammonium surfactants. An especially common tertiary alkylamine surfactant used in aqueous solution concentrate formulations of glyphosate IPA salt has been the very hydrophilic surfactant polyoxyethylene (15) tallowamine, i.e., tallowamine having in total about 15 moles of ethylene oxide in two polymerized ethylene oxide chains attached to the amine group as shown in formula (3):

wherein R is a mixture of predominantly $C_{16}$ and $C_{18}$ alkyl and alkenyl chains derived from tallow and the total of m+n is an average number of about 15.

For certain applications, it has been found desirable to use a somewhat less hydrophilic alkylamine surfactant, such as one having less than about 10 moles of ethylene oxide, as suggested in U.S. Pat. No. 5,668,085 to Forbes et al., for example polyoxyethylene (2) cocoamine. That patent discloses illustrative aqueous compositions comprising such a surfactant together with the IPA, ammonium or potassium salts of glyphosate. The highest concentration of glyphosate in the potassium salt formulations shown in Table 3 of the '085 patent is 300 g glyphosate a.e./l, with a weight ratio of glyphosate a.e. to surfactant of 2:1.

A class of alkoxylated alkylamines is disclosed in WO 00/59302 for use in herbicidal spray compositions. Potassium glyphosate solutions including various Jeffamine™ EO/PO propylamines or propyidiamines are described therein.

A wide variety of quaternary ammonium surfactants have been disclosed as components of aqueous solution concentrate formulations of glyphosate IPA salt. Illustrative examples are N-methylpolyoxyethylene (2) cocoammonium chloride, disclosed in European Patent No. 0274369, N-methylpolyoxyethylene (15) cocoammonium chloride, disclosed in U.S. Pat. No. 5,317,003, and various quaternary ammonium compounds having formula (4):

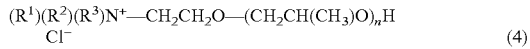

where $R^1$, $R^2$ and $R^3$ are each $C_{1-3}$ alkyl groups and n is an average number from 2 to 20, disclosed in U.S. Pat. No. 5,464,807.

PCT Publication No. WO 97/16969 discloses aqueous solution concentrate compositions of glyphosate, in the form of the IPA, methylammonium and diammonium salts, comprising a quaternary ammonium surfactant and an acid salt of a primary, secondary or tertiary alkylamine compound.

Other cationic surfactants which have been indicated as useful in aqueous solution concentrate compositions of glyphosate salts include those disclosed in PCT Publication No. WO 95/33379. It is further disclosed in PCT Publication No. WO 97/32476 that highly concentrated aqueous compositions of glyphosate salts can be made with certain of these same cationic surfactants, with the further addition of a defined component that enhances stability of the compositions. Glyphosate salts exemplified therein are the IPA salt and the mono- and diammonium salts.

A class of alkyl etheramine, alkylether ammonium salt and alkyl etheramine oxide surfactants has been disclosed in U.S. Pat. No. 5,750,468 to be suitable for preparation of aqueous solution concentrate formulations of various glyphosate salts, the potassium salt being included in the list of salts mentioned. It is disclosed therein that an advantage of the subject surfactants when used in an aqueous composition with glyphosate salts is that these surfactants permit the glyphosate concentration of the composition to be increased to very high levels.

Anionic surfactants, except in combination with cationic surfactants as disclosed in U.S. Pat. No. 5,389,598 and U.S. Pat. No. 5,703,015, are generally of little interest in SL formulations of glyphosate IPA salt. The '015 patent discloses a surfactant blend of a dialkoxylated alkylamine and an anionic eye irritancy reducing compound. The surfactant blend is disclosed as being suitable for preparation of aqueous solution concentrate formulations of various glyphosate salts, the potassium salt being included in the list of salts mentioned. Concentrates of the '015 patent contain from about 5 to about 50%, preferably about 35% to about 45% glyphosate a.i. and from about 5 to about 25% surfactant. Further, PCT Publication No. WO 00/08927 discloses the use of certain polyalkoxylated phosphate esters in combination with certain polyalkoxylated amidoamines in glyphosate containing formulations. Potassium is identified as one of several salts of glyphosate noted as being "suitable."

Nonionic surfactants are generally reported to be less effective in enhancing herbicidal activity than cationic or amphoteric surfactants when used as the sole surfactant component of SL formulations of glyphosate IPA salt; exceptions appear to include certain alkyl polyglucosides, as disclosed for example in Australian Patent No. 627503, and polyoxyethylene (10-100) $C_{16-22}$ alkylethers, as disclosed in PCT Publication No. WO 98/17109. Other nonionic surfactants are generally mixed with cationic surfactants to form a compatible surfactant system for use in liquid herbicidal concentrates. However, cationic/nonionic surfactant systems generally do not provide acceptable low temperature storage stability. Concentrates containing these surfactant systems can crystallize at temperatures at or below about 0° C., limiting the use of such concentrates in cold climates.

Glyphosate concentrates containing nonionic alkylether and cationic amine surfactants are described in U.S. Pat. No. 6,245,713. The surfactant mixture is said to enhance biological effectiveness of the glyphosate and provide enhanced rainfastness. Suitable glyphosates for use in the concentrates include sodium, potassium, ammonium, dimethylammonium, IPA, monoethanolammonium and TMS glyphosate salts. This patent is incorporated herein in its entirety by reference.

It is likely that serious consideration of glyphosate potassium salt as a herbicidal active ingredient has been inhibited by the relative difficulty in formulating this salt as a highly concentrated SL product together with preferred surfactant types. For example, a widely used surfactant in glyphosate IPA salt compositions, namely polyoxyethylene (15) tallowamine of formula (3) above, is highly incompatible in aqueous solution with glyphosate potassium salt. Further, PCT Publication No. WO 00/15037 notes the low compatibility of alkoxylated alkylamine surfactants in general with high-strength glyphosate concentrates. As disclosed therein, in order to "build in" an effective level of surfactant, an alkylglycoside surfactant is used in combination with an alkoxy- lated alkylamine surfactant to obtain high-strength concentrates containing the potassium salt of glyphosate.

The addition of such alkylglycosides resulted in higher viscosity formulations (as compared to formulations without alkylglycosides). Such an increase in the viscosity of these high-strength formulations is undesirable for various reasons. In addition to being more difficult to conveniently pour from the container or to wash residues therefrom, the deleterious effects resulting from higher viscosity formulations is more dramatically observed with respect to pumping requirements. Increasing volumes of liquid aqueous glyphosate products are being purchased by end-users in large refillable containers sometimes known as shuttles, which typically have an integral pump or connector for an external pump to permit transfer of liquid. Liquid aqueous glyphosate products are also shipped in bulk, in large tanks having a capacity of up to about 100,000 liters. The liquid is commonly transferred by pumping to a storage tank at a facility operated by a wholesaler, retailer or cooperative, from which it can be further transferred to shuttles or smaller containers for onward distribution. Because large quantities of glyphosate formulations are purchased and transported in early spring, the low temperature pumping characteristics of such formulations are extremely important.

When such alkylglycosides (e.g., AgriMul™ APG-2067 and 2-ethyl-hexyl glucoside) are added to a glyphosate concentrate, the concentrate is dark brown in color. It is desirable for a glyphosate concentrate to be lighter in color than the alkylglycoside-containing concentrates as disclosed in WO 00/15037, which have a color value of about 10 to 18 as measured by a Gardner calorimeter. When dye is added to a glyphosate concentrate having a Gardner color of 18, the concentrate remains dark brown in color. Concentrates having a Gardner color value of 10 are difficult to dye a wide variety of colors, for example blue, green, red or yellow, as is often desired to distinguish the glyphosate product from other herbicidal products.

It would be desirable to provide a storage-stable aqueous concentrate composition of the potassium salt of glyphosate having an agronomically useful surfactant content, or that is "fully loaded" with surfactant. These formulations exhibit a reduced viscosity such that they may be pumped with standard bulk pumping equipment at 0° C. at rates of at least 7.5 gallons per minute, usually more than 10 gallons per minute and preferably greater than 12.5 gallons per minute. An "agronomically useful surfactant content" means containing one or more surfactants of such a type or types and in such an amount that a benefit is realized by the user of the composition in terms of herbicidal effectiveness by comparison with an otherwise similar composition containing no surfactant. By "fully loaded" is meant having a sufficient concentration of a suitable surfactant to provide, upon conventional dilution in water and application to foliage, herbicidal effectiveness on one or more important weed species without the need for further surfactant to be added to the diluted composition.

By "storage-stable," in the context of an aqueous concentrate composition of glyphosate salt further containing a surfactant, is meant not exhibiting phase separation on exposure to temperatures up to about 50° C., and preferably not forming crystals of glyphosate or salt thereof on exposure to a temperature of about 0° C. for a period of up to about 7 days (i.e., the composition must have a crystallization point of 0° C. or lower). For aqueous solution concentrates, high temperature storage stability is often indicated by a cloud point of about 50° C. or more. Cloud point of a composition is normally determined by heating the composition until the solution becomes cloudy, and then allowing the composition to cool, with agitation, while its temperature is continuously monitored. A temperature reading taken when the solution clears is a measure of cloud point. A cloud point of 50° C. or more is normally considered acceptable for most commercial purposes for a glyphosate SL formulation. Ideally the cloud point should be 60° C. or more, and the composition should withstand temperatures as low as about −10° C., preferably as low as about −20° C., for up to about 7 days without crystal growth, even in the presence of seed crystals of the glyphosate salt.

A surfactant that is described herein as "compatible" with a glyphosate salt at specified surfactant and glyphosate a.e. concentrations is one that provides a storage-stable aqueous concentrate as defined immediately above containing that surfactant and salt at the specified concentrations.

Users of liquid herbicidal products typically meter the dosage by volume rather than by weight, and such products are usually labeled with directions for suitable use rates expressed in volume per unit area, e.g., liters per hectare (l/ha) or fluid ounces per acre (oz/acre). Thus the concentration of herbicidal active ingredient that matters to the user is not percent by weight, but weight per unit volume, e.g., grams per liter (g/l) or pounds per gallon (lb/gal). In the case of glyphosate salts, concentration is often expressed as grams of acid equivalent per liter (g a.e./l).

Historically, surfactant-containing glyphosate IPA salt products such as Roundup® and Roundup® Ultra herbicides of Monsanto Company have most commonly been formulated at a glyphosate concentration of about 360 g a.e./l. The surfactant-containing glyphosate TMS salt product Touchdown® of Syngenta has been formulated at a glyphosate concentration of about 330 g a.e./l. Products at lower a.e. concentration, i.e., more dilute, are also sold in some markets, but carry a cost penalty per unit of glyphosate they contain, primarily reflecting packaging, shipping and warehousing costs.

Further benefits in cost savings and in convenience to the user are possible if a "fully loaded" aqueous concentrate composition, or at least one having an agronomically useful surfactant content, can be provided at a glyphosate concentration of at least about 320 g a.e./l, 340 g a.e./l, or significantly more than 360 g a.e./l, for example at least about 420 g a.e./l or more, or at least 440, 450, 460, 470, 480, 490, 500, 510, 520, 530, 540, 550, 560, 570, 580, 590, 660 g a.e./l or more.

At very high glyphosate a.e. concentrations such as these, a significant problem normally occurs. This is the difficulty in pouring and/or pumping of the aqueous concentrate arising from the high viscosity of the concentrate, especially as manifested at low temperatures. It would therefore be highly desirable to have a highly concentrated aqueous solution of glyphosate potassium salt fully loaded with an agronomically useful surfactant, such formulation preferably being less viscous than glyphosate potassium salt formulations containing alkylglycoside surfactants, such as those disclosed in PCT Publication No. WO 00/15037.

It would be a significant commercial advantage if the efficacy of potassium glyphosate formulations could be increased. Higher efficacy affords lower application rates of the herbicide to achieve the same degree of weed control. Application of less herbicide is cost effective to the consumer since less product provides equivalent weed control. Moreover, such an enhanced efficacy formulation is environmentally responsible because packaged volume is reduced, less storage space is required, shipping cost savings may be realized, and most importantly, environmental burden is minimized. As will be clear from the disclosure that follows, these and other benefits are provided by the present invention.

SUMMARY OF THE INVENTION

Among the several features of the invention, therefore, may be noted the provision of a pesticidal composition useful in agriculture wherein cellular uptake of the water-soluble pesticide into the foliage of a plant is increased by formulating the composition so as to include a compound which increases cell membrane permeability; the provision of herbicidal compositions exhibiting improved control of a broad spectrum of broadleaf plants including velvetleaf and morningglory; the provision of storage stable herbicidal concentrates which can be formulated with minimal surfactant to reduce the aquatic toxicity of the formulation without reducing its performance; and the provision of storage-stable solid or liquid concentrates that is relatively easy to dilute and use.

Briefly, therefore, the present invention is directed to an aqueous pesticidal concentrate composition comprising a water-soluble pesticide dissolved in an aqueous medium, a surfactant component and a compound which increases the cellular uptake of pesticide in a plant. The water-soluble pesticide is present in a concentration that is biologically effective when the composition is diluted in a suitable volume of water to form an enhanced application mixture and applied to the foliage of a susceptible plant. The surfactant component is in solution or stable suspension, emulsion, or dispersion in the aqueous medium. The surfactant component comprises one or more surfactants and a compound which increases cell membrane permeability within the plant to increase cellular uptake of the pesticide in the plant treated with the enhanced application mixture as compared to a plant treated with a reference application mixture devoid of the compound but otherwise having the same composition as the enhanced application mixture. The compound and surfactant component are present in a molar ratio exceeding 10:1.

The invention is also directed to an aqueous herbicidal concentrate composition comprising glyphosate, or a salt or ester thereof, and a compound which increases cell membrane permeability within a plant. The glyphosate component is in solution in an aqueous medium in a concentration in excess of 455 grams glyphosate a.e. per liter. When the composition is diluted in a suitable volume of water to form an enhanced application mixture and applied to the foliage of a susceptible plant, cellular uptake of glyphosate is increased in the plant treated with the enhanced application mixture as compared to a plant treated with a reference application mixture devoid of the compound but otherwise having the same composition as the enhanced application mixture.

Yet another embodiment of the present invention is directed to an aqueous herbicidal concentrate composition comprising glyphosate and a compound which increases the cellular uptake of glyphosate. Glyphosate is predominantly in the form of the potassium, monoammonium, dominum, sodium, monoethanolamine, n-propylamine, ethylamine, ethylenediamine, hexamethylenediamine or trimethylsulfonium salt in solution in the aqueous medium. The cellular uptake of glyphosate is increased by increasing cell membrane permeability within the plant treated with the enhanced application mixture as compared to a plant treated with a reference application mixture devoid of the compound but otherwise having the same composition as the enhanced application mixture. The concentrate is biologically effective when the composition is diluted in a suitable volume of water to form an enhanced application mixture and applied to the foliage of a susceptible plant.

Another embodiment of the invention is directed to an aqueous herbicidal concentrate composition comprising glyphosate and a compound that increases the cellular uptake of glyphosate. Glyphosate is predominantly in the form of the potassium salt thereof in solution in the aqueous medium. The cellular uptake of glyphosate is increased by increasing the cell membrane permeability within the plant treated with the enhanced application mixture as compared to a plant treated with a reference application mixture devoid of the compound but otherwise having the same composition as the enhanced application mixture. The composition is biologically effective when diluted in a suitable volume of water to form an enhanced application mixture and applied to the foliage of a susceptible plant.

The present invention is also directed to an aqueous pesticidal concentrate composition comprising a water-soluble pesticide dissolved in an aqueous medium, a surfactant component, and a compound that suppresses oxidative burst. The water-soluble pesticide is present in a concentration that is biologically effective when the composition is diluted in a suitable volume of water to form an enhanced application mixture and applied to the foliage of a susceptible plant. The surfactant component comprises one or more surfactants in solution or stable suspension, emulsion, or dispersion in the medium. The compound which suppresses oxidative burst in cells of the plant interferes with plant defense response in the plant treated with the enhanced application mixture as compared to a plant treated with a reference application mixture devoid of the compound but otherwise having the same composition as the enhanced application mixture. The compound and surfactant components are present in a molar ratio exceeding 10:1.

The present invention is yet further directed to an aqueous herbicidal concentrate composition comprising glyphosate or a salt or ester thereof, and a compound which suppresses oxidative burst in cells of a plant. Glyphosate is in solution in an aqueous medium in a concentration in excess of 455 grams glyphosate a.e. per liter. When the composition is diluted in a suitable volume of water to form an enhanced application mixture and applied to the foliage of a susceptible plant, the plant defense response is abated in the plant treated with the enhanced application mixture as compared to a plant treated with a reference application mixture devoid of the compound but otherwise having the same composition as the enhanced application mixture.

Yet another embodiment of the invention is directed to an aqueous herbicidal concentrate composition comprising glyphosate and a compound that suppresses oxidative burst in plant cells. Glyphosate is predominantly in the form of the potassium, monoammonium, dominum, sodium, monoethanolamine, n-propylamine, ethylamine, ethylenediamine, hexamethylenediamine or trimethylsulfonium salt thereof, in solution in an aqueous medium in a concentration that is biologically effective when the composition is diluted in a suitable volume of water to form an enhanced application mixture and applied to the foliage of a susceptible plant. The compound which suppresses oxidative burst interferes with the plant defense response in the plant treated with the enhanced application mixture as compared to a plant treated with a reference application mixture devoid of the compound but otherwise having the same composition as the enhanced application mixture.

An additional embodiment of the invention is directed to an aqueous herbicidal concentrate composition comprising glyphosate predominantly in the form of the potassium salt thereof, in solution in an aqueous medium in a concentration that is biologically effective when the composition is diluted in a suitable volume of water to form an enhanced application mixture and applied to the foliage of a susceptible plant. The composition further comprises a compound which suppresses oxidative burst in cells of the plant to interfere with plant defense response in the plant treated with the enhanced application mixture as compared to a plant treated with a reference application mixture devoid of the compound but otherwise having the same composition as the enhanced application mixture.

Another embodiment of the present invention is directed to an aqueous herbicidal concentrate composition comprising glyphosate or a salt or ester thereof, and oxalic acid or a salt thereof. Glyphosate is in solution in a concentration in excess of 455 grams glyphosate a.e. per liter. When the composition is diluted in a suitable volume of water to form an enhanced application mixture and applied to the foliage of a susceptible plant, growth of the plant is controlled to a greater extent than in a plant treated with a reference application mixture devoid of oxalic acid and the salt but otherwise having the same composition as the enhanced application mixture.

Yet a further embodiment of the invention is directed to an aqueous solution comprising glyphosate and oxalic acid. Glyphosate is predominantly in the form of the potassium salt thereof, and is in a concentration that is biologically effective when the composition is diluted in a suitable volume of water to form an enhanced application mixture and applied to the foliage of a susceptible broadleaf plant. Oxalic acid or a salt thereof is in a concentration such that growth of the plant is controlled to a greater extent as compared to a plant treated with a reference application mixture devoid of oxalic acid and the salt but otherwise having the same composition as the enhanced application mixture.

An additional embodiment of the present invention is directed to an aqueous solution comprising glyphosate and oxalic acid. Glyphosate is predominantly in the form of the dominum salt and is in a concentration that is biologically effective when the composition is diluted in a suitable volume of water to form an enhanced application mixture and applied to the foliage of a susceptible broadleaf plant. Oxalic acid or a salt thereof is in a concentration such that growth of the plant is controlled to a greater extent as compared to a plant treated with a reference application mixture devoid of oxalic acid and the salt but otherwise having the same composition as the enhanced application mixture.

Another embodiment of the present invention is directed to an aqueous solution comprising glyphosate and a salt of oxalic acid. Glyphosate or a salt or ester thereof is in solution in a concentration that is biologically effective when the composition is diluted in a suitable volume of water to form an enhanced application mixture and applied to the foliage of a susceptible plant is prepared. The salt of oxalic acid comprises the tetraalkylammonium or aryltrialkylammonium salt and is in a concentration such that growth of the plant treated with the enhanced application mixture is controlled to a greater extent as compared to a plant treated with a reference application mixture devoid of the salt but otherwise having the same composition as the enhanced application mixture.

Another embodiment of the present invention is directed to an aqueous herbicidal composition comprising glyphosate, one or more surfactants, and oxalic acid. Glyphosate or a salt or ester thereof is in solution in a concentration that is biologically effective when the composition is diluted in a suitable volume of water to form an enhanced application mixture and applied to the foliage of a susceptible plant. The surfactants are in solution or stable suspension, emulsion, or dispersion in the aqueous medium with oxalic acid or a salt thereof, wherein the concentration of oxalic acid or the salt and the nature of the surfactant are such that a first difference between:
  (i) the growth rate of a plant treated with a first enhanced application mixture prepared by dilution of the aqueous herbicidal composition with water and
  (ii) the growth rate of a plant treated with a first reference application mixture devoid of oxalic acid and any of the salt but otherwise having the same composition as the first enhanced application mixture is greater than a second difference between:
  (iii) the growth rate of a plant treated with a second enhanced application mixture and
  (iv) the growth rate of a plant treated with a second reference application mixture devoid of oxalic acid and any of the salt but otherwise having the same composition as the second enhanced application mixture.

The composition of the second enhanced application mixture differs from the composition of the first enhanced application mixture only with respect to the nature of the surfactant system contained therein, with the second enhanced application mixture containing an ethoxylated tallowamine surfactant having the formula:

(3)

wherein R is a mixture of predominantly $C_{16}$ and $C_{18}$ alkyl and alkenyl chains derived from tallow and the total of m+n is an average number of about 15, wherein the weight ratio of glyphosate a.e. to surfactant in the second enhanced application mixture is about 2:1.

Yet another embodiment of the present invention is directed to an aqueous herbicidal composition comprising glyphosate and oxalic acid. Glyphosate or a salt or ester thereof, is in solution in a concentration in excess of 360 grams glyphosate a.e. per liter. Oxalic acid or a salt thereof is in a concentration such that, when the composition is diluted in a suitable volume of water to form an enhanced application mixture and applied to the foliage of a susceptible broadleaf plant, growth of the plant is controlled to a greater extent as compared to a broadleaf plant treated with a reference application mixture, wherein the composition of the reference application mixture differs from the composition of the enhanced application mixture only in that it is devoid of oxalic acid and the salt and it contains ethylenediaminetetraacetic acid or sodium citrate.

A further embodiment of the present invention is directed to an aqueous herbicidal composition comprising glyphosate and oxalic acid. Glyphosate or a salt or ester thereof is in solution in a concentration that is biologically effective when the composition is diluted in a suitable volume of water to form an enhanced application mixture and applied to the foliage of a susceptible plant. Oxalic acid or a salt thereof is in a concentration such that growth of the plant is controlled to a greater extent as compared to a plant treated with a reference application mixture devoid of oxalic acid and the salt but otherwise having the same composition as the enhanced application mixture, and wherein the composition has a density of at least about 1.210 grams/liter.

Yet another embodiment of the present invention is directed to, an aqueous herbicidal concentrate composition comprising glyphosate and oxalic acid. Glyphosate is predominantly in the form of the potassium, monoammonium, dominum, sodium, monoethanolamine, n-propylamine, ethylamine, ethylenediamine, hexamethylenediamine or trimethylsulfonium salt thereof, and is in a concentration that is biologically effective when the composition is diluted in a suitable volume of water to form an enhanced application mixture and applied to the foliage of a susceptible plant. Oxalic acid or a salt thereof is in a concentration such that growth of the plant is controlled to a greater extent as compared to a plant treated with a reference application mixture devoid of oxalic acid and the salt but otherwise having the same composition as the enhanced application mixture.

The present invention is also directed to an aqueous herbicidal composition comprising glyphosate and oxalic acid. Glyphosate or a salt or ester thereof is in solution in a concentration that is biologically effective when the composition is diluted in a suitable volume of water and applied to the foliage of a susceptible plant. Glyphosate a.e. and the oxalic acid, or a salt thereof, are present in a weight ratio greater than 21:1.

Another embodiment of the present invention is directed to an aqueous pesticidal concentrate composition comprising a water-soluble pesticide dissolved in an aqueous medium, a surfactant, and a compound which increases expression of hydroxyproline-rich glycoproteins. The water-soluble pesticide is present in a concentration that is biologically effective when the composition is diluted in a suitable volume of water to form an enhanced application mixture and applied to the foliage of a susceptible plant. The surfactant component comprises one or more surfactants and is in solution or stable suspension, emulsion, or dispersion in the medium. The compound which increases expression of hydroxyproline-rich glycoproteins increases movement of the pesticide to the phloem in the plant treated with the enhanced application mixture as compared to a plant treated with a reference application mixture devoid of the compound but otherwise having the same composition as the enhanced application mixture. The compound and surfactant component are present in a molar ratio exceeding 10:1.

Yet another embodiment of the present invention is directed to an aqueous herbicidal concentrate composition comprising glyphosate and a compound which increases expression of hydroxyproline-rich glycoproteins. Glyphosate or a salt or ester thereof is in solution in a concentration in excess of 455 grams glyphosate a.e. per liter. The compound which increases expression of hydroxyproline-rich glycoproteins is in a concentration such that, when the composition is diluted in a suitable volume of water to form an enhanced application mixture and applied to the foliage of a susceptible plant, movement of the glyphosate to the phloem is increased in the plant treated with the enhanced application mixture as compared to a plant treated with a reference application mixture devoid of the compound but otherwise having the same composition as the enhanced application mixture.

Another embodiment of the present invention is directed to an aqueous herbicidal concentrate composition comprising glyphosate, a surfactant component and oxalic acid wherein:
  (i) glyphosate or a salt or ester thereof, is in solution in a concentration that is biologically effective when the composition is diluted in a suitable volume of water and applied to the foliage of a susceptible plant;
  (ii) a surfactant component is in solution or stable suspension, emulsion, or dispersion in the medium, and comprises one or more surfactant(s); and
  (iii) oxalic acid or a salt thereof.

The surfactant component comprises at least one surfactant selected from the group consisting of:

(a) a phosphate ester having the formula:

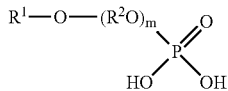 (57)

wherein $R^1$ is a linear or branched alkyl, linear or branched alkenyl, linear or branched alkenyl, aryl, or aralkyl group having from about 4 to about 30 carbon atoms; $R^2$ in each of the m ($R^2O$) groups is independently $C_2$-$C_4$ alkylene; and m is from 1 to about 30;

(b) a phosphate diester having the formula:

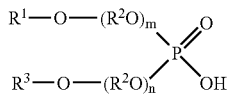 (56)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2O$) and the n ($R^2O$) groups is independently $C_2$-$C_4$ alkylene; and m and n are independently from 1 to about 30;

(c) etheramines having the formula:

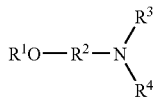 (32)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —($R^5O$)$_x R^6$, $R^5$ in each of the x($R^5$—O) groups is independently $C_2$-$C_4$ alkylene, $R^6$ is hydrogen, or a linear or branched alkyl group having from 1 to about 4 carbon atoms, and x is an average number from 1 to about 50; and (d) monoalkoxylated quaternary ammonium salts having the formula:

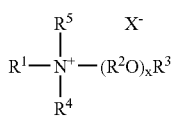 (30)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x($R^2O$) groups is independently $C_2$-$C_4$ alkylene, $R^3$ is hydrogen, or a linear or branched alkyl group having from 1 to about 30 carbon atoms, x is an average number from 1 to about 60, and X— is an agriculturally acceptable anion.

Yet another embodiment of the present invention is directed to a method of decreasing surfactant content of an aqueous herbicidal concentrate composition required to provide a given degree of growth control observed when the composition is diluted with water and applied to foliage of a plant. The method comprises adding oxalic acid or a salt thereof to the composition, the composition comprising glyphosate or a salt or ester thereof and one or more surfactants.

In a further embodiment of the present invention, a method of decreasing aquatic toxicity of an aqueous herbicidal composition without decreasing growth control observed when the composition is diluted with water and applied to foliage of a plant is provided. The method comprises adding oxalic acid or a salt thereof to the composition, the composition comprising glyphosate or a salt or ester thereof.

In another embodiment of the present invention, a method of controlling growth of morningglory is provided. The method comprises applying an aqueous composition to foliage of morningglory, the composition comprising glyphosate or a salt or ester thereof and oxalic acid or a salt thereof.

A further embodiment of the present invention is directed to an aqueous herbicidal concentrate composition comprising glyphosate, a surfactant component and oxalic acid wherein:

(i) glyphosate or a salt or ester thereof, is in solution in an aqueous medium in a concentration that is biologically effective when the composition is diluted in a suitable volume of water and applied to the foliage of a susceptible plant;

(ii) a surfactant component in solution or stable suspension, emulsion, or dispersion in the medium, and comprising one or more surfactant(s); and (iii) oxalic acid or a salt thereof.

The surfactant component comprises at least one surfactant selected from various cationic, nonionic and anionic surfactants.

Yet another embodiment of the present invention is directed to a solid pesticidal concentrate composition comprising a water-soluble pesticide and a compound which increases cell membrane permeability. The pesticide is present in a concentration that is biologically effective when the composition is diluted in a suitable volume of water to form an enhanced application mixture and applied to the foliage of a susceptible plant. The compound which increases cell membrane permeability is a compound that increases cellular uptake of the pesticide in the plant treated with the enhanced application mixture as compared to a plant treated with a reference application mixture devoid of the compound but otherwise having the same composition as the enhanced application mixture, and wherein the weight ratio of the pesticide to the compound is at least 2.5:1.

In another embodiment of the present invention, a solid herbicidal concentrate composition comprising a glyphosate and a compound which increases cell membrane permeability. Glyphosate, or salt or ester, is present in a concentration that is biologically effective when the composition is diluted in a suitable volume of water to form an enhanced application mixture and applied to the foliage of a susceptible plant is formulated. The compound which increases cell membrane permeability within the plant is a compound that increases cellular uptake of the pesticide in the plant treated with the enhanced application mixture as compared to a plant treated with a reference application mixture devoid of the compound but otherwise having the same composition as the enhanced application mixture.

Another embodiment of the present invention is directed to a solid pesticidal concentrate composition comprising a water-soluble pesticide and a compound which suppresses oxidative burst. The pesticide is present in a concentration that is biologically effective when the composition is diluted in a suitable volume of water to form an enhanced application mixture and applied to the foliage of a susceptible plant. The compound which suppresses oxidative burst in cells of the plant is a compound that interferes with plant defense response in the plant treated with the enhanced application mixture as compared to a plant treated with a reference application mixture devoid of the compound but otherwise having the same composition as the enhanced application mixture, and wherein the weight ratio of the pesticide to the compound is at least 2.5:1.

A further embodiment of the present invention is directed to a solid herbicidal concentrate composition comprising a glyphosate salt or ester and a compound that suppresses oxidative burst. The glyphosate salt or ester is present in a concentration that is biologically effective when the composition is diluted in a suitable volume of water to form an enhanced application mixture and applied to the foliage of a susceptible plant. The compound which suppresses oxidative burst in cells of the plant is a compound that interferes with plant defense response in the plant treated with the enhanced application mixture as compared to a plant treated with a reference application mixture devoid of the compound but otherwise having the same composition as the enhanced application mixture.

Another embodiment of the present invention is directed to a solid pesticidal concentrate composition comprising a water-soluble pesticide and a compound that increases the expression of hydroxyproline-rich glycoproteins. The pesticide is present in a concentration that is biologically effective when the composition is diluted in a suitable volume of water to form an enhanced application mixture and applied to the foliage of a susceptible plant. The compound which increases expression of hydroxyproline-rich glycoproteins is a compound which increases movement of the pesticide to the phloem in the plant treated with the enhanced application mixture as compared to a plant treated with a reference application mixture devoid of the compound but otherwise having the same composition as the enhanced application mixture, and wherein the weight ratio of the pesticide to the compound is at least 2.5:1.

An additional embodiment of the present invention is directed to a solid herbicidal concentrate composition comprising a glyphosate salt or ester and a compound that increases the expression of hydroxyproline-rich glycoproteins. Glyphosate is present in a concentration that is biologically effective when the composition is diluted in a suitable volume of water to form an enhanced application mixture and applied to the foliage of a susceptible plant. The compound which increases expression of hydroxyproline-rich glycoproteins is a compound which increases movement of the pesticide to the phloem in the plant treated with the enhanced application mixture as compared to a plant treated with a reference application mixture devoid of the compound but otherwise having the same composition as the enhanced application mixture.

Yet a further embodiment of the present invention is directed to a solid pesticidal concentrate composition comprising a water-soluble pesticide and oxalic acid or a salt thereof. The pesticide present in a concentration that is biologically effective when the composition is diluted in a suitable volume of water and applied to the foliage of a susceptible plant. The glyphosate and oxalic acid are present in a weight ratio of at least 2.5:1.

Another embodiment of the present invention is directed to a solid pesticidal concentrate composition comprising a glyphosate salt or ester and oxalic acid or a salt thereof. Glyphosate is present in a concentration that is biologically effective when the composition is diluted in a suitable volume of water and applied to the foliage of a susceptible plant.

A final embodiment of the present invention is directed to a solid pesticidal concentrate composition comprising a water-soluble pesticide, a surfactant and oxalic acid or a salt thereof. The pesticide is present in a concentration that is biologically effective when the composition is diluted in a suitable volume of water and applied to the foliage of a susceptible plant. The surfactant component comprises one or more cationic or nonionic surfactants.

DETAILED DESCRIPTION OF THE PREFERRED EMBODIMENTS

Some aqueous pesticidal concentrates, especially those containing potassium glyphosate, are difficult to compatibilize with surfactants. It is desirable to minimize or sometimes eliminate surfactants from such compositions since surfactants are quite costly and sometimes cause aquatic toxicity. It has been discovered that the addition of oxalic acid or salts thereof to glyphosate compositions increases the cell membrane permeability of plant cells or suppresses oxidative burst to increase cellular uptake of glyphosate. The increase is not caused by the ability of oxalic acid to chelate calcium and other metal ions in hard water. In fact, oxalic acid improves efficacy significantly more than conventional chelators such as EDTA or sodium citrate. The oxalic acid efficacy advantage over EDTA is present even though EDTA possesses a chelating capability about five orders of magnitude greater than oxalic acid. The addition of a relatively small amount of oxalic acid significantly reduces the amount of surfactant needed to provide a stable composition which, upon dilution and application to foliage of a plant, provides desired plant growth control. It also significantly improves the performance of many surfactants which otherwise provide poor growth control, enabling the use of a broader range of surfactants in herbicidal formulations. The compositions have been effective in controlling a broad spectrum of broadleaf plants including velvetleaf, sicklepod and morningglory.

While not wishing to be bound to any particular theory, there are several mechanisms by which oxalic acid, its salts and other compounds are likely to improve glyphosate bioefficacy. First, oxalic acid increases cell membrane permeability in a plant by chelating calcium in the cell walls and/or apoplast which compromises calcium dependent defense responses. Second, enhanced expression of hydroxyproline-rich glycoproteins (HRGPs) enhances glyphosate movement to the phloem. Third, oxalic acid suppresses the oxidative burst in the cells of a plant. The oxidative burst is an early resistance response mounted by plant tissue resulting in controlled release of $O_2^-$ and hydrogen peroxide. In other words, oxalic acid inhibits the free-radical generating oxidase directly, or by blocking a signaling step leading to the activation of the oxidase. Suppression of the oxidative burst interferes with plant defense response which would otherwise limit glyposate bioefficacy.

In an embodiment of the invention, an aqueous pesticidal concentrate composition is provided which comprises a water-soluble pesticide dissolved in water. The water-soluble pesticide is present in a concentration that is biologically effective when the composition is diluted in a suitable volume of water and applied to the foliage of a susceptible plant. The composition also comprises a surfactant component in solution or stable suspension, emulsion, or dispersion in the water. The surfactant component comprises one or more surfactants. The surfactant component is present in a concentration sufficient to provide acceptable temperature stability of the composition such that the composition has a cloud point of at least about 50° C. and a crystallization point not greater than about 0° C. The composition also includes a compound which increases cell membrane permeability within the plant to increase cellular uptake of the pesticide as compared to a similarly loaded water-soluble pesticide composition which includes the same surfactant component without the compound.

In another embodiment of the invention, the aqueous pesticidal concentrate contains the pesticide, the surfactant component, and a compound which suppresses oxidative burst in cells of a plant to increase cellular uptake of the pesticide as compared to a similarly loaded water-soluble pesticide composition which includes the same surfactant system without the compound. Oxalic acid and its salts are effective in increasing cell membrane permeability and/or suppressing oxidative burst in compositions of the invention.

Solid pesticidal concentrate compositions of the invention comprise the pesticide and a compound which increases cell membrane permeability within the plant or suppresses oxidative burst in cells of a plant to increase cellular uptake of the pesticide as compared to a similarly loaded water-soluble pesticide composition which includes the same surfactant system without the compound. The surfactant component is an optional component of the solid concentrate compositions. In some jurisdictions, aquatic toxicity or other environmental regulatory issues such as caution or warning labeling may dictate how much, if any, surfactant is incorporated in the solid concentrates of the invention.

Although oxalic acid has proven most effective in improving the performance of the compositions of the invention, other components are also effective in formulating the pesticide compositions. Organic acids, particularly polycarboxylic acids, may be added to the compositions to enhance herbicidal effectiveness. Preferred polycarboxylic acids include dicarboxylic acids, Suitable dicarboxylic acids that may be added to the formulations include oxalic acid, malonic acid, succinic acid, glutaric acid, maleic acid, adipic acid, and fumaric acid, salts thereof and mixtures thereof, with oxalic acid being preferred. Suitable salts include, for example, alkali metal salts such as sodium and potassium salts, alkanolamine salts and alkylamine salts such as IPA. Preferred salts include potassium oxalate, dipotassium oxalate, sodium oxalate, disodium oxalate, diammonium oxalate, diethanolamine oxalate, dimethylamine oxalate, alkanolamine salts of oxalic acid, and lower alkylamine salts of oxalic acid. Formulations contain such compounds in an amount sufficient to enhance the resulting efficacy of the formulation. Typically, in liquid systems the weight ratio of total surfactant to dicarboxylic acid compound may be from about 1:1 to about 50:1, more preferably 5:1 to 40:1 and most preferably from about 5:1 to about 20:1. This ratio of total surfactant to dicarboxylic acid significantly enhances the herbicidal performance of the resulting formulation. Preferably, the weight ratio of glyphosate in the free acid, or a.e., form to dicarboxylic acid is between about 1:1 and about 500:1, more preferably about 2:1 to about 100:1, and most preferably between about 2:1 to about 50:1. In dry formulations, the weight ratio of total surfactant to dicarboxylic acid compound is between about 50:1 and about 1:30, more preferably between about 1:1 and about 5:1, and most preferably between about 1:1 and about 3:1.

The liquid concentrate compositions of the invention preferably comprise a water-soluble herbicide in a concentration between about 20 and about 45% by weight of the composition, a surfactant component in a concentration between about 0.1 and about 25% by weight of the composition, and a dicarboxylic acid in a concentration between about 0.01 and about 20% by weight of the composition. More preferably, the compositions comprise glyphosate or a salt or ester thereof in a concentration between about 25 and about 40% by weight of the composition, a surfactant component in a concentration between about 0.1 and about 20% by weight of the composition, and a dicarboxylic acid in a concentration between about 0.01 and about 15% by weight of the composition. Even more preferably, the compositions comprise glyphosate or a salt or ester thereof in a concentration between about 30 and about 40% by weight of the composition, a surfactant component in a concentration between about 0.1 and about 10% by weight of the composition, and a dicarboxylic acid in a concentration between about 0.01 and about 10% by weight of the composition. Most preferably, the compositions comprise glyphosate or a salt or ester thereof in a concentration between about 31 and about 40% by weight of the composition, a surfactant component in a concentration between about 0.1 and about 7% by weight of the composition, and oxalic acid or a salt thereof in a concentration between about 0.01 and about 5% by weight of the composition.

The solid concentrate compositions of the invention preferably comprise a water-soluble herbicide in a concentration between about 40 and about 90% by weight of the composition, a surfactant component in a concentration up to about 30% by weight of the composition, and a dicarboxylic acid in a concentration between about 1 and about 30% by weight of the composition. More preferably, the compositions comprise glyphosate or a salt or ester thereof in a concentration between about 50 and about 80% by weight of the composition, a surfactant component in a concentration between about 5 and about 25% by weight of the composition, and a dicarboxylic acid in a concentration between about 1 and about 25% by weight of the composition. Even more preferably, the compositions comprise glyphosate or a salt or ester thereof in a concentration between about 60 and about 80% by weight of the composition, a surfactant component in a concentration between about 7.5 and about 20% by weight of the composition, and a dicarboxylic acid in a concentration between about 1 and about 20% by weight of the composition. Most preferably, the compositions comprise glyphosate or a salt or ester thereof in a concentration between about 60 and about 80% by weight of the composition, a surfactant component in a concentration between about 7.5 and about 25% by weight of the composition, and oxalic acid or a salt thereof in a concentration between about 5 and about 20% by weight of the composition.

Compositions of the invention have a viscosity of not greater than about 1000 cPs at 10° C., preferably not greater than about 900 cPs at 10° C., more preferably not greater than about 800, 700, 600, 500, 400 or 300 cPs at 10° C., and even more preferably not greater than about 200 cPs at 10° C., at 45/s shear rate.

The term "water-soluble" as used herein in relation to a herbicide or salt or ester thereof means having a solubility in deionized water at 20° C. of not less than about 50 g/l. Preferred water-soluble herbicides have a solubility in deionized water at 20° C. of not less than about 200 g/l. Particularly preferred water-soluble herbicides have a herbicidal active acid or anionic moiety and are most usefully present in a composition of the invention in the form of one or more water-soluble salts. The aqueous phase of the composition can optionally contain, in addition to the water-soluble herbicide, other salts contributing to the ionic strength of the aqueous phase.

A particularly preferred group of water-soluble herbicides are those that are normally applied post-emergence to the foliage of plants. While the invention is not limited to any particular class of foliar-applied water-soluble herbicide, it has been found to provide useful benefits for compounds that rely at least in part for their herbicidal effectiveness on systemic movement in plants. Systemic movement in plants can take place via apoplastic (non-living) pathways, including within xylem vessels and in intercellular spaces and cell walls, via symplastic (living) pathways, including within phloem elements and other tissues composed of cells connected symplastically by plasmodesmata, or via both apoplastic and symplastic pathways. For foliar-applied systemic herbicides, the most important pathway is the phloem, and the present invention is believed to provide the greatest benefits where the water-soluble herbicide is phloem-mobile. However, compositions of the invention can also be useful where the water-soluble herbicide is non-systemic, as in the case of paraquat.

Water-soluble herbicides suitable for use in compositions of the invention include acifluorfen, acrolein, amitrole, asulam, benazolin, bentazon, bialaphos, bromacil, bromoxynil, chloramben, chloroacetic acid, clopyralid, 2,4-D, 2,4-DB, dalapon, dicamba, dichlorprop, difenzoquat, diquat, endothall, fenac, fenoxaprop, flamprop, flumiclorac, fluoroglycofen, flupropanate, fomesafen, fosamine, glufosinate, glyphosate, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, quinclorac, sulfamic acid, 2,3,6-TBA, TCA, triclopyr and water-soluble salts thereof.

Phloem-mobile herbicides that are preferred for use in compositions of the invention include but are not limited to aminotriazole, asulam, bialaphos, clopyralid, dicamba, glufosinate, glyphosate, imidazolinones such as imazameth, imazamethabenz, imazamox, imazapic, imazapyr, imazaquin and imazethapyr, phenoxies such as 2,4-D, 2,4-DB, dichlorprop, MCPA, MCPB and mecoprop, picloram and triclopyr. A particularly preferred group of water-soluble herbicides are salts of bialaphos, glufosinate and glyphosate. Another particularly preferred group of water-soluble herbicides are salts of imidazolinone herbicides.

Compositions of the invention can optionally contain more than one water-soluble herbicide in solution in the aqueous phase.

An especially preferred water-soluble herbicide useful in a composition of the present invention is glyphosate, the acid form of which is alternatively known as N-(phosphonomethyl)glycine. For example, glyphosate salts useful in compositions of the present invention are disclosed in U.S. Pat. No. 3,799,758 and U.S. Pat. No. 4,405,531. Glyphosate salts that can be used according to the present invention include but are not restricted to alkali metal, for example sodium and potassium, salts; ammonium salt; $C_{1-6}$ alkylammonium, for example dimethylammonium and isopropylammonium, salts; $C_{1-6}$ alkanolammonium, for example monoethanolammonium, salt; $C_{1-6}$ alkylsulfonium, for example trimethylsulfonium, salts; and mixtures thereof. The N-phosphonomethylglycine molecule has three acid sites having different pKa values; accordingly mono-, di- and tribasic salts, or any mixture thereof, or salts of any intermediate level of neutralization, can be used. Especially preferred glyphosate salts include the potassium salt, isopropylamine salt, ammonium salt, diammonium salt, monoethanolamine salt, and trimethylsulfonium salt. The potassium salt is most preferred.

The relative amount of potassium glyphosate loading in the pesticidal compositions of the present invention will vary depending upon many factors including the surfactant system employed, the rheological characteristics of the composition, and the temperature range at which the composition will be exposed. The potassium glyphosate loading in the herbicidal compositions of the invention is preferably at least 320 g a.e./L, and more preferably at least 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690 or 700 g a.e./L.

Compositions of the invention can optionally contain one or more water-insoluble herbicides in solution in an organic solvent or in suspension in a concentration that is biologically effective when the composition is diluted in a suitable volume of water and applied to the foliage of a susceptible plant. Preferred water-insoluble herbicide is selected from the group consisting of acetochlor, aclonifen, alachlor, ametryn, amidosulfuron, anilofos, atrazine, azafenidin, azimsulfuron, benfluralin, benfuresate, bensulfuron-methyl, bensulide, benzfendizone, benzofenap, bromobutide, bromofenoxim, butachlor, butafenacil, butamifos, butralin, butroxydim, butylate, cafenstrole, carfentrazone-ethyl, carbetamide, chlorbromuron, chloridazon, chlorimuron-ethyl, chlorotoluron, chlornitrofen, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluazifop-P-butyl, fluazoate, fluchloralin, flumetsulam, flumiclorac-pentyl, flumioxazin, fluometuron, fluorochloridone, flupoxam, flurenol, fluridone, fluroxypyr-1-methylheptyl, flurtamone, fluthiacet-methyl, graminicides, halosulfuron, haloxyfop, hexazinone, imazosulfuron, indanofan, isoproturon, isouron, isoxaben, isoxaflutole, isoxapyrifop, lenacil, linuron, mefenacet, metamitron, metazachlor, methabenzthiazuron, methyldymron, metobenzuron, metobromuron, metolachlor, S-metolachlor, metosulam, metoxuron, metribuzin, metsulfuron, molinate, monolinuron, naproanilide, napropamide, neburon, nicosulfuron, norflurazon, orbencarb, oryzalin, oxadiargyl, oxadiazon, oxasulfuron, pebulate, pendimethalin, pentanochlor, pentoxazone, phenmedipham, piperophos, pretilachlor, primisulfuron, prodiamine, profluazol, prometon, prometryn, propachlor, propanil, propaquizafop, propazine, propham, propisochlor, propyzamide, prosulfocarb, prosulfuron, pyraflufen-ethyl, pyrazogyl, pyrazolynate, pyrazosulfuron-ethyl, pyrazoxyfen, pyributicarb, pyridate, pyriminobac-methyl, quinclorac, quinmerac, quizalofop, quizalofop-P, rimsulfuron, sethoxydim, siduron, simazine, simetryn, sulcotrione, sulfentrazone, sulfometuron, sulfosulfuron, tebutam, tebuthiuron, tepraloxydim, terbacil, terbumeton, terbuthylazine, terbutryn, thenylchlor, thiazopyr, thidiazimin, thifensulfuron, thiobencarb, tiocarbazil, tralkoxydim, triallate, triasulfuron, tribenuron, trietazine, trifluralin, triflusulfuron and vernolate.

The surfactant component of the composition of the present invention when applied with the above-mentioned herbicidal components of the invention is of the type and present in a sufficient concentration to allow the plant to cellularly uptake and translocate a herbicidally effective amount of glyphosate. One way to accomplish this is to provide more intimate contact between the applied herbicidal composition and the microtopographically rough surface of the plant, for example by flattening the contact angle of the composition, so as to permit the composition to spread into crevices and pores in the plant. For example, the surfactant composition should preferably also enhance sticking or adhesion to a plant surface when used in aqueous solution, and it should allow the solution to dry on a time scale that is effective to permit penetration.

Various surfactants have been found to be effective in formulating herbicidal compositions and concentrates of the invention, particularly in formulating compositions and concentrates containing potassium glyphosate.

Cationic surfactants effective in forming herbicide formulations include:

(a) aminated alkoxylated alcohol having the formula:

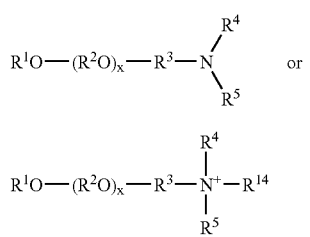

wherein $R^1$ is hydrogen or hydrocarbyl or substituted hydrocarbyl having from 1 to about 30 carbon atoms; $R^2$ in each of the $x(R^2O)$ and $y(R^2O)$ groups is independently $C_2$-$C_4$ alkylene; $R^3$ and $R^6$ are each independently hydrocarbylene or substituted hydrocarbylene having from 1 to about 6 carbon atoms; $R^4$ is hydrogen, hydrocarbyl or substituted hydrocarbyl having from 1 to about 30 carbon atoms, hydroxy substituted hydrocarbyl, $—(R^6)_n—(R^2O)_yR^7$, $—C(=NR^{11})NR^{12}R^{13}$, $—C(=O)NR^{12}R^{13}$, $—C(=S)NR^{12}R^{13}$ or together with $R^5$ and the nitrogen atom to which they are attached, form a cyclic or heterocyclic ring; $R^5$ is hydrogen, hydrocarbyl or substituted hydrocarbyl having from 1 to about 30 carbon atoms, hydroxy substituted hydrocarbyl, $(R^6)_n—(R^2O)_yR^7$, $—C(=NR^{11})NR^{12}R^{13}$, $—C(=O)NR^{12}R^{13}$, $—C(=S)NR^{12}R^{13}$, or together with $R^4$ and the nitrogen atom to which they are attached, form a cyclic or heterocyclic ring; $R^7$ is hydrogen or a linear or branched alkyl group having 1 to about 4 carbon atoms; $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, $—(R^6)_n—(R^2O)_yR^7$, $—C(=NR^{11})NR^{12}R^{13}$, $—C(=O)NR^{12}R^{13}$, or $—C(=S)NR^{12}R^{13}$, n is 0 or 1, x and y are independently an average number from 1 to about 60, and A- is an agriculturally acceptable anion. In this context, preferred $R^1$, $R^3$, $R^4$, $R^5$, $R^6$, $R^{11}$, $R^{12}$ and $R^{13}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment, $R^3$ is linear alkylene, preferably ethylene, and $R^1$, $R^2$, $R^4$ and $R^5$ are as previously defined. In another embodiment, $R^4$ is H, alkyl, or $—R^2OR^7$ and $R^1$, $R^2$, $R^3$, $R^5$ and $R^7$ are as previously defined. In yet another embodiment, $R^1$ is a linear or branched alkyl or linear or branched alkenyl group having from about 8 to about 25 carbon atoms, $R^2$ in each of the $x(R^2O)$ groups is independently $C_2$-$C_4$ alkylene, $R^3$ is a linear or branched alkylene group having from 1 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene group having from 1 to about 4 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is an ethylene or a 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the $x(R^2O)$ groups is independently ethylene or propylene, $R^3$ is an ethylene or a 2-hydroxypropylene group, $R^4$ and $R^5$ are methyl, and x is an average number from about 4 to about 20. Compounds of formula (2) have the preferred groups as described above and $R^{14}$ is preferably hydrogen or a linear or branched alkyl or alkenyl group, more preferably alkyl, and most preferably methyl. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10,15 or 20 or 25 $C_{16-18}$ ether dimethyl propylamines (from Tomah).

(b) hydroxylated amides having the formula:

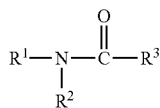

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and $R^3$ is hydroxyalkyl, polyhydroxyalkyl, or poly(hydroxyalkyl)alkyl. In this context, preferred $R^1$ and $R^2$ hydrocarbyl groups are linear or branched alkyl, linear or branched alkenyl, linear or branched alkynyl, aryl, or aralkyl groups. Preferably, the hydroxylated amides have the formula:

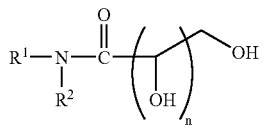

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and n is 1 to about 8. In this context, preferred $R^1$ and $R^2$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ is hydrogen, a linear or branched alkyl or linear or branched alkenyl group having from 1 to about 30 carbon atoms, and n is about 4 to about 8; or $R^1$ and $R^2$ are independently linear or branched alkyl or linear or branched alkenyl groups having from about 4 to about 30 carbon atoms and n is about 4 to about 8. More preferably, $R^1$ is a linear or branched alkyl or linear or branched alkenyl group having from about 8 to about 22 carbon atoms, $R^2$ is hydrogen or a linear or branched alkyl or linear or branched alkenyl group having from 1 to about 6 carbon atoms, and n is about 4 to about 8; or $R^1$ and $R^2$ are independently linear or branched alkyl or linear or branched alkenyl groups having from about 4 to about 8 carbon atoms, and n is about 4 to about 8.

(c) diamines having the formula:

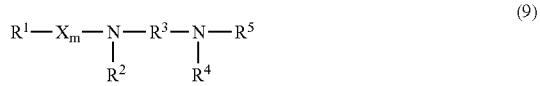
(9)

wherein $R^1$, $R^2$ and $R^5$ are independently hydrogen or hydrocarbyl or substituted hydrocarbyl having from 1 to about 30 carbon atoms or $-R^8(OR^9)_nOR^{10}$, $R^3$ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^4$ and $R^{10}$ are independently hydrogen or hydrocarbyl or substituted hydrocarbyl having from 1 to about 30 carbon atoms, m is 0 or 1, n is an average number from 0 to about 40, and X is $-C(O)-$ or $-SO_2-$. In this context, preferred $R^1$, $R^2$, $R^3$, $R^4$, $R^5$ and $R^{10}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$ and $R^5$ are independently hydrogen, a linear or branched alkyl or alkenyl group having from 1 to about 6 carbon atoms, and $R^3$ is a linear or branched alkylene having from 2 to about 6 carbon atoms. More preferably, $R^1$, $R^2$, $R^4$ and $R^5$ are independently hydrogen, or a linear or branched alkyl group having from 1 to about 6 carbon atoms, and $R^3$ is a linear or branched alkylene having from 2 to about 6 carbon atoms. Most preferably, $R^1$, $R^2$, $R^4$, and $R^5$ are independently hydrogen or methyl, and $R^3$ is ethylene or propylene.

(d) mono- or di-ammonium salts having the formula:

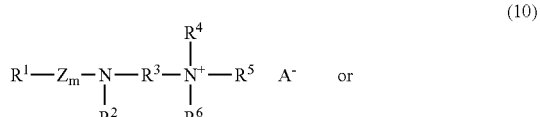
(10)

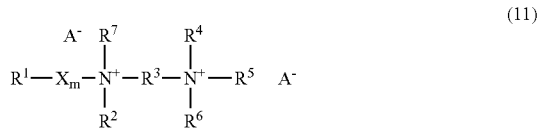
(11)

wherein $R^1$, $R^2$, $R^4$, $R^5$ and $R^7$ are independently hydrogen or hydrocarbyl or substituted hydrocarbyl having from 1 to about 30 carbon atoms or $-R^8(OR^9)_nOR^{10}$, $R^6$ is hydrocarbyl or substituted hydrocarbyl having from 1 to about 30 carbon atoms, $R^3$ is hydrocarbylene or substituted hydrocarbylene having from 2 to about 30 carbon atoms, $R^8$ and $R^9$ are individually hydrocarbylene or substituted hydrocarbylene having from 2 to about 4 carbon atoms, $R^{10}$ is hydrogen or hydrocarbyl or substituted hydrocarbyl having from 1 to about 30 carbon atoms, m is 0 or 1, n is an average number from 0 to about 40, X is $-C(O)-$ or $-SO_2-$, Z is $-C(O)-$ and A- is an agriculturally acceptable anion. In this context, preferred $R^1$-$R^{10}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$, $R^5$ and $R^7$ are independently hydrogen, or a linear or branched alkyl or alkenyl group having from 1 to about 6 carbon atoms, $R^6$ is a linear or branched alkyl or alkenyl group having from about 8 to about 30 carbon atoms, m is 0 or 1, and $R^3$ is a linear or branched alkylene having from 2 to about 22 carbon atoms. More preferably, $R^1$, $R^2$, $R^4$, $R^5$ and $R^7$ are independently hydrogen, or a linear or branched alkyl group having from 1 to about 6 carbon atoms, $R^6$ is a linear or branched alkyl group having from about 8 to about 22 carbon atoms, m is 0 or 1, and $R^3$ is a linear or branched alkylene having from 2 to about 20 carbon atoms. Most preferably, $R^1$, $R^2$, $R^4$, $R^5$ and $R^7$ are independently hydrogen or methyl, $R^6$ is a linear or branched alkyl group having from about 8 to about 18 carbon atoms, m is 0 or 1, and $R^3$ is ethylene or propylene.

(e) poly(hydroxyalkyl)amines having the formula:

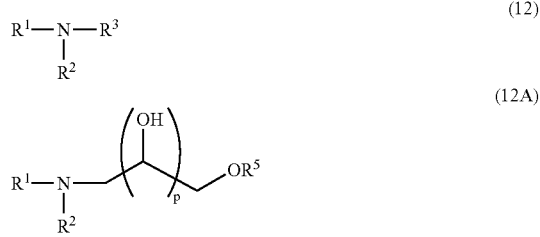
(12)

(12A)

wherein $R^1$ is hydrocarbyl or substituted hydrocarbyl having from about 4 to about 30 carbon atoms or $-R^4OR^8$, $R^2$ is hydrogen or hydrocarbyl or substituted hydrocarbyl having from 1 to about 30 carbon atoms, $R^3$ is hydroxyalkyl, polyhydroxyalkyl, or poly(hydroxyalkyl)alkyl, $R^4$ is hydrocarbylene or substituted hydrocarbylene having from 2 to about 18 carbon atoms, $R^8$ is hydrogen or hydrocarbyl or substituted hydrocarbyl having from 1 to about 30 carbon atoms, $R^5$ is $-(R^6O)_yR^7$; $R^6$ in each of the y($R^6O$) groups is independently $C_2$-$C_4$ alkylene; $R^7$ is hydrogen or a linear or branched alkyl group having 1 to about 4 carbon atoms; and y is an average number from 0 to about 30. Preferably, the poly(hydroxyalkyl)amines have the formula:

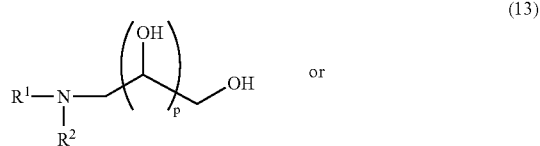
(13)

-continued

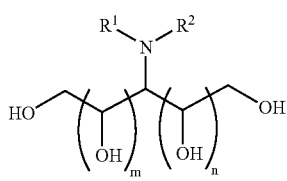
(14)

wherein $R^1$ is hydrocarbyl or substituted hydrocarbyl having from about 4 to about 30 carbon atoms or —$R^3$–$OR^4$; $R^2$ is hydrogen or hydrocarbyl or substituted hydrocarbyl having from 1 to about 30 carbon atoms, $R^3$ is hydrocarbylene or substituted hydrocarbylene having from 2 to about 18 carbon atoms, $R^4$ is hydrogen or hydrocarbyl or substituted hydrocarbyl having from 1 to about 30 carbon atoms, m and n are independently integers from 0 to about 7, the sum of m and n is not greater than about 7, and p is an integer from 1 to about 8. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 30 carbon atoms or —$R^3OR^4$, $R^2$ is hydrogen, a linear or branched alkyl or linear or branched alkenyl group having from 1 to about 30 carbon atoms, $R^3$ is a linear or branched alkylene or alkenylene group having from 2 to about 6 carbon atoms, $R^4$ is a linear or branched alkyl or alkenyl group having from about 8 to about 22 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 30 carbon atoms, m and n are independently integers from 0 to about 7, the sum of m and n is from about 3 to 7, and p is an integer from about 4 to about 8. More preferably, $R^1$ is a linear or branched alkyl or linear or branched alkenyl group having from about 8 to about 22 carbon atoms or —$R^3OR^4$, $R^2$ is hydrogen or a linear or branched alkyl or linear or branched alkenyl group having from 1 to about 6 carbon atoms, $R^3$ is a linear or branched alkylene or alkenylene group having from 2 to about 6 carbon atoms, $R^4$ is a linear or branched alkyl or alkenyl group having from about 8 to about 18 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms or —$R^3OR^4$, $R^2$ is hydrogen or methyl, m and n are independently integers from 0 to about 4, $R^3$ is a linear or branched alkylene group having from 2 to about 6 carbon atoms, $R^4$ is a linear or branched alkyl group having from about 8 to about 18 carbon atoms, the sum of m and n is about 4, and p is an integer of about 4. Most preferably, $R^1$ is a linear or branched alkyl group having from about 8 to about 18 carbon atoms or —$R^3OR^4$, $R^2$ is methyl, $R^3$ is ethylene, propylene, hydroxyethylene or 2-hydroxypropylene, $R^4$ is a linear or branched alkyl group having from about 8 to about 18 carbon atoms, m and n are independently integers from 0 to about 4, the sum of m and n is about 4, and p is an integer of about 4. Such compounds are commercially available from Aldrich and Clariant.

(f) alkoxylated poly(hydroxyalkyl)amines having the formula:

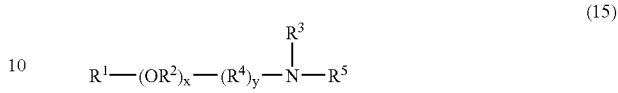
(15)

wherein $R^1$ and $R^3$ are independently hydrogen, hydrocarbyl or substituted hydrocarbyl having from 1 to about 30 carbon atoms, $R^2$ in each of the $x(R^2O)$ groups is independently $C_2$-$C_4$ alkylene; $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl; x is an average number from 0 to about 30, and y is 0 or 1. In this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferred alkoxylated poly(hydroxyalkyl)amines have the formula:

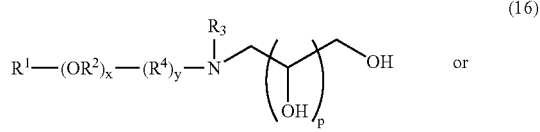
(16)

or

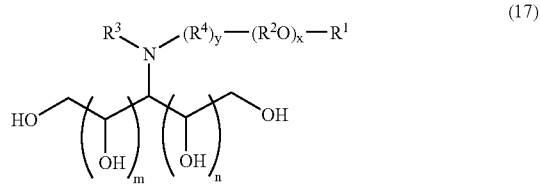
(17)

wherein $R^1$ and $R^3$ are independently hydrogen, hydrocarbyl or substituted hydrocarbyl having from 1 to about 30 carbon atoms, $R^2$ in each of the $x(R^2O)$ groups is independently $C_2$-$C_4$ alkylene; $R^4$ is hydrocarbylene or substituted hydrocarbylene having from 1 to about 30 carbon atoms, m and n are independently integers from 0 to about 7, the sum of m and n is not greater than about 7, p is an integer from 1 to about 8, x is an average number from 0 to about 30, and y is 0 or 1. In this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferably, $R^1$ is a linear or branched alkyl or linear or branched alkenyl group having from about 8 to about 30 carbon atoms; $R^2$ in each of the $x(R^2O)$ groups is independently $C_2$-$C_4$ alkylene; $R^3$ is hydrogen, a linear or branched alkyl or linear or branched alkenyl group having from 1 to about 30 carbon atoms; $R^4$ is a linear or branched alkylene having from 1 to about 30 carbon atoms, m and n are independently integers from 0 to about 7, the sum of m and n is from about 3 to 7, p is an integer from 1 to about 8, x is an average number from 0 to about 30, and y is 0 or 1. More preferably, $R^1$ is a linear or branched alkyl group having from about 8 to about 22 carbon atoms; $R^2$ in each of the $x(R^2O)$ groups is independently ethylene or propylene; $R^3$ is hydrogen, or a linear or branched alkyl group having from 1 to about 6 carbon atoms; $R^4$ is a linear or branched alkylene having from 1 to about 6 carbon atoms, m and n are independently integers from 0 to about 7, the sum of m and n is from about 3 to 7, p is an integer from 1 to about 8, x is an average number from 0 to about 30, and y is 0 or 1. Most preferably, $R^1$ is a linear or branched alkyl group having from about 8 to about 18 carbon atoms; $R^2$ in each of the x ($R^2O$) groups is independently ethylene or propylene; $R^3$ is hydrogen or methyl; m and n are independently integers from 0 to about 7, the sum of m and n is from about 3 to 7, p is an integer from 1 to about 8, x is an average number from 0 to about 30, and y is 0.

(g) di-poly(hydroxyalkyl)amine having the formula:

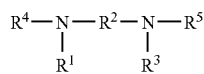
(18)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and $R^4$ and $R^5$ are independently hydroxyalkyl, polyhydroxyalkyl, or poly(hydroxyalkyl)alkyl. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, the di-poly(hydroxyalkyl)amine has the formula:

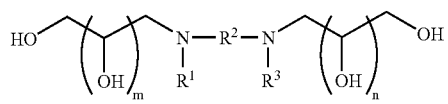
(19)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and m and n are independently integers from 1 to about 8. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^3$ are independently hydrogen or a linear or branched alkyl group having from 1 to about 18 carbon atoms, $R^2$ is a linear or branched alkylene or linear or branched alkenylene group having from 2 to about 18 carbon atoms, and m and n are independently integers from 1 to about 8. More preferably, $R^1$ and $R^3$ are independently hydrogen or a linear or branched alkyl group having from 6 to about 12 carbon atoms, $R^2$ is a linear or branched alkylene group having from 2 to about 6 carbon atoms, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 16 carbon atoms, and m and n are independently integers from about 4 to about 8. Most preferably, $R^1$ and $R^3$ are independently hydrogen or a linear or branched alkyl group having from 6 to about 12 carbon atoms, $R^2$ is ethylene or propylene, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 12 carbon atoms, and m and n are independently integers from about 4 to about 8.

(h) quaternary poly(hydroxyalkyl)amine salts having the formula:

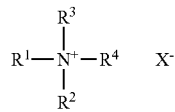
(20)

wherein $R^1$ is hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, $R^4$ is hydroxyalkyl, polyhydroxyalkyl, or poly(hydroxyalkyl)alkyl, and X— is an agriculturally acceptable anion. In this context, preferred $R^1$, $R^2$, and $R^3$ hydrocarbyl groups are linear or branched alkyl, linear or branched alkenyl, linear or branched alkynyl, aryl, or aralkyl groups. Preferably, the quaternary poly(hydroxyalkyl) amine salts have the formula:

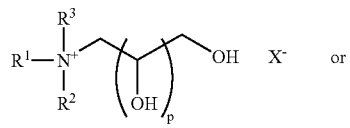
(21)

or

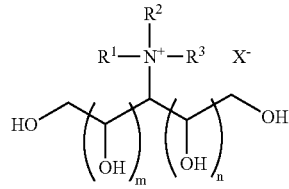
(22)

wherein $R^1$ is $—X_m—(R^4O)_yR^5$, hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, m and n are independently integers from 0 to about 7, the sum of m and n is not greater than about 7, p is an integer from 1 to about 8, X— is an agriculturally acceptable anion, $R^4$ in each of the y($R^4O$) groups is independently $C_2$-$C_4$ alkylene; $R^5$ is hydrogen or a linear or branched alkyl group having 1 to about 4 carbon atoms; X is hydrocarbylene or substituted hydrocarbylene having from 2 to about 18 carbon atoms; m is 0 or 1; and y is an average number from 0 to about 30. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ and $R^3$ are independently hydrogen or a linear or branched alkyl or linear or branched alkenyl group having from 1 to about 30 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 30 carbon atoms, m and n are independently integers from 0 to about 7, the sum of m and n is not greater than about 7, and p is an integer from about 4 to about 8. More preferably, $R^1$ is a linear or branched alkyl or linear or branched alkenyl group having from about 8 to about 22 carbon atoms, $R^2$ and $R^3$ are independently hydrogen or a linear or branched alkyl or linear or branched alkenyl group having from 1 to about 6 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms, $R^2$ and $R^3$ are independently hydrogen or methyl, m and n are independently integers from 0 to about 4, the sum of m and n is about 4, and p is an integer of about 4. Most preferably, $R^1$ is a linear or branched alkyl group having from about 8 to about 18 carbon atoms, $R^2$ and $R^3$ are methyl, m and n are independently integers from 0 to about 4, the sum of m and n is about 4, and p is an integer of about 4.

(i) triamines having the formula:

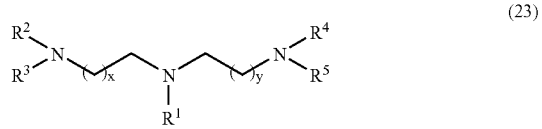

(23)

wherein $R^1$ is hydrocarbyl or substituted hydrocarbyl having from 1 to about 30 carbon atoms; $R^2$, $R^3$, $R^4$ and $R^5$ are independently hydrogen, hydrocarbyl or substituted hydrocarbyl having from 1 to about 30 carbon atoms, or —$(R^8)_s$ $(R^7O)_nR^6$; $R^6$ is hydrogen or a linear or branched alkyl group having from 1 to about 4 carbon atoms, $R^7$ in each of the n $(R^7O)$ groups is independently $C_2$-$C_4$ alkylene; $R^8$ is hydrocarbylene or substituted hydrocarbylene having from 1 to about 6 carbon atoms, n is an average number from 1 to about 10, s is 0 or 1, and x and y are independently an integer from 1 to about 4. In this context, preferred $R^1$, $R^2$, $R^3$, $R^4$, $R^5$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl groups having from about 8 to about 30 carbon atoms, $R^2$, $R^3$, $R^4$ and $R^5$ are independently hydrogen, a linear or branched alkyl or linear or branched alkenyl group having from 1 to about 30 carbon atoms, or —$(R^7O)_nR^6$, $R^6$ is hydrogen, methyl or ethyl; $R^7$ in each of the n $(R^7O)$ groups is independently $C_2$-$C_4$ alkylene, n is an average number from 1 to about 10, and x and y are independently an integer from 1 to about 4. More preferably, $R^1$ is a linear or branched alkyl group having from about 8 to about 18 carbon atoms, $R^2$, $R^3$, $R^4$ and $R^5$ are independently hydrogen, a linear or branched alkyl group having from 1 to about 6 carbon atoms, or —$(R^7O)_nR^6$, $R^6$ is hydrogen or methyl, $R^7$ in each of the n $(R^7O)$ groups is independently ethylene or propylene, n is an average number from 1 to about 5, and x and y are independently an integer from 1 to about 4. Most preferably, $R^1$ is a linear or branched alkyl group having from about 8 to about 18 carbon atoms, $R^2$, $R^3$, $R^4$ and $R^5$ are independently hydrogen, or —$(R^7O)_nR^6$, $R^6$ is hydrogen, $R^7$ in each of the n $(R^7O)$ groups is independently ethylene or propylene, n is an average number from 1 to about 5, and x and y are independently an integer from 1 to about 4. Commercially available triamines include Acros and Clariant Genamin 3119.

(j) diamines having the formula:

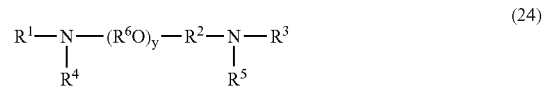

(24)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, $C(=NR^{11})NR^{12}R^{13}$—, —$C(=O)NR^{12}R^{13}$—, —$C(=S)NR^{12}R^{13}$—, —$C(=NR^{12})$—, —$C(S)$—, or —$C(O)$—, $R^6$ in each of the x $(R^6O)$ and y $(R^6O)$ groups is independently $C_2$-$C_4$ alkylene, $R^7$ is hydrogen, or a linear or branched alkyl group having from 1 to about 30 carbon atoms, $R^{11}$, $R^{12}$ and $R^{13}$ are hydrogen, hydrocarbyl or substituted hydrocarbyl having from 1 to about 30 carbon atoms, x is an average number from 1 to about 50, and y is an average number from 0 to about 60. In this context, preferred $R^1$, $R^2$, $R^3$, $R^4$, and $R^5$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$ and $R^5$ are independently hydrogen or a linear or branched alkyl or linear or branched alkenyl group having from 1 to about 22 carbon atoms or —$(R^6O)_xR^7$, $R^2$ is a linear or branched alkylene or linear or branched alkenylene group having from 1 to about 6 carbon atoms, $R^6$ in each of the x$(R^6O)$ and y $(R^6O)$ groups is independently $C_2$-$C_4$ alkylene, $R^7$ is hydrogen, or a linear or branched alkyl group having from 1 to about 4 carbon atoms, x is an average number from 1 to about 30, and y is an average number from 0 to about 60. More preferably, $R^1$, $R^3$, $R^4$ and $R^5$ are independently hydrogen or a linear or branched alkyl group having from about 1 to about 18 carbon atoms or —$(R^6O)_xR^7$, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 15, and y is an average number from 0 to about 60. Most preferably, $R^1$ and $R^3$ are independently linear or branched alkyl groups having from about 8 to about 18 carbon atoms and $R^4$ and $R^5$ are independently hydrogen, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 10, and y is an average number from 0 to about 50.

(k) mono- or di-quaternary ammonium salts having the formula:

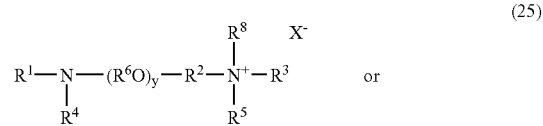

(25)

-continued

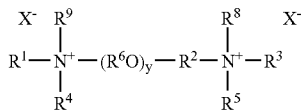

(26)

wherein $R^1$, $R^3$, $R^4$, $R^5$, $R^8$ and $R^9$ are independently hydrogen, polyhydroxyalkyl, hydrocarbyl or substituted hydrocarbyl having from 1 to about 30 carbon atoms, or $—(R^6O)_xR^7$, $R^2$ is hydrocarbylene or substituted hydrocarbylene having from 2 to about 30 carbon atoms, $R^6$ in each of the x $(R^6O)$ and y $(R^6O)$ groups is independently $C_2$-$C_4$ alkylene, $R^7$ is hydrogen, or a linear or branched alkyl group having from 1 to about 4 carbon atoms, x is an average number from 1 to about 30, y is an average number from about 3 to about 60, and $X^-$ is an agriculturally acceptable anion. In this context, preferred $R^1$, $R^2$, $R^3$, $R^4$, $R^5$, $R^8$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$, $R^5$, $R^8$ and $R^9$ are independently hydrogen or a linear or branched alkyl or alkenyl group having from about 1 to about 22 carbon atoms or $—(R^6O)_xR^7$, $R^2$ is a linear or branched alkylene or alkenylene group having from about 1 to about 6 carbon atoms, $R^6$ in each of the $x(R^6O)$ and y $(R^6O)$ groups is independently $C_2$-$C_4$ alkylene, $R^7$ is hydrogen, or a linear or branched alkyl group having from 1 to about 4 carbon atoms, x is an average number from 1 to about 30, and y is an average number from 1 to about 60. More preferably, $R^1$, $R^3$, $R^4$, $R^5$, $R^8$ and $R^9$ are independently hydrogen or a linear or branched alkyl group having from about 1 to about 18 carbon atoms or $—(R^6O)_xR^7$, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 10, and y is an average number from 1 to about 60. Most preferably, $R^1$ and $R^3$ are independently linear or branched alkyl groups having from about 8 to about 18 carbon atoms and $R^4$, $R^5$, $R^8$ and $R^9$ are independently hydrogen or methyl, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 10, and y is an average number from 10 to about 50.

(l) a secondary or tertiary amine having the formula:

(27)

wherein $R^1$ and $R^2$ are hydrocarbyl having from 1 to about 30 carbon atoms, and $R^3$ is hydrogen or hydrocarbyl having from 1 to about 30 carbon atoms. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from 8 to about 30 carbon atoms, and $R^2$ and $R^3$ are independently hydrogen or a linear or branched alkyl or linear or branched alkenyl group having from 1 to about 6 carbon atoms. More preferably, $R^1$ is a linear or branched alkyl group having from about 12 to about 22 carbon atoms, and $R^2$ and $R^3$ are independently hydrogen, methyl or ethyl. In one embodiment of the amine of formula (23), $R^1$ is a linear or branched alkyl group having from about 12 to about 22 carbon atoms, and $R^2$ and $R^3$ are independently linear or branched hydroxyalkyl groups having from 1 to about 6 carbon atoms.

In one embodiment, the surfactant has the formula (23) wherein $R^1$ is hydrocarbyl or substituted hydrocarbyl having from about 8 to about 30 carbon atoms, $R^2$ is a hydroxyalkyl, polyhydroxyalkyl or poly(hydroxyalkyl)alkyl group, and $R^3$ is hydrogen, hydroxyalkyl, polyhydroxyalkyl or poly(hydroxyalkyl)alkyl. In this context, preferred $R^1$ hydrocarbyl groups are linear or branched alkyl, linear or branched alkenyl, linear or branched alkynyl, aryl, or aralkyl groups. In one embodiment, $R^1$ is a linear or branched alkyl, linear or branched alkenyl, linear or branched alkynyl, aryl, or aralkyl group having from about 8 to about 30 carbon atoms, $R^2$ is a linear or branched hydroxyalkyl group having from 1 to about 6 carbon atoms, and $R^3$ is hydrogen or a linear or branched hydroxyalkyl group having from 1 to about 6 carbon atoms. Preferably, $R^1$ is a linear or branched alkyl, linear or branched alkenyl, linear or branched alkynyl, aryl, or aralkyl group having from about 8 to about 22 carbon atoms, $R^2$ is a linear or branched hydroxyalkyl group having from 1 to about 4 carbon atoms, and $R^3$ is hydrogen or a linear or branched hydroxyalkyl group having from 1 to about 4 carbon atoms. More preferably, $R^1$ is a linear or branched alkyl, linear or branched alkenyl, linear or branched alkynyl, aryl, or aralkyl group having from about 8 to about 18 carbon atoms, $R^2$ is hydroxymethyl or hydroxyethyl, and $R^3$ is hydrogen, hydroxymethyl or hydroxyethyl.

(m) monoalkylated amines having the formula:

(28)

wherein $R^1$ and $R^4$ are independently hydrocarbyl or substituted hydrocarbyl groups having from 1 to about 30 carbon atoms or $—R^5SR^6$, $R^2$ in each of the x $(R^2O)$ groups is independently $C_2$-$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60. In this context, preferred $R^1$, $R^4$, and $R^6$ hydrocarbyl groups are linear or branched alkyl, linear or branched alkenyl, linear or branched alkynyl, aryl, or aralkyl groups. In one embodiment, $R^1$ includes from about 7 to about 30 carbon atoms, preferably from about 8 to about 22 carbon atoms, and the remaining groups are as described above. Preferably, $R^1$ and $R^4$ are independently a linear or branched alkyl or linear or branched alkenyl group having from 1 to about 25 carbon atoms, $R^2$ in each of the x $(R^2O)$ groups is independently $C_2$-$C_4$ alkylene, $R^3$ is hydrogen, methyl or ethyl, and x is an average number from 1 to about 40. More preferably, $R^1$ and $R^4$ are independently a linear or branched alkyl group having from 1 to about 22 carbon atoms, $R^2$ in each of the x $(R^2O)$ groups is independently ethylene or propylene, $R^3$ is hydrogen or methyl, and x is an average number from 1 to about 30. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) groups is independently ethylene or propylene, $R^3$ is hydrogen or methyl, and x is an average number from about 1 to about 10. Most preferably, $R^1$ is a linear or branched alkyl group having from about 16 to about 22 carbon atoms and $R^4$ is methyl, $R^2$ in each of the x ($R^2O$) groups is ethylene, $R^3$ is hydrogen, and x is an average number from about 1 to about 5, or $R^1$ is a linear or branched alkyl group having from about 8 to about 15 carbon atoms and $R^4$ is methyl, $R^2$ in each of the x ($R^2O$) groups is ethylene, $R^3$ is hydrogen, and x is an average number from about 5 to about 10.

(n) dialkoxylated quaternary ammonium salts having the formula:

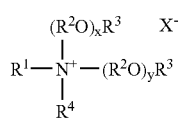

(29)

wherein $R^1$ is hydrocarbyl or substituted hydrocarbyl having from 1 to about 30 carbon atoms, $R^2$ in each of the x ($R^2O$) and y ($R^2O$) groups is independently $C_2$-$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X- is an agriculturally acceptable anion. In this context, preferred $R^1$ and $R^4$ hydrocarbyl groups are linear or branched alkyl, linear or branched alkenyl, linear or branched alkynyl, aryl, or aralkyl groups. Preferably, $R^1$ and $R^4$ are independently a linear or branched alkyl or linear or branched alkenyl group having from 1 to about 25 carbon atoms, $R^2$ in each of the x ($R^2O$) and y ($R^2O$) groups is independently $C_2$-$C_4$ alkylene, $R^3$ is hydrogen, methyl or ethyl, and the sum of x and y is an average number from about 2 to about 30. More preferably, $R^1$ and $R^4$ are independently a linear or branched alkyl group having from 1 to about 22 carbon atoms, $R^2$ in each of the x ($R^2O$) and y ($R^2O$) groups is independently ethylene or propylene, $R^3$ is hydrogen or methyl, and the sum of x any y is an average number from about 2 to about 20. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) and y ($R^2O$) groups is independently ethylene or propylene, $R^3$ is hydrogen or methyl, and x is an average number from about 2 to about 20. Most preferably, $R^1$ is a linear or branched alkyl group having from about 8 to about 22 carbon atoms and $R^4$ is a linear or branched alkyl group having from 1 to about 6 carbon atoms, $R^2$ in each of the x ($R^2O$) and y ($R^2O$) groups is independently ethylene or propylene, $R^3$ is hydrogen or methyl, and x is an average number from about 2 to about 15, or $R^1$ and $R^4$ are independently a linear or branched alkyl group having from about 8 to about 22 carbon atoms, $R^2$ in each of the x ($R^2O$) and y ($R^2O$) groups is independently ethylene or propylene, $R^3$ is hydrogen or methyl, and x is an average number from about 5 to about 15. Preferred dialkoxylated quatemary ammonium surfactants include Ethoquad™ C12 (a PEG 2 coco methyl ammonium chloride from Akzo Nobel), PEG 5 coco methyl ammonium chloride, PEG 5 tallow methyl ammonium chloride, PEG 5 ditallow ammonium bromide, and PEG 10 ditallow ammonium bromide.

(o) monoalkoxylated quaternary ammonium salts having the formula:

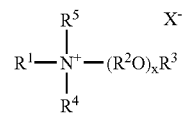

(30)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 30 carbon atoms, x is an average number from 1 to about 60, and X— is an agriculturally acceptable anion. In this context, preferred $R^1$, $R^4$, and $R^5$ hydrocarbyl groups are linear or branched alkyl, linear or branched alkenyl, linear or branched alkynyl, aryl, or aralkyl groups. Preferably, $R^1$, $R^4$ and $R^5$ are independently a linear or branched alkyl or linear or branched alkenyl group having from 1 to about 25 carbon atoms, $R^2$ in each of the x ($R^2O$) groups is independently $C_2$-$C_4$ alkylene, $R^3$ is hydrogen, methyl or ethyl, and x is an average number from 1 to about 40. More preferably, $R^1$, $R^4$ and $R^5$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 22 carbon atoms, and x is an average number from 1 to about 30. Even more preferably, $R^1$ is a linear or branched alkyl group having from about 8 to about 22 carbon atoms, $R^2$ in each of the x ($R^2O$) groups is independently ethylene or propylene, $R^3$ is hydrogen or methyl, $R^4$ and $R^1$ are independently a linear or branched alkyl group having from 1 to about 6 carbon atoms, and x is an average number from about 5 to about 25. Most preferably, $R^1$ is a linear or branched alkyl group having from about 16 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 3 carbon atoms, and x is an average number from about 5 to about 25. Preferred monoalkoxylated quaternary ammonium surfactants include PEG 7 $C_{18}$ dimethyl ammonium chloride and PEG 22 $C_{18}$ dimethyl ammonium chloride.

(p) quaternary ammonium salts having the formula:

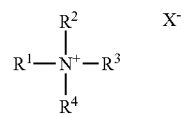

(31)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X— is an agriculturally acceptable anion. In this context, preferred $R^1$, $R^2$, $R^3$, and $R^4$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$, $R^3$ and $R^4$ are independently a linear or branched alkyl or linear or branched alkenyl group having from 1 to about 30 carbon atoms. More preferably, $R^1$ is a linear or branched alkyl or linear or branched alkenyl group having from about 8 to about 22 carbon atoms, and $R^2$, $R^3$ and $R^4$ are independently a linear or branched alkyl or linear or branched alkenyl group having from 1 to about 6 carbon atoms. Even more preferably, $R^1$ is a linear or branched alkyl group having from about 8 to about 16 carbon atoms, and $R^2$, $R^3$ and $R^4$ are independently a linear or branched alkyl group having from 1 to about 6 carbon atoms. Most preferably, $R^1$ is a linear or branched alkyl group having from about 8 to about 14 carbon atoms, and $R^2$, $R^3$ and $R^4$ are methyl. Preferred commercially available quaternary ammonium surfactants include Arquad™ C-50 (a dodecyl trimethyl ammonium chloride from Akzo Nobel) and Arquad™ T-50 (a tallow trimethyl ammonium chloride from Akzo Nobel).

(q) etheramines having the formula:

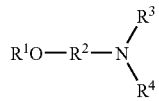

(32)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —$(R^5O)_xR^6$, $R^5$ in each of the x($R^5$—O) groups is independently $C_2$-$C_4$ alkylene, $R^6$ is hydrogen, or a linear or branched alkyl group having from 1 to about 4 carbon atoms, and x is an average number from 1 to about 50. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl, linear or branched alkenyl, linear or branched alkynyl, aryl, or aralkyl group having from 8 to about 25 carbon atoms, $R^2$ is a linear or branched alkylene or alkenylene group having from 2 to about 30 carbon atoms, $R^3$ and $R^4$ are independently hydrogen, a linear or branched alkyl, linear or branched alkenyl, linear or branched alkynyl, aryl, or aralkyl group having from 1 to about 30 carbon atoms, or —$(R^5O)_xR^6$, $R^5$ in each of the x ($R^5O$) groups is independently $C_2$-$C_4$ alkylene, $R^6$ is hydrogen, methyl or ethyl, and x is an average number from 1 to about 30. More preferably, $R^1$ is a linear or branched alkyl or alkenyl group having from 8 to about 22 carbon atoms, $R^2$ is a linear or branched alkylene or alkenylene group having from 2 to about 6 carbon atoms, $R^3$ and $R^4$ are independently hydrogen, a linear or branched alkyl or alkenyl group having from 1 to about 6 carbon atoms, or —$(R^5O)_xR^6$, $R^5$ in each of the x ($R^5O$) groups is independently ethylene or propylene, $R^6$ is hydrogen or methyl, and x is an average number from 1 to about 15. Most preferably, $R^1$ is a linear or branched alkyl or alkenyl group having from 8 to about 18 carbon atoms, $R^2$ is ethylene or propylene, $R^3$ and $R^4$ are independently hydrogen, methyl, or —$(R^5O)_xR^6$, $R^5$ in each of the x ($R^5O$) groups is independently ethylene or propylene, $R^6$ is hydrogen, and x is an average number from 1 to about 5.

(r) diamines having the formula:

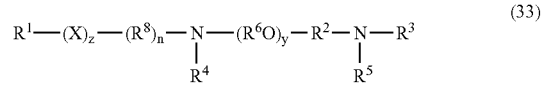

(33)

wherein $R^1$, $R^3$, $R^4$ and $R^5$ are independently hydrogen, hydrocarbyl or substituted hydrocarbyl having from 1 to about 30 carbon atoms, or —$(R^6O)R^7$; $R^2$ and $R^8$ are independently hydrocarbylene or substituted hydrocarbylene having from 2 to about 30 carbon atoms, $R^6$ in each of the x ($R^6O$) and y ($R^6O$) groups is independently $C_2$-$C_4$ alkylene, $R^7$ is hydrogen, or a linear or branched alkyl group having from 1 to about 30 carbon atoms, x is an average number from 1 to about 30, X is —O—, —N($R^6$)—, —C(O)—, —C(O)O—, —OC(O)—, —N($R^9$)C(O)—, —C(O)N($R^9$)—, —S—, —SO—, or —$SO_2$—, y is 0 or an average number from 1 to about 30, n and z are independently 0 or 1, and $R^9$ is hydrogen or hydrocarbyl or substituted hydrocarbyl. In this context, preferred $R^1$, $R^2$, $R^3$, $R^4$, $R^5$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^4$ are independently a linear or branched alkyl or linear or branched alkenyl group having from about 1 to about 22 carbon atoms, $R^2$ and $R^8$ are independently linear or branched alkylene groups having from about 2 to about 25 carbon atoms, $R^3$ and $R^5$ are each independently hydrogen or a linear or branched alkyl group having from 1 to about 6 carbon atoms and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 8 to about 25 carbon atoms, and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 1 to about 6 carbon atoms, $R^6$ in each of the y ($R^6O$) groups is independently $C_2$-$C_4$ alkylene, y is an average number from 1 to about 20 and n and z are 0; or $R^1$ and $R^3$ are independently a linear or branched alkyl or linear or branched alkenyl group having from about 8 to about 22 carbon atoms, $R^2$ is a linear or branched alkylene group having from about 2 to about 25 carbon atoms; and $R^4$ and $R^5$ are each independently hydrogen, a linear or branched alkyl or alkenyl group having from 1 to about 6 carbon atoms, or —$(R^6O)_xR^7$, $R^6$ in each of the x ($R^6O$) groups is independently $C_2$-$C_4$ alkylene, $R^7$ is hydrogen, or a linear or branched alkyl group having from 1 to about 4 carbon atoms, x is an average number from 1 to about 30, and n, y and z are 0; or $R^1$ is a linear or branched alkyl or linear or branched alkenyl group having from about 1 to about 22 carbon atoms, $R^2$ is a linear or branched alkylene group having from about 2 to about 25 carbon atoms, $R^3$, $R^4$ and $R^5$ are each independently hydrogen or a linear or branched alkyl group having from 1 to about 6 carbon atoms, X is —C(O)— or —$SO_2$—, n and y are 0 and z is 1. More preferably, $R^1$ and $R^4$ are independently a linear or branched alkyl or linear or branched alkenyl group having from about 4 to about 18 carbon atoms, $R^2$ is a linear or branched alkylene group having from about 2 to about 6 carbon atoms, $R^3$ and $R^5$ are each independently hydrogen or a linear or branched alkyl group having from 1 to about 6 carbon atoms, and n, y and z are 0; or $R^1$, $R^2$, $R^3$ and $R^4$ are independently hydrogen or a linear or branched alkyl group having from about 1 to about 6 carbon atoms, $R^2$ is a linear or branched alkylene group having from about 8 to about 25 carbon atoms, and y is 0; or $R^1$, $R^2$, $R^3$ and $R^4$ are independently hydrogen or a linear or branched alkyl group having from about 1 to about 6 carbon atoms, $R^2$ is a linear or branched alkylene group having from about 1 to about 6 carbon atoms, $R^6$ in each of the y ($R^6O$) groups is independently ethylene or propylene, y is an average number from 1 to about 10 and n and z is 0; or $R^1$ and $R^3$ are independently a linear or branched alkyl group having from about 8 to about 22 carbon atoms, $R^2$ is a linear or branched alkylene group having from about 2 to about 6 carbon atoms, and $R^4$ and $R^5$ are each independently hydrogen, a linear or branched alkyl group having from 1 to about 6 carbon atoms, or —$(R^6O)_xR^7$, $R^6$ in each of the x ($R^6O$) groups is independently ethylene or propylene, $R^7$ is hydrogen or methyl, x is an average number from 1 to about 15, and n, y and z are 0; or $R^1$ is a linear or branched alkyl group having from about 1 to about 22 carbon atoms, $R^2$ is a linear or branched alkylene group having from about 2 to about 6 carbon atoms, $R^3$, $R^4$ and $R^5$ are each independently hydrogen, X is —C(O)— or —$SO_2$—, n and y are 0 and z is 1. Preferred diamines include Gemini 14-2-14, Gemini 14-3-14, Gemini 10-2-10, Gemini 10-3-10, Gemini 10-4-10, and Gemini 16-2-16 ($C_{10}$, $C_{14}$ or $C_{16}$ ethylene, propylene or butylene N-methyl diamines from Monsanto), Ethoduomeens™, and Jeffamine™ EDR-148.

(s) amine oxides having the formula:

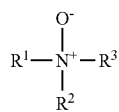

(34)

wherein $R^1$, $R^2$ and $R^3$ are independently hydrogen, hydrocarbyl or substituted hydrocarbyl having from 1 to about 30 carbon atoms, —$(R^4O)_xR^5$, or —$R^6(OR^4)_xOR^5$; $R^4$ in each of the x ($R^4O$) groups is independently $C_2$-$C_4$ alkylene, $R^5$ is hydrogen, or a hydrocarbyl or substituted hydrocarbyl having from 1 to about 30 carbon atoms, $R^6$ is a hydrocarbylene or substituted hydrocarbylene having from 1 to about 6 carbon atoms, x is an average number from 1 to about 50, and the total number of carbon atoms in $R^1$, $R^2$ and $R^3$ is at least 8. In this context, preferred $R^1$, $R^2$, $R^3$, $R^5$ and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^2$ are independently hydrogen, a linear or branched alkyl or linear or branched alkenyl group having from 1 to about 30 carbon atoms, or —$(R^4O)_xR^5$; $R^3$ is a linear or branched alkyl or linear or branched alkenyl group having from about 8 to about 30 carbon atoms, $R^4$ in each of the x ($R^4O$) groups is independently $C_2$-$C_4$ alkylene; $R^5$ is hydrogen or a linear or branched alkyl or linear or branched alkenyl group having from 1 to about 30 carbon atoms, and x is an average number from 1 to about 30. More preferably, $R^1$ and $R^2$ are independently hydrogen, or a linear or branched alkyl group having from 1 to about 6 carbon atoms, and $R^3$ is a linear or branched alkyl group having from about 8 to about 22 carbon atoms; or $R^1$ and $R^2$ are independently —$(R^4O)_xR^5$, $R^3$ is a linear or branched alkyl group having from about 8 to about 22 carbon atoms, $R^4$ in each of the x ($R^4O$) groups is ethylene or propylene, $R^5$ is hydrogen or a linear or branched alkyl or linear or branched alkenyl group having from 1 to about 30 carbon atoms, and x is an average number from 1 to about 10. Most preferably, $R^1$ and $R^2$ are independently methyl, and $R^3$ is a linear or branched alkyl group having from about 8 to about 18 carbon atoms; or $R^1$ and $R^2$ are independently —$(R^4O)_xR^5$, $R^3$ is a linear or branched alkyl group having from about 8 to about 18 carbon atoms, $R^4$ in each of the x ($R^4O$) groups is ethylene or propylene, $R^5$ is hydrogen or an alkyl group having from about 8 to about 18 carbon atoms, and x is an average number from 1 to about 5. Commercially available amine oxide surfactants include Chemoxide L70.

(t) alkoxylated amine oxides having the formula:

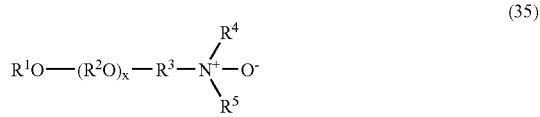

(35)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —$(R^6)_n$—$(R^2O)_yR^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60. In this context, preferred $R^1$, $R^4$, $R^5$ and $R^6$ hydrocarbyl (hydrocarbylene) groups include linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2O$) groups is independently $C_2$-$C_4$ alkylene, $R^3$ is a linear or branched alkylene or alkenylene group having from 2 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene or alkenylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is an ethylene, propylene or 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is an ethylene, propylene, or 2-hydroxypropylene group, $R^4$ and $R^5$ are methyl, and x is an average number from about 4 to about 20.

(u) dialkoxylated amines having the formula:

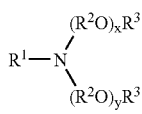
(36)

wherein $R^1$ is hydrogen or hydrocarbyl or substituted hydrocarbyl having from 1 to about 30 carbon atoms, —$R^4SR^5$, or —$(R^2O)_zR^3$, $R^2$ in each of the x ($R^2O$), y ($R^2O$) and z ($R^2O$) groups is independently $C_2$-$C_4$ alkylene, $R^3$ is hydrogen, or a linear or branched alkyl group having from 1 to about 22 carbon atoms, $R^4$ is a linear or branched alkyl group having from about 6 to about 30 carbon atoms, $R^5$ is a linear or branched alkyl group having from about 4 to about 15 carbon atoms, and x, y and z are independently an average number from 1 to about 40. In this context, preferred $R^1$ hydrocarbyl groups are hydrogen, linear or branched alkyl, linear or branched alkenyl, linear or branched alkynyl, aryl, or aralkyl groups. Preferably, $R^1$ is hydrogen, a linear or branched alkynyl, aryl, or aralkyl group having from about 1 to about 30 carbon atoms, $R^2$ in each of the x ($R^2O$), y ($R^2O$) and z ($R^2O$) groups is independently $C_2$-$C_4$ alkylene, $R^3$ is hydrogen, methyl or ethyl, and x and y are independently an average number from 1 to about 20. More preferably, $R^1$ is hydrogen or a linear or branched alkynyl, aryl, or aralkyl group having from about 8 to about 25 carbon atoms, $R^2$ in each of the x ($R^2O$), y ($R^2O$) and z ($R^2O$) groups is independently ethylene or propylene, $R^3$ is hydrogen or methyl, and x and y are independently an average number from 1 to about 30. Even more preferably, $R^1$ is hydrogen or a linear or branched alkynyl, aryl, or aralkyl group having from about 8 to about 22 carbon atoms, $R^2$ in each of the x ($R^2O$), y ($R^2O$) and z ($R^2O$) groups is independently ethylene or propylene, $R^3$ is hydrogen or methyl, and x and y are independently an average number from 1 to about 5. Preferred commercially available dialkoxylated amines include Trymeen™ 6617 (from Cognis) and Ethomeen™ C/12, C/15, C/20, C/25, T/12, T/15, T/20 and T/25 (from Akzo Nobel).

and (v) aminated alkoxylated alcohols having the following chemical structure:

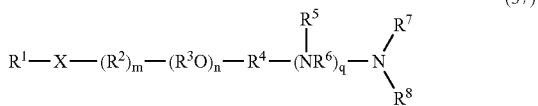
(37)

wherein $R^1$, $R^7$, $R^8$, and $R^9$ are each independently hydrogen, hydrocarbyl or substituted hydrocarbyl having from 1 to about 30 carbon atoms, or —$(R^{11})_s(R^3O)_vR^{10}$; X is —O—, —OC(O)—, —C(O)O—, —N($R^{12}$)C(O)—, —C(O)N($R^{12}$)—, —S—, —SO—, —$SO_2$— or —N($R^9$)—; $R^3$ in each of the n ($R^3O$) groups and the v ($R^3O$) groups is independently $C_2$-$C_4$ alkylene; $R^{10}$ is hydrogen, or a linear or branched alkyl group having from 1 to about 30 carbon atoms; n is an average number from 1 to about 60; v is an average number from 1 to about 50; $R^2$ and $R^{11}$ are each independently hydrocarbylene or substituted hydrocarbylene having from 1 to about 6 carbon atoms; $R^4$ is hydrocarbylene or substituted hydrocarbylene having from 2 to about 6 carbon atoms; $R^{12}$ is hydrogen or hydrocarbyl or substituted hydrocarbyl having from 1 to about 30 carbon atoms; m and s are each independently 0 or 1; $R^6$ is hydrocarbylene or substituted hydrocarbylene having from 2 to about 30 carbon atoms, —C(=N$R^{12}$)—, —C(S)—, or —C(O)—; q is an integer from 0 to 5; and $R^5$ is hydrogen or hydrocarbyl or substituted hydrocarbyl having from 1 to about 30 carbon atoms. In this context, preferred $R^1$, $R^2$, $R^4$, $R^5$, $R^6$, $R^7$, $R^8$, $R^9$, $R^{11}$ and $R^{12}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

In one embodiment, any of the amine or quaternary ammonium surfactants as described in sections (a)-(v) above are included in liquid glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 10 wt. % glyphosate a.e., more preferably at least about 15%, 20%, 25%, 30%, 35%, 40% or more wt.% a.e., or at least about 120 g a.e. glyphosate per liter, more preferably at least 130, 140, 150, 160, 170, 180, 190, 200, 210, 220, 230, 240, 250, 260, 270, 280, 290, 300, 310, 320, 330, 340, 350, 360, 370, 380, 390, or 400 g a.e./l or more.

In another embodiment, any of the cationic surfactants as described in (a)-(v) above are preferably formulated in concentrates that are free of alkyl polyglycosides, or that only contain alkyl polyglycosides having a light color of less than 10, preferably less than 9, 8, 7, 6, or 5 as measured using a Gardner colorimeter. 1 When dye is added to a formulated glyphosate product having a Gardner color greater than about 10, the concentrate remains dark brown in color. Concentrates having a Gardner color value of 10 are difficult to dye blue or green as is often desired to distinguish the glyphosate product from other herbicidal products.

A subclass of such cationic surfactants described above includes a monoalkoxylated amine having the formula:

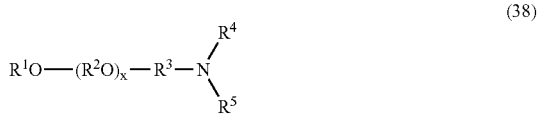
(38)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ is hydrocarbylene or substituted hydrocarbylene having from 2 to about 30 carbon atoms; $R^4$ and $R^5$ are each independently hydrogen, hydrocarbyl or substituted hydrocarbyl having from 1 to about 30 carbon atoms, —$(R^6)_n$—$(R^2O)_yR^7$, or $R^4$ and $R^5$, together with the nitrogen atom to which they are attached, form a cyclic or heterocyclic ring; $R^6$ is hydrocarbylene or substituted hydrocarbylene having from 1 to about 30 carbon atoms; $R^7$ is hydrogen or a linear or branched alkyl group having 1 to about 4 carbon atoms, n is 0 or 1, x and y are independently an average number from 1 to about 60. In this context, preferred $R^1$, $R^3$, $R^4$, $R^5$, and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2O$) groups is independently $C_2$-$C_4$ alkylene, $R^3$ is a linear or branched alkylene group having from 2 to about 20 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is ethylene or propylene, $R^4$ and $R^5$ are each independently hydrogen, methyl or tris(hydroxymethyl)methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is ethylene, $R^4$ and $R^5$ are methyl, and x is an average number from about 4 to about 20. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10, 13,15, 20 or25 $C_{14-18}$ether dimethyl propylamines (from Tomah) and Surfonic™ AGM-550 from Huntsman.

Quaternary ammonium, sulfonium and sulfoxonium salts are also effective cationic surfactants in forming potassium glyphosate concentrates and have a chemical structure:

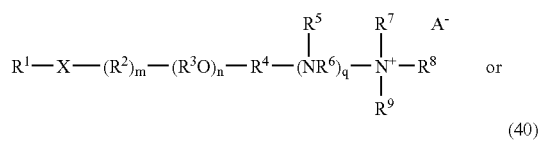

(39)

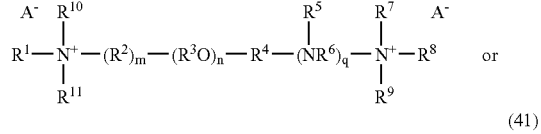

(40)

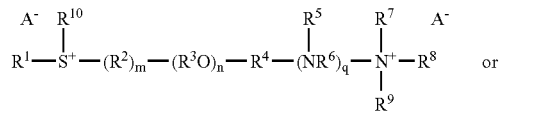

(41)

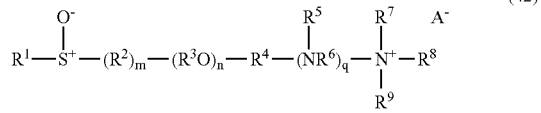

(42)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or —($R^{13}$)$_s$($R^3O$)$_v R^{12}$; X is —O—, —OC(O)—, —N($R^{14}$)C(O)—, —C(O)N($R^{14}$)—, —C(O)O—, or —S—; $R^3$ in each of the n ($R^3O$) groups and v ($R^3O$) groups is independently $C_2$-$C_4$ alkylene; $R^{12}$ is hydrogen, or a linear or branched alkyl group having from 1 to about 30 carbon atoms; n is an average number from 1 to about 50; v is an average number from 1 to about 50; $R^2$ and $R^{13}$ are each independently hydrocarbylene or substituted hydrocarbylene having from 1 to about 6 carbon atoms; m and s are each independently 0 or 1; $R^4$ is hydrocarbylene or substituted hydrocarbylene having from 2 to about 6 carbon atoms; $R^6$ is hydrocarbylene or substituted hydrocarbylene having from 2 to about 30 carbon atoms, —C(=$NR^{12}$)—, —C(S)—, or —C(O)—; $R^{14}$ is hydrogen or hydrocarbyl or substituted hydrocarbyl having from 1 to about 30 carbon atoms, q is an integer from 0 to 5; $R^5$ is hydrogen or hydrocarbyl or substituted hydrocarbyl having from 1 to about 30 carbon atoms; and each A- is an agriculturally acceptable anion. In this context, preferred $R^1$, $R^2$, $R^4$, $R^5$, $R^6$, $R^7$, $R^8$, $R^9$, $R^{10}$, $R^{11}$, $R^{13}$, and $R^{14}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

Another cationic surfactant effective in the formulations of the invention is a diamine or diammonium salt having the formula:

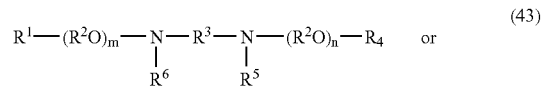

(43)

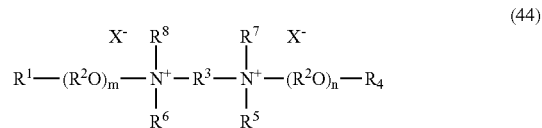

(44)

wherein $R^1$, $R^4$, $R^5$, $R^6$, $R^7$ and $R^8$ are independently hydrogen or hydrocarbyl or substituted hydrocarbyl having from 1 to about 30 carbon atoms, $R^2$ in each of the m ($R^2O$) and n ($R^2O$) groups and $R^9$ are independently $C_2$-$C_4$ alkylene, $R^3$ is hydrocarbylene or substituted hydrocarbylene having from about 2 to about 6 carbon atoms or —($R^2O$)$_p R_9$—, m and n are individually an average number from 0 to about 50, and p is an average number from 0 to about 60. In this context, preferred $R^1$, $R^3$, $R^4$, $R^5$, $R^6$, $R^7$ and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment of formula (40), $R^3$ is hydrocarbylene having from about 2 to about 6 carbon atoms, and the remaining groups are as defined above.

Some preferred cationic surfactants include alkylamine ethoxylates (including etheramines and diamines) such as tallowamine ethoxylate, cocoamine ethoxylate, etheramine ethoxylate, N-tallow ethylenediamine ethoxylate and amidoamine ethoxylates; alkylamine quaternary amines such as alkoxylated quaternary amines (e.g., ethoxylated quaternary amines or propoxylated quaternary amines); alkylamine acetates such as tallowamine acetate or octylamine acetate; and amine oxides such as ethoxylated amine oxides (e.g., N,N-bis(2-hydroxyethyl) cocoamine N-oxide), nonethoxylated amine oxides (e.g., cethyldimethylamine N-oxide) and amidoamine oxides.

Preferred nonionic surfactants suitable for use in formulating the herbicidal compositions and concentrates of the invention include:

(a) alkoxylated alcohols having the formula:

(45)

wherein $R^1$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 4 carbon atoms, and x is an average number from 1 to about 60. In this context, preferred $R^1$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ in each of the x ($R^2$O) groups is independently $C_2$-$C_4$ alkylene, $R^3$ is hydrogen, methyl or ethyl, and x is an average number from about 5 to about 50. More preferably, $R^1$ is a linear or branched alkyl group having from about 8 to about 25 carbon atoms, $R^2$ in each of the x ($R^2$O) groups is independently ethylene or propylene, $R^3$ is hydrogen or methyl, and x is an average number from about 8 to about 40. Even more preferably, $R^1$ is a linear or branched alkyl group having from about 12 to about 22 carbon atoms, $R^2$ in each of the x ($R^2$O) groups is independently ethylene or propylene, $R^3$ is hydrogen or methyl, and x is an average number from about 8 to about 30. Preferred commercially available alkoxylated alcohols include Procol™ LA-15 (from Protameen), Brij™ 35, Brij™ 76, Brij™ 78, Brij™ 97 and Brij™ 98 (from Sigma Chemical Co.), Neodol™ 25-12 (from Shell), Hetoxol™ CA-10, Hetoxol™ CA-20, Hetoxol™ CS-9, Hetoxol™ CS-15, Hetoxol™ CS-20, Hetoxol™ CS-25, Hetoxol™ CS-30, and Plurafac™ A38 (from BASF), ST-8303 (from Cognis), and Arosurf™ 66 E20 (from Goldschmidt).

(b) dialkoxylated alcohols having the formula:

$$R^1(OR^2)_xO-R^3-O-(R^2O)_yR^1 \quad (46)$$

wherein $R^1$ is independently hydrogen, or a linear or branched alkyl group having from 1 to about 4 carbon atoms, $R^2$ in each of the x ($R^2$O) and the y ($R^2$O) groups is independently $C_2$-$C_4$ alkylene, $R^3$ is hydrocarbylene or substituted hydrocarbylene having from 2 to about 30 carbon atoms, and x and y are independently an average number from 1 to about 60. In this context, preferred $R^3$ hydrocarbylene groups are linear or branched alkylene, linear or branched alkenylene, linear or branched alkynylene, arylene, or aralkylene groups. Preferably, $R^1$ is hydrogen, methyl or ethyl, $R^2$ in each of the x ($R^2$O) and the y ($R^2$O) groups is independently $C_2$-$C_4$ alkylene, $R^3$ is a linear or branched alkenylene or linear or branched alkenylene group having from about 8 to about 25 carbon atoms, and x and y are independently an average number from about 1 to about 20. More preferably, $R^1$ is hydrogen or methyl, $R^2$ in each of the x ($R^2$O) and the y ($R^2$O) groups is independently ethylene or propylene, $R^3$ is a linear or branched alkylene or linear or branched alkenylene group having from about 8 to about 18 carbon atoms, and x and y are independently an average number from 1 to about 10. Even more preferably, $R^1$ is hydrogen, $R^2$ in each of the x ($R^2$O) and the y ($R^2$O) groups is independently ethylene or propylene, $R^3$ is a linear or branched alkylene group having from about 8 to about 18 carbon atoms, and x and y are independently an average number from 1 to about 5.

(c) alkloxylated dialkylphenols having the formula:

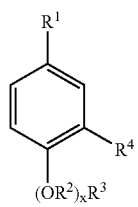

(47)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x ($R^2$O) groups is independently $C_2$-$C_4$ alkylene, $R^3$ is hydrogen, or a linear or branched alkyl group having from 1 to about 4 carbon atoms, and x is an average number from 1 to about 60. Preferably, $R^1$ and $R^4$ are independently linear or branched alkyl groups having from 8 to about 30 carbon atoms, $R^2$ in each of the x ($R^2$O) groups is independently $C_2$-$C_4$ alkylene, $R^3$ is hydrogen, methyl or ethyl, and x is an average number from about 5 to about 50. More preferably, $R^1$ and $R^4$ are independently linear or branched alkyl groups having from about 8 to about 22 carbon atoms, $R^2$ in each of the x ($R^2$O) groups is independently ethylene or propylene, $R^3$ is hydrogen or methyl, and x is an average number from about 8 to about 40. Even more preferably, $R^1$ and $R^4$ are independently linear or branched alkyl groups having from about 8 to about 16 carbon atoms, $R^2$ in each of the x ($R^2$O) groups is independently ethylene or propylene, $R^3$ is hydrogen or methyl, and x is an average number from about 10 to about 30. Preferred commercially available alkoxylated dialkylphenols include ethoxylated dinonyl phenols such as Surfonic™ DNP 100, Surfonic™ DNP 140, and Surfonic™ DNP 240 (from Huntsman).

Other suitable nonionic surfactants include alkylpolyglucosides; glycerol esters such as glyceryl monolaurate, and ethyoxylated glyceryl monococoate; ethoxylated castor oil; ethoxylated reduced sugar esters such as polyoxyethylene sorbitol monolaurate; esters of other polyhydric alcohols such as sorbitan monolaurate and sucrose monostearate; ethoxylated amides such as polyoxyethylene cocoamide; ethoxylated esters such as monolaurate of polyethylene glycol 1000 and dilaurate of polyethylene glycol 6000; ethoxylated alkyl or arylphenols such as nonylphenol ethoxylate, octylphenol ethoxylates, dodecylphenol ethoxylates, dinonylphenol ethoxylates and tristyrylphenol ethoxylates; alcohol ethoxylates such as fatty alcohol ethoxylates (e.g., oleyl alcohol ethoxylate), tridecylalcohol ethoxylates and other alcohol ethoxylates such as Neodols and oxoalcohol ethoxylates; and ethylene oxide/propylene oxide copolymers such as Pluronic type, Tetronic type, or Tergitol XH type.

Additional nonionic surfactants for inclusion in surfactant compositions that may be used in the invention are polyoxyethylene (5-30) $C_{8-22}$ alkylethers and polyoxyethylene (5-30) $C_{8-12}$ alkylphenylethers, wherein "(5-30)" means that the average number of ethylene oxide units in the polyoxyethylene chains of these surfactants is from about 5 to about 30. Examples of such nonionic surfactants include polyoxyethylene nonylphenols, octanols, decanols and trimethyinonanols. Particular nonionic surfactants that have proved useful include NEODOL™ 91-6 of Shell (a polyoxyethylene (6) $C_{9-11}$ linear primary alcohol), NEODOL™ 1-7 of Shell (a polyoxyethylene (7) $C_{11}$ linear primary alcohol), TERGITOL™ 15-S-9 of Union Carbide (a polyoxyethylene (9) $C_{12-15}$ secondary alcohol) and SURFONIC™ NP95 of Huntsman (a polyoxyethylene (9.5) nonylphenol).

The herbicidal compositions of the invention may also include a compound capable of reducing eye irritancy. Such compounds are generally effective in combination with the alkylamine surfactants described herein, and have the formula:

$$R_1O(R_2O)_nX_1 \quad (47A)$$

wherein $R_1$ is a hydrocarbyl group having from about 8 to about 22 carbon atoms, each of the n ($R_2$O) groups is independently $C_2$-$C_4$ alkylene, n is a number from 0 to about 60, and $X_1$ is a carboxylate, sulfate or phosphate. These compounds are described in U.S. Pat. No. 6,063,733, which is incorporated herein by reference.

Suitable amphoteric surfactants include betaines such as simple betaines (e.g., cocodimethylbetaine), sulfobetaines, amidobetaines, and cocoamidosulfobetaines; imidazolinium compounds such as disodium lauroamphodiacetate, sodium cocoamphoacetate, sodium cocoamphopropionate, disodium cocoaminodipropionate, and sodium cocoamphohydoxypropyl sulfonate; and other amphoteric surfactants such as N-alkyl, N,-bis(2-hydroxyethyl)glycine and alkylaminedipropionates.

Other surfactants for use in herbicidal compositions and concentrates of the invention include compounds of the formula:

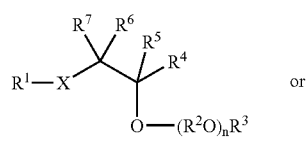
(48)

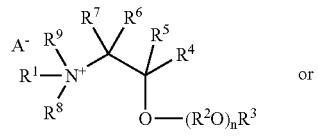
(49)

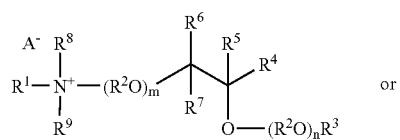
(50)

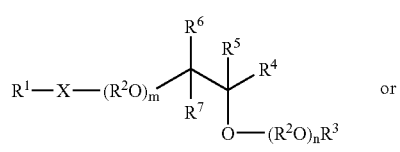
(51)

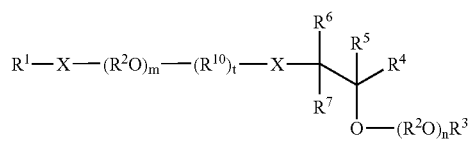
(52)

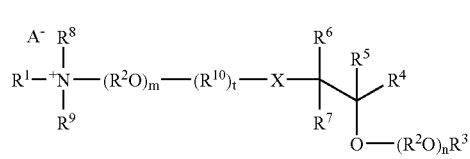
(53)

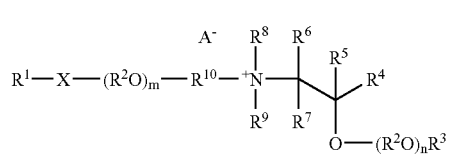
(54)

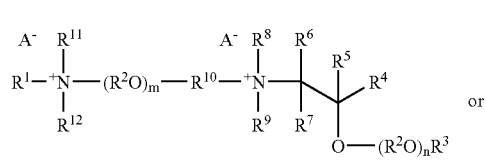
(55)

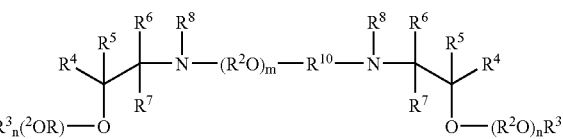
(55A)

wherein $R^1$, $R^9$, and $R^{12}$ are independently hydrocarbyl or substituted hydrocarbyl having from 1 to about 30 carbon atoms, or $-(R^2O)_pR^{13}$; $R^2$ in each of the m ($R^2O$), n ($R^2O$), p ($R^2O$) and q ($R^2O$) groups is independently $C_2$-$C_4$ alkylene; $R^3$, $R^8$, $R^{11}$, $R^{13}$ and $R^{15}$ are independently hydrogen, or a hydrocarbyl or substituted hydrocarbyl having from 1 to about 30 carbon atoms; $R^4$ is $-(CH_2)_yOR^{13}$ or $-(CH_2)_yO(R^2O)_qR^3$; $R^5$, $R^6$ and $R^7$ are independently hydrogen, hydrocarbyl or substituted hydrocarbyl having from 1 to about 30 carbon atoms, or $R^4$; $R^{10}$ is hydrocarbylene or substituted hydrocarbylene having from 2 to about 30 carbon atoms; $R^{14}$ is hydrogen, hydrocarbyl or substituted hydrocarbyl having from 1 to about 30 carbon atoms, or $-(CH_2)_zO(R^2O)_pR^3$; m, n, p and q are independently an average number from 1 to about 50; X is independently $-O-$, $-N(R^{14})-$, $-C(O)-$, $-C(O)O-$, $-OC(O)-$, $-N(R^{15})C(O)-$, $-C(O)N(R^{15})-$, $-S-$, $-SO-$, or $-SO_2-$; t is 0 or 1; A- is an agriculturally acceptable anion; and y and z are independently an integer from 0 to about 30. In this context, preferred $R^1$, $R^3$, and $R^5$-$R^{15}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^9$, and $R^{12}$ are independently linear or branched alkyl or alkenyl groups having from 1 to about 22 carbon atoms, or $-(R^2O)_pR^{13}$; $R^2$ in each of the m ($R^2O$), n ($R^2O$), p ($R^2O$) and q ($R^2O$) groups is independently $C_2$-$C_4$ alkylene; $R^3$ is hydrogen, methyl or ethyl; $R^4$ is $-(CH_2)_yOR^{13}$ or $-(CH_2)_yO(R^2O)_qR^3$; $R^5$, $R^6$ and $R^7$ are independently hydrogen, linear or branched alkyl or alkenyl groups having from 1 to about 22 carbon atoms, or $R^4$; $R^8$, $R^{11}$, $R^{13}$ and $R^{15}$ are independently hydrogen, or linear or branched alkyl or alkenyl groups having from 1 to about 22 carbon atoms; $R^{10}$ is a linear or branched alkylene or alkenylene group having from 2 to about 18 carbon atoms; $R^{14}$ is a linear or branched alkyl or alkenyl group having from 1 to about 22 carbon atoms, or $-(CH_2)_zO(R^2O)_pR^3$; m, n, p and q are independently an average number from 1 to about 30; X is independently $-O-$, $-N(R^{14})-$, $-C(O)-$, $-C(O)O-$, $-OC(O)-$, $-N(R^{15})C(O)-$, $-C(O)N(R^{15})-$, $-S-$, $-SO-$, or $-SO_2-$, t is 0 or 1; A- is an agriculturally acceptable anion; and y and z are independently an integer from 0 to about 30. More preferably, $R^1$ is a linear or branched alkyl or alkenyl groups having from about 8 to about 18 carbon atoms, or $-(R^2O)_pR^{13}$; $R^9$ and $R^{12}$ are independently linear or branched alkyl or alkenyl groups having from 1 to about 22 carbon atoms, or $-(R^2O)_pR^{13}$; $R^2$ in each of the m ($R^2O$), n ($R^2O$), p ($R^2O$) and q ($R^2O$) groups is independently ethylene or propylene; $R^3$ is hydrogen or methyl; $R^4$ is -$(CH_2)_yOR^{13}$ or $-(CH_2)_yO(R^2O)_qR^3$; $R^8$, $R^{11}$, $R^{15}$ are independently hydrogen, or linear or branched alkyl or alkenyl groups having from 1 to about 22 carbon atoms; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to about 22 carbon atoms, or —$(CH_2)_z$ $O(R^2O)_pR^3$; m, n, p and q are independently an average number from 1 to about 20; X is independently —O—, —N($R^{14}$)—, —C(O)—, —C(O)O—, —OC(O)—, —N($R^{15}$) C(O)—, —C(O)N($R^{15}$)—, —S—, —SO—, or —$SO_2$—, t is 0 or 1; A- is an agriculturally acceptable anion; and y and z are independently an integer from 0 to about 10. Most preferably, $R^1$ is a linear or branched alkyl or alkenyl groups having from about 12 to about 18 carbon atoms, or —$(R^2O)_pR^{13}$; $R^9$ and $R^{12}$ are independently linear or branched alkyl or alkenyl groups having from 1 to about 6 carbon atoms, or —$(R^2O)_p$ $R^{13}$; $R^2$ in each of the m ($R^2O$), n ($R^2O$), p ($R^2O$) and q ($R^2O$) groups is independently ethylene or propylene; $R^3$ is hydrogen; $R^4$ is —$(CH_2)_yOR^{13}$ or —$(CH_2)_yO(R^2)_qR^3$; $R^8$, $R^{11}$, $R^{15}$ are independently hydrogen, or linear or branched alkyl or alkenyl groups having from 1 to about 6 carbon atoms; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to about 22 carbon atoms, or —$(CH_2)_zO(R^2O)_pR^3$; m, n, p and q are independently an average number from 1 to about 5; X is independently —O— or —N($R^{14}$)—, t is 0 or 1; A- is an agriculturally acceptable anion; and y and z are independently an integer from 1 to about 3.

Preferred anionic surfactants effective in forming formulations of the invention include saturated carboxylic acids such as butyric, caproic, caprylic, capric, lauric, palmitic, myristic or stearic acid, and unsaturated carboxylic acids such as palmitoleic, oleic, linoleic or linolenic acid. Preferred carboxylic acids include palmitic, oleic or stearic acid. Other preferred anionic surfactants include alkyl sulfates such as sodium lauryl sulfate, and phosphate esters or diesters having the formulae:

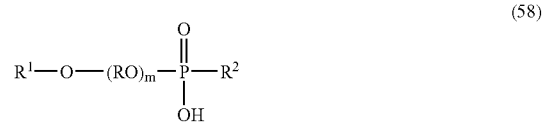

(56)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2O$) and the n ($R^2O$) groups is independently $C_2$-$C_4$ alkylene; and m and n are independently from 1 to about 30; or

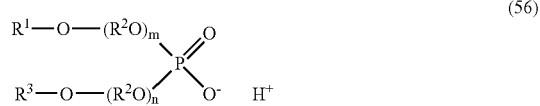

(57)

wherein $R^1$ is a linear or branched alkyl, linear or branched alkenyl, linear or branched alkynyl, aryl, or aralkyl group having from about 8 to about 30 carbon atoms; $R^2$ in each of the m ($R^2O$) groups is independently $C_2$-$C_4$ alkylene; and m is from 1 to about 30. Representative phosphate esters include oleth-10 phosphate, oleth-20 phosphate and oleth-25 phosphate.

Preferred phosphate ester surfactants include mono- and dialcohol phosphates, mono- and di- (polyoxyalkylene alcohol) phosphates and the mono- and dialcohol phosphates, (polyoxyalkylene alkylphenol) phosphates, and are represented by the formula:

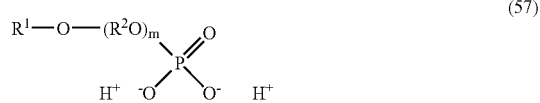

(58)

wherein $R^1$ is $C_8$-$C_{20}$ alkyl or $C_8$-$C_{20}$ alkylphenyl; R is an alkylene having from 2 to about 4 carbon atoms, usually ethylene or propylene, m is zero or a number up to about 60, preferably less than 10 and more preferably about 4, and $R^2$ is hydroxyl or $R^1$—O—$(RO)_m$— radical wherein $R^1$ and R are as just indicated and m is 0 to about 30. If $R^2$ is hydroxyl, then the compound is monoester. If $R^2$ is a $R^1$—O—$(RO)_m$-radical, then the compound is a diester. Mixtures of phosphate esters or diesters of formula (52), (53), and/or (54) and a cationic surfactant, particularly the alkylamine surfactants of formula (61), (62), (63) or (64) are preferred for use in the compositions of the invention. Mixtures of monoesters and diesters are also useful, together with the polyoxyalkylene alkylamines. Where mixtures of monoesters and diesters are present, the weight percentage of the monoester, or monoesters, exceeds that of the diester or diesters.

Other suitable anionic surfactants include fatty soaps such as ammonium tallowate and sodium stearate; alkyl sulfates such as sodium $C_{8-10}$ alcohol sulfate, and sodium oleyl sulfate; sulfated oils such as sulfated castor oil; ether sulfates such as sodium lauryl ether sulfate, ammonium lauryl ether sulfate, and ammonium nonylphenol ether sulfate; sulfonates such as petroleum sulfonates, alkylbenzene sulfonates (e.g., sodium (linear) dodecylbenzene sulfonate or sodium (branched) dodecylbenzene sulfonate), alkylnapthalene sulfonates (e.g., sodium dibutylnapthalene sulfonate), alkyl sulfonates (e.g., alpha olefin sulfonates), sulfosuccinates such as dialkylsulfosuccinates (e.g., sodium dioctylsulfosuccinate) and monoalkylsulfosuccinates and succinamides (e.g., disodium laurylsulfosuccinate and disodium N-alkylsulfosuccinamate); sulfonated amides such as sodium N-methyl N-coco taurate; isethionates such as sodium cocoyl isethionate; sarcosinates such as N-lauroyl sarcosine; and phosphates such as alkylether ethoxylate phosphates and alkylarylether ethoxyated phosphates.

Exemplary surfactants that may be used in accordance with the present invention include the following species:

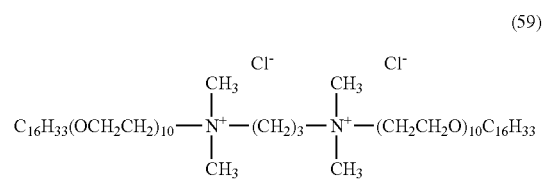

(59)

and

-continued

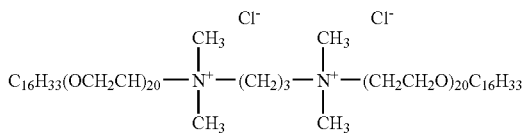
(60)

Other surfactants for use in herbicidal compositions and concentrates of the invention include N-acyl sarcosinates, which are described in U.S. Pat. No. 5,985,798, which is incorporated herein by reference. Such surfactants are represented by the formula:

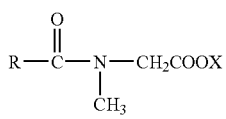
(61)

wherein R is $C_8$ to $C_{22}$ N-acyl, preferably a fatty acid of chain length $C_{10}$ to $C_{18}$, and X is salt forming cation including alkali metal, ammonia or alkanolamine. More preferably R is lauroyl, cocoyl, palmitoyl, myristoyl or oleoyl, and X is sodium, potassium, ammonium, an isopropylamine, or an amino alcohol. Preferred sarcosinates include sodium lauroyl sarcosinate, sodium cocoyl sarcosinate and sodium myristoyl sarcosinate, which are commercially available under the trademark HAMPOSYL from Hampshire Chemical Corp.

Alkylpolyglycosides are also suitable for use in the compositions and concentrates of the invention, and are described, for example, in U.S. Pat. No. 6,117,820. As used herein the term "alkylglycoside" includes mono- and polyalkylglycosides. Glycosides are represented by the formula:

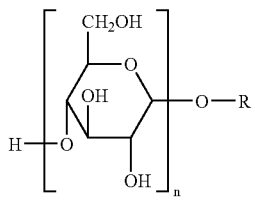
(62)

wherein n is the degree of polymerization, or number of glycose groups, and R is a branched or straight chain alkyl group preferably having from 4 to 18 carbon atoms, or a mixture of alkyl groups having an average value within the given range. The number of glycose groups per alkyl group may vary and alkyl mono- or di-, or polyglucose or saccharide derivatives are possible. Commercial alkylpolyglycosides usually contain a mixture of derivatives with n expressed as an average. Preferably n is between 1 and about 5, and more preferably between 1 and about 3. Typical of alkylglycosides is the product commercially available under the trade names AL2042 (Imperial Chemical Industries PLC) wherein n is an average of 1.7 and R is a mixture of octyl (45%) and decyl (55%), the product commercially available under the trade name AGRIMUL PG2069 (Henkel Corp) wherein n is an average of 1.6 and R is a mixture of nonyl (20%), decyl (40%) and undecyl (40%), and the product commercially available under the trade name BEROL AG6202 (Akzo Nobel) which is 2-ethyl-1-hexylglycoside.

The more preferred surfactant for use in the particulate solid concentrates are of the "superspreading" type. The superspreading surfactants include, but are not limited to organosilicones and fluoro-organic surfactant. The organosilicone surfactants comprise a polysiloxane. More specifically, the organosilicone surfactants comprise a polysiloxane wherein at least one of the siloxane groups possesses a moiety comprising one or more polyalkyleneoxy or polyalkyleneoxyalkyl groups.

The polysiloxane surfactants are represented by the following formula:

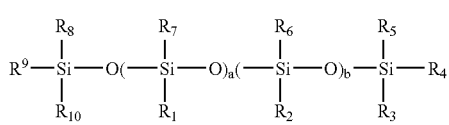
(63)

wherein $R^1$ is $-C_nH_{2n}O(CH_2CH_2O)_m(CH_2CH(CH_3)O)_qX$, n is 0 to 6, a is 0 to about 100 b is 0 to about 10, m is 0 to about 30, q is 0 to about 30, X is hydrogen or a $C_{1-20}$ hydrocarbyl or $C_{2-6}$ acyl group, and $R_2, R_3, R_4, R_5, R_6, R_7, R_8, R_9, R_{10}$ groups are independently substituted or unsubstituted $C_{1-20}$ hydrocarbyl or nitrogen containing groups.

Generally, in preferred embodiments, n is 0 to 6, a is 1 to about 30, b is 0 to about 10, m is 0 to about 30, q is 0 to about 3, X is hydrogen or a $C_{1-6}$ hydrocarbyl or $C_{2-6}$ acyl group, and $R_2, R_3, R_4, R_5, R_6, R_7, R_8, R_9, R_{10}$ groups are independently substituted or unsubstituted $C_{1-4}$ hydrocarbyl or nitrogen containing groups.

In one preferred embodiment, the polysiloxane is a polyoxyethylene heptamethyl trisiloxane wherein $R_1$ is $-C_nH_{2n}O(CH_2CH_2O)_m(CH_2CH(CH_3)O)_qX$, n is 3 or 4, a is 1, b is 0, m is 1 to about 30, q is 0, X is hydrogen or a methyl, ethyl or acetyl group, and $R_2, R_3, R_4, R_5, R_6, R_7, R_8, R_9, R_{10}$ groups are independently substituted or unsubstituted $C_{1-4}$ hydrocarbyl or nitrogen containing groups.

In a preferred embodiment of the invention in the formula for the polysiloxane surfactant(s), a is 1 to 5, b is 0 to 10, n is 3 or 4, m is 1 to about 30, q is 0, X is hydrogen or a methyl, ethyl or acetyl group, and $R_2, R_3, R_4, R_5, R_6, R_7, R_8, R_9$, and $R_{10}$ are methyl groups.

In another preferred embodiment of the invention in the formula for said polysiloxane surfactant(s), a is 1 to 5, b is 0 to 10, n is 3 or 4, m is 4 to 12, q is 0, X is hydrogen or a methyl or acetyl group, $R_2, R_3, R_4, R_5, R_6, R_7, R_8, R_9$, and $R_{10}$ are methyl groups.

In a more preferred embodiment of the invention in the formula for said polysiloxane surfactant(s), a is 1, b is 0, n is 3 or 4, m is 1 to about 30, b is 0, X is hydrogen or a methyl, ethyl or acetyl group, and $R_2, R_3, R_4, R_5, R_6, R_7, R_8, R_9$, and $R_{10}$ are methyl groups.

In a further preferred embodiment of the invention in the formula for said polysiloxane surfactant(s), a is 1, b is 0, n is 3, m is 8, b is 0, X is methyl and $R_2, R_3, R_4, R_5, R_6, R_7, R_8, R_9$, and $R_{10}$ are methyl groups.

Trisiloxanes of the above formula are generally described in product literature of Crompton Corporation and in U.S. Pat. No. 3,505,377. Several of such trisiloxanes are ethoxylated organosilicone wetting agents available from Crompton Corporation as Silwet® silicone glycol copolymers. Both liquid organosilicones and dry organosilicones can be used in the surfactant composition; both are included within the scope of the invention.

More preferred trisiloxanes are those sold commercially in the United States or elsewhere by Crompton Corporation as Silwet® L-77, Silwet® 408 and Silwet® 800, by Dow-Corning as Sylgard® 309, by Exacto, Inc., as Qwikwet® 100, and by Goldschmidt as Breakthru S-240ä. In the most preferred polyoxyethylene heptamethyl trisiloxanes, $R^2$ is hydrogen.

A preferred surfactant composition useful in this invention contains about 75% to about 100%, more preferably about 80% to about 100% by weight of the polyoxyalkylene trisiloxane. A blend of more than one polyoxyalkylene trisiloxane can be used, in which case the preferred total amount of all polyoxyalkylene trisiloxanes present in the surfactant composition is as above.

The polysiloxane surfactants can be combined with any of the surfactants described herein. In one embodiment, a polysiloxane of formula (59) is combined with an alkyl diphenyloxide sulfonate having the formula:

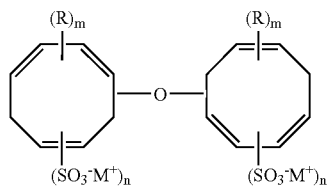

(63A)

wherein each R is independently a hydrocarbyl having 1 to about 30 carbon atoms (preferably 6-10 carbon atoms), each n is independently 0 or 1, each $M^+$ is an agriculturally acceptable cation, and each n is independently 0 or 1, provided that the surfactant include at least one sulfonate group. The cation can be ammonium (including alkylammonium and hydroxyalkylammonium), alkali metal, alkaline earth metal, or hydrogen. Such surfactant combinations generally include from about 5-55 wt. % polysiloxane surfactant and from about 45-95 wt. % diphenyloxide sulfonate, and are described in EP 1064844. Commercially available diphenyloxide sulfonates include sodium alkyl diphenyloxide sulfonates sold as DOW-FAX™ from Dow Chemical.

Fluoro-organic wetting agents useful in this invention are organic molecules represented by the formula:

(64)

wherein $R_f$ is a fluoroaliphatic radical and G is a group which contains at least one hydrophilic group such as cationic, anionic, nonionic, or amphoteric groups. $R_f$ is a fluorinated, monovalent, aliphatic organic radical containing at least four carbon atoms. Preferably, it is a saturated perfluoroaliphatic monovalent organic radical. However, hydrogen or chlorine atoms can be present as substituents on the skeletal chain. Although radicals containing a large number of carbon atoms can function adequately, compounds containing not more than about 20 carbon atoms are preferred because large radicals usually represent a less efficient utilization of fluorine than is possible with shorter skeletal chains. Preferably, $R_f$ contains about 5 to 14 carbon atoms.

The cationic groups which are usable in the fluoro-organic wetting agents employed in this invention can include an amine or a quaternary ammonium cationic group. Such amine and quaternary ammonium cationic hydrophilic groups can have formulas such as $NH_2$, $NHR^2$, $—N(R^2)_2$, $—(NH_3)X$, $—(NH_2R^2)X$, $—(NH(R^2)_2X)$, or $—(N(R^2)_3)X$, where X is an anionic counterion such as halide, hydroxide, sulfate, bisulfate, acetate or carboxylate, and each $R^2$ is independently a $C_{1-18}$ alkyl group. Preferably, X is halide, hydroxide, or bisulfate. Preferably, the cationic fluoro-organic wetting agents used in this invention contain hydrophilic groups which are quaternary ammonium cationic groups. The anionic groups which are usable in the fluoro-organic wetting agents employed in this invention include groups which by ionization can become radicals of anions. The anionic groups can have formulas such as $—COOM$, $—SO_3M$, $^-OSO_3M$, $—PO_3M_2$, $—PO_3HM$, $—OPO_3M_2$, or $OPO_3HM$, where M is H, an alkali metal ion, $(NR^1_4)^+$, or $(SR^1_3)^+$, where each $R^1$ is independently H or substituted or unsubstituted $C_1$-$C_6$ alkyl. Preferably M is $Na^+$ or $K^+$. The preferred anionic groups of the fluoro-organic wetting agents used in this invention have the formula $—COOM$ or $—SO_3M$.

The amphoteric groups which are usable in the fluoro-organic wetting agents employed in this invention include groups which contain at least one cationic group as defined above and at least one anionic group as defined above. Other useful amphoteric groups are amine oxides.

The nonionic groups which are usable in the fluoro-organic wetting agents employed in this invention include groups which are hydrophilic but which under pH conditions of normal agronomic use are not ionized. The nonionic groups can have formulas such as $—O(CH2CH2)XH$ wherein x is greater than zero, preferably 1-30, $—SO_2NH_2$, $SO_2NHCH_2CH_2OH$, $SO_2N(CH_2CH_2OH)_2$, $—CONH_2$, $—CONHCH_2CH_2OH$, or $—ON(CH_2CH_2OH)_2$.

Cationic fluoro-organic wetting agents useful herein include those cationic fluorochemicals described, for example, in U.S. Pat. Nos. 2,764,602, 2,764,603, 3,147,064, and 4,069,158. Amphoteric fluoro-organic wetting agents useful herein include those amphoteric fluorochemicals described, for example, in U.S. Pat. Nos. 2,764,602, 4,042, 522, 4,069,158, 4,069,244, 4,090,967, 4,161,590 and 4,161, 602. Anionic fluoro-organic wetting agents useful herein include those anionic fluorochemicals described, for example, in U.S. Pat. Nos. 2,803,656, 3,255,131, 3,450,755 and 4,090,967. The pertinent disclosure of the above patents is incorporated herein by reference.

Several fluoro-organic wetting agents suitable for use in the invention are available from 3M under the Fluorad trademark. They include anionic agents Fluorad FC-120, Fluorad FC-129 and Fluorad FC-99, cationic agent Fluorad FC-750, and nonionic agents Fluorad FC-170C, Fluorad FC-171 and Fluorad FC-430.

Representative surfactants of the type mentioned above are described in U.S. Pat. Nos. 5,703,015, 5,750,468 and 5,389, 598, the entirety of each being incorporated herein by reference.

The surfactant component of the compositions of the present invention may optionally contain a glycol or glycol ester of formula:

(70)

wherein $R^4$ in each of the x $(R^4O)$ groups is independently a linear or branched $C_{2-6}$ alkylene group, x is 1 to about 4, and $R^5$ is hydrogen or a $C_1$-$C_4$ hydrocarbyl group. Contemplated glycols and glycol esters include but are not limited to monoethylene glycol, diethylene glycol, propylene glycol or the methyl, ethyl, n-propyl, -butyl or t-butyl ethers thereof, dipropylene glycol or the methyl, ethyl, n-propyl, n-butyl or t-butyl ethers thereof, tripropylene glycol, or the methyl, ethyl, n-propyl, n-butyl or t-butyl ethers thereof, 1,3-butanediol, 1,4-butanediol, 2-methyl-1,3-propanediol, 2,2-dimethyl-1,3-propanediol, 2-methyl-1,3-pentanediol and 2-methyl-2,4-pentanediol.

Other nonionic surfactants may likewise be found useful, including without restriction polyoxyethylene polyoxypropylene block copolymers and alkyl polyglucosides. Cationic, anionic or amphoteric surfactants may also be included if desired.

In one embodiment of the invention, the herbicidal compositions include at least one nonionic surfactant and at least one cationic surfactant such as those described herein. Such surfactant combinations are described in U.S. Pat. No. 5,998,332, which is incorporated herein by reference.

Additional cationic surfactants suitable for use in the herbicidal compositions of the invention are those described in U.S. Pat. Nos. 5,563,111, 5,622,911, 5,849,663, 5,863,909, 5,985,794, 6,030,923 and 6,093,679, which are incorporated herein by reference.

The surfactant compositions typically are intended for mixing with a water soluble herbicide composition. It is preferred that there be substantially no water present in the surfactant composition.

A surfactant composition of the invention comprises any combination of the surfactants as described above. The surfactant composition is particularly preferred for use in formulating compositions or concentrates containing potassium, di-ammonium, ammonium, sodium, monoethanolamine, n-propylamine, methylamine, ethylamine, hexamethylenediamine, dimethylamine and/or trimethylsulfonium glyphosate.

The density of any glyphosate-containing formulation of the invention is preferably at least 1.050 grams/liter, more preferably at least about 1.055, 1.060, 1.065, 1.070, 1.075, 1.080, 1.085, 1.090, 1.095, 1.100, 1.105, 1.110, 1.115, 1.120, 1.125, 1.130, 1.135, 1.140, 1.145, 1.150, 1.155, 1.160, 1.165, 1.170, 1.175, 1.180, 1.185, 1.190, 1.195, 1.200, 1.205, 1.210, 1.215, 1.220, 1.225, 1.230, 1.235, 1.240, 1.245, 1.250, 1.255, 1.260, 1.265, 1.270, 1.275, 1.280, 1.285, 1.290, 1.295, 1.300, 1.305, 1.310, 1.315, 1.320, 1.325, 1.330, 1.335, 1.340, 1.345, 1.350, 1.355, 1.360, 1.365, 1.370, 1.375, 1.380, 1.385, 1.390, 1.395, 1.400, 1.405, 1.410, 1.415, 1.420, 1.425, 1.430, 1.435, 1.440, 1.445, or 1.450 grams/liter.

Other additives, adjuvants, or ingredients may be introduced into the formulations of the present invention to improve certain properties of the resulting formulations. Although the formulations of the present invention generally show good overall stability and viscosity properties without the addition of any further additives, the addition of a solubilizer (also commonly referred to as a cloud point enhancer or stabilizer) can significantly improve the properties of the formulations of the present invention. Suitable solubilizers for use with the novel formulations of the present invention include, for example, cocoamine (Armeen C), dimethylcocoamine (Arquad DMCD), cocoammonium chloride (Arquad C), PEG 2 cocoamine (Ethomeen C12), and PEG 5 cocoamine (Ethomeen C15), all of which are manufactured by Akzo Nobel (California).

Additionally, it has been found that the addition of a $C_4$ to $C_{16}$ alkyl or aryl amine compound, or the corresponding quaternary ammonium compound, greatly enhances the compatibility of certain glyphosate salts (e.g., potassium or isopropylamine) with surfactants that otherwise exhibit low or marginal compatibility at a given glyphosate loading. Suitable stabilizers include primary, secondary or tertiary $C_4$ to $C_{16}$ alkyl or aryl amine compounds, or the corresponding quaternary ammonium compounds. Such stabilizers greatly enhance the compatibility of certain glyphosate salts (e.g., potassium or isopropylamine) with surfactants that otherwise exhibit low or marginal compatibility at a given glyphosate loading. Suitable alkyl or aryl amine compounds may also contain 0 to about 5 $C_2$-$C_4$ alkylene oxide groups, preferably ethylene oxide groups. Preferred alkylamine compounds include $C_6$ to $C_{12}$ alkylamines having 0 to 2 ethylene oxide groups. Similarly, etheramine compounds having 4 to 12 carbons and 0 to about 5 ethylene oxide groups, as well as the corresponding quaternary ammonium compounds, also enhance the compatibility of such formulations. In one embodiment, the compounds which enhance the compatibility of such surfactants include amines or quaternary ammonium salts having the formula:

(71)

(72)

(73)

(74)

wherein $R^1$ is linear or branched alkyl or aryl having from about 4 to about 16 carbon atoms, $R^2$ is hydrogen, methyl, ethyl, or —$(CH_2CH_2O)_xH$, $R^3$ is hydrogen, methyl, ethyl, or —$(CH_2CH_2O)_yH$ wherein the sum of x and y is not more than about 5; $R^4$ is hydrogen or methyl; $R^6$ in each of the n ($R^6O$) groups is independently $C_2$-$C_4$ alkylene; $R^5$ is hydrocarbylene or substituted hydrocarbylene having from 2 to about 6 carbon atoms; and A- is an agriculturally acceptable anion.

The present invention also includes a method for killing or controlling weeds or unwanted vegetation comprising the steps of diluting a liquid concentrate in a convenient amount of water to form a tank mix and applying a herbicidally effective amount of the tank mix to the foliage of the weeds or unwanted vegetation. Similarly included in the invention is the method of killing or controlling weeds or unwanted vegetation comprising the steps of diluting a solid particulate concentrate in a convenient amount of water to form a tank mix and applying a herbicidally effective amount of the tank mix to the foliage of the weeds or unwanted vegetation.

In a herbicidal method of using a composition of the invention, the composition is diluted in a suitable volume of water to provide an application solution which is then applied to foliage of a plant or plants at an application rate sufficient to give a desired herbicidal effect. This application rate is usually expressed as amount of glyphosate per unit area treated, e.g., grams acid equivalent per hectare (g a.e./ha). What constitutes a "desired herbicidal effect" is, typically and illustratively, at least 85% control of a plant species as measured by growth reduction or mortality after a period of time during which the glyphosate exerts its full, herbicidal or phytotoxic effects in treated plants. Depending on plant species and growing conditions, that period of time can be as short as a week, but normally a period of at least two weeks is needed for glyphosate to exert its full effect.

The selection of application rates that are herbicidally effective for a composition of the invention is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing this invention. With respect to the use of glyphosate compositions, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate salts are used to control a very wide variety of plants worldwide, and it is believed the potassium salt will prove no different from other salts of glyphosate in this regard.

Particularly important annual dicotyledonous plant species for control of which a composition of the invention can be used are exemplified without limitation by velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis arvensis*) and cocklebur (*Xanthium* spp.).

Particularly important annual monocotyledonous plant species for control of which a composition of the invention can be used are exemplified without limitation by wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial dicotyledonous plant species for control of which a composition of the invention can be used are exemplified without limitation by mugwort (*Artemisia* spp.), milkweed (*Asclepias* spp.), canada thistle (*Cirsium arvense*), field bindweed (*Convolvulus arvensis*) and kudzu (*Pueraria* spp.).

Particularly important perennial monocotyledonous plant species for control of which a composition of the invention can be used are exemplified without limitation by brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial plant species for control of which a composition of the invention can be used are exemplified without limitation by horsetail (*Equisetum* spp.), bracken (*Pteridium aquilinum*), blackberry (*Rubus* spp.) and gorse (*Ulex europaeus*).

If desired, the user can mix one or more adjuvants with a composition of the invention and the water of dilution when preparing the application composition. Such adjuvants can include additional surfactant and/or an inorganic salt such as ammonium sulfate with the aim of further enhancing herbicidal efficacy. However, under most conditions a herbicidal method of use of the present invention gives acceptable efficacy in the absence of such adjuvants.

In a particular contemplated method of use of a composition of the invention, the composition, following dilution in water, is applied to foliage of crop plants genetically transformed or selected to tolerate glyphosate, and simultaneously to foliage of weeds or undesired plants growing in close proximity to such crop plants. This method of use results in control of the weeds or undesired plants while leaving the crop plants substantially unharmed. Crop plants genetically transformed or selected to tolerate glyphosate include those whose seeds are sold by Monsanto Company or under license from Monsanto Company bearing the Roundup Ready® trademark. These include, without restriction, varieties of cotton, soybean, canola, sugar beet, wheat and corn.

Plant treatment compositions can be prepared simply by diluting a concentrate composition of the invention in water. Application of plant treatment compositions to foliage is preferably accomplished by spraying, using any conventional means for spraying liquids, such as spray nozzles, atomizers or the like. Compositions of the invention can be used in precision farming techniques, in which apparatus is employed to vary the amount of pesticide applied to different parts of a field, depending on variables such as the particular plant species present, soil composition, etc. In one embodiment of such techniques, a global positioning system operated with the spraying apparatus can be used to apply the desired amount of the composition to different parts of a field.

The composition at the time of application to plants is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (l/ha) by spray application. The preferred application rates for aqueous solutions are in the range from about 50 to about 300 l/ha.

Many exogenous chemicals (including glyphosate herbicide) must be taken up by living tissues of the plant and translocated within the plant in order to produce the desired biological (e.g., herbicidal) effect. Thus, it is important that a herbicidal composition not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

A large number of compositions of the invention are illustrated in the Examples that follow. Many concentrate compositions of glyphosate have provided sufficient herbicidal effectiveness in greenhouse tests to warrant field testing on a wide variety of weed species under a variety of application conditions.

DEFINITIONS

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "hydrocarbylene" as used herein describes radicals joined at two ends thereof to other radicals in an organic compound, and which consist exclusively of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The "substituted hydrocarbylene" moieties described herein are hydrocarbylene moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are preferably lower alkyl containing from one to 18 carbon atoms in the principal chain and up to 30 carbon atoms. They may be straight or branched chain or cyclic and include methyl, ethyl, propyl, isopropyl, n-butyl, isobutyl, hexyl, 2-ethylhexyl, and the like.

Unless otherwise indicated, the alkenyl groups described herein are preferably lower alkenyl containing from two to 18 carbon atoms in the principal chain and up to 30 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to 18 carbon atoms in the principal chain and up to 30 carbon atoms. They may be straight or branched chain and include ethynyl, propynyl, butynyl, isobutynyl, hexynyl, and the like.

The terms "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the potassium glyphosate formulation without adversely affecting the storage stability of the formulation.

The terms "halogen" or "halo" as used herein alone or as part of another group refer to chlorine, bromine, fluorine, and iodine. Fluorine substituents are often preferred in surfactant compounds.

Unless otherwise indicated, the term "hydroxyalkyl" includes alkyl groups substituted with at least one hydroxy group, and includes bis(hydroxyalkyl)alkyl, tris(hydroxyalkyl)alkyl and poly(hydroxyalkyl)alkyl groups. Preferred hydroxyalkyl groups include hydroxymethyl (—CH$_2$OH), and hydroxyethyl (—C$_2$H$_4$OH), bis(hydroxymethyl)methyl (—CH(CH$_2$OH )$_2$), and tris(hydroxymethyl)methyl (—C(CH$_2$OH)$_3$).

The term "cyclic" as used herein alone or as part of another group denotes a group having at least one closed ring, and includes alicyclic, aromatic (arene) and heterocyclic groups.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like, and non-aromatic heterocyclics such as tetrahydrofuryl, tetrahydrothienyl, piperidinyl, pyrrolidino, etc. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioester, thioether, ketal, acetal, ester and ether.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioether, thioester, ketal, acetal, ester and ether.

The term "acyl," as used herein alone or as part of another group, denotes the moiety formed by removal of the hydroxyl group from the group —COOH of an organic carboxylic acid, e.g., RC(O)—, wherein R is R$^1$, R$^1$O—, R$^1$R$^2$N—, or R$^1$S—, R$^1$ is hydrocarbyl, heterosubstituted hydrocarbyl, or heterocyclo and R$^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number." The presence in a composition of individual surfactant molecules having an integer number of such units outside the stated range in "average number" does not remove the composition from the scope of the present invention, so long as the "average number" is within the stated range and other requirements are met.

By "storage-stable," in the context of a liquid concentrate of the invention, is meant not exhibiting phase separation on exposure to temperatures up to about 50° C. for 14-28 days, and preferably not forming crystals of glyphosate or salt thereof on exposure to a temperature of about 0° C. for a period of up to about 7 days (i.e., the composition must have a crystallization point of 0° C. or lower). For aqueous solution concentrates, high temperature storage stability is often indicated by a cloud point of about 50° C. or more. Cloud point of a composition is normally determined by heating the composition until the solution becomes cloudy, and then allowing the composition to cool, with agitation, while its temperature is continuously monitored. A temperature reading taken when the solution clears is a measure of cloud point. A cloud point of 50° C. or more is normally considered acceptable for most commercial purposes for a glyphosate aqueous solution concentrate. Ideally the cloud point should be 60° C. or more, and the composition should withstand temperatures as low as about −10° C. for up to about 7 days without crystal growth, even in the presence of seed crystals of the glyphosate salt.

As used herein, the term "surfactant" is intended to include a wide range of adjuvants that can be added to herbicidal glyphosate compositions to enhance the herbicidal efficacy thereof, as compared to the activity of the glyphosate salt in the absence of such adjuvant, stability, formulability or other beneficial solution property, irrespective of whether such adjuvant meets a more traditional definition of "surfactant."

EXAMPLES

The following Examples are provided for illustrative purposes only and are not intended to limit the scope of the present invention. The Examples will permit better understanding of the invention and perception of its advantages and certain variations of execution.

Spray compositions of the Examples contained an exogenous chemical, such as glyphosate potassium salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Concentrate compositions were tested by dilution, dissolution or dispersion in water to form spray compositions. In these spray compositions prepared from concentrates, the concentration of excipient ingredients varied with that of exogenous chemical.

In the following Examples illustrative of the invention, greenhouse and field tests were conducted to evaluate the relative herbicidal effectiveness of glyphosate compositions. Compositions included for comparative purposes may be identified as follows:

| Composition | Formulation |
|---|---|
| Roundup ® Ultra | Roundup ® Ultra (Dry) |
| Composition 570I | 570 g/l of glyphosate IPA salt in aqueous solution with no added surfactant |
| Composition 390K | 391 g a.e./l of glyphosate potassium salt in aqueous solution with monoethoxylated amine surfactant |
| Composition 360I | 360 g a.e./ of glyphosate IPA salt in aqueous solution together with a surfactant system as described in U.S. Pat. No. 5,652,197 |
| Composition 480I | 480 g a.e./l of glyphosate IPA salt in aqueous solution, together with 120 g/l of ethoxylated etheramine surfactant |
| Composition 450IS | 450 g a.e./ of glyphosate IPA salt in aqueous solution together with an etheramine surfactant as described in U.S. Pat. No. 5,750,468 |
| Composition 487K | 487 g a.e./l of glyphosate potassium salt in aqueous solution, together with 65 g/l of ceteth(2PO)(9EO) alcohol alkoxylate, 97 g/l ethoxylated (10EO) tallowamine and 85 g/l n-octylamine |
| Composition 41I | 41% by weight of glyphosate IPA salt in aqueous solution, together with phosphate ester and tallow amine surfactants. This formulation is sold by Monsanto Company under the Roundup ® Ultra trademark |
| Ultramax Dry | Roundup ® UltraMax (Dry) |
| Composition AMM-GLY1S | Ammonium glyphosate salt (solid) with ethoxylated tallow amine surfactant |
| Composition 540K | 540 g a.e./l of glyphosate potassium salt in aqueous solution with etheramine surfactant |
| Composition 360I | 360 g a.e./l of glyphosate IPA salt in solution, together with 111 g/l ethoxylated quaternary surfactant based tallowamine with 25EO, 74 g/l polyoxyethylene 10 EO cetyl ether and 12 g/l myristyl dimethyl amineoxide |
| Composition 725K | 725 g/l of glyphosate potassium salt in aqueous solution with no added surfactant |
| Composition 540KS | 540 g a.e./l of glyphosate potassium salt in solution, together with 135 g/l of ethoxylated etheramine surfactant (M121) |
| Composition | 450 g a.e./l of glyphosate IPA salt in aqueous solution, together |

-continued

| Composition | Formulation |
| --- | --- |
| 450I | with 168 g/l of phosphate ester and phosphate diester surfactants as described in U.S. Pat. No. 5,703,015 |
| Composition AMM-GLY2S | 91% ammonium glyphosate salt (solid) |
| Composition IPA Dry | Glyphosate IPA (Dry) |
| Roundup ® UltraMax | 50% by weight (445 g a.e./l) of glyphosate IPA salt in aqueous solution, together with surfactant, which is sold by Monsanto Company under the Roundup ® UltraMax trademark |
| Composition 470K | 472 g a.e./l of glyphosate potassium salt in aqueous solution, together with 117 g/l cocoamine 5 EO, 52 g/l iso-stearyl 10 EO and 13 g/l cocoamine |
| TD IQ | Touchdown IQ ®, which is an aqueous concentrate containing 28 wt. % a.e of the glyphosate diammonium salt, and 8 wt. % alkylpolyglucoside surfactant |

Various excipients were used in compositions of the examples. They may be identified as follows:

| Ref. | Trade Name | Manufacturer | Chemical Description |
| --- | --- | --- | --- |
| S1 | M-T1415E13-2 | Tomah | $C_{14-15}$ alkyl-(EO)13-dimethylpropylamine |
| S2 | | | C18NMe(EO)5.9H |
| S3 | | | C18NMe(EO)11H |
| S4 | | | C18NMe(EO)7.5H |
| S5 | Ethomeen C12 | Akzo | Ethoxylated cocoamine 2EO |
| S6 | T45E18PA | Tomah | $C_{14-15}$ EO 10 propyl amine |
| S7 | T45E18DA | Tomah | $C_{14-15}$ EO 10 propyl diamine |
| S8 | | | C18NMe(EO)9.5H |
| S9 | | | C18NMe(EO)11.1H |
| S10 | 1816E20PA | Tomah | ethoxylated (20 EO) cetyl/stearyl etheramine |
| S11 | 1816E10PA | Tomah | ethoxylated (10 EO) cetyl/stearyl etheramine |
| S12 | Witcamine 405 | Witco | PEG 5 tallow amine |
| S13 | 1816E15PA | Tomah | ethoxylated (15 EO) cetyl/stearyl etheramine |
| S14 | Arquad 12-37W | Akzo | dodecyl trimethyl ammonium chloride |
| S15 | | | A mixture of cationic tallowamines and phosphate esters as described in U.S. Pat. No. 5,703,015 |
| S16 | 1816E10DA | Tomah | ethoxylated (10 EO) cetyl/stearyl ether dipropylamine |
| S17 | T45P3E10PA | | $C_{14-15}$ O(PO)3(EO) 10 propylamine |
| S18 | Armeen DMCD | Akzo | N,N-dimethylcocoamine |
| S19 | Ethomeen C15 | Akzo | Ethoxylated cocoamine 5EO |
| S20 | Ethomeen C25 | Akzo | Ethoxylated cocoamine (25)EO |
| S21 | | Witco | Coco 2EO quat and branched PEG 7 $C_{12}$ alcohol blend |
| S22 | Witconol IS 100 | Witco | PEG 10EO iso $C_{18}$ alcohol |
| S23 | Witcamine 305 | Witco | PEG 5EO cocoamine |
| S24 | Armeen C | Akzo | coco ($C_{12}$–$C_{18}$ unsaturated) primary amine |
| S25 | Phos A-100 | Lambent | ethoxylated silicone phosphate ester |
| S26 | Phos A-150 | Lambent | ethoxylated silicone phosphate ester |
| S27 | Phos A-200 | Lambent | ethoxylated silicone phosphate ester |
| S28 | Amine PD | Lambent | branched silicone amine |
| S29 | Quat 400 M | Lambent | silicone quat |
| S30 | M-T25E9-2 | Tomah | $C_{12-15}$ PEG 9 (EO) dimethyl etheramine |
| S31 | Neodol 1-9 | Shell | PEG 9 $C_{11}$ alcohol |
| S32 | APG 2067 | Cognis | linear alkylpolyglucoside |
| S33 | Tryfac 5560-A TDA-6 | Cognis | PEG 6 isotridecyl phosphate ester |
| S34 | AV 01/37-2 | Clariant | monoethoxylated alkylamine |
| S35 | AV 01/37-3 | Clariant | monoethoxylated alkylamine |
| S36 | E-14-2 | Tomah | bis-(2-hydroxyethyl) isodecyloxypropyl amine |
| S37 | E-17-2 | Tomah | bis-(2-hydroxyethyl) isotridecyloxypropyl amine |

-continued

| Ref. | Trade Name | Manufacturer | Chemical Description |
|---|---|---|---|
| S38 | E-19-2 | Tomah | bis-(2-hydroxyethyl) linear alkyloxypropyl amine |
| S39 | E-14-5 | Tomah | poly (5) oxyethylene isodecyloxypropyl amine |
| S40 | M-1618-E15-2 | Tomah | $C_{16-18}$ O(EO) 15 dimethypropyl amine |
| S41 | 5595-120A | Witco | $C_{12}OPO_3$ (EO)5 |
| S42 | Arosurf 66 E10 | Goldschmidt | PEG-10 Isostearyl ether |
| S43 | | | Cocoquat 2 EO |
| S43 | Varonic K205 | | polyoxyethylene(5)cocoamine, |
| S44 | Silwet L-77 | | heptamethyltrisiloxane 7EO methyl ether |
| S45 | M-45P3E10-2 | | $C_{14-15}$ O(PO)3(EO) 10 dimethylpropylamine |
| S46 | T1415E18DA | Tomah | PEG 18 $C_{14-15}$ ether dipropyldiamine |
| S47 | APG 2069 | Cognis | alkylpolyglucoside |
| S48 | AG 6202 | Akzo Nobel | alkylpolyglucoside |
| S49 | AV 01/37-3 | Clariant | tallowamine ethoxylate 15 EO |
| S50 | Hetoxol CS20 | | $C_{16-18}$ alcohol ethoxylate 20 EO |
| S51 | MEAA 13 | | monoethoxylated alkylamine: $C_{18}H_{37}NMe(13\ EO)H$ |
| S52 | 1816P5E15PA | Tomah | $C_{16-18}$ propyl etheramine (5 PO)(15 EO) |
| S53 | HDTMH | Sigma | Hexadecyl trimethylammonium hydroxide |
| S54 | HDTMBr | Aldrich | Hexadecyl trimethylammonium bromide |
| S55 | 1816P5E15DA | Tomah | $C_{16-18}$ etherdiamine (5 PO)(15 EO) |
| S56 | M-T25E9-2 | Tomah | $C_{12-15}$ (9 EO) dimethyl etheramine |
| S57 | M-91P3E10-2 | Tomah | $C_{9-11}$ dimethyl etheramine (3 PO)(10 EO) |
| S58 | 91P3E10DA | Tomah | C9–11 (3 PO)(10 EO) ether diamine |
| S59 | BTAH | Aldrich | Benzyltrimethylammonium hydroxide |
| S60 | BTACl | Aldrich | Benzyltrimethylammonium chloride |
| S61 | Neodol 23-5 | Shell | C12–15 ethoxylated (5 EO) alcohol |
| S62 | Mackine 101 | McIntyre | Cocoaminodipropyl dimethylamine |
| S63 | Hetoxol CAW | | $C_{16}$ alcohol alkoxylate (5 PO)(20 EO) |
| S64 | C91P3E10PA | Tomah | $C_{9-11}$ alkoxylated propylamine (3 PO)(10 EO) |
| S65 | Surfonic ™ AGM-550 | Huntsman | $C_{12-14}$ alkoxylated (1 PO) propylamine (5EO) ethoxylate |
| S66 | M-1816E15-2 | Tomah | C16–18 PEG 15 (EO) dimethyl etheramine |
| S67 | PF 8000 | Witco | ethoxylated phosphate ester |
| S68 | TBAH | Sigma | Tetrabutylammonium hydroxide |

The following procedure was used for testing compositions of the Examples to determine herbicidal effectiveness, except where otherwise indicated.

Seeds of the plant species indicated were planted in 85 mm square pots in a soil mix which was previously steam sterilized and prefertilized with a 14-14-14 NPK slow release fertilizer at a rate of 3.6 kg/m3. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and about 18° C. during the night. Plants were sub-irrigated throughout the test to ensure adequate soil moisture levels.

Pots were assigned to different treatments in a randomized experimental design with 6 replications. A set of pots was left untreated as a reference against which effects of the treatments could later be evaluated.

Application of glyphosate compositions was made by spraying with a track sprayer fitted with a 9501E nozzle calibrated to deliver a spray volume of 93 liters per hectare (l/ha) at a pressure of 166 kilopascals (kPa). After treatment, pots were returned to the greenhouse until ready for evaluation.

Treatments were made using dilute aqueous compositions. These could be prepared as spray compositions directly from their ingredients, or by dilution with water of preformulated concentrate compositions.

For evaluation of herbicidal effectiveness, all plants in the test were examined by a single practiced technician, who recorded percent control, a visual measurement of the effectiveness of each treatment by comparison with untreated plants. Control of 0% indicates no effect, and control of 100% indicates that all of the plants are completely dead. Control of 85% or more is in most cases considered acceptable for normal herbicide use; however in greenhouse tests such as those for the Examples it is normal to apply compositions at rates which give less than 85% control, as this makes it easier to discriminate among compositions having different levels of effectiveness. The reported % control values represent the average for all replicates of each treatment.

Example 1

The effect of small acids on the efficacy of aminated alkoxylated alcohols of formulae (5) or (6) above was tested. Aqueous concentrate compositions were prepared containing potassium glyphosate salt ("Glyph"), reported in g a.e./liter, and excipient ingredients as shown in Table 1a.

TABLE 1a

| Composition | Glyph. g a.e./l | Component 1 | w/v % | Component 2 | w/v % |
|---|---|---|---|---|---|
| 346A8T | 62.7 | S1 | 2.0 | — | — |
| 346B4E | 62.7 | S1 | 2.0 | Acetic Acid | 0.1 |
| 346C0Z | 62.7 | S1 | 2.0 | Phosphoric Acid | 0.15 |
| 346D2B | 62.7 | S1 | 2.0 | Gluconic Acid | 0.35 |
| 346E9L | 62.7 | S1 | 2.0 | Lactic Acid | 0.15 |
| 346F8T | 62.7 | S1 | 2.0 | Oxalic Acid | 0.1 |
| 346G3S | 62.7 | S1 | 2.0 | Fumaric Acid | 0.14 |
| 346H6Y | 62.7 | S1 | 2.0 | Citric Acid | 0.14 |

The compositions of Table 1a and comparative compositions Roundup® UltraMax and Composition 41I were applied to velvetleaf (*Abutilon theophrasti*, ABUTH) plants. Results, averaged for all replicates of each treatment, are shown in Table 1b.

TABLE 1b

| | ABUTH % Control | | | |
|---|---|---|---|---|
| Composition | 100 g a.e./ha | 200 g a.e./ha | 300 g a.e./ha | 400 g a.e./ha |
| 346A8T | 56.7 | 80.8 | 90.0 | 95.0 |
| 346B4E | 58.3 | 80.8 | 90.0 | 93.3 |
| 346C0Z | 53.3 | 80.8 | 90.8 | 95.5 |
| 346D2B | 63.3 | 77.5 | 90.0 | 93.0 |
| 346E9L | 50.0 | 80.0 | 87.5 | 93.8 |
| 346F8T | 80.8 | 85.8 | 95.5 | 97.8 |
| 346G3S | 67.5 | 77.5 | 89.2 | 91.7 |
| 346H6Y | 61.7 | 81.7 | 88.3 | 94.7 |
| Roundup ® UltraMax | 10.0 | 74.2 | 81.7 | 88.3 |
| Composition 41I | 23.3 | 76.7 | 85.0 | 93.8 |

Potassium glyphosate formulations containing oxalic acid and S1 provided significant efficacy improvement over Roundup® UltraMax and Composition 41I standards, and composition 346A8T which did not contain oxalic acid at all applied rates. All formulations, with or without dicarboxylic acids, were more effective than Roundup® UltraMax and Composition 41I for velvetleaf control.

Example 2

The herbicidal efficacy against velvetleaf of the addition of small organic acids to potassium glyphosate formulations containing aminated alkoxylated alcohols of formulae (5) or (6) was tested. Aqueous concentrate compositions ("Comp") were prepared containing potassium glyphosate salt, reported in g a.e./liter, and excipient ingredients as shown in Table 2a. All components were added together and agitated in a shaker batch for 30 min at 60° C. All samples were then cooled to room temperature and the stability after 24 hours was determined.

TABLE 2a

| Comp. Number | Glyphosate g/l | Component 1 | w/v % | Component 2 | w/v % |
|---|---|---|---|---|---|
| 342A6J | 62.7 | S10 | 2.0 | — | — |
| 342B9V | 62.7 | S1 | 2.0 | Acetic Acid | 0.1 |
| 342C3H | 62.7 | S1 | 2.0 | Phosphoric Acid | 0.15 |
| 342D7D | 62.7 | S1 | 2.0 | Gluconic Acid | 0.35 |
| 342E7U | 62.7 | S1 | 2.0 | Lactic Acid | 0.15 |
| 342F8K | 62.7 | S1 | 2.0 | Oxalic Acid | 0.1 |
| 342G6R | 62.7 | S1 | 2.0 | Fumaric Acid | 0.14 |
| 342H1A | 62.7 | S1 | 2.0 | Citric Acid | 0.14 |

The compositions of Table 2a and comparative compositions Composition 570I and Composition 41I were applied to velvetleaf (*Abutilon theophrasti*, ABUTH) plants. Results, averaged for all replicates of each treatment, are shown in Table 2b.

TABLE 2b

| | ABUTH % Control | | | |
|---|---|---|---|---|
| Composition | 100 g a.e./ha | 200 g a.e./ha | 300 g a.e./ha | 400 g a.e./ha |
| 342A6J | 65 | 87.3 | 91.8 | 95.8 |
| 342B9V | 50 | 85.3 | 91.5 | 95.2 |
| 342C3H | 50.3 | 84 | 92.3 | 94.8 |
| 342D7D | 63.5 | 86.5 | 90.8 | 95.2 |
| 342E7U | 54.7 | 87.7 | 92.8 | 94.7 |
| 342F8K | 75.8 | 91.7 | 94.8 | 97.2 |
| 342G6R | 70 | 84 | 92.2 | 94.8 |
| 342H1A | 60 | 83 | 92.5 | 95.7 |
| Composition 570I | 0.8 | 14.2 | 37.5 | 60.5 |
| Composition 41I | 2.5 | 79.5 | 86.8 | 93.5 |

Composition 342F8K, containing oxalic acid, provided the greatest velvetleaf control.

Example 3

The efficacy of the addition of citric and phosphoric acid to potassium glyphosate formulations was tested. Aqueous concentrate compositions were prepared containing potassium glyphosate salt, reported in g a.e./liter, and excipient ingredients as shown in Table 3a. All components were added together and agitated in a shaker batch for 30 minutes at 60° C. After 24 hours at RT all samples were stable, clear and yellow.

TABLE 3a

| Comp. Number | Glyphosate g/l | Component 1 | w/v % | Component 2 | w/v % |
|---|---|---|---|---|---|
| 344A2G | 62.7 | S6 | 2.0 | — | — |
| 344B8I | 62.7 | S7 | 2.0 | — | — |
| 344C6R | 62.7 | S7 | 2.0 | Citric Acid | 0.08 |
| 344D9Z | 62.7 | S7 | 2.0 | Citric Acid | 0.24 |
| 344E7U | 62.7 | S7 | 2.0 | Citric Acid | 0.45 |
| 344F5X | 62.7 | S7 | 2.0 | Phosphoric Acid | 0.10 |
| 344G5T | 62.7 | S7 | 2.0 | Phosphoric Acid | 0.20 |

The compositions of Table 3a and comparative compositions of Composition 570I and Composition 41I were applied to velvetleaf (*Abutilon theophrasti*, ABUTH) plants. Results, averaged for all replicates of each treatment, are shown in Table 3b.

TABLE 3b

ABUTH % inhibition 14 days after treatment

| Composition | 100 g a.e./ha | 200 g a.e./ha | 300 g a.e./ha | 400 g a.e./ha |
|---|---|---|---|---|
| 344A2G | 42.5 | 78.3 | 91.8 | 93.3 |
| 344B8I | 17.5 | 66.7 | 86.2 | 93.2 |
| 344C6R | 24.2 | 76.3 | 85.7 | 91 |
| 344D9Z | 40 | 76.8 | 87.2 | 90.2 |
| 344E7U | 40 | 76.7 | 87.2 | 91.7 |
| 344F5X | 36.7 | 76.7 | 85.8 | 91.5 |
| 344G5T | 30.8 | 74.2 | 85 | 91 |
| Composition 570I | 0 | 25 | 58.3 | 70.8 |
| Composition 41I | 35.8 | 74.7 | 86.8 | 94.3 |

Addition of small acids such as citric acid and phosphoric acid did not have significant impact on the efficacy of the aminated alkoxylated alcohols of formulae (5).

Example 4

The efficacy of the performance of oxalic acid versus EDTA on velvetleaf was tested. In Table 4a aqueous concentrate compositions were prepared with potassium glyphosate salt. Glyphosate concentrations are reported in g a.e./liter. Oxalic acid and EDTA were first dissolved in water and then potassium glyphosate and surfactant were added. The formulation was then placed in a shaker batch for 30 min at 60° C. 24 hours after cooling to RT all samples were stable, clear and slightly yellow.

TABLE 4a

| Comp. Number | Glyphosate g/l | Component 1 | w/v % | Component 2 | w/v % |
|---|---|---|---|---|---|
| 381A9N | 62.7 | S1 | 2.0 | Oxalic acid | 0.2 |
| 381B3K | 62.7 | S1 | 2.0 | Oxalic acid | 0.4 |
| 381C4R | 62.7 | S1 | 2.0 | EDTA | 0.2 |
| 381D0Q | 62.7 | S1 | 2.0 | EDTA | 0.4 |
| 381E4I | 62.7 | S12 | 2.0 | Oxalic acid | 0.2 |
| 381F1A | 62.7 | S12 | 2.0 | Oxalic acid | 0.4 |
| 381G5C | 62.7 | S12 | 2.0 | EDTA | 0.2 |
| 381H8S | 62.7 | S12 | 2.0 | EDTA | 0.4 |

The compositions of Table 4a, Composition 725K, Composition 570I and Roundup® UltraMax, were applied to velvetleaf (ABUTH) plants. Results, averaged for all replicates of each treatment, are shown in Table 4b.

TABLE 4b

| Composition | 100 g a.e./ha | 200 g a.e./ha | 300 g a.e./ha | 400 g a.e./ha |
|---|---|---|---|---|
| 381A9N | 71.7 | 93.2 | 97.8 | 99 |
| 381B3K | 74.2 | 90.5 | 99 | 99.5 |
| 381C4R | 70 | 85.8 | 93.5 | 95.8 |
| 381D0Q | 64.2 | 81.7 | 94.8 | 97.3 |
| 381E4I | 66.7 | 86.7 | 93.3 | 98 |
| 381F1A | 63.3 | 87.5 | 94.2 | 97.3 |
| 381G5C | 49.2 | 72.5 | 86.7 | 89.2 |
| 381H8S | 23.3 | 60.8 | 83.3 | 88.3 |
| Comp. 725K | 0 | 9.2 | 36.7 | 61.7 |
| Composition 570I | 0 | 19.2 | 48.3 | 66.7 |
| Roundup® UltraMax | 25 | 75.8 | 90 | 94.7 |

Oxalic acid and EDTA in combination with $C_{14-15}$ PEG 13(EO) etheramine showed similar efficacy. Oxalic acid formulations containing PEG 5 tallow amine gave enhanced efficacy over analogous EDTA formulations. $C_{14-15}$ PEG 13(EO) etheramine gave enhanced efficacy over analogous PEG 5 tallow amine formulations. All formulations except PEG 5 tallow amine containing EDTA outperformed the Roundup® UltraMax standard.

Example 5

The efficacy of different dicarboxylic acids with cocoamine surfactant was tested. In Table 5a, aqueous concentrate compositions were prepared with potassium glyphosate. Glyphosate concentrations are reported in g a.e./liter. Dicarboxylic acids were added to the formulations in various weight ratios. Acids were first dissolved in water and then potassium glyphosate and surfactant were added. The formulation was agitated in a shaker batch for 30 minutes at 60° C. 24 hours after cooling to RT all samples were stable, clear and colorless.

TABLE 5a

| Comp. Number | Glyphosate g/l | Surfactant | w/v % | Dicarboxylic Acid (DA) | w/v % | Gly:DA |
|---|---|---|---|---|---|---|
| 611A5V | 62.7 | S5 | 2.0 | — | — | — |
| 611B9S | 62.7 | S5 | 2.0 | Formic acid | 0.15 | 40:1 |
| 611C6L | 62.7 | S5 | 2.0 | Oxalic acid | 0.3 | 20:1 |
| 611D3H | 62.7 | S5 | 2.0 | Malonic acid | 0.4 | 15:1 |
| 611E8C | 62.7 | S5 | 2.0 | Succinic acid | 0.4 | 15:1 |
| 611F8K | 62.7 | S5 | 2.0 | Glutaric acid | 0.4 | 15:1 |
| 611G1Z | 62.7 | S5 | 2.0 | Adipic acid | 0.5 | 12:1 |
| 611H3J | 63.7 | S5 | 1.2 | Oxalic acid | 0.3 | 20:1 |

The compositions of Table 5a and comparative compositions of Composition 725K, Composition 570I and Roundup® UltraMax were applied to velvetleaf (*Abutilon theophrasti*, ABUTH) and Japanese millet (*Echinochloa crus-galli* var. *frumentae*, ECHCF) plants. Results, averaged for all replicates of each treatment, are shown in Tables 5b and 5c.

TABLE 5b

ABUTH % inhibition 14 days after treatment

| Composition | 100 g a.e./ha | 200 g a.e./ha | 300 g a.e./ha | 400 g a.e./ha |
|---|---|---|---|---|
| 611A5V | 60 | 77.5 | 88.3 | 91.7 |
| 611B9S | 46.7 | 80 | 88.3 | 90 |
| 611C6L | 81.7 | 83.3 | 89.2 | 90 |
| 611D3H | 47.5 | 82.5 | 87.5 | 90 |
| 611E8C | 64.2 | 78.3 | 85.8 | 90.8 |
| 611F8K | 47.5 | 82.5 | 85.8 | 90 |
| 611G1Z | 75 | 80.8 | 86.7 | 87.5 |
| 611H3J | 60 | 82.5 | 89.2 | 92.8 |
| Comp. 725K | 20.8 | 70 | 80.8 | 82.5 |
| Composition 570I | 40 | 72.5 | 84.2 | 84.2 |
| Roundup ® UltraMax | 72.5 | 87.5 | 90.8 | 92.2 |

TABLE 5c

ECHCF % inhibition 14 days after treatment

| Composition | 100 g a.e./ha | 200 g a.e./ha | 300 g a.e./ha | 400 g a.e./ha |
|---|---|---|---|---|
| 611A5V | 55 | 60 | 66.7 | 82.5 |
| 611B9S | 55 | 66.7 | 82.5 | 85.8 |
| 611C6L | 55 | 63.3 | 78.3 | 82.5 |
| 611D3H | 52.5 | 60 | 71.7 | 77.5 |
| 611E8C | 55 | 60.8 | 65 | 74.2 |
| 611F8K | 52.5 | 58.3 | 70.8 | 74.2 |
| 611G1Z | 53.3 | 59.2 | 70 | 77.5 |
| 611H3J | 52.5 | 60.8 | 73.3 | 80.8 |
| Composition 725K | 2.5 | 15.8 | 48.3 | 52.5 |
| Composition 570I | 15.8 | 40 | 50 | 55 |
| Roundup ® UltraMax | 55 | 59.2 | 71.7 | 86.3 |

Oxalic acid gave increased efficacy on velvetleaf, while the other dicarboxylic acids tested did not. None of the dicarboxylic acids provided efficacy enhancement on barnyardgrass. In table 5b, some increased efficacy was noted with adipic acid.

Example 6

The efficacy of iminodiacetic acid (IDA) versus oxalic acid on potassium glyphosate performance was tested. In Table 6a aqueous concentrate compositions were prepared with potassium glyphosate salt. Glyphosate concentrations are reported in g a.e./liter.

TABLE 6a

| Comp. Number | Glyphosate g/l | Component 1 | w/v % | Component 2 | w/v % |
|---|---|---|---|---|---|
| 060AA3D | 62 | — | — | Oxalic acid | 2.0 |
| 060AB8J | 62 | — | — | Oxalic acid | 0.6 |
| 060AC3H | 62 | — | — | Iminodiacetic acid | 2.0 |
| 060AD5N | 62 | — | — | Iminodiacetic acid | 0.6 |
| 060AE7Q | 62 | S5 | 2.0 | Oxalic acid | 0.6 |
| 060AF6B | 62 | S5 | 2.0 | Iminodiacetic acid | 0.6 |
| 060AG0L | 62 | S5 | 2.0 | — | — |

The compositions of Table 6a and comparative compositions of Composition 725K, Composition 570I and Roundup® UltraMax were applied to velvetleaf (*Abutilon theophrasti*, ABUTH) and Japanese millet (*Echinochloa crus-galli* var. *frumentae*, ECHCF) plants. Results, averaged for all replicates of each treatment, are shown in Tables 6b and 6c.

TABLE 6b

ABUTH % inhibition 14 days after treatment

| Composition | 100 g a.e./ha | 200 g a.e./ha | 300 g a.e./ha | 400 g a.e./ha |
|---|---|---|---|---|
| 060AA3D | 73.3 | 80 | 85.8 | 90 |
| 060AB8J | 66.7 | 80 | 84.2 | 92.5 |
| 060AC3H | 31.7 | 70 | 77.5 | 86.7 |
| 060AD5N | 13.3 | 70 | 80 | 85.8 |
| 060AE7Q | 71.7 | 85 | 87.5 | 97.5 |
| 060AF6B | 55.8 | 80 | 87.5 | 94.8 |
| 060AG0L | 60 | 74.2 | 87.5 | 92.5 |
| Comp. 725K | 23.3 | 61.7 | 72.5 | 77.5 |
| Composition 570I | 36.7 | 65.8 | 77.5 | 84.2 |
| Roundup ® UltraMax | 45 | 83.3 | 91.7 | 93.3 |

TABLE 6c

ECHCF % inhibition 14 days after treatment

| Composition | 100 g a.e./ha | 200 g a.e./ha | 300 g a.e./ha | 400 g a.e./ha |
|---|---|---|---|---|
| 060AA3D | 10 | 30.8 | 43.3 | 50 |
| 060AB8J | 13.3 | 40.8 | 54.2 | 55 |
| 060AC3H | 14.2 | 30.8 | 55.8 | 57.5 |
| 060AD5N | 20.8 | 39.2 | 51.7 | 62.5 |
| 060AE7Q | 60 | 78.3 | 85 | 91.3 |
| 060AF6B | 50 | 76.7 | 80.8 | 82.5 |
| 060AG0L | 59.2 | 70 | 84.2 | 92.5 |
| Comp. 725K | 0.8 | 32.5 | 56.7 | 58.3 |
| Composition 570I | 14.2 | 30 | 54.2 | 57.5 |
| Roundup ® UltraMax | 60 | 67.5 | 85.7 | 87.3 |

Oxalic acid is more effective than iminodiacetic acid at enhancing glyphosate efficiency on velvetleaf. Ethomeen C12 was necessary to achieve efficacy enhancement on barnyardgrass in oxalic acid and iminodiacetic acid formulations.

Example 7

The ability of oxalic acid to enhance potassium glyphosate performance was evaluated as compared to other common chelators. In Table 7a aqueous concentrate compositions were prepared with potassium glyphosate salt. Glyphosate concentrations are reported in g a.e./liter. The weight ratio of glyphosate a.e. to sodium citrate, oxalic acid, and EDTA was 2.2:1, 2:1 and 1.5:1, respectively, and at 22:1, 20:1 and 15:1, respectively. Chelators were first dissolved in water and then potassium glyphosate was added. The formulation was agitated in a shaker batch for 30 minutes at 60° C. 24 hours after cooling to RT all samples were stable and clear.

TABLE 7a

| Composition | Glyphosate g/l | Component 1 | w/v % |
|---|---|---|---|
| 605A0X | 64.2 | di-K oxalic acid | 4.09 |
| 605B5T | 62.7 | di-K oxalic acid | 0.41 |
| 605C8U | 63.6 | EDTA | 4.23 |
| 605D5A | 62.7 | EDTA | 0.42 |
| 605E9I | 63.6 | Sodium Citrate | 2.68 |
| 605F2E | 62.7 | Sodium Citrate | 0.27 |

The compositions of Table 7a, Composition 470K, Composition 725K, Composition 570I and Roundup® UltraMax, were applied to velvetleaf (*Abutilon theophrasti*, ABUTH) plants. Results, averaged for all replicates of each treatment, are shown in Table 7b.

TABLE 7b

ABUTH % inhibition 15 days after treatment

| Composition | 100 g a.e./ha | 200 g a.e./ha | 300 g a.e./ha | 400 g a.e./ha |
|---|---|---|---|---|
| 605A0X | 80.8 | 86.7 | 91.7 | 92.8 |
| 605B5T | 68.3 | 81.7 | 84.2 | 86.7 |
| 605C8U | 65 | 74.2 | 80 | 83.3 |
| 605D5A | 59.2 | 70.8 | 82.5 | 81.7 |
| 605E9I | 50 | 73.3 | 80 | 83.3 |
| 605F2E | 48.3 | 75.8 | 81.7 | 84.2 |
| Comp. 470K | 79.2 | 84.2 | 89.2 | 93 |
| Comp. 725K | 3.3 | 51.7 | 69.2 | 76.7 |
| Composition 570I | 18.3 | 64.2 | 75.8 | 78.3 |
| Roundup® UltraMax | 70.8 | 88.8 | 94.3 | 97.7 |

Oxalic acid was superior to sodium citrate and EDTA for enhancement of glyphosate efficacy on velvetleaf. Oxalic acid at 2:1 and 20:1 ratios of glyphosate a.e.:oxalic acid performed similarly to Roundup® UltraMax and Composition 470K standards.

Example 8

The efficacy of dicarboxylic acids with aminated alkoxylated alcohols of formulae (5) and potassium glyphosate was evaluated. In Table 8a aqueous concentrate compositions were prepared with potassium glyphosate salt. Glyphosate concentrations are reported in g a.e./liter. Acids were first dissolved in water, potassium glyphosate was added, and the surfactant was melted into solution. The formulation was agitated in a shaker batch for 30 minutes at 60° C. 24 hours after cooling to RT all samples were stable, clear and slightly yellow.

TABLE 8a

| Composition | Glyphosate g/l | Component 1 | w/v % | Component 2 | w/v % |
|---|---|---|---|---|---|
| 396A3J | 62.7 | S46 | 2.0 | — | — |
| 396B5R | 62.7 | S46 | 2.0 | Acetic acid | 0.2 |
| 396C9A | 62.7 | S46 | 2.0 | Phosphoric acid | 0.3 |
| 396D3V | 62.7 | S46 | 2.0 | Lactic acid | 0.3 |
| 396E3R | 62.7 | S46 | 2.0 | Oxalic acid | 0.2 |
| 396F9K | 62.7 | S46 | 2.0 | Succinic acid | 0.26 |
| 396G5B | 62.7 | S46 | 2.0 | Citric acid | 0.27 |
| 396H7U | 62.7 | S46 | 2.0 | Gluconic acid | 0.5 |

The compositions of Table 8a, Composition 725K, Composition 570I and Roundup® UltraMax, were applied to velvetleaf (*Abutilon theophrasti*, ABUTH) plants. Results, averaged for all replicates of each treatment, are shown in Table 8b.

TABLE 8b

ABUTH % inhibition 14 days after treatment

| Composition | 100 g a.e./ha | 200 g a.e./ha | 300 g a.e./ha | 400 g a.e./ha |
|---|---|---|---|---|
| 396A3J | 53.3 | 79.2 | 87.5 | 90 |
| 396B5R | 39.2 | 80.8 | 87.5 | 93 |
| 396C9A | 53.3 | 80 | 85 | 91.5 |
| 396D3V | 59.2 | 77.5 | 85 | 89.2 |
| 396E3R | 71.7 | 85.8 | 86.7 | 92.5 |
| 396F9K | 56.7 | 78.3 | 87.5 | 90 |
| 396G5B | 52.5 | 80.8 | 85.8 | 89.2 |
| 396H7U | 47.5 | 80.8 | 85.8 | 92.5 |
| Comp. 725K | 6.7 | 63.3 | 75.8 | 80.8 |
| Composition 570I | 28.3 | 69.2 | 76.7 | 80.8 |
| Roundup® UltraMax | 60 | 80 | 88.3 | 9.25 |

Acetic, phosphoric, lactic, succinic, citric and gluconic acids did not significantly effect the efficacy of their respective formulations on velvetleaf. The oxalic acid formulation exhibited enhanced efficacy.

Example 9

The efficacy of dicarboxylic acids with aminated alkoxylated alcohols of formulae (5) was evaluated. In Table 9a aqueous concentrate compositions were prepared with potassium glyphosate salt. Glyphosate concentrations are reported in g a.e./liter. Acids were first dissolved in water, potassium glyphosate was added, and the surfactant was melted into solution. The formulation was agitated in a shaker batch for 30 minutes at 60° C. 24 hours after cooling to RT all samples were stable, clear and slightly yellow.

TABLE 9a

| Composition | Glyphosate g/l | Component 1 | w/v % | Component 2 | w/v % |
|---|---|---|---|---|---|
| 390A7B | 62.7 | S1 | 2.0 | Oxalic acid | 0.2 |
| 390B8W | 62.7 | S1 | 2.0 | Succinic acid | 0.26 |
| 390C3A | 62.7 | S1 | 2.0 | Maleic acid | 0.26 |
| 390D0K | 62.7 | S1 | 2.0 | Fumaric acid | 0.26 |
| 390E9D | 62.7 | S1 | 2.0 | Succinamic acid | 0.26 |
| 390F4G | 62.7 | S1 | 2.0 | — | — |
| 390G4P | 62.7 | S30 | 2.0 | Oxalic acid | 0.26 |

The compositions of Table 9a, Composition 725K, Composition 570I and Roundup® UltraMax, were applied to velvetleaf (*Abutilon theophrasti*, ABUTH) plants. Results, averaged for all replicates of each treatment, are shown in Table 9b.

TABLE 9b

ABUTH % inhibition 15 days after treatment

| Composition | 100 g a.e./ha | 200 g a.e./ha | 300 g a.e./ha | 400 g a.e./ha |
|---|---|---|---|---|
| 390A7B | 78.3 | 87.5 | 92.8 | 95.7 |
| 390B8W | 70.8 | 84.2 | 91 | 93 |
| 390C3A | 72.5 | 86.7 | 94.5 | 95 |
| 390D0K | 75 | 85.8 | 93.5 | 98 |
| 390E9D | 25.8 | 51.7 | 67.5 | 72.5 |
| 390F4G | 70 | 85 | 90.8 | 94.5 |
| 390G4P | 80 | 90.5 | 92.2 | 96.7 |
| TD IQ | 38.3 | 73.3 | 85 | 86.7 |
| Comp. 725K | 0 | 2.5 | 21.7 | 56.7 |
| Composition 570I | 8.3 | 30 | 55 | 68.3 |
| Roundup ® UltraMax | 41.7 | 75 | 88.3 | 90.8 |

The oxalic acid, maleic acid and fumaric acid formulations provided similar efficacy for velvetleaf control with performance levels greater than the Roundup UltraMax standard. Succinamic acid demonstrated an antagonistic effect on glyphosate efficacy when combined with the $C_{14-15}$ PEG 13(EO) dimethyl etheramine surfactant.

Example 10

The efficacy of oxalic acid addition to glyphosate commercial standard compositions on sicklepod (CASOB) was evaluated. Three different weight ratios of 2:1, 10:1 and 30:1 glyphosate a.e.:oxalic acid were evaluated. Results, averaged for all replicates of each treatment, are shown in Table 10a.

TABLE 10a

CASOB % Control 18 Days After Treatment

| Composition | Glyph. Salt | 200 g a.e./ha | 400 g a.e./ha | 800 g a.e./ha |
|---|---|---|---|---|
| Composition 725K | K | 35 | 61.7 | 75 |
| Roundup UltraMax | IPA | 80 | 92.5 | 97.5 |
| Roundup UltraMax:oxalic acid @ 2:1 | IPA | 85 | 96.7 | 99.7 |
| Roundup UltraMax:oxalic acid @ 10:1 | IPA | 84.2 | 92.5 | 96.5 |
| Roundup UltraMax:oxalic acid @ 30:1 | IPA | 80.8 | 91.7 | 95 |
| TD IQ | di-NH$_4$ | 75 | 89.8 | 96.5 |
| TD IQ:oxalic acid @ 2:1 | di-NH$_4$ | 82.5 | 90 | 96.5 |
| TD IQ:oxalic acid @ 10:1 | di-NH$_4$ | 82.5 | 85.7 | 97.5 |
| TD IQ:oxalic acid @ 30:1 | di-NH$_4$ | 77.5 | 85 | 97.5 |
| Composition 540K | K | 80.8 | 87.3 | 95 |

TABLE 10a-continued

CASOB % Control 18 Days After Treatment

| Composition | Glyph. Salt | 200 g a.e./ha | 400 g a.e./ha | 800 g a.e./ha |
|---|---|---|---|---|
| Composition 540K:oxalic acid @ 2:1 | K | 87.5 | 93.8 | 99.2 |
| Composition 540K:oxalic acid @ 10:1 | K | 85.8 | 96.7 | 99.8 |
| Composition 540K:oxalic acid @ 30:1 | K | 80 | 93.2 | 97.5 |

Overall, oxalic acid did not give statistically significant efficacy enhancement on sicklepod when tank mixed with the commercial standards. Oxalic acid did give efficacy improvements for high load IPA and potassium glyphosate formulations.

Example 11

The effect of oxalic acid on aminated alkoxylated alcohols of formulae (5) and short EO tallowamine surfactants in dilute IPA and potassium glyphosate formulations was evaluated. Glyphosate concentrations are reported in g a.e./liter. All components were added and the formulation was agitated in a shaker batch for 30 minutes at 60° C. 24 hours after cooling to RT all samples were stable, clear and slightly yellow.

TABLE 11a

| Comp. Number | Glyph. g/l | Glyph. salt | Component 1 | w/v % | Component 2 | w/v % |
|---|---|---|---|---|---|---|
| 366A1P | 60.0 | IPA | S13 | 2.0 | — | — |
| 366B4R | 60.0 | IPA | S13 | 2.0 | Oxalic acid | 0.1 |
| 366C4K | 62.7 | K | S13 | 2.0 | — | — |
| 366D5N | 62.7 | K | S13 | 2.0 | Oxalic acid | 0.1 |
| 366E3M | 60.0 | IPA | S12 | 2.0 | — | — |
| 366F0Q | 60.0 | IPA | S12 | 2.0 | Oxalic acid | 0.2 |
| 366G6J | 62.7 | K | S12 | 2.0 | — | — |
| 366H6D | 62.7 | K | S12 | 2.0 | Oxalic acid | 0.2 |

The compositions of Table 11a and comparative compositions of Composition 725K, Composition 570I and Roundup UltraMax were applied to velvetleaf (*Abutilon theophrasti*, ABUTH) plants. Results, averaged for all replicates of each treatment, are shown in Table 11b.

TABLE 11b

| Composition | 100 g a.e./ha | 200 g a.e./ha | 300 g a.e./ha | 400 g a.e./ha |
|---|---|---|---|---|
| 366A1P | 75.8 | 88.3 | 91.7 | 96.8 |
| 366B4R | 79.2 | 90.8 | 97.5 | 97.7 |
| 366C4K | 77.5 | 87.5 | 92.5 | 94.7 |
| 366D5N | 77.5 | 87.5 | 92.5 | 96.3 |
| 366E3M | 55.8 | 72.5 | 77.5 | 82.5 |
| 366F0Q | 43.3 | 83.3 | 86.7 | 90 |
| 366G6J | 43.3 | 60 | 75.8 | 84.2 |
| 366H6D | 15 | 80.8 | 90 | 94.7 |
| Comp. 725K | 0 | 5 | 28.3 | 67.5 |
| Composition 570I | 0 | 9.2 | 62.5 | 73.3 |
| Roundup UltraMax | 43.3 | 80 | 87.5 | 91.3 |

All formulations containing oxalic acid showed efficacy over the analogous formulations not containing oxalic acid. Formulations 366A1P, 366B4R, 366C4K and 366D5N, all containing aminated alkoxylated alcohols of formulae (5) with or without added oxalic acid, gave higher efficacy than the Witcamine 405 or glyphosate standard formulations. Potassium and IPA glyphosate formulations performed similarly.

Example 12

The effect of oxalic acid on aminated alkoxylated alcohols of formulae (5) in IPA and potassium glyphosate formulations was evaluated. Aqueous concentrate compositions 368A8F, 368B7I, 368C5O and 368D7Q were formulated with potassium glyphosate salt. Concentrate compositions 368E4V, 368F3C, 368G7G and 368H6L were formulated with IPA glyphosate salt. Glyphosate concentrations are reported in g a.e. per liter. Compositions 368A8F and 368C5O each additionally contained 0.5% oxalic acid. All components ("Compon") were added and the formulation was agitated in a shaker batch for 1 hour at 60° C. 24 hours after cooling to RT all samples were stable, clear and slightly yellow.

TABLE 12a

| Comp. Number | Glyph. g/l | Compon. 1 | wt % | Compon. 2 | wt % | Compon. 3 | wt % |
|---|---|---|---|---|---|---|---|
| 368A8F | 484 | S13 | 7.0 | S5 | 3.0 | S14 | 1.5 |
| 368B7I | 63 | S13 | 2.0 | Oxalic acid | 0.1 | — | |
| 368C5O | 484 | S1 | 7.0 | S5 | 3.0 | S14 | 1.5 |
| 368D7Q | 63 | S1 | 2.0 | Oxalic acid | 0.1 | — | |
| 368E4V | 360 | S13 | 10.0 | S14 | 1.5 | Oxalic acid | 0.5 |
| 368F3C | 360 | S13 | 10.0 | S14 | 1.5 | — | |
| 368G7G | 60 | S13 | 2.0 | Oxalic acid | 0.1 | — | |
| 368H6L | 60 | S13 | 2.0 | — | | — | |

The compositions of Table 12a and comparative compositions of Composition 725K, Composition 570I and Roundup UltraMax were applied to velvetleaf (*Abutilon theophrasti*, ABUTH) plants. Results, averaged for all replicates of each treatment, are shown in Table 12b.

TABLE 12b

| | ABUTH % Control | | | |
|---|---|---|---|---|
| Composition | 100 g a.e./ha | 200 g a.e./ha | 300 g a.e./ha | 400 g a.e./ha |
| 368A8F | 61.7 | 81.7 | 88.3 | 95.8 |
| 368B7I | 68.3 | 80.8 | 92.5 | 96.7 |
| 368C5O | 70.8 | 80.8 | 90.8 | 95.3 |
| 368D7Q | 78.3 | 93 | 96.3 | 99.2 |
| 368E4V | 83.3 | 87.5 | 96 | 99.2 |
| 368F3C | 65.8 | 80 | 92.5 | 97.2 |
| 368G7G | 75 | 90 | 95.3 | 99.2 |
| 368H6L | 70.7 | 85.8 | 93.3 | 99.7 |
| Comp. 725K | 0 | 0 | 11.7 | 38.3 |
| Composition 570I | 0 | 0 | 21.7 | 42.5 |
| Roundup UltraMax | 14.2 | 72.5 | 84.2 | 93.3 |

All 1816E15PA formulations, with or without oxalic acid, were superior to Roundup UltraMax. 368D7Q and 368E4V, containing glyphosate a.e. to surfactant ratios of 3:1 and 2.7:1 respectively, and each with a glyphosate a.e. to oxalic acid ratio of 60:1, provided the greatest efficacy.

Example 13

The effect of oxalic acid on various glyphosate salts was evaluated. In Table 13a, aqueous tank mixture compositions were prepared with the potassium, IPA and ammonium salts of glyphosate in weight ratios of 2:1,10:1 and 30:1 with 98% oxalic acid from Aldrich (OA). Tank mixture herbicidal activity was analyzed versus tank mixes of the respective salts without added oxalic acid.

TABLE 13a

| Composition | Glyphosate salt | Component 1 | Gly:OA |
|---|---|---|---|
| Composition 725K A | K | — | — |
| Composition 725K B | K | Oxalic Acid | 2:1 |
| Composition 725K C | K | Oxalic Acid | 10:1 |
| Composition 725K D | K | Oxalic Acid | 30:1 |
| Composition 570IA | IPA | — | — |
| Composition 570IB | IPA | Oxalic Acid | 2:1 |
| Composition 570IC | IPA | Oxalic Acid | 10:1 |
| Composition 570ID | IPA | Oxalic Acid | 30:1 |

TABLE 13a-continued

| Composition | Glyphosate salt | Component 1 | Gly:OA |
|---|---|---|---|
| Composition AMM-GLY2S A | $NH_4$ | — | — |
| Composition AMM-GLY2S B | $NH_4$ | Oxalic Acid | 2:1 |
| Composition AMM-GLY2S C | $NH_4$ | Oxalic Acid | 10:1 |
| Composition AMM-GLY2S D | $NH_4$ | Oxalic Acid | 30:1 |

Velvetleaf (*Abutilon theophrasti*, ABUTH) was grown and treated by the standard procedures above. The compositions of Table 13a were applied with results, averaged for all replicates of each treatment, shown in Table 13b.

TABLE 13b

| | ABUTH % Inhibition 15 days after treatment | | |
|---|---|---|---|
| Composition | 75 g a.e./ha | 100 g a.e./ha | 200 g a.e./ha |
| Composition 725K A | 0 | 0 | 34.2 |
| Composition 725K B | 20.8 | 70.8 | 80 |
| Composition 725K C | 0 | 7.5 | 72.5 |
| Composition 725K D | 0 | 0 | 60 |
| Composition 570IA | 0.8 | 5 | 52.5 |
| Composition 570IB | 56.7 | 75.8 | 85 |
| Composition 570IC | 25.8 | 45 | 75.8 |
| Composition 570ID | 16.7 | 37.5 | 75 |
| Composition AMM-GLY2S A | 28.3 | 45.8 | 67.5 |
| Composition AMM-GLY2S B | 75 | 80 | 84.2 |

TABLE 13b-continued

ABUTH % Inhibition 15 days after treatment

| Composition | 75 g a.e./ha | 100 g a.e./ha | 200 g a.e./ha |
|---|---|---|---|
| Composition AMM-GLY2S C | 48.3 | 60.8 | 80 |
| Composition AMM-GLY2S D | 47.5 | 48.3 | 75.8 |

The efficacy of the potassium, IPA and ammonium salts of glyphosate were enhanced with added oxalic acid. The efficacy of the glyphosate and oxalic acid formulation was most effective at a ratio of 2:1 glyphosate a.e.:oxalic acid, and least effective at a ratio of 30:1 glyphosate a.e:oxalic acid.

Example 14

The effect of oxalic acid on glyphosate formulations containing various surfactants was evaluated. In Table 14a, aqueous tank mixture compositions were prepared with the potassium, IPA and di-ammonium salts of glyphosate in ratios of 2:1, 10:1 and 30:1 with 98% oxalic acid from Aldrich (OA). Each of the glyphosate formulations contained a different surfactant component. Tank mixture herbicidal activity was analyzed versus tank mixes of the respective salts without added oxalic acid.

TABLE 14a

| Composition | Glyph. Salt | Surfactant | Gly:S | Component 1 | Gly:OA |
|---|---|---|---|---|---|
| Composition 540K A | K | S65 | 4:1 | — | — |
| Composition 540K B | K | S65 | 4:1 | Oxalic Acid | 2:1 |
| Composition 540K C | K | S65 | 4:1 | Oxalic Acid | 10:1 |
| Composition 540K D | K | S65 | 4:1 | Oxalic Acid | 30:1 |
| Roundup UltraMax A | IPA | proprietary | — | — | — |
| Roundup UltraMax B | IPA | proprietary | — | Oxalic Acid | 2:1 |
| Roundup UltraMax C | IPA | proprietary | — | Oxalic Acid | 10:1 |
| Roundup UltraMax D | IPA | proprietary | — | Oxalic Acid | 30:1 |
| TD IQ-A | di-NH$_4$ | nonionic APG | 3.6:1 | — | — |
| TD IQ-B | di-NH$_4$ | nonionic APG | 3.6:1 | Oxalic Acid | 2:1 |
| TD IQ-C | di-NH$_4$ | nonionic APG | 3.6:1 | Oxalic Acid | 10:1 |
| TD IQ-D | di-NH$_4$ | nonionic APG | 3.6:1 | Oxalic Acid | 30:1 |

The compositions of Table 14a and comparative compositions of Composition 725K were applied to velvetleaf (*Abutilon theophrasti*, ABUTH) plants. Results, averaged for all replicates of each treatment, are shown in Table 14b.

TABLE 14b

ABUTH % Inhibition 17 days after treatment

| Composition | 75 g a.e./ha | 100 g a.e./ha | 200 g a.e./ha |
|---|---|---|---|
| Composition 540KA | 12.5 | 38.3 | 72.5 |
| Composition 540KB | 76.7 | 84.2 | 91.7 |
| Composition 540KC | 70 | 79.2 | 87.5 |
| Composition 540KD | 34.2 | 76.7 | 84.2 |
| Roundup UltraMax A | 7.9 | 28 | 62.1 |
| Roundup UltraMax B | 80 | 85 | 90.8 |
| Roundup UltraMax C | 76.7 | 84.2 | 90.8 |
| Roundup UltraMax D | 70 | 78.3 | 87.5 |
| TD IQ-A | 16.7 | 26.7 | 65.8 |
| TD IQ-B | 75 | 84.2 | 90 |
| TD IQ-C | 45 | 77.5 | 87.5 |
| TD IQ-D | 41.7 | 67.5 | 85.8 |

TABLE 14b-continued

ABUTH % Inhibition 17 days after treatment

| Composition | 75 g a.e./ha | 100 g a.e./ha | 200 g a.e./ha |
|---|---|---|---|
| Composition 725K[1] | 0 | 9.2 | 44.2 |
| Composition 725K[2] | 15.8 | 46.7 | 80 |

[1]Tank mix formulated from Composition 725K at 725 grams/l.
[2]Tank mix formulated from Composition 725K at 445 grams/l.

The efficacy of all formulations were enhanced with added oxalic acid. The efficacy of the glyphosate and oxalic acid formulation was most effective at a ratio of 2:1 glyphosate a.e.:oxalic acid. Overall efficacy of Roundup® UltraMax was greatest with oxalic acid, followed by the potassium glyphosate formulation containing a cationic etheramine surfactant and TD IQ containing a nonionic alkylpolyglucoside.

Example 15

The efficacy of three commercial glyphosate products and oxalic acid as tank mixtures was evaluated. In Table 15a, aqueous tank mixture compositions were prepared with the potassium, IPA and di-ammonium salts of glyphosate in ratios of 2:1, 10:1 and 30:1 with oxalic acid (OA). Tank mixture herbicidal activity was analyzed versus tank mixes of the respective salts without added oxalic acid.

TABLE 15a

| Composition | Glyphosate salt | Component 1 | Gly:OA |
|---|---|---|---|
| Composition 540KA | K | — | — |
| Composition 540KB | K | Oxalic Acid | 2:1 |
| Composition 540KC | K | Oxalic Acid | 10:1 |
| Composition 540KD | K | Oxalic Acid | 30:1 |
| Roundup UltraMax A | IPA | — | — |
| Roundup UltraMax B | IPA | Oxalic Acid | 2:1 |
| Roundup UltraMax C | IPA | Oxalic Acid | 10:1 |
| Roundup UltraMax D | IPA | Oxalic Acid | 30:1 |
| TD IQ-A | di-NH$_4$ | — | — |
| TD IQ-B | di-NH$_4$ | Oxalic Acid | 2:1 |
| TD IQ-C | di-NH$_4$ | Oxalic Acid | 10:1 |
| TD IQ-D | di-NH$_4$ | Oxalic Acid | 30:1 |

The compositions of Table 15a and comparative compositions of Composition 725K, Composition 570I and Roundup UltraMax were applied to green foxtail (SETVI) plants. Results, averaged for all replicates of each treatment, are shown in Table 15b.

TABLE 15b

SETVI % Inhibition 14 days after treatment

| Composition | 75 g a.e./ha | 100 g a.e./ha | 200 g a.e./ha |
|---|---|---|---|
| Composition 540KA | 69.2 | 75 | 87.5 |
| Composition 540KB | 68.3 | 79.2 | 94.7 |
| Composition 540KC | 71.7 | 81.7 | 93 |
| Composition 540KD | 65 | 72.5 | 94 |
| Roundup UltraMax A | 70 | 72.5 | 86.7 |
| Roundup UltraMax B | 71.7 | 72.5 | 91.3 |
| Roundup UltraMax C | 71.7 | 78.3 | 89.2 |
| Roundup UltraMax D | 66.7 | 76.7 | 90.8 |
| TD IQ-A | 63.3 | 71.7 | 85 |
| TD IQ-B | 65.8 | 73.3 | 90.5 |
| TD IQ-C | 53.3 | 67.5 | 84.2 |
| TD IQ-D | 53.3 | 67.5 | 90.3 |
| Composition 725K[1] | 50 | 55 | 69.2 |
| Composition 725K[2] | 70 | 72.5 | 86.7 |

[1] Tank mix formulated from Composition 725K at 725 grams/l.
[2] Tank mix formulated from Composition 725K at 445 grams/l.

No significant enhancement or antagonism with the oxalic acid combinations was found.

Example 16

The efficacy of three commercial glyphosate products and oxalic acid as tank mixtures was evaluated. In Table 16a, aqueous tank mixture compositions were prepared with the potassium, IPA and di-ammonium salts of glyphosate in ratios of 2:1, 10:1 and 30:1 with oxalic acid (OA). Tank mixture herbicidal activity was analyzed versus tank mixes of the respective salts without added oxalic acid.

TABLE 16a

| Composition | Glyphosate salt | Component 1 | Gly:OA |
|---|---|---|---|
| Composition 540KA | K | — | — |
| Composition 540KB | K | Oxalic Acid | 2:1 |
| Composition 540KC | K | Oxalic Acid | 10:1 |
| Composition 540KD | K | Oxalic Acid | 30:1 |
| Roundup UltraMax A | IPA | — | — |
| Roundup UltraMax B | IPA | Oxalic Acid | 2:1 |
| Roundup UltraMax C | IPA | Oxalic Acid | 10:1 |
| Roundup UltraMax D | IPA | Oxalic Acid | 30:1 |
| TD IQ-A | di-NH$_4$ | — | — |
| TD IQ-B | di-NH$_4$ | Oxalic Acid | 2:1 |
| TD IQ-C | di-NH$_4$ | Oxalic Acid | 10:1 |
| TD IQ-D | di-NH$_4$ | Oxalic Acid | 30:1 |

The compositions of Table 16a and comparative compositions of Composition 725K, Composition 570I and Roundup UltraMax were applied to annual ryegrass (LOLMG) plants. Results, averaged for all replicates of each treatment, are shown in Table 16b.

TABLE 16b

LOLMG % Inhibition 13 days after treatment

| Composition | 75 g a.e./ha | 100 g a.e./ha | 200 g a.e./ha |
|---|---|---|---|
| Composition 540KA | 72.5 | 87.5 | 94 |
| Composition 540KB | 74.2 | 88 | 98.7 |
| Composition 540KC | 75 | 88.3 | 96.2 |
| Composition 540KD | 72.5 | 92.2 | 93.7 |
| Roundup UltraMax A | 71.7 | 88.5 | 92.2 |
| Roundup UltraMax B | 70 | 88 | 93.5 |
| Roundup UltraMax C | 73.3 | 85 | 94.7 |
| Roundup UltraMax D | 67.5 | 83.3 | 87.5 |
| TD IQ-A | 64.2 | 80 | 89.2 |

TABLE 16b-continued

LOLMG % Inhibition 13 days after treatment

| Composition | 75 g a.e./ha | 100 g a.e./ha | 200 g a.e./ha |
|---|---|---|---|
| TD IQ-B | 65 | 87.2 | 92.2 |
| TD IQ-C | 65 | 82.5 | 91.7 |
| TD IQ-D | 64.2 | 81.7 | 85 |
| Composition 725K[1] | 20 | 75.8 | 84.2 |
| Composition 725K[2] | 71.7 | 88.5 | 92.2 |

[1] Tank mix formulated from Composition 725K at 725 grams/l.
[2] Tank mix formulated from Composition 725K at 445 grams/l No significant enhancement or antagonism with the oxalic acid combinations was found.

Example 17

The efficacy of commercial glyphosate products and oxalic acid as tank mixtures was evaluated. In Table 17a, aqueous tank mixture compositions were prepared with the IPA and di-ammonium salts of glyphosate in weight ratios of 2:1, 10:1 and 30:1 with oxalic acid (OA). Tank mixture herbicidal activity was analyzed versus tank mixes of the respective salts without added oxalic acid.

TABLE 17a

| Composition | Glyphosate salt | Component 1 | Gly:OA |
|---|---|---|---|
| Roundup UltraMax A | IPA | — | — |
| Roundup UltraMax B | IPA | Oxalic Acid | 2:1 |
| Roundup UltraMax C | IPA | Oxalic Acid | 10:1 |
| Roundup UltraMax D | IPA | Oxalic Acid | 30:1 |
| TD IQ-A | di-NH$_4$ | — | — |
| TD IQ-B | di-NH$_4$ | Oxalic Acid | 2:1 |
| TD IQ-C | di-NH$_4$ | Oxalic Acid | 10:1 |
| TD IQ-D | di-NH$_4$ | Oxalic Acid | 30:1 |

The compositions of Table 16a and a comparative Composition 725K was applied to velvetleaf (*Abutilon theophrasti*, ABUTH) and Japanese millet (*Echinochloa crus-galli* var. *frumentae*, ECHCF) plants. Results, averaged for all replicates of each treatment, are shown in Tables 17b and 17c.

TABLE 17b

ABUTH % Inhibition 15 days after treatment

| Composition | 75 g a.e./ha | 100 g a.e./ha | 200 g a.e./ha |
|---|---|---|---|
| Roundup UltraMax A | 5.8 | 56.7 | 82.5 |
| Roundup UltraMax B | 78.3 | 80 | 90 |
| Roundup UltraMax C | 71.7 | 79.2 | 89.2 |
| Roundup UltraMax D | 40 | 79.2 | 89.2 |
| TD IQ-A | 0 | 45 | 75 |
| TD IQ-B | 40 | 80 | 89.2 |
| TD IQ-C | 25.8 | 50.8 | 80 |
| TD IQ-D | 0 | 19.2 | 80 |
| Composition 725K[1] | 0 | 5 | 29.2 |
| Composition 725K[2] | 5.8 | 56.7 | 82.5 |

[1] Tank mix formulated from Composition 725K at 725 grams/l.
[2] Tank mix formulated from Composition 725K at 445 grams/l.

TABLE 17c

ECHCF % Inhibition 15 days after treatment

| Composition | 75 g a.e./ha | 100 g a.e./ha | 200 g a.e./ha |
|---|---|---|---|
| Roundup UltraMax A | 20.8 | 56.7 | 70 |
| Roundup UltraMax B | 44.2 | 60.8 | 67.5 |

TABLE 17c-continued

ECHCF % Inhibition 15 days after treatment

| Composition | 75 g a.e./ha | 100 g a.e./ha | 200 g a.e./ha |
|---|---|---|---|
| Roundup UltraMax C | 42.5 | 57.5 | 67.5 |
| Roundup UltraMax D | 38.3 | 57.5 | 67.5 |
| TD IQ-A | 6.7 | 30 | 62.5 |
| TD IQ-B | 25 | 35 | 63.3 |
| TD IQ-C | 23.3 | 45 | 60.8 |
| TD IQ-D | 29.2 | 41.7 | 62.5 |
| Composition 725K[1] | 0 | 0 | 28.3 |
| Composition 725K[2] | 20.8 | 56.7 | 70.0 |

[1]Tank mix formulated from Composition 725K at 725 grams/l.
[2]Tank mix formulated from Composition 725K at 445 grams/l.

Oxalic acid enhanced glyphosate efficacy on velvetleaf, with a 2:1 ratio of glyphosate a.e.:oxalic acid being the most effective. Oxalic acid did not significantly enhance glyphosate efficacy on barnyardgrass.

Example 18

The efficacy performance of Silwet L-77 surfactant formulated with Roundup UltraMax and oxalic acid on morningglory was evaluated. Aqueous concentrate compositions containing the IPA salt of glyphosate as Roundup UltraMax were formulated as tank mixes with oxalic acid and with or without Silwet L-77 (S44) surfactant as summarized in Table 18a.

TABLE 18a

| Composition | Compon. 1 | Gly a.e.:Compon. 1 | Compon. 2 | Gly a.e.:Compon. 2 |
|---|---|---|---|---|
| Roundup UltraMax A | — | — | — | — |
| Roundup UltraMax B | — | — | S44 | 1000:1 |
| Roundup UltraMax C | Oxalic Acid | 2:1 | — | — |
| Roundup UltraMax D | Oxalic Acid | 10:1 | — | — |
| Roundup UltraMax E | Oxalic Acid | 30:1 | — | — |
| Roundup UltraMax F | Oxalic Acid | 2:1 | S44 | 1000:1 |
| Roundup UltraMax G | Oxalic Acid | 10:1 | S44 | 1000:1 |
| Roundup UltraMax H | Oxalic Acid | 30:1 | S44 | 1000:1 |

The compositions of Table 18a and the comparative composition of Composition 725K was applied to morningglory (IPOSS) plants. Results, averaged for all replicates of each treatment, are shown in Tables 18b.

TABLE 18b

IPOSS % Control 14 days after treatment

| Composition | 300 g a.e./ha | 400 g a.e./ha | 600 g a.e./ha |
|---|---|---|---|
| Roundup UltraMax A | 70 | 78.3 | 84.2 |
| Roundup UltraMax B | 80 | 80 | 82.5 |
| Roundup UltraMax C | 82.5 | 82.5 | 85 |
| Roundup UltraMax D | 80.8 | 83.3 | 85 |
| Roundup UltraMax E | 80 | 82.5 | 84.2 |
| Roundup UltraMax F | 84.2 | 82.5 | 85 |
| Roundup UltraMax G | 80.8 | 84.2 | 84.2 |

TABLE 18b-continued

IPOSS % Control 14 days after treatment

| Composition | 300 g a.e./ha | 400 g a.e./ha | 600 g a.e./ha |
|---|---|---|---|
| Roundup UltraMax H | 80 | 84.2 | 85 |
| Composition 725K[1] | 44.2 | 70 | 80 |
| Composition 725K[2] | 70 | 78.3 | 84.2 |

[1]Tank mix formulated from Composition 725K at 725 grams/l.
[2]Tank mix formulated from Composition 725K at 445 grams/l.

Oxalic acid as a tank mix additive at 2:1, 10:1 or 30:1 glyphosate a.e.:oxalic acid ratios were equally effective in enhancing Roundup UltraMax efficacy on morningglory

Example 19

The efficacy effect of oxalic acid on glyphosate salts was evaluated. Aqueous compositions were prepared with as indicated in Table 19a. Glyphosate concentrations are reported in g a.e./liter.

TABLE 19a

| Composition | Glyphosate g/l | Glyphosate Salt | Component 1 | w/v % |
|---|---|---|---|---|
| 053A9M | 62 | K | di K oxalate | 2.0 |
| 053B2C | 62 | K | — | — |
| 053C5T | 62 | IPA | di K oxalate | 2.0 |
| 053D8N | 62 | IPA | — | — |
| 053E2M | 62 | $NH_4$ | di K oxalate | 2.0 |
| 053F1R | 62 | $NH_4$ | — | — |
| 053G0K | 62 | $(NH_4)_2$ | di K oxalate | 2.0 |
| 053H7A | 62 | $(NH_4)_2$ | — | — |

The compositions of Table 19a and comparative compositions of Composition 725K, Composition 570I and Roundup UltraMax were applied to velvetleaf (*Abutilon theophrasti*, ABUTH) and Japanese millet (*Echinochloa crus-galli* var. *frumentae*, ECHCF) plants. Results, averaged for all replicates of each treatment, are shown in Tables 19b and 19c.

TABLE 19b

ABUTH % inhibition 16 days after treatment

| Composition | 100 g a.e./ha | 200 g a.e./ha | 300 g a.e./ha | 400 g a.e./ha |
|---|---|---|---|---|
| 053A9M | 41.7 | 77.5 | 84.2 | 90 |
| 053B2C | 14.2 | 62.5 | 78.3 | 81.7 |
| 053C5T | 64.2 | 80.8 | 84.2 | 87.5 |
| 053D8N | 16.7 | 65.8 | 78.3 | 79.2 |
| 053E2M | 43.3 | 75 | 83.3 | 88.3 |
| 053F1R | 27.5 | 62.5 | 70 | 79.2 |
| 053G0K | 44.2 | 80.8 | 86.7 | 90.5 |
| 053H7A | 17.5 | 61.7 | 75.8 | 77.5 |
| Comp. 725K | 5 | 54.2 | 62.5 | 75.8 |
| Composition 570I | 6.7 | 58.3 | 73.3 | 80 |
| Roundup UltraMax | 20 | 80 | 85 | 90 |

TABLE 19c

ECHCF % inhibition 16 days after treatment

| Composition | 100 g a.e./ha | 200 g a.e./ha | 300 g a.e./ha | 400 g a.e./ha |
|---|---|---|---|---|
| 053A9M | 26.7 | 45 | 47.5 | 51.7 |
| 053B2C | 24.2 | 43.3 | 48.3 | 51.7 |
| 053C5T | 20 | 45.8 | 48.3 | 51.7 |
| 053D8N | 21.7 | 42.5 | 49.2 | 51.7 |

TABLE 19c-continued

ECHCF % inhibition 16 days after treatment

| Composition | 100 g a.e./ha | 200 g a.e./ha | 300 g a.e./ha | 400 g a.e./ha |
|---|---|---|---|---|
| 053E2M | 16.7 | 42.5 | 46.7 | 51.7 |
| 053F1R | 10 | 40 | 47.5 | 52.5 |
| 053G0K | 21.7 | 45 | 49.2 | 50.8 |
| 053H7A | 11.7 | 31.7 | 45 | 49.2 |
| Comp. 725K | 5 | 30 | 44.2 | 50 |
| Composition 570I | 11.7 | 40 | 47.5 | 50 |
| Roundup UltraMax | 36.7 | 55 | 65.8 | 75.8 |

All formulations containing dipotassium oxalate were superior for velvetleaf control versus the analogous formulations not containing oxalic acid, and performed better than the Roundup UltraMax standard. Dipotassium oxalate enhanced efficacy regardless of the glyphosate salt. Dipotassium oxalate was relatively ineffective for enhancing efficacy against barnyardgrass.

Example 20

The effect of oxalic acid and aminated alkoxylated alcohols of formulae (5) in ammonium glyphosate solid formulations was evaluated. Comparative solid formulations of commercial standards were also prepared. Ammonium glyphosate concentrations for compositions 664A4D and 664C6G were 71% a.e., and 664B5T was 65% a.e. Oxalic acid and ammonium sulfate were added to ammonium glyphosate, to which solvents were then added. Melted surfactant was then added. The composition was mixed in a blender and extruded. The extrudate grains were dried at 50° C. for 10 minutes. The material was then sieved to obtain the required grain size.

TABLE 20a

| Composition | Compon. 1 | wt % | Compon. 2 | wt % | Compon. 3 | wt % |
|---|---|---|---|---|---|---|
| 664A4D | S64 | 10 | S61 | 2 | Oxalic Acid | 8 |
| 664B5T | S13 | 8 | S63 | 8 | Ammonium SO$_4$ | 10 |
| 664C6G | S62 | 10 | S61 | 2 | Oxalic Acid | 8 |

The compositions of Table 20a and comparative compositions of Composition AMM-GLY2S, Composition 570I and Roundup UltraMax were applied to velvetleaf (*Abutilon theophrasti*, ABUTH) plants. The average results of each treatment, are shown in Table 20b.

TABLE 20b

ABUTH % Control 16 days after treatment

| Composition | 75 g a.e./ha | 100 g a.e./ha | 200 g a.e./ha | 400 g a.e./ha |
|---|---|---|---|---|
| 664A4D | 80 | 81.7 | 96.5 | 99.5 |
| 664B5T | 75 | 76.7 | 91.7 | 98.5 |
| 664C6G | 80 | 82.5 | 90.8 | 99.3 |
| Comp. IPA Dry | 79.2 | 80 | 93 | 99.5 |
| Comp. 470K | 40.8 | 55 | 75 | 90.8 |
| Composition AMM-GLY1S | 34.2 | 42.5 | 80.8 | 94.5 |
| Roundup Ultra | 75 | 81.7 | 95 | 98.5 |

TABLE 20b-continued

ABUTH % Control 16 days after treatment

| Composition | 75 g a.e./ha | 100 g a.e./ha | 200 g a.e./ha | 400 g a.e./ha |
|---|---|---|---|---|
| Roundup UltraMax Dry | 57.5 | 67.5 | 82.5 | 95.5 |
| Composition AMM-GLY2S | 0 | 8.3 | 50.8 | 79.2 |
| Composition 570I | 6.7 | 19.2 | 57.5 | 80 |
| Roundup UltraMax | 56.7 | 60.8 | 81.7 | 93.8 |

The three compositions each had higher efficacy than did comparative dried commercial standards.

Example 21

The effect of oxalic acid and an oxalic acid salt on monoethoxylated alkylamine surfactants alone or in combination with an alcohol ethoxylate surfactant in ammonium glyphosate formulations was evaluated. The molar ratio of oxalate:monoethoxylated alkylamine surfactant in each composition was at least 10:1. Glyphosate concentrations for each composition were 62 g a.e. per liter. All components were added and the composition was agitated in a shaker batch for 1 hour at 60° C. 24 hours after cooling to RT all samples were stable, clear and slightly yellow.

TABLE 21a

| Composition | Compon. 1 | wt % | Compon. 2 | wt % | Compon. 3 | wt % |
|---|---|---|---|---|---|---|
| 071A5V | S51 | 1.1 | — | — | — | — |
| 071B7H | S51 | 0.8 | S50 | 0.3 | — | — |
| 071C3S | S51 | 1.1 | — | — | Oxalic Acid | 0.9 |
| 071D0L | S51 | 0.8 | S50 | 0.3 | Oxalic Acid | 0.9 |
| 071E1M | S51 | 0.6 | S50 | 0.4 | — | — |
| 071F5W | S51 | 0.6 | S50 | 0.4 | Oxalic Acid | 0.9 |
| 071G4B | S51 | 1.1 | — | — | NH$_4$ Oxalate | 0.9 |
| 071H9M | S51 | 0.6 | S50 | 0.4 | NH$_4$ Oxalate | 0.9 |
| 071I6B | S51 | 1.1 | — | — | — | — |
| 071J5D | S51 | 0.7 | S50 | 0.5 | — | — |
| 071K6J | S51 | 1.1 | — | — | Oxalic Acid | 0.9 |
| 071L1K | S51 | 0.7 | S50 | 0.5 | Oxalic Acid | 0.9 |
| 071M3X | S51 | 1.2 | — | — | — | — |
| 071N7U | S51 | 0.7 | S50 | 0.5 | — | — |
| 071O2W | S51 | 1.2 | — | — | Oxalic Acid | 0.8 |
| 071P9G | S51 | 0.7 | S50 | 0.5 | Oxalic Acid | 0.8 |
| 071Q1A | S49 | 1.1 | — | — | — | — |
| 071R5V | S49 | 0.9 | S50 | 0.2 | — | — |
| 071T6N | S49 | 0.9 | S50 | 0.2 | Oxalic Acid | 0.9 |
| 071U8M | S49 | 0.8 | S50 | 0.3 | — | — |
| 071V3Y | S49 | 0.8 | S50 | 0.3 | Oxalic Acid | 0.9 |
| 071W2X | S49 | 0.6 | S50 | 0.4 | — | — |
| 071X0D | S49 | 0.6 | S50 | 0.4 | Oxalic Acid | 0.9 |
| 071Z2C | S49 | 0.6 | S50 | 0.4 | NH$_4$ Oxalate | 0.9 |
| 071AA2N | S49 | 1.1 | — | — | — | — |
| 071AB7H | S49 | 0.9 | S50 | 0.3 | — | — |
| 071AD4N | S49 | 0.9 | S50 | 0.3 | Oxalic Acid | 0.9 |
| 071AE3F | S49 | 0.7 | S50 | 0.5 | — | — |
| 071AF7B | S49 | 0.7 | S50 | 0.5 | Oxalic Acid | 0.9 |
| 071AG8O | S49 | 1.2 | — | — | — | — |
| 071AH6X | S49 | 0.7 | S50 | 0.5 | — | — |
| 071AJ1Q | S49 | 0.7 | S50 | 0.5 | Oxalic Acid | 0.8 |

The compositions of Table 21a and comparative compositions of Composition AMM-GLY2S, Composition AMM-GLY1S and Roundup UltraMax were applied to velvetleaf (*Abutilon theophrasti*, ABUTH) plants, and some of the Table 21a compositions were applied to Japanese millet (*Echi-* nochloa crus-galli var. frumentae, ECHCF) plants. Results, averaged for all replicates of each treatment, are shown in Tables 21b and 21c.

TABLE 21b

ABUTH % Control 15 days after treatment

| Composition | 75 g a.e./ha | 100 g a.e./ha | 200 g a.e./ha | 400 g a.e./ha |
|---|---|---|---|---|
| 071A5V | 35 | 37.5 | 81.7 | 93.2 |
| 071B7H | 20.8 | 47.5 | 83.3 | 95.3 |
| 071C3S | 65 | 71.7 | 93 | 98.5 |
| 071D0L | 81.7 | 85 | 93.3 | 99.2 |
| 071E1M | 70.8 | 75 | 84.2 | 95.5 |
| 071F5W | 83.3 | 88.3 | 90.7 | 99.7 |
| 071G4B | 80 | 83.3 | 91.3 | 99.5 |
| 071H9M | 80 | 85.8 | 93.5 | 99.3 |
| 071I6B | 15.8 | 39.2 | 82.5 | 92.5 |
| 071J5D | 25.8 | 72.5 | 85.8 | 96.3 |
| 071K6J | 80 | 85 | 90 | 96.5 |
| 071L1K | 81.7 | 86.7 | 90 | 97.5 |
| 071M3X | 30 | 61.7 | 86.7 | 91.7 |
| 071N7U | 36.7 | 64.2 | 88.3 | 96.5 |
| 071O2W | 80 | 85 | 91.7 | 96.5 |
| 071P9G | 84.2 | 85 | 92.5 | 98.5 |
| 071Q1A | 10 | 33.3 | 75 | 87.5 |
| 071R5V | 27.5 | 30 | 78.3 | 87.5 |
| 071T6N | 79.2 | 81.7 | 89.2 | 95.8 |
| 071U8M | 48.3 | 78.3 | 80 | 90.8 |
| 071V3Y | 84.2 | 85 | 90 | 96.7 |
| 071W2X | 47.5 | 68.3 | 83.3 | 92.2 |
| 071X0D | 82.5 | 82.5 | 91.7 | 98.7 |
| 071Z2C | 85.8 | 86.7 | 94.2 | 98.7 |
| 071AA2N | 24.2 | 52.5 | 80 | 88.3 |
| 071AB7H | 50 | 65.8 | 85 | 93.7 |
| 071AD4N | 84.2 | 87.5 | 92.5 | 98.7 |
| 071AE3F | 65.8 | 74.2 | 85.8 | 93 |
| 071AF7B | 81.7 | 86.7 | 94.2 | 99.2 |
| 071AG8O | 50 | 65 | 84.2 | 87.5 |
| 071AH6X | 55 | 64.2 | 85.8 | 94.7 |
| 071AJ1Q | 84.2 | 86.7 | 92.5 | 99.2 |
| Composition AMM-GLY2S | 0 | 0 | 50.8 | 78.5 |
| Composition AMM-GLY1S | 0 | 28.1 | 75.2 | 87.8 |
| Roundup UltraMax | 14.2 | 53.3 | 82.1 | 91.6 |

The Hetoxol CS20 surfactant, with or without oxalic additions to the monoethoxylated alkyl amine surfactant, provided synergy. All compositions containing monoethoxylated alkyl amine surfactant with oxalic acid or $NH_4$ oxalate were superior to those without oxalate, and to the glyphosate standards.

TABLE 21c

ECHCF % Control 15 days after treatment

| Composition | 75 g a.e./ha | 100 g a.e./ha | 200 g a.e./ha | 400 g a.e./ha |
|---|---|---|---|---|
| 071I6B | 20 | 57.5 | 75 | 85.5 |
| 071J5D | 25 | 52.5 | 72.5 | 88 |
| 071K6J | 9.2 | 50 | 67.5 | 75.8 |
| 071L1K | 32.5 | 59.2 | 75 | 89.7 |
| 071M3X | 45.8 | 59.2 | 70.8 | 83.3 |
| 071N7U | 40 | 50.8 | 70 | 83.3 |
| 071O2W | 28.3 | 45 | 64.2 | 75 |
| 071P9G | 48.3 | 61.7 | 76.7 | 94.7 |
| Composition AMM-GLY2S | 0 | 5 | 35 | 60.8 |
| Composition AMM-GLY1S | 25 | 47.5 | 67.5 | 85 |
| Roundup UltraMax | 30 | 49.2 | 68.3 | 86.7 |

The Hetoxol CS20 and monoethoxylated alkyl amine surfactant combination with oxalic additions preformed best with efficacy superior to the glyphosate standards. The surfactant blend outperformed either surfactant individually.

Example 22

The effect of organic bases in combination with oxalic acid in tank mixes comprising potassium glyphosate and alkyl etheramine surfactant 1816P5E15PA (from Tomah) was evaluated. Glyphosate concentrations for each composition were 62.8 g a.e. per liter. Oxalic acid was first dissolved in water and the melted surfactant and the remaining components were added and the composition was agitated in a shaker batch for 30 minute at 60° C. 24 hours after cooling to RT all samples were stable, clear and slightly yellow.

TABLE 22a

| Composition | Compon. 1 | wt % | Compon. 2 | wt % | Compon. 3 | wt % |
|---|---|---|---|---|---|---|
| 666A9M | S52 | 2.0 | — | — | — | — |
| 666B6N | S52 | 2.0 | Oxalic acid | 0.25 | — | — |
| 666C4F | S52 | 2.0 | Oxalic acid | 0.25 | S53 | 0.25 |
| 666D3T | S52 | 2.0 | Oxalic acid | 0.25 | S53 | 0.5 |
| 666E0W | S52 | 1.8 | Oxalic acid | 0.25 | S53 | 0.75 |
| 666F7V | S52 | 2.0 | Oxalic acid | 0.25 | S53 | 1 |
| 666G3C | S52 | 2.0 | Oxalic acid | 0.25 | S54 | 1.2 |
| 666H1P | S52 | 2.0 | Oxalic acid | 0.25 | S54 | 0.6 |

The compositions of Table 22a and comparative compositions of Composition 725K, Composition 570I and Roundup UltraMax were applied to velvetleaf (*Abutilon theophrasti*, ABUTH) plants. Results, averaged for all replicates of each treatment, are shown in Table 22b.

TABLE 22b

ABUTH % Control 16 days after treatment

| Composition | 75 g a.e./ha | 100 g a.e./ha | 200 g a.e./ha | 400 g a.e./ha |
|---|---|---|---|---|
| 666A9M | 62.5 | 75 | 86.7 | 95.2 |
| 666B6N | 75 | 80 | 92.5 | 95.7 |
| 666C4F | 78.3 | 85 | 91.7 | 97.8 |
| 666D3T | 76.7 | 81.7 | 87.5 | 98.3 |
| 666E0W | 75 | 77.5 | 87.5 | 98 |
| 666F7V | 73.3 | 80.8 | 90 | 96.2 |
| 666G3C | 77.5 | 82.5 | 88.7 | 98.3 |
| 666H1P | 72.5 | 82.5 | 90.8 | 97.2 |
| Comp. 725K | 0 | 0 | 31.7 | 70 |
| Comp. 570I | 0 | 0.8 | 45.8 | 67.5 |
| Roundup UltraMax | 20 | 40 | 80.8 | 93.3 |

Addition of oxalic acid to the alkoxylated amine surfactant and potassium glyphosate tank mixes provided some synergy. Further synergy was obtained with the addition of the organic bases.

Example 23

The effect of organic bases in combination with oxalic acid in tank mixes comprising potassium glyphosate and alkyl etheramine surfactant 1816P5E15PA (from Tomah) was evaluated. Glyphosate concentrations for each composition were 62.8 g a.e. per liter. Oxalic acid was first dissolved in water and the melted surfactant and the remaining components were added and the composition was agitated in a shaker batch for 30 minute at 60° C. 24 hours after cooling to RT all samples were stable, clear and slightly yellow.

TABLE 23a

| Composition | Compon. 1 | wt % | Compon. 2 | wt % | Compon. 3 | wt % |
|---|---|---|---|---|---|---|
| 668A3C | S52 | 2 | — | — | — | — |
| 668B6H | S52 | 2 | Oxalic Acid | 0.25 | — | — |
| 668C3P | S52 | 2 | Oxalic Acid | 0.25 | S59 | 0.25 |
| 668D1Z | S52 | 2 | Oxalic Acid | 0.25 | S59 | 0.5 |
| 668E0L | S52 | 2 | Oxalic Acid | 0.25 | S59 | 0.75 |
| 668F8N | S52 | 2 | Oxalic Acid | 0.25 | S59 | 1 |
| 668G2Q | S52 | 2 | — | — | S59 | 1.2 |
| 668H0B | S52 | 2 | Oxalic Acid | 0.25 | S60 | 0.6 |

The compositions of Table 23a and comparative compositions of Composition 725K, Composition 570I and Roundup UltraMax were applied to velvetleaf (*Abutilon theophrasti*, ABUTH) plants. Results, averaged for all replicates of each treatment, are shown in Table 23b.

TABLE 23b

| | ABUTH % Control 15 days after treatment | | | |
|---|---|---|---|---|
| Composition | 75 g a.e./ha | 100 g a.e./ha | 200 g a.e./ha | 400 g a.e./ha |
| 668A3C | 63.3 | 74.2 | 87.5 | 95.5 |
| 668B6H | 68.3 | 74.2 | 88.3 | 96.3 |
| 668C3P | 70.8 | 79.2 | 89.2 | 95.5 |
| 668D1Z | 62.5 | 78.3 | 91.3 | 95.2 |
| 668E0L | 74.2 | 79.2 | 88.3 | 96.8 |
| 668F8N | 54.2 | 70 | 88.3 | 98.8 |
| 668G2Q | 58.3 | 67.5 | 84.2 | 92.7 |
| 668H0B | 59.2 | 72.5 | 87.5 | 94.5 |
| Comp. 725K | 0 | 0 | 27.5 | 64.2 |
| Comp. 570I | 0 | 0 | 35.8 | 70 |
| Roundup UltraMax | 0 | 20 | 80 | 91.7 |

Addition of oxalic acid and the organic base to the alkoxylated amine surfactant and potassium glyphosate tank mixes provided synergy versus all of the comparative standards.

Example 24

The effect of organic bases in combination with oxalic acid in tank mixes comprising potassium glyphosate, with and without alkoxylated alcohol surfactant Neodol 23-5 (from Shell), was evaluated. Glyphosate concentrations for each composition was 62.8 g a.e. per liter. Oxalic acid was first dissolved in water and the melted surfactant and the remaining components were added and the composition was agitated in a shaker batch for 30 minute at 60° C. 24 hours after cooling to RT all samples, except 670G1P, were stable, clear and slightly yellow. 670G1P gave an unstable hazy dispersion.

TABLE 24a

| Composition | Compon. 1 | wt % | Compon. 2 | wt % | Compon. 3 | wt % |
|---|---|---|---|---|---|---|
| 670A2K | S59 | 2 | — | — | — | — |
| 670B7H | S60 | 2 | — | — | — | — |
| 670C3Z | S60 | 1.6 | — | — | Oxalic Acid | 0.8 |
| 670D1Q | S60 | 1.4 | — | — | Oxalic Acid | 0.7 |
| 670E0F | S60 | 1.2 | — | — | Oxalic Acid | 0.6 |
| 670F2M | S60 | 1 | — | — | Oxalic Acid | 0.5 |
| 670G1P | S60 | 0.8 | S61 | 0.4 | Oxalic Acid | 0.4 |
| 670H0K | S59 | 0.8 | S61 | 0.4 | Oxalic Acid | 0.4 |

The compositions of Table 24a and comparative compositions of Composition 725K, Composition 570I and Roundup UltraMax were applied to velvetleaf (*Abutilon theophrasti*, ABUTH) plants. Results, averaged for all replicates of each treatment, are shown in Table 24b.

TABLE 24b

| | ABUTH % Control 14 days after treatment | | | |
|---|---|---|---|---|
| Composition | 75 g a.e./ha | 100 g a.e./ha | 200 g a.e./ha | 400 g a.e./ha |
| 670A2K | 20 | 33.3 | 78.3 | 92.5 |
| 670B7H | 15 | 35 | 72.5 | 85.8 |
| 670C3Z | 61.7 | 64.2 | 86.7 | 91.7 |
| 670D1Q | 47.5 | 63.3 | 85 | 93 |
| 670E0F | 47.5 | 64.2 | 86.7 | 93.7 |
| 670F2M | 35 | 78.3 | 86.7 | 93.8 |
| 670G1P | 4.2 | 55.8 | 71.7 | 90 |
| 670H0K | 0 | 41.7 | 83.3 | 93.7 |
| Comp. 725K | 0 | 8.3 | 60 | 79.2 |
| Comp. 570I | 0 | 16.7 | 50 | 81.7 |
| Roundup UltraMax | 11.7 | 47.5 | 82.5 | 93.8 |

Benzyltrimethylammonium hydroxide and Benzyltrimethylammonium chloride as stand-alone surfactants showed better efficacy than did the commercial Roundup UltraMax standard. Addition of oxalic acid further increased efficacy. The addition of Neodol 23-5 did not provide additional efficacy.

Example 25

The effect of organic bases in combination with oxalic acid in tank mixes comprising potassium glyphosate was evaluated. Glyphosate concentrations for each composition was 62.4 g a.e. per liter.

TABLE 25a

| Composition | Component 1 | wt % | Component 2 | wt % |
|---|---|---|---|---|
| 672A2B | S59 | 2 | — | — |
| 672B8J | S59 | 2 | Oxalic Acid | 1 |
| 672C6G | S59 | 1.7 | Oxalic Acid | 0.8 |
| 672D0P | S59 | 1.5 | Oxalic Acid | 0.7 |
| 672E4F | S59 | 1.3 | Oxalic Acid | 0.6 |
| 672F7N | S59 | 1.2 | Oxalic Acid | 0.5 |
| 672G3X | S59 | 1 | Oxalic Acid | 0.4 |

The compositions of Table 25a and comparative compositions of Composition 725K, Composition 570I and Roundup UltraMax were applied to velvetleaf (*Abutilon theophrasti*, ABUTH) plants. Results, averaged for all replicates of each treatment, are shown in Table 25b.

TABLE 25b

| | ABUTH % Control 15 days after treatment | | | |
|---|---|---|---|---|
| Composition | 100 g a.e./ha | 200 g a.e./ha | 400 g a.e./ha | 600 g a.e./ha |
| 672A2B | 17.5 | 45.8 | 87.5 | 87.5 |
| 672B8J | 45 | 80 | 91.7 | 96.3 |
| 672C6G | 65 | 82.5 | 90.8 | 94.2 |
| 672D0P | 62.5 | 85 | 92.5 | 95.8 |
| 672E4F | 70.8 | 85 | 91.7 | 93.8 |
| 672F7N | 43.3 | 83.3 | 92.3 | 94.2 |
| 672G3X | 55 | 82.5 | 93 | 94.2 |
| Comp. 725K | 0 | 1.7 | 30 | 78.3 |
| Comp. 570I | 0 | 5 | 52.5 | 84.2 |
| Roundup UltraMax | 26.7 | 80.8 | 91.7 | 95.5 |

The addition of oxalic acid and the organic base to the potassium glyphosate tank mixes provided synergy at all application rates. The highest efficacy was found at an organic base:oxalic acid ratio of 2:1.

Example 26

The effect of oxalic acid on the efficacy of tank mix formulations comprising potassium glyphosate and alkoxylated amine surfactants was evaluated. Glyphosate concentrations for each composition was 62.7 g a.e. per liter. Oxalic acid was first dissolved in water and then the melted surfactant and glyphosate were added. The composition was then agitated in a shaker batch for 30 minutes at 60° C. 24 hours after cooling to RT all samples, except 640E1A were stable, clear and slightly yellow. 640E1A was an unstable, hazy dispersion.

TABLE 26a

| Composition | Component 1 | wt % | Component 2 | wt % |
|---|---|---|---|---|
| 640A3C | S40 | 2 | Oxalic Acid | 0.2 |
| 640B7H | S55 | 2 | Oxalic Acid | 0.2 |
| 640C9M | S1 | 2 | Oxalic Acid | 0.2 |
| 640D3X | S56 | 2 | Oxalic Acid | 0.3 |
| 640E1A | S16 | 2 | Oxalic Acid | 0.25 |
| 640F5V | S57 | 2 | Oxalic Acid | 0.25 |
| 640G8J | S58 | 2 | Oxalic Acid | 0.25 |

The compositions of Table 26a and comparative compositions of Composition 725K, Composition 570I and Roundup UltraMax were applied to velvetleaf (*Abutilon theophrasti*, ABUTH) and Japanese millet (*Echinochloa crus-galli* var. *frumentae*, ECHCF) plants. Results, averaged for all replicates of each treatment, are shown in Tables 26b, 26c and 26d.

TABLE 26b

| | ABUTH % Control 15 days after treatment | | | |
|---|---|---|---|---|
| Composition | 100 g a.e./ha | 200 g a.e./ha | 300 g a.e./ha | 400 g a.e./ha |
| 640A3C | 80.8 | 90 | 98.3 | 98.3 |
| 640B7H | 76.7 | 87.5 | 95.3 | 99 |
| 640C9M | 70.8 | 89.7 | 91.3 | 95.2 |
| 640D3X | 81.7 | 89.2 | 97.7 | 99.2 |
| 640E1A | 52.5 | 85.8 | 93 | 95.3 |
| 640F5V | 79.2 | 86.7 | 97 | 98.2 |
| 640G8J | 75 | 85.8 | 95.3 | 97.8 |
| Comp. 725K | 0 | 30.8 | 73.3 | 80.8 |
| Comp. 570I | 5 | 50 | 77.5 | 83.3 |
| Roundup UltraMax | 21.7 | 80 | 89.7 | 92.8 |

Addition of oxalic acid to the alkoxylated amine potassium glyphosate tank mixes provided synergy for all compositions except 640E1A. Efficacy difference due to surfactant structures are mediated by oxalic acid addition.

TABLE 26c

| | ECHCF % Control 15 days after treatment | | | |
|---|---|---|---|---|
| Composition | 100 g a.e./ha | 200 g a.e./ha | 300 g a.e./ha | 400 g a.e./ha |
| 640A3C | 58.3 | 73.3 | 76.7 | 85.8 |
| 640B7H | 57.5 | 70 | 79.2 | 83.2 |
| 640C9M | 62.5 | 77.5 | 81.7 | 87.5 |
| 640D3X | 62.5 | 75.8 | 82.5 | 88.3 |
| 640E1A | 58.3 | 65 | 69.2 | 75.8 |
| 640F5V | 60.8 | 74.2 | 88.8 | 92.3 |
| 640G8J | 60 | 73.3 | 88.2 | 89.7 |
| Comp. 725K | 6.7 | 44.2 | 50.8 | 62.5 |
| Comp. 570I | 18.3 | 50 | 56.7 | 60.8 |
| Roundup UltraMax | 53.3 | 67.5 | 75 | 81.7 |

TABLE 26d

| | IPOSS % Control 14 days after treatment | | | |
|---|---|---|---|---|
| Composition | 100 g a.e./ha | 200 g a.e./ha | 300 g a.e./ha | 400 g a.e./ha |
| 640A3C | 80.8 | 86.7 | 86.7 | 87.5 |
| 640B7H | 81.7 | 85 | 86.7 | 87.5 |
| 640C9M | 83.3 | 83.3 | 85.8 | 87.5 |
| 640D3X | 82.5 | 85.8 | 89.2 | 88.3 |
| 640E1A | 83.3 | 85 | 87.5 | 88.3 |
| 640F5V | 80.8 | 86.7 | 86.7 | 86.7 |
| 640G8J | 82.5 | 85.8 | 85.8 | 87.5 |
| Comp. 725K | 70 | 82.5 | 82.5 | 81.7 |
| Comp. 570I | 70 | 82.5 | 83.3 | 84.2 |
| Roundup UltraMax | 82.5 | 82.5 | 84.2 | 87.5 |

Addition of oxalic acid to the alkoxylated amine potassium glyphosate tank mixes provided synergy for all compositions except 640E1A. Efficacy difference due to surfactant structures are mediated by oxalic acid addition.

Example 27

The efficacy of high load potassium glyphosate formulations containing aminated alkoxylated alcohols of formulae (5) was evaluated. Aqueous concentrate compositions 609D4V and 609E8E were formulated with IPA glyphosate salt, all others were formulated with potassium glyphosate salt. Glyphosate concentrations are reported in g a.e. per liter. Oxalic acid was first dissolved in water, KOH and melted surfactant were added and potassium glyphosate was added last. The formulation was agitated in a shaker batch for 30 minutes at 60° C. 24 hours after cooling to RT all samples were stable and clear with the exception of 609A8F which was stable and cloudy.

TABLE 27a

| Comp. | Glyph. g/l | Compon. 1 | wt % | Compon. 2 | wt % | Compon. 3 | wt % |
|---|---|---|---|---|---|---|---|
| 609A8F | 484 | S40 | 6.0 | S5 | 6.0 | — | — |
| 609B4E | 484 | S1 | 6.0 | S5 | 6.0 | — | — |
| 609C2P | 484 | S41 | 3.0 | S12 | 7.0 | S5 | 2.0 |

TABLE 27a-continued

| Comp. | Glyph. g/l | Compon. 1 | wt % | Compon. 2 | wt % | Compon. 3 | wt % |
|---|---|---|---|---|---|---|---|
| 609D4V | 434 | S1 | 10.0 | S43 | 1.5 | — | |
| 609E8E | 434 | S1 | 10.0 | S43 | 1.5 | Oxalic acid | 1.2 |
| 609F2X | 480 | S41 | 4.0 | S23 | 7.0 | S5 | 3.0 |
| Comp. 470K | 472 | S42 | 4.0 | S43 | 9.0 | S24 | 1.0 |

The compositions of Table 27a and comparative compositions of Composition 725K, Composition 570I and Roundup UltraMax were applied to velvetleaf (*Abutilon theophrasti*, ABUTH) plants. Results, averaged for all replicates of each treatment, are shown in Tables 27b.

TABLE 27b

ABUTH % Control 15 days after treatment

| Composition | 100 g a.e./ha | 200 g a.e./ha | 300 g a.e./ha | 400 g a.e./ha |
|---|---|---|---|---|
| 609A8F | 61.7 | 83.3 | 92.5 | 94 |
| 609B4E | 60 | 80.8 | 88.3 | 91.7 |
| 609C2P | 65.8 | 80.8 | 87.5 | 90.5 |
| 609D4V | 70 | 83.3 | 92.5 | 95.7 |
| 609E8E | 81.7 | 90.5 | 97 | 98 |
| 609F2X | 52.5 | 79.2 | 84.2 | 90.8 |
| Comp. 470K | 55 | 79.2 | 83.3 | 92.2 |
| Comp. 725K | 11.7 | 68.3 | 74.2 | 81.7 |
| Comp. 570I | 38.3 | 67.5 | 80 | 84.2 |
| Roundup UltraMax | 55.8 | 81.7 | 91.3 | 92.2 |

Formulation 609E8E, containing oxalic acid, gave the highest efficacy, including enhancement over formulation 609D4V, an analogous formulation not containing oxalic acid.

Example 28

The efficacy of oxalic acid and glyphosate salts in hard water was evaluated. In Table 28a aqueous concentrate compositions were prepared with potassium, IPA, ammonium and di-ammonium glyphosate salts. Glyphosate concentrations are reported in g a.e./liter.

The compositions of Table 28a, with compositions 045G2W, 045H7A and 045I4R used as comparative compositions, were applied to velvetleaf (*Abutilon theophrasti*, ABUTH) plants. The compositions of Table 28a were reapplied with 500 ppm $CaCl_2$ added to simulated hard water. Results, averaged for all replicates of each treatment, are shown in Table 28b.

TABLE 28b

ABUTH % inhibition 15 days after treatment

| Composition | 100 g a.e./ha | 200 g a.e./ha | 300 g a.e./ha | 400 g a.e./ha |
|---|---|---|---|---|
| 045A1B | 31.7 | 58.3 | 75 | 85 |
| 045A1B-H | 15 | 31.7 | 55 | 78.3 |
| 045B6E | 53.3 | 70 | 83.3 | 86.7 |
| 045B6E-H | 66.7 | 75 | 81.7 | 90 |
| 045C4R | 55 | 60 | 75 | 83.3 |
| 045C4R-H | 25 | 46.7 | 51.7 | 71.7 |
| 045D2J | 75 | 83.3 | 85 | 93.3 |
| 045D2J-H | 6.7 | 35 | 50 | 80 |
| 045E9D | 60 | 65 | 81.7 | 86.7 |
| 045E9D-H | 41.7 | 48.3 | 53.3 | 70 |
| 045F8K | 60 | 80 | 83.3 | 86.7 |
| 045F8K-H | 36.7 | 50 | 60 | 83.3 |
| 045G2W | 53.3 | 63.3 | 76.7 | 85 |
| 045G2W-H | 40 | 48.3 | 53.3 | 81.7 |
| 045H7A | 66.7 | 75 | 81.7 | 90 |
| 045H7A-H | 41.7 | 58.3 | 66.7 | 88.3 |
| 045I4R | 51.7 | 60 | 78.3 | 85 |
| 045I4R-H | 3.3 | 35 | 68.3 | 85 |

500 ppm $CaCl_2$ reduced the activity of all formulations. Oxalic acid effectively increased the efficacy of all formulations.

Example 29

The effect of hard water on the efficacy of formulations of oxalic acid and glyphosate salts was evaluated. In Table 29a aqueous concentrate compositions were prepared with potassium, IPA, ammonium and di-ammonium glyphosate salts. Glyphosate concentrations are reported in g a.e./liter.

TABLE 28a

| Comp. | Glyph. g/l | Glyph. Salt | Compon. 1 | w/v % | Compon. 2 | w/v % |
|---|---|---|---|---|---|---|
| 045A1B | 62 | K | Oxalic acid | 0.41 | — | — |
| 045B6E | 62 | K | Oxalic acid | 0.41 | S5 | 2.0 |
| 045C4R | 62 | IPA | Oxalic acid | 0.41 | — | — |
| 045D2J | 62 | Roundup UltraMax | Oxalic acid | 0.41 | — | — |
| 045E9D | 62 | di-$NH_4$ | Oxalic acid | 0.41 | — | — |
| 045F8K | 62 | TD IQ | Oxalic acid | 0.41 | — | — |
| 045G2W | 62 | TD IQ | — | — | — | — |
| 045H7A | 62 | Roundup UltraMax | — | — | — | — |
| 045I4R | 62 | Comp. 725K | — | — | S5 | 2.0 |

TABLE 29a

| Comp. | Glyph. g/l | Glyph. Salt | Compon. 1 | w/v % | Compon. 2 | w/v % |
|---|---|---|---|---|---|---|
| 045A7R | 62 | K | Oxalic acid | 0.41 | — | — |
| 045B3U | 62 | K | Oxalic acid | 0.41 | S5 | 2.0 |
| 045C3X | 62 | IPA | Oxalic acid | 0.41 | — | — |
| 045D0L | 62 | Roundup UltraMax | Oxalic acid | 0.41 | — | — |
| 045E4C | 62 | di-$NH_4$ | Oxalic acid | 0.41 | — | — |
| 045F7J | 62 | TD IQ | Oxalic acid | 0.41 | — | — |
| 045G2K | 62 | TD IQ | — | — | — | — |
| 045H5F | 62 | Roundup UltraMax | — | — | — | — |
| 045I3P | 62 | Comp. 725K | — | — | S5 | 2.0 |

The compositions of Table 29a, with compositions 045G2K, 045H5F and 045I3P used as comparative compositions, were applied to velvetleaf (*Abutilon theophrasti*, ABUTH) plants. The compositions of Table 29a were reapplied to velvetleaf (*Abutilon theophrasti*, ABUTH) plants with 500 ppm $CaCl_2$ added to simulate hard water. Results, averaged for all replicates of each treatment, are shown in Table 29b.

TABLE 29b

ABUTH % inhibition 16 days after treatment

| Composition | 100 g a.e./ha | 150 g a.e./ha | 300 g a.e./ha | 400 g a.e./ha |
|---|---|---|---|---|
| 045A7R | 41.7 | 60 | 76.7 | 86.7 |
| 045A7R-H | 13.3 | 30 | 63.3 | 66.7 |
| 045B3U | 60 | 63.3 | 83.3 | 86.7 |
| 045B3U-H | 53.3 | 63.3 | 73.3 | 83.3 |
| 045C3X | 66.7 | 71.7 | 80 | 86.7 |
| 045C3X-H | 26.7 | 55 | 61.7 | 71.7 |
| 045D0L | 80 | 81.7 | 85 | 91.7 |
| 045D0L-H | 35 | 46.7 | 55 | 78.3 |
| 045E4C | 65 | 66.7 | 78.3 | 85 |
| 045E4C-H | 43.3 | 56.7 | 60 | 68.3 |
| 045F7J | 66.7 | 70 | 83.3 | 86.7 |
| 045F7J-H | 46.7 | 56.7 | 61.7 | 83.3 |
| 045G2K | 58.3 | 71.7 | 78.3 | 83.3 |
| 045G2K-H | 46.7 | 60 | 75 | 76.7 |
| 045H5F | 61.7 | 70 | 85 | 90 |
| 045H5F-H | 45 | 58.3 | 68.3 | 83.3 |
| 045I3P | 48.3 | 66.7 | 75 | 88.3 |
| 045I3P-H | 0 | 40 | 65 | 83.3 |

500 ppm $CaCl_2$ reduced the activity of all formulations. Oxalic acid effectively increased the efficacy of all formulations.

Example 30

Th efficacy of oxalic acid with different surfactants on morningglory was tested. In Table 30a, dilute aqueous compositions were prepared with potassium glyphosate salt in hard water (i.e., all compositions contained 500 ppm calcium chloride). Glyphosate concentrations are reported in g a.e./liter. The weight ratio of glyphosate a.e. to surfactant was about 3:1 and the weight ratio of glyphosate a.e. to oxalic acid was about 60:1, 40:1, 30:1, 24:1, 20:1 or 3:1. Oxalic acid was dissolved, potassium glyphosate added, and melted surfactant added. Formulations were then agitated in a shaker batch for 30 minutes at 60° C. 24 hours after cooling to RT all samples were stable, clear and colorless.

TABLE 30a

| Composition | Glyphosate g/l | Component 1 | w/v % | Component 2 | w/v % |
|---|---|---|---|---|---|
| 383A2T | 62.7 | S1 | 2.0 | Oxalic acid | 0.2 |
| 383B7K | 62.7 | S1 | 2.0 | — | — |
| 383C4D | 62.7 | S13 | 2.0 | Oxalic acid | 0.2 |
| 383D3E | 62.7 | S13 | 2.0 | — | — |
| 383E8N | 62.7 | S5 | 2.0 | Oxalic acid | 0.4 |
| 383F6V | 62.7 | S5 | 2.0 | — | — |
| 383G7Q | 62.7 | S18 | 2.0 | Oxalic acid | 0.4 |
| 383H0O | 62.7 | S18 | 2.0 | — | — |

The compositions of Table 30a, Composition 725K, Composition 570I and Roundup UltraMax, were applied to morningglory (IPOSS) plants. Results, averaged for all replicates of each treatment, are shown in Table 30b.

TABLE 30b

IPOSS % inhibition 15 days after treatment

| Composition | 100 g a.e./ha | 200 g a.e./ha | 300 g a.e./ha | 400 g a.e./ha |
|---|---|---|---|---|
| 383A2T | 0 | 9.2 | 17.5 | 41.7 |
| 383B7K | 0 | 1.7 | 7.5 | 28.3 |
| 383C4D | 0 | 28.3 | 65 | 77.5 |
| 383D3E | 0 | 3.3 | 7.5 | 20 |
| 383E8N | 4.2 | 18.3 | 25 | 55 |
| 383F6V | 0 | 5 | 7.5 | 46.7 |
| 383G7Q | 2.5 | 20 | 26.7 | 49.2 |
| 383H0O | 0 | 0 | 1.7 | 13.3 |
| Comp. 725K | 0 | 0 | 2.5 | 10 |
| Comp. 570I | 0 | 0 | 2.5 | 18.3 |
| Roundup UltraMax | 0 | 1.7 | 7.5 | 20.8 |

All formulations containing oxalic acid outperformed formulations without oxalic acid. The addition of oxalic acid to Composition 725K significantly improved its weed growth control of morningglory.

Example 31

The efficacy of oxalic acid with surfactants on velvetleaf was evaluated. In Table 31a aqueous concentrate compositions were prepared with potassium glyphosate salt. Glyphosate concentrations are reported in g a.e./liter. Oxalic acid was dissolved, potassium glyphosate added, and melted surfactant then added. Formulations were then agitated in a shaker batch for 30 minutes at 60° C. 24 hours after cooling to RT all samples were stable, clear and yellow.

TABLE 31a

| Composition | Glyphosate g/l | Component 1 | w/v % | Component 2 | w/v % |
|---|---|---|---|---|---|
| 383A7U | 62.7 | S1 | 2.0 | Oxalic acid | 0.2 |
| 383B5D | 62.7 | S1 | 2.0 | — | — |
| 383C3N | 62.7 | S13 | 2.0 | Oxalic acid | 0.2 |
| 383D8H | 62.7 | S13 | 2.0 | — | — |
| 383E5A | 62.7 | S5 | 2.0 | Oxalic acid | 0.4 |
| 383F0L | 62.7 | S5 | 2.0 | — | — |
| 383G5K | 62.7 | S18 | 2.0 | Oxalic acid | 0.4 |
| 383H1Z | 62.7 | S18 | 2.0 | — | — |

The compositions of Table 31a, Composition 725K, Composition 570I and Roundup UltraMax, were applied to velvetleaf (ABUTH) plants. Results, averaged for all replicates of each treatment, are shown in Table 31b.

TABLE 31b

ABUTH % inhibition 17 days after treatment

| Composition | 100 g a.e./ha | 200 g a.e./ha | 300 g a.e./ha | 400 g a.e./ha |
|---|---|---|---|---|
| 383A2T | 69.2 | 88.3 | 90.8 | 95.5 |
| 383B7K | 46.7 | 80.8 | 85.8 | 93.3 |
| 383C4D | 66.7 | 88.3 | 93.3 | 95 |
| 383D3E | 55.8 | 85 | 90 | 96.8 |
| 383E8N | 33.3 | 80 | 89.2 | 91.7 |
| 383F6V | 5 | 35 | 75 | 83.3 |
| 383G7Q | 5 | 33.3 | 75.8 | 89.2 |
| 383H1Z | 0 | 9.2 | 60.8 | 75.8 |
| Comp. 725K | 0 | 0 | 24.2 | 45 |
| Comp. 570I | 0 | 0 | 45.8 | 64.2 |
| Roundup UltraMax | 5 | 79.2 | 82.5 | 89.2 |

$C_{14-15}$ PEG 13(EO) etheramine and PEG 15(EO) etheramine surfactants in combination with oxalic acid gave the greatest efficacy.

Example 32

The efficacy of oxalic acid with surfactants in potassium glyphosate formulations was evaluated. In Table 32a aqueous concentrate compositions were prepared with potassium glyphosate salt. Glyphosate concentrations are reported in g a.e./liter. Oxalic acid was dissolved, potassium glyphosate added, and melted surfactant then added. Formulations were then agitated in a shaker batch for 30 minutes at 60° C. 24 hours after cooling to RT all samples were stable, clear and yellow.

TABLE 32a

| Composition | Glyphosate g/l | Component 1 | w/v % | Component 2 | w/v % |
|---|---|---|---|---|---|
| 383A2T | 62.7 | S1 | 2.0 | Oxalic acid | 0.2 |
| 383B7K | 62.7 | S1 | 2.0 | — | — |
| 383C4D | 62.7 | S13 | 2.0 | Oxalic acid | 0.2 |
| 383D3E | 62.7 | S13 | 2.0 | — | — |
| 383E8N | 62.7 | S5 | 2.0 | Oxalic acid | 0.4 |
| 383F6V | 62.7 | S5 | 2.0 | — | — |
| 383G7Q | 62.7 | S18 | 2.0 | Oxalic acid | 0.4 |
| 383H0O | 62.7 | S18 | 2.0 | — | — |

The compositions of Table 32a, Composition 725K, Composition 570I and Roundup UltraMax, were applied to Prickly sida (SIDSP) plants. Results, averaged for all replicates of each treatment, are shown in Table 32b.

TABLE 32b

Prickly Sida % inhibition 18 days after treatment

| Composition | 100 g a.e./ha | 200 g a.e./ha | 300 g a.e./ha | 400 g a.e./ha |
|---|---|---|---|---|
| 383A2T | 65.8 | 78.3 | 85 | 90 |
| 383B7K | 55 | 75 | 85 | 90 |
| 383C4D | 65 | 80.8 | 88.3 | 92.2 |
| 383D3E | 65 | 79.2 | 90 | 93 |
| 383E8N | 68.3 | 80 | 82.5 | 85.8 |
| 383F6V | 60.8 | 78.3 | 80 | 83.3 |
| 383G7Q | 50.8 | 75 | 80.8 | 85.7 |
| 383H0O | 21.7 | 66.7 | 77.5 | 81.7 |
| Comp. 725K | 10 | 38.3 | 63.3 | 70 |
| Comp. 570I | 40 | 55 | 67.5 | 77.5 |
| Roundup UltraMax | 55 | 75 | 82.5 | 93.3 |

Addition of oxalic acid at glyphosate a.e.:oxalic acid ratios of 30:1 or 15:1 gave efficacy enhancement.

Example 33

The effect of oxalic acid on the efficacy of potassium glyphosate and aminated alkoxylated alcohols of formulae (5) was evaluated. Aqueous concentrate compositions were prepared containing potassium glyphosate salt, reported in g a.e./liter, and excipient ingredients as shown in Table 33a. Acids were first dissolved in water and then potassium glyphosate and surfactant were added. The formulation was agitated in a shaker batch for 30 minutes at 60° C. 24 hours after cooling to RT all samples were stable, clear and yellow except for 359B3W which was unstable and hazy.

TABLE 33a

| Composition | Glyphosate g/l | Component 1 | w/v % | Component 2 | w/v % |
|---|---|---|---|---|---|
| 359A5L | 62.7 | S1 | 2.0 | — | — |
| 359B3W | 62.7 | S1 | 0 | Oxalic Acid | 2.0 |
| 359C3M | 62.7 | S1 | 2.0 | Oxalic Acid | 0.1 |
| 359D8C | 62.7 | S1 | 2.0 | Oxalic Acid | 0.15 |
| 359E7B | 62.7 | S1 | 2.0 | Oxalic Acid | 0.2 |
| 359F4P | 62.7 | S1 | 2.0 | Oxalic Acid | 0.25 |
| 359G4S | 62.7 | S1 | 2.0 | Oxalic Acid | 0.3 |
| 359H2L | 62.7 | S1 | 1.5 | Oxalic Acid | 0.2 |

The compositions of Table 33a and comparative compositions of Composition 725K, Composition 570I, Roundup UltraMax and Composition 411 were applied to velvetleaf (*Abutilon theophrasti*, ABUTH) plants. Results, averaged for all replicates of each treatment, are shown in Table 33b.

TABLE 33b

ABUTH % Inhibition 14 days after treatment

| Composition | 100 g a.e./ha | 200 g a.e./ha | 300 g a.e./ha | 400 g a.e./ha |
|---|---|---|---|---|
| 359A5L | 55 | 80 | 90 | 97.8 |
| 359B3W | 65 | 79.2 | 84.2 | 86.7 |
| 359C3M | 80 | 92.7 | 97.3 | 99.5 |
| 359D8C | 79.2 | 96.3 | 98 | 99.3 |
| 359E7B | 85.5 | 95.3 | 99 | 99.8 |
| 359F4P | 81.7 | 90.8 | 96.5 | 98.5 |
| 359G4S | 81.7 | 95.5 | 96.3 | 99.2 |
| 359H2L | 80 | 95.3 | 96.2 | 99 |
| Comp. 725K | 0 | 10 | 32.5 | 70.8 |
| Comp. 570I | 0 | 15 | 54.2 | 75.8 |

TABLE 33b-continued

ABUTH % Inhibition 14 days after treatment

| Composition | 100 g a.e./ha | 200 g a.e./ha | 300 g a.e./ha | 400 g a.e./ha |
|---|---|---|---|---|
| Roundup UltraMax | 23.3 | 80 | 87.5 | 92.2 |
| Comp. 41I | 31.7 | 81.7 | 94.7 | 96.8 |

All formulations containing oxalic acid and surfactant provided superior efficacy versus glyphosate standards Roundup UltraMax and Composition 41I. Only formulation 359B3W, containing no surfactant, gave reduced efficacy. Formulations containing oxalic acid in a range of 0.1% to 0.3% in combination with $C_{14-5}$, PEG 13(EO) ether dimethylpropyl- amine performed similarly.

Example 34

The efficacy of oxalic acid, monochain ethoxylated etheramine surfactants and potassium glyphosate on Indian Mustard was evaluated. In Table 34a dilute aqueous compositions were prepared with potassium glyphosate salt. Glyphosate concentrations are reported in g a.e./liter. The weight ratio of glyphosate a.e. to surfactant was about 3:1 and the weight ratio of glyphosate a.e. to oxalic acid was about 60:1, 40:1, 30:1, 24:1, 20:1 or 3:1. All components were added and the formulation was agitated in a shaker batch for 30 minutes at 60° C. 24 hours after cooling to RT all samples were stable, clear and colorless except for 369B6S which was unstable and hazy.

TABLE 34a

| Composition | Glyphosate g/l | Component 1 | w/v % | Component 2 | w/v % |
|---|---|---|---|---|---|
| 359A0G | 62.7 | S1 | 2.0 | — | — |
| 369B6S | 62.7 | S1 | 0 | Oxalic acid | 2.0 |
| 369C7K | 62.7 | S1 | 2.0 | Oxalic acid | 0.1 |
| 369D4W | 62.7 | S1 | 2.0 | Oxalic acid | 0.15 |
| 369E6U | 62.7 | S1 | 2.0 | Oxalic acid | 0.2 |
| 369F9I | 62.7 | S1 | 2.0 | Oxalic acid | 0.25 |
| 369G3A | 62.7 | S1 | 2.0 | Oxalic acid | 0.3 |
| 369H5C | 62.7 | S1 | 1.5 | Oxalic acid | 0.2 |

The compositions of Table 34a and comparative compositions of Composition 725K, Composition 570I and Roundup UltraMax were applied to Indian Mustard (BRSJU) plants. Results, averaged for all replicates of each treatment, are shown in Table 34b.

TABLE 34b

BRSJU % Inhibition 23 days after treatment

| Composition | 200 g a.e./ha | 400 g a.e./ha | 600 g a.e./ha | 800 g a.e./ha |
|---|---|---|---|---|
| 359A0G | 66.7 | 81.7 | 86.7 | 89.2 |
| 369B6S | 61.7 | 72.5 | 73.3 | 75 |
| 369C7K | 54.2 | 79.2 | 83.3 | 85 |
| 369D4W | 71.7 | 78.3 | 88.3 | 90 |
| 369E6U | 65 | 77.5 | 84.2 | 90 |
| 369F9I | 62.5 | 80.8 | 81.7 | 85 |
| 369G3A | 69.2 | 80 | 81.7 | 85 |
| 369H5C | 65 | 78.3 | 80.8 | 82.5 |
| Comp. 725K | 5 | 9.2 | 52.5 | 66.7 |
| Comp. 570I | 5 | 36.7 | 72.5 | 75 |

TABLE 34b-continued

BRSJU % Inhibition 23 days after treatment

| Composition | 200 g a.e./ha | 400 g a.e./ha | 600 g a.e./ha | 800 g a.e./ha |
|---|---|---|---|---|
| Roundup UltraMax | 46.7 | 76.7 | 78.3 | 80 |
| Comp. 41I | 48.3 | 76.7 | 78.3 | 83.3 |

Oxalic acid did not provide significant efficacy enhancement on Indian mustard. Performance did not depend on the oxalic acid concentration.

Example 35

The efficacy of oxalic acid and aminated alkoxylated alcohols of formulae (5) in dilute potassium glyphosate formulations was evaluated. In Table 35a aqueous concentrate compositions were prepared with potassium glyphosate salt. Glyphosate concentrations are reported in g a.e./liter. All components were added and the formulation was agitated in a shaker batch for 30 minutes at 60° C. 24 hours after cooling to RT 376A3X, 3765BI and 376C4W were stable, clear and colorless. All others were unstable and hazy.

TABLE 35a

| Composition | Glyphosate g/l | Component 1 | w/v % | Component 2 | w/v % |
|---|---|---|---|---|---|
| 376A3X | 62.7 | S16 | 2.0 | — | — |
| 376B5L | 62.7 | S16 | 2.0 | Oxalic acid | 0.05 |
| 376C4W | 62.7 | S16 | 2.0 | Oxalic acid | 0.1 |
| 376D0S | 62.7 | S16 | 2.0 | Oxalic acid | 0.2 |
| 376E6D | 62.7 | S16 | 2.0 | Oxalic acid | 0.3 |
| 376F5G | 62.7 | S16 | 2.0 | Oxalic acid | 0.4 |
| 376G8N | 62.7 | S16 | 2.0 | Oxalic acid | 0.5 |
| 376H7A | 62.7 | S16 | 2.0 | Oxalic acid | 0.6 |

The compositions of Table 35a and comparative compositions of Composition 725K, Composition 570I and Roundup UltraMax were applied to velvetleaf (*Abutilon theophrasti*, ABUTH) plants. Results, averaged for all replicates of each treatment, are shown in Table 35b.

TABLE 35b

ABUTH % inhibition 16 days after treatment

| Composition | 100 g a.e./ha | 200 g a.e./ha | 300 g a.e./ha | 400 g a.e./ha |
|---|---|---|---|---|
| 376A3X | 10 | 56.7 | 75.8 | 85.8 |
| 376B5L | 39.2 | 72.5 | 84.2 | 85.8 |
| 376C4W | 49.2 | 77.5 | 86.7 | 88.3 |
| 376D0S | 55 | 85 | 86.7 | 89.2 |
| 376E6D | 69.2 | 85.8 | 88.3 | 92.5 |
| 376F5G | 66.7 | 85 | 86.7 | 94.2 |
| 376G8N | 66.7 | 85 | 88.3 | 93.3 |
| 376H7A | 70.8 | 86.7 | 89 | 95 |
| Comp. 725K | 0 | 24.2 | 59.2 | 65.8 |
| Comp. 570I | 3.3 | 20 | 71.7 | 65.8 |
| Roundup UltraMax | 35 | 75 | 85.8 | 88.3 |

The results indicate that highly efficacious, high-load potassium glyphosate formulations may be achieved by adding oxalic acid to $C_{16-18}$ PEG 10(EO) surfactants containing a polyamine head group. Polyamine head groups are known to produce stable high load formulatioins. Oxalic acid addition enhanced the efficacy of $C_{16-18}$ PEG 10(EO) ether dipropylamine surfactants formulated with a glyphosate a.e. to surfactant ratio of 3:1, efficacy was greatest with a glyphosate a.e. to oxalic acid ratio of 20:1, and the performance of the oxalic acid formulations exceed that of comparative standards.

Example 36

The efficacy of oxalic acid with aminated alkoxylated alcohols of formulae (5) in dilute potassium glyphosate formulations was evaluated. In Table 36a aqueous concentrate compositions were prepared with potassium glyphosate salt. Glyphosate concentrations are reported in g a.e./liter. Oxalic acid was dissolved, melted surfactant added, and potassium glyphosate then added. Formulations were then agitated in a shaker batch for 30 minutes at 60° C. 24 hours after cooling to RT all samples were stable, clear and colorless except for 618B8F which was unstable, hazy and formed a precipitated.

TABLE 36a

| Composition | Glyphosate g/l | Component 1 | w/v % | Component 2 | w/v % |
| --- | --- | --- | --- | --- | --- |
| 618A3D | 62.7 | S30 | 2.0 | — | — |
| 618B8F | 62.7 | — | — | Oxalic acid | 2.0 |
| 618C7S | 62.7 | S30 | 1.9 | Oxalic acid | 0.1 |
| 618D2K | 62.7 | S30 | 1.8 | Oxalic acid | 0.2 |
| 618E1U | 62.7 | S30 | 1.6 | Oxalic acid | 0.4 |
| 618F4P | 62.7 | S30 | 1.4 | Oxalic acid | 0.6 |
| 618G6W | 62.7 | S30 | 1.2 | Oxalic acid | 0.8 |
| 618H1Q | 62.7 | S30 | 1.0 | Oxalic acid | 1.0 |

The compositions of Table 36a, Composition 725K, Composition 570I and Roundup UltraMax, were applied to velvetleaf (*Abutilon theophrasti*, ABUTH) plants. Results, averaged for all replicates of each treatment, are shown in Table 36b.

TABLE 36b

| | ABUTH % inhibition 15 days after treatment | | | |
| --- | --- | --- | --- | --- |
| Composition | 100 g a.e./ha | 200 g a.e./ha | 300 g a.e./ha | 400 g a.e./ha |
| 618A3D | 30 | 80 | 85.8 | 88.3 |
| 618B8F | 16.7 | 61.7 | 82.5 | 91.3 |
| 618C7S | 57.5 | 82.5 | 90.8 | 95.5 |
| 618D2K | 75 | 88.3 | 93.8 | 95.2 |
| 618E1U | 75 | 88.3 | 96.2 | 96 |
| 618F4P | 72.5 | 90 | 95.3 | 97.2 |
| 618G6W | 80.8 | 90 | 94.8 | 96.5 |
| 618H1Q | 80.8 | 90.8 | 96.5 | 98.3 |
| Comp. 725K | 0 | 0.8 | 30 | 52.5 |
| Comp. 570I | 0 | 3.3 | 47.5 | 63.3 |
| Roundup UltraMax | 5 | 77.5 | 85 | 88.3 |

Oxalic acid provided efficacy enhancement over the surfactant system alone, and greater efficacy than the Roundup UltraMax standard. Increasing oxalic acid concentration and simultaneously decreasing surfactant concentrations resulted in an efficacy increase. Glyphosate a.e.:oxalic acid ratios of 30:1, 15:1, 7.5:1 and 6:1 gave similar efficacy results. The surfactant and oxalic acid combination is indicated to be synergistic as the combination at an equal concentration was superior to either one alone.

Example 37

The efficacy effect of oxalic acid on tank mixes of monoethoxylated alkylamine and aminated alkoxylated alcohols of formulae (5) in combination with potassium glyphosate was evaluated. Additionally, the efficacy effect of oxalic acid as a pretreatment and as a tankmix adjuvant with monoethoxylated alkylamine surfactants was evaluated. Oxalic acid pretreatments were applied one hour before the application of the aqueous concentrate compositions. Aqueous concentrate compositions were prepared containing potassium glyphosate salt, reported in g a.e./liter, and excipient ingredients as shown in Table 37a. Formulation 026Z2H contains the IPA salt of glyphosate.

TABLE 37a

| Composition | Glyphosate g/l | Component 1 | w/v % | Component 2 | w/v % |
| --- | --- | --- | --- | --- | --- |
| 026A2W | 62 | S8 | 2.0 | Oxalic Acid | 0.41 |
| 026B8B | 62 | S8 | 2.0 | — | — |
| 026C5Z | 62 | S11 | 2.0 | Oxalic Acid | 0.40 |
| 026D5K | 62 | S11 | 2.0 | — | — |
| 026E0A | — | — | — | Oxalic Acid | 0.40 |
| 026Z2H | 62 | — | — | Oxalic Acid | 0.40 |

The compositions of Table 37a and comparative compositions of Composition 725K, Composition 570I, Roundup UltraMax and Composition 41I were applied to velvetleaf (*Abutilon theophrasti*, ABUTH) plants. Results, averaged for all replicates of each treatment, are shown in Table 37b.

TABLE 37b

| | ABUTH % inhibition 17 days after treatment | | | |
| --- | --- | --- | --- | --- |
| Composition | 100 g a.e./ha | 200 g a.e./ha | 300 g a.e./ha | 400 g a.e./ha |
| 026A2W | 64.2 | 85.5 | 94.5 | 98.5 |
| 026B8B | 50.8 | 80 | 85 | 98.2 |
| 026C5Z | 72.5 | 86.7 | 95 | 96.5 |
| 026D5K | 28.3 | 68.3 | 75.8 | 84.2 |
| 026E0A | 41.7 | 77.5 | 91.3 | 99.2 |
| 026Z2H | 71.7 | 86.7 | 94.5 | 98.5 |
| Comp. 725K | 0 | 0 | 28.3 | 45 |
| Comp. 570I | 0 | 5.0 | 33.3 | 46.7 |
| Roundup UltraMax | 26.7 | 75 | 84.2 | 91.3 |
| Comp. 41I | 26.7 | 75 | 87.5 | 97.3 |

UltraMax with added 0.4% oxalic acid provided the highest efficacy. Pretreating velvetleaf plants with oxalic acid one hour prior to treatments with monoethoxylated alkylamine or aminated alkoxylated alcohol glyphosate formulations showed no efficacy advantages versus the monoethoxylated alkylamine or aminated alkoxylated alcohol and glyphosate formulations without the pretreatment.

Example 38

The efficacy performance of oxalic acid with aminated alkoxylated alcohols of formulae (5) on morningglory was evaluated. In Table 38a aqueous concentrate compositions were prepared with potassium glyphosate salt. Glyphosate concentrations are reported in g a.e./liter. Oxalic acid was dissolved, potassium glyphosate added, and melted surfactant then added. Formulations were then agitated in a shaker batch for 30 minutes at 60° C. 24 hours after cooling to RT all samples were stable, clear and yellow.

TABLE 38a

| Composition | Glyphosate g/l | Component 1 | w/v % | Component 2 | w/v % |
|---|---|---|---|---|---|
| 383A2T | 62.7 | S1 | 2.0 | Oxalic acid | 0.2 |
| 383B7K | 62.7 | S1 | 2.0 | — | — |
| 383C4D | 62.7 | S13 | 2.0 | Oxalic acid | 0.2 |
| 383D3E | 62.7 | S13 | 2.0 | — | — |
| 383E8N | 62.7 | S5 | 2.0 | Oxalic acid | 0.4 |
| 383F6V | 62.7 | S5 | 2.0 | — | — |
| 383G7Q | 62.7 | S18 | 2.0 | Oxalic acid | 0.4 |
| 383H0O | 62.7 | S18 | 2.0 | — | — |

The compositions of Table 38a, Composition 725K, Composition 570I and Roundup UltraMax, were applied to morningglory (IPOSS) plants. Results, averaged for all replicates of each treatment, are shown in Table 38b.

TABLE 38b

IPOSS % inhibition 14 days after treatment

| Composition | 200 g a.e./ha | 400 g a.e./ha | 600 g a.e./ha | 800 g a.e./ha |
|---|---|---|---|---|
| 383A2T | 63.3 | 80.8 | 82.5 | 86.7 |
| 383B7K | 54.2 | 79.2 | 82.5 | 83.3 |
| 383C4D | 76.7 | 84.2 | 88 | 90.5 |
| 383D3E | 60.8 | 80 | 82.5 | 87.5 |
| 383E8N | 79.2 | 86.7 | 87.5 | 90.5 |
| 383F6V | 76.7 | 82.5 | 85 | 86.7 |
| 383G7Q | 78.3 | 82.5 | 86.7 | 85.8 |
| 383H0O | 45 | 79.2 | 80.8 | 84.2 |
| Comp. 725K | 6.7 | 54.2 | 70 | 73.3 |
| Comp. 570I | 17.5 | 54.2 | 77.5 | 79.2 |
| Roundup UltraMax | 27.5 | 76.7 | 80.8 | 85 |

All oxalic acid formulations outperformed the analogous formulations not containing oxalic acid. Ethoxylated cocoamine 2EO surfactant and $C_{16-18}$ O(EO) 15 dimethylpropyl surfactants in combination with oxalic acid provided the highest efficacy.

Example 39

The efficacy effect of oxalic acid on Monoethoxylated alkylamine surfactant in dilute potassium glyphosate formulations was evaluated. Aqueous concentrate compositions were prepared containing potassium glyphosate salt, reported in g a.e. per liter, and excipient ingredients as shown in Table 39a.

TABLE 39a

| Comp. | Glyph. g/l | Compon. 1 | wt % | Compon. 2 | wt % | Compon. 3 | wt % |
|---|---|---|---|---|---|---|---|
| 026F0A | 62 | S4 | 2.0 | — | — | — | — |
| 026G4T | 62 | S4 | 2.0 | Oxalic Acid | 0.41 | — | — |
| 026H7J | 62 | S4 | 2.0 | Oxalic Acid | 0.21 | — | — |
| 026I4F | 62 | S5 | 2.0 | Oxalic Acid | 0.46 | — | — |
| 026J3Y | 62 | S5 | 2.0 | — | — | — | — |
| 026K6X | 62 | S4 | 1.0 | Oxalic Acid | 0.33 | S5 | 1.0 |
| 026L9O | 62 | S4 | 1.0 | — | — | S5 | 1.0 |

The compositions of Table 39a and comparative compositions of Composition 725K, Composition 570I, Roundup UltraMax and Composition 41I were applied to velvetleaf (*Abutilon theophrasti*, ABUTH) and Japanese millet (*Echinochloa crus-galli* var. *frumentae*, ECHCF) plants. Results, averaged for all replicates of each treatment, are shown in Tables 39b and 39c.

TABLE 39b

ABUTH % Inhibition 17 days after treatment

| Composition | 100 g a.e./ha | 200 g a.e./ha | 300 g a.e./ha | 400 g a.e./ha |
|---|---|---|---|---|
| 026F0A | 56.7 | 78.3 | 88.3 | 91.7 |
| 026G4T | 74.2 | 85.8 | 89.2 | 93.3 |
| 026H7J | 74.2 | 90.8 | 96.2 | 97.8 |
| 026I4F | 76.7 | 83.3 | 84.2 | 91.7 |
| 026J3Y | 28.3 | 70 | 79.2 | 85 |
| 026K6X | 58.3 | 87.5 | 88.3 | 95 |
| 026L9O | 32.5 | 75 | 82.5 | 87.5 |
| Comp. 725K | 0 | 23.3 | 60.8 | 72.5 |
| Comp. 570I | 0 | 25 | 63.3 | 75.8 |
| Roundup UltraMax | 16.7 | 77.5 | 85.8 | 89.2 |
| Comp. 41I | 36.7 | 78.3 | 83.3 | 91.7 |

TABLE 39c

ECHCF % Inhibition 17 days after treatment

| Composition | 100 g a.e./ha | 200 g a.e./ha | 300 g a.e./ha | 400 g a.e./ha |
|---|---|---|---|---|
| 026F0A | 52.5 | 75 | 83.3 | 88 |
| 026G4T | 50 | 58.3 | 68.3 | 77.5 |
| 026H7J | 56.7 | 74.2 | 83.3 | 92.7 |
| 026I4F | 57.5 | 75 | 85 | 84.2 |
| 026J3Y | 56.7 | 74.2 | 81.7 | 88.3 |
| 026K6X | 60.8 | 79.2 | 82.5 | 91 |
| 026L9O | 58.3 | 74.2 | 85 | 90 |
| Comp. 725K | 1.7 | 34.2 | 49.2 | 50.8 |
| Comp. 570I | 2.5 | 47.5 | 52.5 | 55 |
| Roundup UltraMax | 40.8 | 66.7 | 84.2 | 86.7 |
| Comp. 41I | 53.3 | 72.5 | 80 | 87 |

The efficacy of all oxalic acid formulations was superior to Roundup Ultra and the formulation of potassium glyphosate+S4. The formulation containing potassium glyphosate+S4+0.21% oxalic acid with a glyphosate a.e. to oxalic acid ratio of 28:1 gave the greatest efficacy. Oxalic acid levels of 0.21% possessed slightly higher efficacy than did formulations at 0.41%. Oxalic acid addition provided higher efficacy with formulations of potassium glyphosate and S4 (Monoethoxylated alkylamine) than with potassium glyphosate and S5 (Ethomeen C12).

Example 40

The performance of Monoethoxylated alkylamine surfactants with diK oxalate at differing surfactant loading was evaluated. In Table 40a aqueous concentrate compositions were prepared with potassium glyphosate salt. Glyphosate concentrations are reported in g a.e./liter.

TABLE 40a

| Composition | Glyphosate g/l | Component 1 | w/v % | Component 2 | w/v % |
|---|---|---|---|---|---|
| 062A4Y | 62 | — | — | — | — |
| 062B0C | 12 | — | — | di-K oxalate | 0.75 |
| 062O2T | 62 | S34 | 1.37 | di-K oxalate | 0.75 |
| 062P7A | 62 | S34 | 1.16 | di-K oxalate | 0.75 |
| 062Q4K | 62 | S34 | 1.02 | di-K oxalate | 0.75 |
| 062R1R | 62 | S35 | 1.37 | di-K oxalate | 0.75 |
| 062S7M | 62 | S35 | 1.16 | di-K oxalate | 0.75 |
| 062T5G | 62 | S35 | 1.02 | di-K oxalate | 0.75 |

The compositions of Table 40a and comparative compositions of Composition 725K, Composition 570I and Roundup UltraMax were applied to velvetleaf (*Abutilon theophrasti*, ABUTH) and Japanese millet (*Echinochloa crus-galli* var. *frumentae*, ECHCF) plants. Results, averaged for all replicates of each treatment, are shown in Tables 40b and 40c.

TABLE 40b

ABUTH % inhibition 15 days after treatment

| Composition | 100 g a.e./ha | 200 g a.e./ha | 300 g a.e./ha | 400 g a.e./ha |
|---|---|---|---|---|
| 062A4Y | 0 | 13.3 | 64.2 | 77.5 |
| 062B0C | 77.5 | 83.3 | 89.2 | 95.5 |
| 062O2T | 65 | 87.5 | 89.2 | 93.2 |
| 062P7A | 68.3 | 85 | 90 | 95.7 |
| 062Q4K | 75.8 | 83.3 | 89.2 | 90.8 |
| 062R1R | 74.2 | 85 | 88.3 | 91.7 |
| 062S7M | 75.8 | 82.5 | 89.2 | 90 |
| 062T5G | 35.8 | 81.7 | 89.2 | 94.7 |
| Composition AMM-GLY2S | 0 | 3.3 | 20.8 | 51.7 |
| Roundup UltraMax | 15 | 75.8 | 82.5 | 89.2 |
| Composition AMM-GLY1S | 0 | 37.5 | 46.7 | 80 |

TABLE 40c

ECHCF % inhibition 15 days after treatment

| Composition | 100 g a.e./ha | 200 g a.e./ha | 300 g a.e./ha | 400 g a.e./ha |
|---|---|---|---|---|
| 062A4Y | 13.3 | 43.3 | 56.7 | 61.7 |
| 062B0C | 46.7 | 52.5 | 57.5 | 58.3 |
| 062O2T | 57.5 | 75.8 | 84.2 | 89.8 |
| 062P7A | 55 | 65 | 83.3 | 88.3 |
| 062Q4K | 57.5 | 70.8 | 78.3 | 84.2 |
| 062R1R | 55 | 70.8 | 83.2 | 88 |
| 062S7M | 56.7 | 70 | 77.5 | 85.5 |
| 062T5G | 52.5 | 64.2 | 78.3 | 86.5 |
| Composition AMM-GLY2S | 2.5 | 31.7 | 42.5 | 52.5 |
| Roundup UltraMax | 59.2 | 75.8 | 85.8 | 93.3 |
| Composition AMM-GLY1S | 28.3 | 55 | 58.3 | 70 |

Reduced loading of surfactants in combination with oxalic acid gave higher efficacy over Composition AMM-GLY1S for both velvetleaf and barnyardgrass, higher than Roundup UltraMax on velvetleaf, and slightly lower than Roundup UltraMax on barnyardgrass. Efficacy remained consistent across all surfactant loadings tested.

Example 41

The efficacy of oxalic acid formulated with short EO tallowamine surfactant in dilute potassium glyphosate was evaluated. Aqueous concentrate compositions were prepared containing potassium glyphosate salt, reported in g a.e./liter, and excipient ingredients as shown in Table 41a. All components were added and then agitated in a shaker batch for 30 minutes at 60° C. 24 hours after cooling to RT all samples were stable, clear and yellow except for 363B7U which was unstable and hazy.

TABLE 41a

| Composition | Glyphosate g/l | Component 1 | w/v % | Component 2 | w/v % |
|---|---|---|---|---|---|
| 363A1B | 62.7 | S12 | 2.0 | — | — |
| 363B7U | 62.7 | — | — | Oxalic Acid | 2.0 |
| 363C5J | 62.7 | S12 | 2.0 | Oxalic Acid | 0.08 |
| 363D4Q | 62.7 | S12 | 2.0 | Oxalic Acid | 0.1 |
| 363E5T | 62.7 | S12 | 2.0 | Oxalic Acid | 0.13 |
| 363F9K | 62.7 | S12 | 2.0 | Oxalic Acid | 0.15 |
| 363G6V | 62.7 | S12 | 2.0 | Oxalic Acid | 0.2 |
| 363H5G | 62.7 | S12 | 1.9 | Oxalic Acid | 0.1 |

The compositions of Table 41a and comparative compositions of Composition 725K, Composition 570I, Roundup UltraMax and Composition 41I were applied to velvetleaf (*Abutilon theophrasti*, ABUTH) plants. Results, averaged for all replicates of each treatment, are shown in Table 41b.

TABLE 41b

ABUTH % inhibition

| Composition | 100 g a.e./ha | 200 g a.e./ha | 300 g a.e./ha | 400 g a.e./ha |
|---|---|---|---|---|
| 363A1B | 15.8 | 73.3 | 82.5 | 86.7 |
| 363B7U | 62.5 | 80.8 | 83.3 | 85 |
| 363C5J | 65 | 79.2 | 86.7 | 87.5 |
| 363D4Q | 41.7 | 80.8 | 87.5 | 90 |
| 363E5T | 54.2 | 80.8 | 86.7 | 90 |
| 363F9K | 60.8 | 80.8 | 87.5 | 91.7 |
| 363G6V | 70 | 85 | 87.5 | 92.5 |
| 363H5G | 41.7 | 79.2 | 85 | 90.8 |
| Comp. 725K | 0 | 26.7 | 63.3 | 70 |
| Comp. 570I | 0 | 43.3 | 60.8 | 72.5 |
| Roundup UltraMax | 40 | 72.5 | 85 | 87.5 |
| Comp. 41I | 64.2 | 80 | 86.7 | 89.2 |

Most Witcamine 405 formulation blends containing oxalic acid showed efficacy equal to Roundup UltraMax on velvetleaf. Oxalic acid, at any level of addition, provided some efficacy benefits to the Witcamine 405 surfactant.

Example 42

The efficacy of oxalic acid on cocoamine ethoxylates in dilute potassium glyphosate formulations in hard water was evaluated. In Table 42a aqueous concentrate compositions were prepared with potassium glyphosate salt. Glyphosate concentrations are reported in g a.e./liter.

TABLE 42a

| Composition | Glyphosate g/l | Component 1 | w/v % | Component 2 | w/v % |
|---|---|---|---|---|---|
| 045A2M | 62 | S5 | 2.0 | — | — |
| 045B2E | 62 | S5 | 2.0 | Oxalic Acid | 0.3 |
| 045C9I | 62 | S19 | 2.0 | — | — |
| 045D0P | 62 | S19 | 2.0 | Oxalic Acid | 0.3 |
| 045G4H | 62 | S20 | 2.0 | — | — |
| 045H5Y | 62 | S20 | 2.0 | Oxalic Acid | 0.3 |
| 045I8J | 62 | — | — | — | — |
| 045J1Z | 62 | — | — | Oxalic Acid | 0.3 |

The compositions of Table 42a, Composition 725K, Composition 570I and Roundup UltraMax, were applied to velvetleaf (ABUTH) plants. Results, averaged for all replicates of each treatment, are shown in Table 42b.

TABLE 42b

ABUTH % inhibition 14 days after treatment

| Composition | 100 g a.e./ha | 150 g a.e./ha | 200 g a.e./ha | 400 g a.e./ha |
|---|---|---|---|---|
| 045A2M | 0 | 0 | 0 | 75 |
| 045B2E | 0 | 5 | 10 | 86.7 |
| 045C9I | 0 | 0 | 30 | 80 |
| 045D0P | 0 | 10 | 62.5 | 87.5 |
| 045G4H | 0 | 3.3 | 16.7 | 83.3 |
| 045H5Y | 1.7 | 5 | 40.8 | 87.5 |
| 045I8J | 13.3 | 25 | 38.3 | 53.3 |
| 045J1Z | 27.5 | 26.7 | 71.7 | 85 |
| Comp. 725K | 0 | 0 | 0 | 40 |
| Comp. 570I | 0 | 0 | 0 | 30 |
| Roundup UltraMax | 0 | 0 | 5 | 75 |

All formulations were diluted with hard water. The differential enhancement by oxalic acid follows the order of C12 (2EO)>C15 (5EO)>C25 (15EO).

Example 43

The efficacy performance of oxalic acid on tallow amine ethoxylate surfactants in dilute potassium glyphosate formulations in hard water was evaluated. In Table 43a aqueous concentrate compositions were prepared with potassium glyphosate salt. Glyphosate concentrations are reported in g a.e./liter.

TABLE 43a

| Composition | Glyphosate g/l | Component 1 | w/v % | Component 2 | w/v % |
|---|---|---|---|---|---|
| 045K3S | 62 | S5 | 2.0 | — | — |
| 045L9O | 62 | S5 | 2.0 | Oxalic Acid | 0.3 |
| 045M3B | 62 | S19 | 2.0 | — | — |
| 045N5T | 62 | S19 | 2.0 | Oxalic Acid | 0.3 |
| 045Q4Y | 62 | S20 | 2.0 | — | — |
| 045R6J | 62 | S20 | 2.0 | Oxalic Acid | 0.3 |
| 045S3L | 62 | — | — | — | — |
| 045T7G | 62 | — | — | Oxalic Acid | 0.3 |

The compositions of Table 43a, Composition 725K, Composition 570I and Roundup UltraMax, were applied to velvetleaf (ABUTH) plants. Results, averaged for all replicates of each treatment, are shown in Table 43b.

TABLE 43b

ABUTH % inhibition 18 days after treatment.

| Composition | 100 g a.e./ha | 150 g a.e./ha | 200 g a.e./ha | 400 g a.e./ha |
|---|---|---|---|---|
| 045K3S | 0 | 0 | 16.7 | 77.5 |
| 045L9O | 7.5 | 21.7 | 34.2 | 86.3 |
| 045M3B | 10 | 23.3 | 38.3 | 80 |
| 045N5T | 15.8 | 48.3 | 56.7 | 90.8 |
| 045Q4Y | 3.3 | 20 | 45.8 | 84.2 |
| 045R6J | 9.2 | 38.3 | 61.7 | 87.5 |
| 045S3L | 0 | 21.7 | 31.7 | 63.3 |
| 045T7G | 10.8 | 32.5 | 38.3 | 82.5 |
| Comp. 725K | 0 | 0 | 0 | 26.7 |
| Comp. 570I | 0 | 0 | 0 | 26.7 |
| Roundup UltraMax | 0 | 0 | 25 | 70 |

Oxalic acid formulations gave higher efficacy than analogous formulations not containing oxalic acid.

Example 44

The efficacy of oxalic acid with diethoxylated etheramine surfactants was evaluated. In Table 44a, aqueous dilute glyphosate compositions were prepared with potassium glyphosate salt. Glyphosate concentrations are reported in g a.e./liter. Oxalic acid was dissolved, potassium glyphosate added and surfactant added. Formulations were then agitated in a shaker batch for 30 minutes at 60° C. 24 hours after cooling to RT all samples were stable, clear and yellow.

TABLE 44a

| Composition | Glyphosate g/l | Component 1 | w/v % | Component 2 | w/v % |
|---|---|---|---|---|---|
| 615A4F | 484.4 | S36 | 12.0 | — | — |
| 615B9K | 484.4 | S36 | 12.0 | Oxalic acid | 1.5 |
| 615C7S | 62.7 | S37 | 2.0 | — | — |
| 615D1B | 62.5 | S37 | 2.0 | Oxalic acid | 0.25 |
| 615E5I | 62.6 | S38 | 2.0 | — | — |
| 615F5A | 62.5 | S38 | 2.0 | Oxalic acid | 0.25 |
| 615G8Y | 62.7 | S39 | 2.0 | — | — |
| 615H5W | 62.7 | S39 | 2.0 | Oxalic acid | 0.25 |

The compositions of Table 44a, Composition 725K, Composition 570I and Roundup UltraMax, were applied to velvetleaf (*Abutilon theophrasti*, ABUTH) plants. Results, averaged for all replicates of each treatment, are shown in Table 44b.

TABLE 44b

ABUTH % inhibition 14 days after treatment

| Composition | 100 g a.e./ha | 200 g a.e./ha | 300 g a.e./ha | 400 g a.e./ha |
|---|---|---|---|---|
| 615A4F | 7.5 | 75.8 | 90 | 89.2 |
| 615B9K | 78.3 | 88.3 | 94.2 | 94.5 |
| 615C7S | 65 | 84.2 | 90 | 90.8 |
| 615D1B | 74.2 | 90 | 92.5 | 92.5 |
| 615E5I | 40 | 84.2 | 89.2 | 90 |
| 615F5A | 68.3 | 89.2 | 92.5 | 92.5 |
| 615G8Y | 32.5 | 75 | 88.3 | 90.8 |
| 615H5W | 65.8 | 85.8 | 91.3 | 92.5 |
| Comp. 725K | 0 | 40 | 78.3 | 82.5 |
| Comp. 570I | 8.3 | 70.8 | 80 | 84.2 |
| Roundup UltraMax | 39.2 | 81.7 | 90 | 92.5 |

Oxalic acid enhanced velvetleaf efficacy for the tested etheramine surfactants. Performance was similar for all of the surfactants and each exceeded the efficacy of the Roundup UltraMax standard in velvetleaf control at a 24:1 glyphosate a.e. to oxalic acid ratio.

The S36-containing formulation without oxalic acid gave the weakest performance, but was one of the strongest performers when oxalic acid was added.

Example 45

The efficacy effect of oxalic acid with diethoxylated etheramine surfactants was evaluated. In Table 45a aqueous concentrate compositions were prepared with potassium glyphosate salt. Glyphosate concentrations are reported in g a.e./liter. Oxalic acid was dissolved, potassium glyphosate added, and melted surfactant added. Formulations were then agitated in a shaker batch for 30 minutes at 60° C. 24 hours after cooling to RT all samples were stable, clear and yellow except for 392H8U which was unstable, hazy and separated.

TABLE 45a

| Composition | Glyphosate g/l | Component 1 | w/v % | Component 2 | w/v % |
|---|---|---|---|---|---|
| 392A0L | 484.4 | S36 | 10.0 | — | — |
| 392B2S | 488.1 | S36 | 10.0 | Oxalic acid | 1.2 |
| 392C5T | 62.7 | S37 | 1.63 | — | — |
| 392D2K | 62.9 | S37 | 1.63 | Oxalic acid | 0.2 |
| 392E5C | 62.5 | S38 | 1.63 | — | — |
| 392F9V | 62.5 | S38 | 1.63 | Oxalic acid | 0.2 |
| 392G1D | 488.1 | S39 | 10.0 | — | — |
| 392H8U | 488.1 | S39 | 10.0 | Oxalic acid | 1.2 |

The compositions of Table 45a, Composition 725K, Composition 570I and Roundup UltraMax, were applied to velvetleaf (*Abutilon theophrasti*, ABUTH) plants. Results, averaged for all replicates of each treatment, are shown in Table 45b.

TABLE 45b

ABUTH % inhibition 14 days after treatment

| Composition | 100 g a.e./ha | 200 g a.e./ha | 300 g a.e./ha | 400 g a.e./ha |
|---|---|---|---|---|
| 392A0L | 52.5 | 80 | 88 | 90.8 |
| 392B2S | 56.5 | 85 | 90.8 | 92.5 |
| 392C5T | 68.3 | 83.3 | 90 | 93 |
| 392D2K | 86.3 | 91.7 | 96.3 | 98.2 |
| 392E5C | 54.2 | 80.8 | 87.5 | 90.8 |
| 392F9V | 83 | 84.2 | 88.3 | 90.8 |
| 392G1D | 50 | 80 | 85.8 | 89.2 |
| 392H8U | 86.3 | 88.3 | 92.5 | 96.3 |
| Comp. 725K | 0 | 19.2 | 60.8 | 70.8 |
| Comp. 570I | 10 | 51.7 | 78.3 | 82.5 |
| Roundup UltraMax | 50 | 82.5 | 90.8 | 92.5 |

Etheramine formulations containing oxalic acid gave higher efficacy than analogous formulations without oxalic acid and performance exceeded the Roundup UltraMax standard. The PEG 2 iso $C_{13}$ ether propylamine with oxalic acid provided the greatest efficacy.

Example 46

The efficacy of silicone surfactants with amine and phosphate head groups with and without oxalic acid in dilute potassium glyphosate formulations was evaluated. In Table 46a aqueous concentrate compositions were prepared with potassium glyphosate salt. Glyphosate concentrations are reported in g a.e./liter. Oxalic acid was dissolved, then surfactant and potassium glyphosate were added. Formulations were then agitated in a shaker batch for 30 minutes at 60° C. 24 hours after cooling to RT 627A6B, 627B9F and 627F1Z were stable, clear and yellow. All other formulations were unstable and hazy.

TABLE 46a

| Composition | Glyphosate g/l | Component 1 | w/v % | Component 2 | w/v % |
|---|---|---|---|---|---|
| 627A6B | 62.7 | S25 | 2.0 | — | — |
| 627B9F | 62.7 | S26 | 2.0 | — | — |
| 627C4J | 62.7 | S27 | 2.0 | — | — |
| 627D4J | 62.7 | S28 | 2.0 | — | — |
| 627E5U | 62.7 | S29 | 2.0 | — | — |
| 627F1Z | 62.7 | S25 | 2.0 | Oxalic Acid | 0.3 |
| 627G0P | 62.7 | S28 | 2.0 | Oxalic Acid | 0.3 |

The compositions of Table 46a and comparative compositions of Composition 725K, Composition 570I and Roundup UltraMax were applied to velvetleaf (*Abutilon theophrasti*, ABUTH), Japanese millet (*Echinochloa crus-galli* var. *frumentae*, ECHCF) and morningglory (IPOSS) plants. Results, averaged for all replicates of each treatment, are shown in Tables 46b, 46c and 46d.

TABLE 46b

ABUTH % Inhibition 14 Days after treatment

| Composition | 100 g a.e./ha | 200 g a.e./ha | 300 g a.e./ha | 400 g a.e./ha |
|---|---|---|---|---|
| 627A6B | 79.2 | 84.2 | 90.8 | 95.2 |
| 627B9F | 75.8 | 84.2 | 92.5 | 95.2 |
| 627C4J | 73.3 | 77.5 | 88.3 | 88.3 |
| 627D4J | 70.8 | 72.5 | 86.7 | 85.8 |
| 627E5U | 79.2 | 80.8 | 87.5 | 90 |
| 627F1Z | 80.8 | 83.3 | 92.3 | 93.3 |
| 627G0P | 80 | 85.8 | 87.5 | 88.3 |
| Comp. 725K | 30 | 60 | 81.7 | 83.3 |
| Comp. 570I | 61.7 | 70 | 83.3 | 85 |
| Roundup UltraMax | 74.2 | 85.8 | 91.8 | 95.5 |

TABLE 46c

ECHCF % Inhibition 14 Days after treatment

| Composition | 100 g a.e./ha | 200 g a.e./ha | 300 g a.e./ha | 400 g a.e./ha |
|---|---|---|---|---|
| 627A6B | 60 | 70.8 | 80.8 | 94.3 |
| 627B9F | 57.5 | 66.7 | 86.7 | 93 |
| 627C4J | 55 | 65.8 | 85 | 87.5 |
| 627D4J | 55 | 60.8 | 76.7 | 80 |
| 627E5U | 56.7 | 64.2 | 75 | 77.5 |
| 627F1Z | 59.2 | 69.2 | 85.8 | 89.8 |
| 627G0P | 57.5 | 64.2 | 73.3 | 76.7 |
| Comp. 725K | 47.5 | 59.2 | 64.2 | 65 |
| Comp. 570I | 47.5 | 60 | 61.7 | 63.3 |
| Roundup Ultra Max | 65 | 75.8 | 93.5 | 98.2 |

TABLE 46d

IPOSS % Inhibition 14 Days after treatment

| Composition | 100 g a.e./ha | 200 g a.e./ha | 300 g a.e./ha | 400 g a.e./ha |
|---|---|---|---|---|
| 627A6B | 78.3 | 85.8 | 85.8 | 85.8 |
| 627B9F | 77.5 | 82.5 | 85 | 85.8 |
| 627C4J | 76.7 | 80.8 | 82.5 | 83.3 |
| 627D4J | 77.5 | 84.2 | 84.2 | 85 |

TABLE 46d-continued

| | IPOSS % Inhibition 14 Days after treatment | | | |
|---|---|---|---|---|
| Composition | 100 g a.e./ha | 200 g a.e./ha | 300 g a.e./ha | 400 g a.e./ha |
| 627E5U | 78.3 | 84.2 | 85 | 87.5 |
| 627F1Z | 82.5 | 82.5 | 85 | 87.5 |
| 627G0P | 78.3 | 82.5 | 84.2 | 85 |
| Comp. 725K | 70 | 82.5 | 84.2 | 85 |
| Comp. 570I | 70.8 | 83.3 | 84.2 | 85.8 |
| Roundup UltraMax | 78.3 | 84.2 | 85.8 | 86.7 |

Lambent Phos A-100+ oxalic acid, Lambent Phos A-100 and Lambent Phos A-150 showed efficacy equal to Roundup UltraMax on velvetleaf and momingglory. The presence of oxalic acid improved velvetleaf performance of the Lambent amine PD surfactant but did not provide benefits over the Lambent phos A surfactant alone.

Example 47

The efficacy of various oxalic acid ratios with alkylamine surfactant ethomeen C12 in dilute potassium glyphosate formulations were evaluated. In Table 47a aqueous concentrate compositions were prepared with potassium glyphosate salt. Glyphosate concentrations are reported in g a.e./liter. Oxalic acid was dissolved, potassium glyphosate added, and melted surfactant then added. Formulations were then agitated in a shaker batch for 30 minutes at 60° C. 24 hours after cooling to RT all samples were stable, clear and colorless except for 621 B4L which was unstable and formed a precipitate.

TABLE 47a

| Composition | Glyphosate g/l | Component 1 | w/v % | Component 2 | w/v % |
|---|---|---|---|---|---|
| 621A0V | 62.7 | S5 | 2.0 | — | — |
| 621B4L | 62.7 | — | — | Oxalic acid | 2.0 |
| 621C3E | 62.7 | S5 | 1.9 | Oxalic acid | 0.1 |
| 621D8H | 62.7 | S5 | 1.8 | Oxalic acid | 0.2 |
| 621E7S | 62.7 | S5 | 1.6 | Oxalic acid | 0.4 |
| 621F3X | 62.7 | S5 | 1.4 | Oxalic acid | 0.6 |
| 621G9K | 62.7 | S5 | 1.2 | Oxalic acid | 0.8 |
| 621H2A | 62.7 | S5 | 1.0 | Oxalic acid | 1.0 |

The compositions of Table 47a, Composition 725K, Composition 570I and Roundup UltraMax, were applied to velvetleaf (*Abutilon theophrasti*, ABUTH) plants. Results, averaged for all replicates of each treatment, are shown in Table 47b.

TABLE 47b

| | ABUTH % inhibition 14 days after treatment | | | |
|---|---|---|---|---|
| Composition | 100 g a.e./ha | 200 g a.e./ha | 300 g a.e./ha | 400 g a.e./ha |
| 621A0V | 15 | 51.7 | 78.3 | 83.3 |
| 621B4L | 36.7 | 60.8 | 72.5 | 84.2 |
| 621C3E | 48.3 | 72.5 | 82.5 | 88.3 |
| 621D8H | 60.8 | 75 | 86.7 | 85 |
| 621E7S | 59.2 | 74.2 | 80.8 | 88.3 |
| 621F3X | 37.5 | 73.3 | 78.3 | 85 |
| 621G9K | 75 | 80 | 83.3 | 86.7 |
| 621H2A | 51.7 | 78.3 | 82.5 | 87.5 |
| Comp. 725K | 0 | 1.7 | 46.7 | 60 |
| Comp. 570I | 0.8 | 24.2 | 60.8 | 73.3 |
| Roundup UltraMax | 35 | 55 | 80 | 85 |

Oxalic acid at any concentration provided some efficacy enhancement over the Ethomeen C12 surfactant system alone. Increasing oxalic acid concentration and simultaneously decreasing Ethomeen C12 surfactant concentrations resulted in no significant efficacy decrease. A 3:1 ratio of potassium glyphosate a.e.:oxalic acid, with no surfactant, provided equivalent efficacy with Roundup UltraMax.

Example 48

The efficacy of oxalic acid with nonionic and anionic surfactants in dilute potassium glyphosate formulations was evaluated. In Table 48a, aqueous concentrate compositions were prepared with potassium glyphosate salt. Glyphosate concentrations are reported in g a.e./liter. Oxalic acid was dissolved, potassium glyphosate added, and surfactant added. Formulations were then agitated in a shaker batch for 30 minutes at 60° C. 24 hours after cooling to RT all samples were stable and clear.

TABLE 48a

| Composition | Glyphosate g/l | Component 1 | w/v % | Component 2 | w/v % |
|---|---|---|---|---|---|
| 613A5B | 62.7 | S31 | 2.0 | — | — |
| 613B9I | 62.8 | S31 | 2.0 | Oxalic acid | 0.25 |
| 613C5G | 62.8 | S31 | 2.0 | Oxalic acid | 0.5 |
| 613D0K | 62.9 | S32 | 2.0 | — | — |
| 613E7B | 62.9 | S32 | 2.0 | Oxalic acid | 0.25 |
| 613F7S | 63 | S32 | 2.0 | Oxalic acid | 0.5 |
| 613G3Z | 62.8 | S33 | 2.0 | — | — |
| 613H8J | 62.9 | S33 | 2.0 | Oxalic acid | 0.5 |

The compositions of Table 48a, Composition 725K, Composition 570I and Roundup UltraMax, were applied to velvetleaf (*Abutilon theophrasti*, ABUTH) and hemp sesbania (SEBEX) plants. Results, averaged for all replicates of each treatment, are shown in Tables 48b and 48c.

TABLE 48b

| | ABUTH % Inhibition 14 days after treatment | | | |
|---|---|---|---|---|
| Composition | 100 g a.e./ha | 200 g a.e./ha | 300 g a.e./ha | 400 g a.e./ha |
| 613A5B | 15 | 67.5 | 80 | 84.2 |
| 613B9I | 45 | 85.8 | 90.8 | 92.5 |
| 613C5G | 64.2 | 85 | 90 | 90 |
| 613D0K | 22.5 | 76.7 | 80 | 85.8 |
| 613E7B | 58.3 | 78.3 | 85.8 | 90 |
| 613F7S | 65 | 80.8 | 87.5 | 90.8 |
| 613G3Z | 22.5 | 62.5 | 70.8 | 78.3 |
| 613H8J | 53.3 | 75.8 | 80 | 86.7 |
| Comp. 725K | 0 | 47.5 | 70 | 79.2 |
| Comp. 570I | 10.8 | 55 | 74.2 | 81.7 |
| Roundup UltraMax | 30.8 | 78.3 | 88.3 | 90 |

Oxalic acid, in combination with any of the surfactants, provided efficacy enhancement with levels greater than the Roundup UltraMax standard.

TABLE 48c

| Composition | SEBEX % inhibition 18 days after treatment | | | |
|---|---|---|---|---|
| | 200 g a.e./ha | 300 g a.e./ha | 400 g a.e./ha | 600 g a.e./ha |
| 613A5B | 60.8 | 70 | 75.8 | 79.2 |
| 613B9I | 47.5 | 63.3 | 76.7 | 80 |
| 613C5G | 57.5 | 59.2 | 70.8 | 79.2 |
| 613D0K | 41.7 | 68.3 | 75 | 75 |
| 613E7B | 30.8 | 57.5 | 66.7 | 75 |
| 613F7S | 20.8 | 58.3 | 63.3 | 75 |
| 613G3Z | 24.2 | 48.3 | 57.5 | 74.2 |
| 613H8J | 23.3 | 43.3 | 50.8 | 72.5 |
| Comp. 725K | 0 | 0 | 0 | 2.5 |
| Comp. 570I | 0 | 0 | 0 | 6.7 |
| Roundup UltraMax | 40 | 56.7 | 74.2 | 80 |

Herbicidal efficacy level on hemp sesbania were equal with the standards regardless of the presence of oxalic acid.

Example 49

The efficacy effect of oxalic acid with nonionic alkyl polyglucoside and anionic ethoxylated phosphate ester surfactants was evaluated. In Table 49a aqueous concentrate compositions were prepared with potassium glyphosate salt. Glyphosate concentrations are reported in g a.e./liter. Oxalic acid was dissolved, potassium glyphosate added and surfactant then added. Formulations were then agitated in a shaker batch for 30 minutes at 60° C. 24 hours after cooling to RT all samples were stable, clear and yellow.

TABLE 49a

| Composition | Glyphosate g/l | Component 1 | w/v % | Component 2 | w/v % |
|---|---|---|---|---|---|
| 394A7B | 62.7 | S32 | 2.0 | — | — |
| 394B7U | 62.7 | S32 | 2.0 | Oxalic acid | 0.3 |
| 394C2Z | 62.7 | S47 | 2.0 | — | — |
| 394D0K | 62.7 | S47 | 2.0 | Oxalic acid | 0.3 |
| 394E6Y | 62.7 | S48 | 2.0 | — | — |
| 394F3X | 62.7 | S48 | 2.0 | Oxalic acid | 0.3 |
| 394G4J | 62.7 | S33 | 2.0 | — | — |
| 394H2I | 62.7 | S33 | 2.0 | Oxalic acid | 0.3 |

The compositions of Table 49a, Composition 725K, Composition 570I and Roundup UltraMax, were applied to velvetleaf (*Abutilon theophrasti*, ABUTH) plants. Results, averaged for all replicates of each treatment, are shown in Table 49b.

TABLE 49b

| Composition | ABUTH % inhibition 15 days after treatment | | | |
|---|---|---|---|---|
| | 100 g a.e./ha | 200 g a.e./ha | 300 g a.e./ha | 400 g a.e./ha |
| 394A7B | 61.7 | 64.2 | 80 | 82.5 |
| 394B7U | 65.8 | 74.2 | 86.7 | 87.5 |
| 394C2Z | 65.8 | 72.5 | 80.8 | 83.3 |
| 394D0K | 50.8 | 74.2 | 85 | 85.8 |
| 394E6Y | 67.5 | 75 | 86.7 | 87.5 |
| 394F3X | 75.8 | 81.7 | 87.5 | 88.3 |
| 394G4J | 61.7 | 70 | 75 | 81.7 |
| 394H2I | 67.5 | 71.7 | 84.2 | 85 |
| Comp. 725K | 1.7 | 49.2 | 75 | 77.5 |
| Comp. 570I | 22.5 | 46.7 | 79.2 | 80.8 |
| Roundup UltraMax | 50 | 77.5 | 88.8 | 90 |

Oxalic acid blends gave enhanced velvetleaf efficacy at the tested glyphosate a.e.:surfactant and glyphosate a.e.:oxalic acid ratios of 3:1 and 20:1, respectively.

Example 50

The efficacy effect of oxalic acid and its organic salts with cationic etheramine surfactants in potassium glyphosate formulations was evaluated. In Table 50a aqueous concentrate compositions were prepared with potassium glyphosate salt. Glyphosate concentrations are reported in g a.e./liter. The bases were added to water, oxalic acid was dissolved therein followed by melted surfactant and potassium glyphosate. Formulations were then agitated in a shaker batch for 30 minutes at 60° C. 24 hours after cooling to RT all samples were stable, clear and colorless.

TABLE 50a

| Comp. | Glyph. g/l | Compon. 1 | w/w % | Compon. 2 | w/w % | Compon. 3 | w/v % |
|---|---|---|---|---|---|---|---|
| 638A2B | 62.7 | S30 | 2 | — | — | — | — |
| 638B9K | 62.7 | S30 | 2 | Oxalic acid | 0.3 | — | — |
| 638C4J | 62.7 | S30 | 2 | Oxalic acid | 0.26 | S59 | 0.5 |
| 638D1L | 62.7 | S30 | 2 | Oxalic acid | 0.26 | S53 | 0.5 |
| 638E3C | 62.7 | S30 | 2 | Oxalic acid | 0.26 | S68 | 0.5 |
| 638F7N | 62.7 | S30 | 1.9 | Oxalic acid | 0.15 | — | — |
| 638G5B | 62.7 | S30 | 1.6 | Oxalic acid | 0.4 | — | — |

The compositions of Table 50a, Composition 725K, Composition 570I and Roundup UltraMax, were applied to velvetleaf (*Abutilon theophrasti*, ABUTH) plants. Results, averaged for all replicates of each treatment, are shown in Table 50b.

TABLE 50b

| Composition | ABUTH % inhibition 14 days after treatment | | | |
|---|---|---|---|---|
| | 200 g a.e./ha | 300 g a.e./ha | 400 g a.e./ha | 600 g a.e./ha |
| 638A2B | 70 | 85.8 | 93.2 | 96.8 |
| 638B9K | 72.5 | 86.7 | 92.7 | 96.3 |
| 638C4J | 79.2 | 90 | 91.2 | 97.8 |
| 638D1L | 80 | 89.7 | 96.5 | 98.5 |
| 638E3C | 74.2 | 83.3 | 90.2 | 93.3 |

TABLE 50b-continued

| ABUTH % inhibition 14 days after treatment | | | | |
|---|---|---|---|---|
| Composition | 200 g a.e./ha | 300 g a.e./ha | 400 g a.e./ha | 600 g a.e./ha |
| 638F7N | 67.5 | 80.8 | 86.7 | 95.2 |
| 638G5B | 63.3 | 77.5 | 82.5 | 94 |
| Comp. 725K | 25.8 | 54.2 | 69.2 | 80.8 |
| Comp. 570I | 39.2 | 63.3 | 73.3 | 83.3 |
| Roundup UltraMax | 59.2 | 75 | 88.3 | 94.7 |

Oxalic acid blends gave enhanced velvetleaf efficacy that exceeded the UltraMax standard.

Example 51

The efficacy of oxalic acid on EO chain length in high load potassium glyphosate formulations was evaluated. Aqueous concentrate compositions were prepared containing potassium glyphosate salt, reported in g a.e./liter, and excipient ingredients as shown in Table 51a.

TABLE 51a

| Comp. | Glyph. g/l | Compon. 1 | g/l | Compon. 2 | g/l | Compon. 3 | g/l |
|---|---|---|---|---|---|---|---|
| 024A1V | 485 | S2 | 131 | S5 | 65 | — | — |
| 024B7N | 485 | S3 | 91 | S5 | 91 | — | — |
| 024C7B | 485 | S3 | 65 | S5 | 65 | S2 | 65 |
| 024D3K | 485 | S3 | 78 | S5 | 52 | S2 | 65 |
| 024E4J | 485 | S3 | 91 | S5 | 91 | Oxalic Acid | 13 |
| 015A0P | 391 | S4 | 131 | — | — | — | — |

The compositions of Table 51a and comparative compositions of Composition 725K, Composition 570I, Roundup UltraMax and Composition 41I were applied to velvetleaf (*Abutilon theophrasti*, ABUTH) and Japanese millet (*Echinochloa crus-galli* var. *frumentae*, ECHCF) plants. Results, averaged for all replicates of each treatment, are shown in Tables 51b and 51c.

TABLE 51b

| ABUTH % Inhibition 15 days after treatment | | | | |
|---|---|---|---|---|
| Composition | 100 g a.e./ha | 200 g a.e./ha | 300 g a.e./ha | 400 g a.e./ha |
| 024A1V | 15.8 | 76.7 | 83.3 | 84.2 |
| 024B7N | 40 | 80.8 | 86.7 | 88.3 |

TABLE 51b-continued

| ABUTH % Inhibition 15 days after treatment | | | | |
|---|---|---|---|---|
| Composition | 100 g a.e./ha | 200 g a.e./ha | 300 g a.e./ha | 400 g a.e./ha |
| 024C7B | 0 | 0 | 1.7 | 1.7 |
| 024D3K | 29.2 | 80.8 | 82.5 | 90 |
| 024E4J | 75 | 82.5 | 91.7 | 92.5 |
| 015A0P | 55 | 80 | 86.7 | 89.2 |
| Comp. 725K | 0 | 15 | 73.3 | 75.8 |
| Composition 570I | 0.8 | 20 | 71.7 | 80.8 |
| Roundup UltraMax | 45.8 | 80.8 | 87.5 | 90 |
| Composition 41I | 33.3 | 81.7 | 87.5 | 90.8 |

TABLE 51c

| ECHCF % Inhibition 15 days after treatment | | | | |
|---|---|---|---|---|
| Composition | 100 g a.e./ha | 200 g a.e./ha | 300 g a.e./ha | 400 g a.e./ha |
| 024A1V | 35 | 51.7 | 65 | 72.5 |
| 024B7N | 46.7 | 53.3 | 62.5 | 69.2 |
| 024C7B | 0 | 0 | 1.7 | 1.7 |
| 024D3K | 38.3 | 55.8 | 70 | 77.5 |
| 024E4J | 50 | 55 | 75.8 | 79.2 |
| 015A0P | 48.3 | 54.2 | 59.2 | 68.3 |
| Comp. 725K | 1.7 | 20 | 45 | 47.5 |
| Composition 570I | 1.7 | 40 | 50 | 53.3 |
| Roundup UltraMax | 21.7 | 54.2 | 65 | 73.3 |
| Composition 41I | 39.2 | 56.7 | 68.3 | 72.5 |

Formulation 024E4J, containing oxalic acid with Monoethoxylated alkylamine 11 EO and Ethomeen C12 provided the highest herbicidal efficacy on ABUTH and ECHCF. Other formulations gave efficacy similar to that of the glyphosate standards. Formulation 024C7B was atypical and became cloudy upon aqueous dilution, and showed no significant level of herbicidal activity.

Example 52

The effect of oxalic acid on the efficacy of monoethoxylated amine surfactants of varying EO chain length in high load potassium glyphosate was evaluated. Aqueous concentrate compositions were prepared containing potassium glyphosate salt, reported in g a.e. per liter, and excipient ingredients as shown in Table 52a.

TABLE 52a

| Comp. | Glyph. g/l | Compon. 1 | g/l | Compon. 2 | g/l | Compon. 3 | g/l |
|---|---|---|---|---|---|---|---|
| 023A6G | 485 | S8 | 105 | S4 | 92 | — | — |
| 023B6U | 486 | S8 | 118 | S4 | 92 | — | — |
| 023C0P | 487 | S9 | 92 | S4 | 92 | — | — |
| 023D4R | 489 | S9 | 92 | S4 | 92 | oxalic acid | 13.2 |
| 023E6C | 480 | S9 | 104 | S4 | 91 | — | — |
| 023F6Y | 391 | S4 | 121 | — | — | oxalic acid | 7.3 |
| 015Y7N | 391 | S4 | 121 | — | — | — | — |

The compositions of Table 52a and comparative compositions of Composition 725K, Composition 570I, Roundup UltraMax and Composition 41I were applied to velvetleaf (*Abutilon theophrasti*, ABUTH) and Japanese millet (*Echinochloa crus-galli* var. *frumentae*, ECHCF) plants. Results, averaged for all replicates of each treatment, are shown in Tables 52b and 52c.

TABLE 52b

ABUTH % Inhibition 14 days after treatment

| Composition | 100 g a.e./ha | 200 g a.e./ha | 300 g a.e./ha | 400 g a.e./ha |
|---|---|---|---|---|
| 023A6G | 21.7 | 56.7 | 76.7 | 84.2 |
| 023B6U | 25.8 | 63.3 | 77.5 | 83.3 |
| 023C0P | 14.2 | 54.2 | 76.7 | 81.7 |
| 023D4R | 36.7 | 61.7 | 80.8 | 87.5 |
| 023E6C | 34.2 | 50.8 | 76.7 | 80.8 |
| 023F6Y | 45.8 | 71.7 | 88.3 | 88.3 |
| 015Y7N | 34.2 | 68.3 | 82.5 | 86.7 |
| Comp. 725K | 1.7 | 20 | 52.5 | 60.8 |
| Comp. 570I | 3.3 | 24.2 | 52.5 | 58.3 |
| Roundup UltraMax | 10 | 60 | 77.5 | 86.7 |
| Comp. 41I | 20.8 | 60 | 76.7 | 86.7 |

TABLE 52c

ECHCF % Inhibition 14 days after treatment

| Composition | 100 g a.e./ha | 200 g a.e./ha | 300 g a.e./ha | 400 g a.e./ha |
|---|---|---|---|---|
| 023A6G | 50 | 68.3 | 75.8 | 81.7 |
| 023B6U | 42.5 | 67.5 | 75 | 88.3 |
| 023C0P | 39.2 | 70 | 73.3 | 83.3 |
| 023D4R | 41.7 | 69.2 | 75 | 80.8 |
| 023E6C | 51.7 | 67.5 | 73.3 | 80.8 |
| 023F6Y | 46.7 | 67.5 | 69.2 | 79.2 |
| 015Y7N | 51.7 | 66.7 | 69.2 | 80 |
| Comp. 725K | 2.5 | 11.7 | 27.5 | 37.5 |
| Comp. 570I | 6.7 | 16.7 | 43.3 | 50 |
| Roundup UltraMax | 42.5 | 61.7 | 43.3 | 50 |
| Comp. 41I | 50 | 69.2 | 77.5 | 84.2 |

Due to testing error formulations, 023F6Y and 015Y7N were overapplied by 10%. Testing indicates no efficacy difference between formulations with Monoethoxylated alkylamine surfactants with 9.5 EO and 11 EO.

Example 53

The efficacy effect of oxalic acid with surfactant blends in high load potassium glyphosate formulations were evaluated. Aqueous concentrate compositions were formulated with potassium glyphosate salt. Glyphosate concentrations are reported in g a.e. per liter.

The compositions of Table 53a and comparative compositions of Composition 725K, Composition 570I and Roundup UltraMax were applied to velvetleaf (*Abutilon theophrasti*, ABUTH) plants. Results, averaged for all replicates of each treatment, are shown in Table 53b.

TABLE 53b

ABUTH % Control 16 days after treatment

| Composition | 100 g a.e./ha | 200 g a.e./ha | 300 g a.e./ha | 400 g a.e./ha |
|---|---|---|---|---|
| 388A6B | 0 | 5.8 | 54.2 | 79.2 |
| 388B5N | 2.5 | 60 | 83.3 | 90 |
| 388C5T | 0 | 13.3 | 70.8 | 81.7 |
| 388D9J | 0 | 4.2 | 56.7 | 74.2 |
| 388E0A | 0 | 32.5 | 78.3 | 85 |
| Comp. 470K | 0 | 45 | 80 | 85 |
| Comp. 390K | 11.7 | 76.7 | 87.5 | 89.2 |
| Comp. 725K | 0 | 0 | 0.8 | 8.3 |
| Comp. 570I | 0 | 0 | 33.3 | 54.2 |
| Roundup UltraMax | 1.7 | 77.5 | 85 | 90 |

Formulations Composition 390K and Coco 2EO quat and branched PEG 7 C12 alcohol blend in combination with oxalic acid and KOH provided the highest efficacy.

Example 54

The effect of high load aminated alkoxylated alcohols of formulae (5) with commercial standards were evaluated. Aqueous concentrate compositions were formulated with potassium glyphosate salt. Glyphosate concentrations are reported in g a.e. per liter. Oxalic acid was dissolved, KOH and melted surfactant added followed by potassium glyphosate. Formulations were then agitated in a shaker batch for 30 minutes at 60° C. 24 hours after cooling to RT all samples were stable and clear except for 607A8N which was stable and cloudy.

TABLE 53a

| Comp | Glyph. g/l | Compon. 1 | wt % | Compon. 2 | wt % | Compon. 3 | wt % |
|---|---|---|---|---|---|---|---|
| 388A6B | 487 | S21 | 12.0 | — | — | — | — |
| 388B5N | 490 | S21 | 10.0 | Oxalic acid | 1.2 | KOH | 1.0 |
| 388C5T | 486 | S21 | 10.0 | S22 | 2.0 | — | — |
| 388D9J | 544 | S21 | 13.0 | — | — | — | — |
| 388E0A | 548 | S21 | 10.0 | Oxalic acid | 1.0 | KOH | 0.45 |
| Comp. 470K | 472 | S23 | 9.0 | S22 | 4.0 | S24 | 1.0 |
| Comp. 390K | 391 | S4 | 10.0 | — | — | — | — |

TABLE 54a

| Comp | Glyph. g/l | Compon. 1 | wt % | Compon. 2 | wt % | Compon. 3 | wt % |
|---|---|---|---|---|---|---|---|
| 607A8N | 484.4 | S40 | 6.0 | S5 | 6.0 | — | — |
| 607B3E | 480.8 | S1 | 6.0 | S5 | 6.0 | — | — |
| 607C0R | 480.8 | S30 | 6.0 | S5 | 6.0 | Oxalic acid | 1.2 |
| 607D2C | 488.1 | S19 | 6.0 | S5 | 6.0 | — | — |
| 607E5G | 488.1 | S19 | 6.0 | S5 | 6.0 | Oxalic acid | 1.2 |
| 607F4K | 484.4 | S45 | 6.0 | S5 | 6.0 | — | — |
| 607G4W | 488.1 | S45 | 6.0 | S5 | 6.0 | Oxalic acid | 1.2 |
| Comp. 470K | 472 | S42 | 4.0 | S43 | 9.0 | Armeen C | 1.0 |

Compositions 607C0R, 607E5g and 607G4W additionally contain 0.7 w/v % KOH.

The compositions of Table 54a and comparative compositions of Composition 725K, Composition 570I and Roundup UltraMax were applied velvetleaf (*Abutilon theophrasti*, ABUTH) plants. Results, averaged for all replicates of each treatment, are shown in Tables 54b.

TABLE 54b

ABUTH % Control 14 days after treatment

| Composition | 100 g a.e./ha | 200 g a.e./ha | 300 g a.e./ha | 400 g a.e./ha |
|---|---|---|---|---|
| 607A8N | 76.7 | 83.3 | 96.2 | 97.5 |
| 607B3E | 55.8 | 80 | 90 | 95.5 |
| 607C0R | 76.7 | 87.5 | 97.5 | 97.8 |
| 607D2C | 30 | 79.2 | 87.5 | 94.3 |
| 607E5G | 82.5 | 85.8 | 98.8 | 97.2 |
| 607F4K | 64.2 | 80.8 | 90 | 94.2 |
| 607G4W | 85.8 | 89.2 | 94.7 | 99 |
| Comp. 470K | 25.8 | 78.3 | 90 | 91.7 |
| Comp. 725K | 11.7 | 31.7 | 75.8 | 77.5 |
| Roundup UltraMax | 62.5 | 83.3 | 90 | 96.5 |

The four high load formulations 607G4W, 607E5G, 607C0R and 607A8N gave higher efficacy that the Roundup UltraMax and Composition 470K standards. Oxalic acid increased the velvetleaf efficacy.

Example 55

The efficacy of the addition of oxalic acid to weak performing surfactants were evaluated relative to commercial standards. Aqueous concentrate compositions were formulated with potassium glyphosate salt. Glyphosate concentrations are reported in g a.e. per liter. Oxalic acid was dissolved, then potassium glyphosate and surfactant were added. Formulations were then agitated in a shaker batch for 30 minutes at 60° C. 24 hours after cooling to RT all samples were stable, clear and yellow.

TABLE 55a

| Comp. | Glyph. g/l | Compon. 1 | wt % | Compon. 2 | wt % | Compon. 3 | wt % |
|---|---|---|---|---|---|---|---|
| 603A8U | 489.1 | S21 | 10.0 | Oxalic acid | 1.2 | — | — |
| 603B4Z | 492.8 | S21 | 10.0 | Oxalic acid | 1.2 | KOH | 1.2 |
| 603C8J | 496.4 | S21 | 10.0 | Oxalic acid | 1.2 | KOH | 1.2 |
| 603D2F | 489.1 | S21 | 10.0 | Oxalic acid | 1.6 | — | — |
| 603E5B | 496.4 | S21 | 10.0 | Oxalic acid | 1.6 | KOH | 1.2 |
| 603F1E | 491.8 | S5 | 10.0 | Oxalic acid | 2.5 | — | — |
| 603G7K | 536 | S5 | 7.0 | Oxalic acid | 2.0 | — | — |
| Comp. 470K | 472 | S42 | 4.0 | S23 | 9.0 | S24 | 1.0 |

The compositions of Table 55a and comparative compositions of Composition 725K, Composition 570I and Roundup UltraMax were applied to velvetleaf (*Abutilon theophrasti*, ABUTH) plants. Results, averaged for all replicates of each treatment, are shown in Tables 55b.

TABLE 55b

ABUTH % Control 14 days after treatment

| Composition | 100 g a.e./ha | 200 g a.e./ha | 300 g a.e./ha | 400 g a.e./ha |
|---|---|---|---|---|
| 603A8U | 78.3 | 85.8 | 90 | 94 |
| 603B4Z | 75 | 83.3 | 90 | 94.8 |
| 603C8J | 80 | 87.5 | 87.5 | 98.5 |
| 603D2F | 45.8 | 82.5 | 89.2 | 93.2 |
| 603E5B | 42.5 | 84.2 | 89.2 | 90 |
| 603F1E | 70 | 84.2 | 86.7 | 90 |
| 603G7K | 80 | 80.8 | 85 | 93.3 |
| Comp. 470K | 66.7 | 80 | 85 | 90 |
| Comp. 725K | 0 | 43.3 | 71.7 | 78.3 |
| Comp. 570I | 11.7 | 56.7 | 76.7 | 78.3 |
| Roundup UltraMax | 70 | 82.5 | 90 | 94.7 |

The efficacy of cocoquat 2EO+PEG 7 with added oxalic acid was equal to Roundup UltraMax and Composition 470K standards on velvetleaf.

Example 56

The hard water effects on various glyphosate formulations containing either a cationic surfactant or a mixture of cationic and anionic surfactants were evaluated with and without added oxalic acid. Dilute aqueous compositions were formulated with potassium glyphosate salt and deionized water. Glyphosate concentrations are reported in grams a.e. per liter. The weight ratio of glyphosate a.e. to surfactant was about 3:1 and the weight ratio of glyphosate a.e. to oxalic acid was about 30:1. Calcium chloride (500 ppm) was added to some formulations to form hard water. All components were added and the formulation was agitated in a shaker batch for 30 minutes at 60° C. 24 hours after cooling to RT all samples were stable, clear and colorless except for 374D5T and 374H1E which were unstable and hazy.

TABLE 56a

| Comp. | Glyph. g/l | Compon. 1 | wt % | Compon. 2 | wt % | Compon. 3 | wt % |
|---|---|---|---|---|---|---|---|
| 374A2B | 62.7 | S1 | 2.0 | — | — | — | — |
| 374B2E | 62.7 | S1 | 2.0 | — | — | CaCl$_2$ | 0.05 |
| 374C8P | 62.7 | S1 | 2.0 | Oxalic acid | 0.2 | — | — |
| 374D5T | 62.7 | S1 | 2.0 | Oxalic acid | 0.2 | CaCl$_2$ | 0.05 |
| 374E3V | 62.7 | S15 | 2.5 | — | — | — | — |
| 374F4R | 62.7 | S15 | 2.5 | — | — | CaCl$_2$ | 0.05 |
| 374G7L | 62.7 | S15 | 2.5 | Oxalic acid | 0.2 | — | — |
| 374H1E | 62.7 | S15 | 2.5 | Oxalic acid | 0.2 | CaCl$_2$ | 0.05 |

The compositions of Table 56a and comparative compositions of Composition 725K, Composition 725K formulated with hard water (Composition 725K H), Roundup UltraMax and Roundup UltraMax formulated with hard water (Roundup UltraMax H) were applied to velvetleaf (*Abutilon theophrasti*, ABUTH) plants. Results, averaged for all replicates of each treatment, are shown in Tables 56b.

TABLE 56b

ABUTH % Control 18 days after treatment

| Composition | 100 g a.e./ha | 200 g a.e./ha | 300 g a.e./ha | 400 g a.e./ha |
|---|---|---|---|---|
| 374A2B | 28.3 | 79.2 | 86.7 | 89.2 |
| 374B2E | 0 | 48.3 | 81.7 | 85.8 |
| 374C8P | 60.8 | 85 | 90.8 | 97 |
| 374D5T | 0 | 66.7 | 85.8 | 87.5 |
| 374E3V | 0 | 56.7 | 76.7 | 82.5 |
| 374F4R | 0 | 8.3 | 48.3 | 70.8 |
| 374G7L | 43.3 | 83.3 | 87.5 | 92.2 |
| 374H1E | 10.8 | 36.7 | 75 | 84.2 |
| Comp. 725K | 0 | 0 | 2.5 | 24.2 |
| Comp. 725K H | 0 | 0 | 0 | 0 |
| Roundup UltraMax | 0 | 53.3 | 76.7 | 85 |
| Roundup UltraMax H | 0 | 0 | 17.5 | 68.3 |

The efficacy advantages of oxalic acid were still present when using hard water, represented by the addition of 500 ppm CaCl$_2$, as a carrier. However, hard water did negatively impact efficacy compared to analogous formulations made with deionized water. This was expected, however, because the oxalic acid would have chelated the calcium present in the hard water, decreasing the amount of oxalic acid present to impact the efficacy of these formulations. $C_{14-15}$ alkyl(EO)13 dimethylpropylamine surfactants in combination with oxalic acid provided higher efficacy than did similarly formulated cationic tallowamine/phosphate ester compositions.

Example 57

The hard water effects on various glyphosate formulations containing a cationic surfactant were evaluated with and without added oxalic acid. Dilute aqueous compositions were formulated with potassium glyphosate salt and deionized water. Glyphosate concentrations are reported in grams a.e. per liter. The weight ratio of glyphosate a.e. to surfactant was about 3:1 and the weight ratio of glyphosate a.e. to oxalic acid was about 15:1 or about 18:1. Calcium chloride (500 ppm) was added to some formulations to form hard water.

TABLE 57a

| Comp. | Glyph. g/l | Compon. 1 | wt % | Compon. 2 | wt % | Compon. 3 | wt % |
|---|---|---|---|---|---|---|---|
| 026F5M | 62 | S4 | 2.0 | — | — | — | — |
| 026G5L | 62 | S4 | 2.0 | Oxalic acid | 0.41 | — | — |
| 026K7B | 62 | S4 | 1.0 | Oxalic acid | 0.33 | S5 | 1.0 |
| 026L3E | 62 | S4 | 1.0 | — | — | S5 | 1.0 |

The compositions of Table 57a, the compositions of Table 57a with added 500 ppm CaCl$_2$ (indicated with an appended "—H"), comparative compositions of Composition 725K and Composition 725K formulated with hard water (Composition 725K H) were applied to velvetleaf (*Abutilon theophrasti*, ABUTH) plants. Results, averaged for all replicates of each treatment, are shown in Tables 57b.

TABLE 57b

ABUTH % Control 17 days after treatment

| Composition | 100 g a.e./ha | 200 g a.e./ha | 300 g a.e./ha | 400 g a.e./ha |
|---|---|---|---|---|
| 026F5M | 46.7 | 71.7 | 80.8 | 93.3 |
| 026F5M-H | 5 | 54.2 | 65 | 85.8 |
| 026G5L | 74.2 | 85 | 90 | 95.5 |
| 026G5L-H | 21.7 | 71.7 | 81.7 | 90 |
| 026K7B | 62.5 | 80.8 | 87.5 | 93.8 |
| 026K7B-H | 21.7 | 52.5 | 75 | 85 |
| 026L3E | 27.5 | 65 | 75 | 92.5 |
| 026L3E-H | 24.2 | 35.8 | 64.2 | 83.3 |
| Roundup UltraMax | 46.7 | 77.5 | 86.7 | 91.7 |
| Roundup UltraMax H | 0 | 28.3 | 60 | 85 |

Hard water reduced the efficacy of all formulations. This was expected, however, because the oxalic acid would have chelated the calcium present in the hard water, decreasing the amount of oxalic acid present to impact the efficacy of these formulations. Oxalic acid in ratios of glyphosate:oxalic acid of 15:1 and 18:1 improved efficacy in both deionized and hard water.

Example 58

The efficacy of oxalic acid formulated with Composition 480I, Composition 725K and TD IQ at varying application rates and ratios of active to oxalic acid were evaluated on morningglory (IPOSS) and common lambsquarters (CHEAL) plants. Composition 480I, Roundup UltraMax and TD IQ formulated with no oxalic acid, and weight ratios of 3:1, 15:1 and 30:1 glyphosate a.e. to oxalic acid were each tested at active application rates of 390, 585, 780 and 1040 g active (a.e.) per hectare. Comparative compositions of Roundup UltraMax with no added oxalic acid were tested at active application rates of 390, 585, 780 and 1040 g active (a.e) per hectare on IPOSS and CHEAL. Results are given in tables 58a, b, c and d.

TABLE 58a

% Control 22 days after treatment with Composition 480I and oxalic acid

| App. Rate (g a.e./ha) | g Active:g oxalic | IPOSS % Control | CHEAL % Control |
|---|---|---|---|
| 390 | — | 41.5 | 83.8 |
| 390 | 3:1 | 52 | 75.5 |
| 390 | 15:1 | 59 | 78.8 |
| 390 | 30:1 | 50.5 | 73.5 |
| 585 | — | 82.5 | 92 |
| 585 | 3:1 | 83 | 85.5 |
| 585 | 15:1 | 82.3 | 91.5 |
| 585 | 30:1 | 82.3 | 91.5 |
| 780 | — | 89 | 89.3 |
| 780 | 3:1 | 86 | 88 |
| 780 | 15:1 | 92.3 | 90.3 |
| 780 | 30:1 | 83.5 | 90.3 |
| 1040 | — | 92.3 | 92 |
| 1040 | 3:1 | 89.8 | 90 |
| 1040 | 15:1 | 83.8 | 90 |
| 1040 | 30:1 | 88.3 | 91 |

TABLE 58b

% Control 22 days after treatment with Composition 725K and oxalic acid

| App. Rate (g a.e./ha) | g Active:g oxalic | IPOSS % Control | CHEAL % Control |
|---|---|---|---|
| 390 | — | 46 | 31.8 |
| 390 | 3:1 | 45.3 | 27.5 |
| 390 | 15:1 | 45 | 21.3 |
| 390 | 30:1 | 51.5 | 36.3 |
| 585 | — | 61.5 | 41.3 |
| 585 | 3:1 | 66.8 | 36.3 |
| 585 | 15:1 | 69 | 31.3 |
| 585 | 30:1 | 69 | 33 |
| 780 | — | 87.8 | 38 |
| 780 | 3:1 | 70.8 | 31.3 |
| 780 | 15:1 | 83.8 | 41.3 |
| 780 | 30:1 | 84 | 36.3 |
| 1040 | — | 93.3 | 41.5 |
| 1040 | 3:1 | 84 | 48.8 |
| 1040 | 15:1 | 82.3 | 41.8 |
| 1040 | 30:1 | 78.8 | 43.8 |

TABLE 58c

% Control 22 days after treatment with TD IQ and oxalic acid

| App. Rate (g a.e./ha) | g Active:g oxalic | IPOSS % Control | CHEAL % Control |
|---|---|---|---|
| 390 | — | 48.8 | 76 |
| 390 | 3:1 | 52.8 | 77.5 |
| 390 | 15:1 | 52 | 80.5 |
| 390 | 30:1 | 52.5 | 83.5 |
| 585 | — | 74.3 | 87.3 |
| 585 | 3:1 | 79.5 | 90.5 |
| 585 | 15:1 | 84 | 88.8 |
| 585 | 30:1 | 76.3 | 89 |
| 780 | — | 88.3 | 88.5 |
| 780 | 3:1 | 86.8 | 93.3 |
| 780 | 15:1 | 95.3 | 87.5 |
| 780 | 30:1 | 92.5 | 91.5 |
| 1040 | — | 85 | 87.5 |
| 1040 | 3:1 | 94.5 | 89.5 |
| 1040 | 15:1 | 86 | 84 |
| 1040 | 30:1 | 88.8 | 90.3 |

TABLE 58d

% Control 22 days after treatment with Roundup UltraMax without added oxalic acid

| App. Rate (g a.e./ha) | IPOSS % Control | CHEAL % Control |
|---|---|---|
| 390 | 50.3 | 82.5 |
| 585 | 79.8 | 92 |
| 780 | 91.5 | 88.5 |
| 1040 | 90.3 | 84 |

TD IQ formulations including oxalic acid generally performed significantly better than TD IQ in IPOSS and CHEAL.

Composition 480I formulations including oxalic acid performed significantly better or the same as Composition 480I in IPOSS.

Example 59

The efficacy of oxalic acid formulated with Composition 360I, composition 450IS and composition 450I at varying application rates and ratios of active to oxalic acid were evaluated on morningglory (IPOSS). Composition 360I, composition 450IS and composition 450I formulated with no oxalic acid, and at weight ratios of 3:1, 15:1 and 30:1 glyphosate a.e. to oxalic acid were each tested at active application rates of 390, 585, 780 and 1040 g active (a.e.) per hectare. Comparative compositions of Roundup UltraMax Dry with no added oxalic acid were tested at active application rates of 390, 585, 780 and 1040 g active (a.e.) per hectare on IPOSS. Results are given in table 59a.

TABLE 59a

IPOSS % Control 21 days after treatment with Composition 360I, composition 450IS, composition 450I and Roundup UltraMax Dry

| App. Rate (g a.e./ha) | Gly:OA | Composition 360I | composition 450IS | composition 450I | Roundup UltraMax Dry |
|---|---|---|---|---|---|
| 390 | — | 50.5 | 51 | 47.5 | 46.8 |
| 390 | 3:1 | 48 | 44 | 42.5 | — |
| 390 | 15:1 | 49.8 | 45.3 | 49.8 | — |
| 390 | 30:1 | 53.8 | 49.3 | 44.3 | — |

TABLE 59a-continued

IPOSS % Control 21 days after treatment with Composition 360I, composition 450IS, composition 450I and Roundup UltraMax Dry

| App. Rate (g a.e./ha) | Gly:OA | Composition 360I | composition 450IS | composition 450I | Roundup UltraMax Dry |
|---|---|---|---|---|---|
| 585 | — | 62.3 | 63.8 | 62 | 66.3 |
| 585 | 3:1 | 65.5 | 59 | 62 | — |
| 585 | 15:1 | 63.8 | 63 | 62 | — |
| 585 | 30:1 | 63.5 | 66 | 65.8 | — |
| 780 | — | 76.5 | 81.5 | 77.5 | 75.8 |
| 780 | 3:1 | 73.3 | 77.8 | 70.8 | — |
| 780 | 15:1 | 68.8 | 72 | 74 | — |
| 780 | 30:1 | 78.5 | 79.3 | 74.3 | — |
| 1040 | — | 83.3 | 90.7 | 79.8 | 90.3 |
| 1040 | 3:1 | 79.8 | 77.5 | 77.8 | — |
| 1040 | 15:1 | 88 | 77.8 | 72 | — |
| 1040 | 30:1 | 78.5 | 80.8 | 78.3 | — |

Overall, the performance of formulations containing oxalic acid was no significantly different than that of the formulation without oxalic acid when treating IPOSS.

Example 60

The efficacy of oxalic acid formulated with Composition 360I, composition 450IS and composition 450I at varying application rates and ratios of glyphosate to oxalic acid were evaluated on pitted morningglory (IPOLA), velvetleaf (ABUTH), sicklepod (CASOB) and hemp sesbania (SEBEX) plants. Composition 360I, composition 450IS and composition 450I formulated with no oxalic acid, and weight ratios of 3:1, 15:1 and 30:1 glyphosate a.e. to oxalic acid were each tested at active application rates of 325, 520, 715 and 910 g active (a.e.) per hectare. Comparative compositions of Roundup UltraMax Dry with no added oxalic acid were tested at active application rates of 325, 520, 715 and 910 g active (a.e.) per hectare on IPOLA, ABUTH, CASOB and SEBEX. % Control results are given in tables 60a, b, c and d.

TABLE 60a

% Control 24 days after treatment with Composition 360I and oxalic acid

| App. Rate (g a.e./ha) | g a.e.:g oxalic | IPOLA | ABUTH | CASOB | SEBEX |
|---|---|---|---|---|---|
| 325 | — | 50 | 52.5 | 76.3 | 43.8 |
| 325 | 3:1 | 62.5 | 63.8 | 76.3 | 47.5 |
| 325 | 15:1 | 60 | 58.8 | 80 | 52.5 |
| 325 | 30:1 | 62.5 | 61.3 | 78.8 | 53.8 |
| 520 | — | 65 | 71.3 | 78.8 | 55 |
| 520 | 3:1 | 71.3 | 72.5 | 80 | 56.3 |
| 520 | 15:1 | 70 | 77.5 | 86.3 | 61.3 |
| 520 | 30:1 | 70 | 70 | 81.7 | 61.7 |
| 715 | — | 76.3 | 76.3 | 90 | 76.3 |
| 715 | 3:1 | 81.3 | 85 | 91.3 | 78.8 |
| 715 | 15:1 | 80 | 81.3 | 91.3 | 75 |
| 715 | 30:1 | 81.3 | 86.3 | 95 | 82.5 |
| 910 | — | 78.3 | 78.3 | 88.3 | 78.3 |
| 910 | 3:1 | 81.3 | 87.5 | 90 | 78.8 |
| 910 | 15:1 | 83.8 | 92.5 | 91.3 | 76.3 |
| 910 | 30:1 | 77.5 | 92.5 | 95 | 76.3 |

TABLE 60b

% Control 24 days after treatment with composition 450IS and oxalic acid

| App. Rate (g a.e./ha) | g a.e.:g oxalic | IPOLA | ABUTH | CASOB | SEBEX |
|---|---|---|---|---|---|
| 325 | — | 52.5 | 53.8 | 75 | 48.8 |
| 325 | 3:1 | 62.5 | 62.5 | 76.3 | 56.3 |
| 325 | 15:1 | 57.5 | 61.3 | 81.3 | 50 |
| 325 | 30:1 | 58.8 | 58.8 | 81.3 | 41.3 |
| 520 | — | 71.3 | 73.8 | 83.8 | 60 |
| 520 | 3:1 | 71.3 | 78.8 | 83.8 | 67.5 |
| 520 | 15:1 | 68.8 | 70 | 82.5 | 57.5 |
| 520 | 30:1 | 68.8 | 70 | 82.5 | 61.3 |
| 715 | — | 73.8 | 85 | 92.5 | 83.8 |
| 715 | 3:1 | 86.3 | 96.3 | 92.5 | 77.5 |
| 715 | 15:1 | 80 | 91.3 | 96.3 | 80 |
| 715 | 30:1 | 77.5 | 85 | 93.8 | 78.8 |
| 910 | — | 81.3 | 77.5 | 90 | 75 |
| 910 | 3:1 | 78.8 | 88.8 | 90 | 78.8 |
| 910 | 15:1 | 83.8 | 90 | 93.8 | 82.5 |
| 910 | 30:1 | 81.3 | 86.3 | 95 | 78.8 |

TABLE 60c

% Control 24 days after treatment with composition 450I and oxalic acid

| App. Rate (g a.e./ha) | g a.e.:g oxalic | IPOLA | ABUTH | CASOB | SEBEX |
|---|---|---|---|---|---|
| 325 | — | 52.5 | 57.5 | 66.3 | 41.3 |
| 325 | 3:1 | 53.8 | 55 | 63.8 | 40 |
| 325 | 15:1 | 56.3 | 61.3 | 62.5 | 40 |
| 325 | 30:1 | 55 | 56.3 | 63.8 | 41.3 |
| 520 | — | 61.3 | 67.5 | 75 | 52.5 |
| 520 | 3:1 | 68.3 | 63.3 | 80 | 43.3 |
| 520 | 15:1 | 71.3 | 68.8 | 78.8 | 47.5 |
| 520 | 30:1 | 67.5 | 68.8 | 81.3 | 55 |
| 715 | — | 78.8 | 77.5 | 82.5 | 66.3 |
| 715 | 3:1 | 82.5 | 90 | 86.3 | 67.5 |
| 715 | 15:1 | 77.5 | 90 | 86.3 | 72.5 |
| 715 | 30:1 | 77.5 | 80 | 88.8 | 73.8 |
| 910 | — | 75 | 80 | 83.8 | 63.8 |
| 910 | 3:1 | 80 | 95 | 90 | 73.8 |
| 910 | 15:1 | 80 | 83.8 | 86.3 | 72.5 |
| 910 | 30:1 | 80 | 78.8 | 83.8 | 70 |

TABLE 60d

% Control 24 days after treatment with Roundup UltraMax Dry without added oxalic acid.

| App. Rate (g a.e./ha) | IPOLA | ABUTH | CASOB | SEBEX |
|---|---|---|---|---|
| 325 | 56.3 | 60 | 78.8 | 50 |
| 520 | 73.8 | 71.3 | 83.8 | 60 |
| 715 | 82.5 | 85 | 87.5 | 76.3 |
| 910 | 83.8 | 87.5 | 90 | 77.5 |

Composition 360I formulations including oxalic acid performed significantly better than Composition 360I in all species tested.

Composition 450IS formulations including oxalic acid performed significantly better or the same as composition 450IS in all species tested, with the formulation including a 3:1 ratio of glyphosate to oxalic acid generally outperforming the other oxalic acid containing formulations.

Composition 450I formulations including oxalic acid performed significantly better or the same as composition 450I in all species tested.

Example 61

The efficacy of oxalic acid formulated with Composition 480I, Composition 725K and TD IQ at varying application rates and ratios of active to oxalic acid were evaluated on pitted morningglory (IPOLA), velvetleaf (ABUTH), hemp sesbania (SEBEX), barnyardgrass (ECHCG) and sicklepod (CASOB) plants. Composition 480I, Composition 725K and TD IQ formulated with no oxalic acid, and weight ratios of 3:1, 15:1 and 30:1 of glyphosate a.e. to oxalic acid were each tested at active application rates of 325, 520, 715 and 910 g active (a.e.) per hectare. Comparative compositions of Roundup UltraMax with no added oxalic acid were tested at active application rates of 325, 520, 715 and 910 g active (a.e.) per hectare on IPOLA, ABUTH, SEBEX and ECHCG and CASOB. % Control results are given in tables 61a, b, c and d.

TABLE 61a

% Control after treatment with Composition 480I and oxalic acid

| App. Rate (g a.e./ha) | g a.e.:g oxalic | IPOLA | ABUTH | SEBEX | ECHCG | CASOB |
|---|---|---|---|---|---|---|
| 325 | — | 66.3 | 61.3 | 53.8 | 93.8 | 80 |
| 325 | 3:1 | 63.8 | 70 | 41.3 | 94.8 | 80 |
| 325 | 15:1 | 56.3 | 67.5 | 50 | 96.3 | 77.5 |
| 325 | 30:1 | 62.5 | 63.8 | 48.3 | 98.5 | 75 |
| 520 | — | 70 | 75 | 60 | 98.8 | 81.3 |
| 520 | 3:1 | 78.8 | 90 | 57.5 | 94.8 | 86.3 |
| 520 | 15:1 | 78.8 | 80 | 58.8 | 99.5 | 85 |
| 520 | 30:1 | 80 | 81.3 | 58.8 | 98.8 | 85 |
| 715 | — | 81.3 | 96 | 62.5 | 100 | 91.3 |
| 715 | 3:1 | 76.3 | 88.3 | 65 | 97.5 | 88.8 |
| 715 | 15:1 | 78.8 | 88.8 | 65 | 97.5 | 93.8 |
| 715 | 30:1 | 81.3 | 93.8 | 68.8 | 100 | 92.5 |
| 910 | — | 86.3 | 98.5 | 67.5 | 100 | 92.5 |
| 910 | 3:1 | 86.3 | 95 | 71.3 | 99.8 | 90 |
| 910 | 15:1 | 85 | 96.5 | 68.8 | 100 | 91.3 |
| 910 | 30:1 | 86.3 | 98 | 65 | 100 | 91.3 |

TABLE 61b

% Control after treatment with Composition 725K and oxalic acid

| App. Rate (g a.e./ha) | g a.e.:g oxalic | IPOLA | ABUTH | SEBEX | ECHCG | CASOB |
|---|---|---|---|---|---|---|
| 325 | — | 50 | 55 | 35 | 70 | 45 |
| 325 | 3:1 | 63.8 | 70 | 33.8 | 72.5 | 52.5 |
| 325 | 15:1 | 56.3 | 61.3 | 31.3 | 68.8 | 48.8 |
| 325 | 30:1 | 60 | 70 | 45 | 77.5 | 50 |
| 520 | — | 67.5 | 62.5 | 42.5 | 81.3 | 67.5 |
| 520 | 3:1 | 73.8 | 75 | 38.3 | 85.3 | 62.5 |
| 520 | 15:1 | 73.8 | 75 | 41.3 | 76.3 | 63.8 |
| 520 | 30:1 | 70 | 75 | 38.8 | 81.3 | 57.5 |
| 715 | — | 71.3 | 73.8 | 38.8 | 80 | 63.8 |
| 715 | 3:1 | 76.3 | 89.8 | 37.5 | 65 | 71.3 |
| 715 | 15:1 | 75 | 81.3 | 37.5 | 76.3 | 67.5 |
| 715 | 30:1 | 77.5 | 86.5 | 38.8 | 77.5 | 65 |
| 910 | — | 76.3 | 84.8 | 40 | 87.5 | 71.3 |
| 910 | 3:1 | 82.5 | 97.5 | 35 | 80 | 67.5 |
| 910 | 15:1 | 80 | 100 | 46.3 | 88.5 | 72.5 |
| 910 | 30:1 | 81.3 | 83.8 | 41.3 | 76.3 | 78.8 |

TABLE 61c

% Control after treatment with TD IQ and oxalic acid

| App. Rate (g a.e./ha) | g a.e.:g oxalic | IPOLA | ABUTH | SEBEX | ECHCG | CASOB |
|---|---|---|---|---|---|---|
| 325 | — | 65 | 72.5 | 55 | 98.8 | 81.3 |
| 325 | 3:1 | 70 | 86.3 | 53.8 | 97.3 | 83.8 |
| 325 | 15:1 | 70 | 76.3 | 52.5 | 92.3 | 80 |
| 325 | 30:1 | 63.8 | 72.5 | 50 | 93.3 | 77.5 |
| 520 | — | 80 | 80 | 60 | 98.8 | 85 |
| 520 | 3:1 | 82.5 | 80 | 60 | 97.5 | 85 |
| 520 | 15:1 | 76.3 | 84.3 | 63.8 | 97 | 85 |
| 520 | 30:1 | 82.5 | 75 | 58.8 | 92 | 77.5 |
| 715 | — | 81.3 | 90.8 | 65 | 100 | 92.5 |
| 715 | 3:1 | 85 | 92.3 | 65 | 100 | 91.3 |
| 715 | 15:1 | 86.3 | 93.5 | 61.3 | 100 | 91.3 |
| 715 | 30:1 | 80 | 78.8 | 66.3 | 99 | 93.8 |
| 910 | — | 86.3 | 95.3 | 67.5 | 100 | 93.8 |
| 910 | 3:1 | 87.5 | 98.8 | 71.3 | 100 | 95 |
| 910 | 15:1 | 85 | 92.5 | 72.5 | 100 | 95 |
| 910 | 30:1 | 86.3 | 97 | 68.8 | 100 | 95 |

TABLE 61d

% Control after treatment with Roundup UltraMax without added oxalic acid

| App. Rate (g a.e./ha) | IPOLA | ABUTH | SEBEX | ECHCG | CASOB |
|---|---|---|---|---|---|
| 325 | 63.8 | 65 | 51.7 | 98.3 | 80 |
| 520 | 80 | 75 | 61.3 | 97.5 | 85 |
| 715 | 80 | 91 | 67.5 | 99 | 93.8 |
| 910 | 86.3 | 97 | 71.3 | 100 | 92.5 |

Composition 725K formulations including oxalic acid performed significantly better than Composition 725K in IPOLA, ABUTH and CASOB.

TD IQ formulations including oxalic acid performed significantly better or the same as TD IQ at glyphosate a.e. to oxalic acid ratios of 3:1 and 15:1 in all species but ECHCG.

Composition 480I formulations including oxalic acid generally performed significantly better or the same as Composition 480I in all species but ECHCG.

Example 62

The efficacy of oxalic acid formulated with Composition 480I, Composition 725K and TD IQ at varying application rates and ratios of active to oxalic acid were evaluated on velvetleaf (ABUTH), hemp sesbania (SEBEX), pitted morningglory (IPOLA), prickly sida (SIDSP), and sicklepod (CASOB) plants. Composition 480I, Composition 725K and TD IQ formulated with no oxalic acid, and weight ratios of 3:1, 15:1 and 30:1 glyphosate a.e. to oxalic acid were each tested at active application rates of 420, 683, 946 and 1366 g active (a.e.) per hectare. Comparative compositions of Roundup UltraMax with no added oxalic acid were tested at active application rates of 420, 683, 946 and 1366 g active (a.e.) per hectare. Results are given in tables 62a, b, c and d.

TABLE 62a

% Control after treatment with Composition 480I and oxalic acid

| App. Rate (g a.e./ha) | g a.e.:g oxalic | ABUTH | SEBEX | IPOLA | SIDSP | CASOB |
|---|---|---|---|---|---|---|
| 420 | — | 88.5 | 79.8 | 55 | 91.8 | 78.8 |
| 420 | 3:1 | 82.3 | 80.5 | 61.3 | 93 | 72.5 |

TABLE 62a-continued

% Control after treatment with Composition 480I and oxalic acid

| App. Rate (g a.e./ha) | g a.e.:g oxalic | ABUTH | SEBEX | IPOLA | SIDSP | CASOB |
|---|---|---|---|---|---|---|
| 420 | 15:1 | 88.3 | 73.5 | 55 | 92.8 | 74.8 |
| 420 | 30:1 | 90.8 | 75.5 | 51.3 | 96 | 81.3 |
| 683 | — | 93.5 | 91.3 | 63.8 | 96.8 | 81.3 |
| 683 | 3:1 | 96.8 | 93.5 | 68.8 | 95.3 | 82.5 |
| 683 | 15:1 | 92 | 93.3 | 68.8 | 96 | 80.5 |
| 683 | 30:1 | 98.5 | 88.5 | 68.8 | 99.3 | 83.8 |
| 946 | — | 97.3 | 86.5 | 70.8 | 95.8 | 84 |
| 946 | 3:1 | 99.3 | 95 | 77.5 | 97 | 83 |
| 946 | 15:1 | 95.3 | 93 | 72 | 93.3 | 82.5 |
| 946 | 30:1 | 98.8 | 95.3 | 72 | 98.3 | 82.3 |
| 1366 | — | 98.3 | 99.3 | 78.3 | 99.3 | 83 |
| 1366 | 3:1 | 99.8 | 95.8 | 81.3 | 98.3 | 82.5 |
| 1366 | 15:1 | 99.7 | 96.3 | 79.7 | 99 | 86.7 |
| 1366 | 30:1 | 99.5 | 99.8 | 83.3 | 99.5 | 83.3 |

TABLE 62b

% Control after treatment with Composition 725K and oxalic acid

| App. Rate (g a.e./ha) | g a.e.:g oxalic | ABUTH | SEBEX | IPOLA | SIDSP | CASOB |
|---|---|---|---|---|---|---|
| 420 | — | 68.8 | 3.8 | 42.5 | 81.3 | 46.3 |
| 420 | 3:1 | 89.3 | 0 | 42.5 | 87.3 | 48.8 |
| 420 | 15:1 | 74.8 | 6.3 | 42.5 | 92.5 | 45 |
| 420 | 30:1 | 71.8 | 0 | 38.8 | 85.8 | 46.3 |
| 683 | — | 86.8 | 3.8 | 47.5 | 92.3 | 46.3 |
| 683 | 3:1 | 97 | 3.8 | 50 | 92.5 | 48.8 |
| 683 | 15:1 | 94 | 6.3 | 51.3 | 92.3 | 47.5 |
| 683 | 30:1 | 93.3 | 5 | 57.5 | 92.3 | 50 |
| 946 | — | 93.5 | 10 | 60 | 96.8 | 51.3 |
| 946 | 3:1 | 99.3 | 6.3 | 56.3 | 98 | 45 |
| 946 | 15:1 | 93 | 7.5 | 67.5 | 98 | 53.8 |
| 946 | 30:1 | 95.8 | 10 | 62.5 | 98 | 51.3 |
| 1366 | — | 97.3 | 7.5 | 70.3 | 98.3 | 55 |
| 1366 | 3:1 | 99.5 | 11.3 | 65 | 90.8 | 51.3 |
| 1366 | 15:1 | 98.3 | 15 | 66.3 | 98 | 52.5 |
| 1366 | 30:1 | 99.5 | 6.3 | 67.5 | 99 | 51.3 |

TABLE 62c

% Control after treatment with TD IQ and oxalic acid

| App. Rate (g a.e./ha) | g a.e.:g oxalic | ABUTH | SEBEX | IPOLA | SIDSP | CASOB |
|---|---|---|---|---|---|---|
| 420 | — | 91.5 | 72.5 | 51.3 | 90.5 | 82.5 |
| 420 | 3:1 | 87.5 | 69.3 | 53.8 | 90.5 | 80.5 |
| 420 | 15:1 | 93.3 | 77.5 | 56.3 | 90.3 | 79.8 |
| 420 | 30:1 | 85.5 | 76.3 | 52.5 | 94.8 | 82.3 |
| 683 | — | 88.8 | 88.8 | 65.8 | 91.3 | 81.3 |
| 683 | 3:1 | 99.3 | 94 | 65.8 | 98 | 78 |
| 683 | 15:1 | 96 | 88.5 | 61.3 | 94 | 80.8 |
| 683 | 30:1 | 93.5 | 89 | 65 | 90.8 | 82.5 |
| 946 | — | 92 | 93.8 | 72.5 | 96.3 | 85.3 |
| 946 | 3:1 | 99.3 | 99.3 | 77.5 | 96.8 | 83.8 |
| 946 | 15:1 | 99.5 | 97.3 | 68.8 | 96.3 | 82.5 |
| 946 | 30:1 | 95.8 | 89.3 | 70 | 94.5 | 81 |
| 1366 | — | 99.5 | 96 | 74.5 | 98.5 | 81.3 |
| 1366 | 3:1 | 99.5 | 97.5 | 77.8 | 98.3 | 81.8 |
| 1366 | 15:1 | 97.5 | 97.5 | 75 | 99.3 | 83.8 |
| 1366 | 30:1 | 100 | 99.8 | 78.3 | 99.3 | 84 |

TABLE 62d

% Control after treatment with Roundup UltraMax without added oxalic acid

| App. Rate (g a.e./ha) | ABUTH | SEBEX | IPOLA | SIDSP | CASOB |
|---|---|---|---|---|---|
| 420 | 84.8 | 69 | 57.5 | 93 | 80.5 |
| 683 | 97 | 86.8 | 68.8 | 95.8 | 82.3 |
| 946 | 99.5 | 96 | 73.8 | 97 | 81 |
| 1366 | 97 | 97.5 | 80 | 96.8 | 83 |

TD IQ formulations including oxalic acid performed significantly better or the same as TD IQ in IPOLA, ABUTH, SEBEX and SIDSP, particularly at a 3:1 ratio of glyphosate to oxalic acid.

Composition 725K formulations including oxalic acid performed significantly better or the same as Composition 725K in IPOLA, ABUTH, SEBEX and SIDSP.

Composition 480I formulations including oxalic acid performed significantly better or the same as Composition 480I in IPOLA, ABUTH, SEBEX and SIDSP.

Example 63

The efficacy of oxalic acid formulated with Composition 480I, Composition 725K and TD IQ at varying application rates and ratios of active to ocalic acid were evaluated on sicklepod (CASOB), beggarweed (DEDTO), pitted morningglory (IPOLA), hemp sesbania (SEBEX) and velvetleaf (ABUTH). Composition 480I, Composition 725K and TD IQ formulated with no oxalic acid, and weight ratios of 3:1, 15:1 and 30:1 glyphosate a.e. to oxalic acid were each tested at active application rates of 420, 683, 946 and 1366 g active (a.e.) per hectare. Comparative compositions of Roundup UltraMax with no added oxalic acid were tested at active application rates of 420, 683, 946 and 1366 g active (a.e.) per hectare. Results are given in tables 63a, b, c and d.

TABLE 63a

% Control after treatment with Composition 480I and oxalic acid

| App. Rate (g a.e./ha) | g a.e.:g oxalic | CASOB | DEDTO | IPOLA | SEBEX | ABUTH |
|---|---|---|---|---|---|---|
| 420 | — | 84 | 97 | 57.5 | 81.5 | 92 |
| 420 | 3:1 | 81.5 | 94.3 | 55 | 80 | 94.3 |
| 420 | 15:1 | 80.3 | 96 | 57.5 | 81 | 93.5 |
| 420 | 30:1 | 78 | 96 | 52.5 | 79 | 89.8 |
| 683 | — | 84.5 | 98 | 66.3 | 87 | 99 |
| 683 | 3:1 | 82 | 98 | 61.3 | 89.8 | 98 |
| 683 | 15:1 | 80 | 96.8 | 65 | 82.5 | 99 |
| 683 | 30:1 | 82.5 | 98 | 67.5 | 84.3 | 99 |
| 946 | — | 87.5 | 99 | 70 | 93.5 | 99 |
| 946 | 3:1 | 86.5 | 99 | 72.5 | 92 | 99 |
| 946 | 15:1 | 84.5 | 97 | 72 | 86.8 | 99 |
| 946 | 30:1 | 85 | 98 | 71.3 | 88.5 | 99 |
| 1366 | — | 88.3 | 97 | 75.3 | 94 | 99 |
| 1366 | 3:1 | 90.5 | 98 | 82.3 | 95.3 | 99 |
| 1366 | 15:1 | 84 | 98 | 75.3 | 90.8 | 99 |
| 1366 | 30:1 | 83.5 | 98 | 80.8 | 93.3 | 99 |

TABLE 63b

% Control after treatment with Composition 725K and oxalic acid

| App. Rate (g a.e./ha) | g a.e.:g oxalic | CASOB | DEDTO | IPOLA | SEBEX | ABUTH |
|---|---|---|---|---|---|---|
| 420 | — | 30 | 86.5 | 37.5 | 10 | 81.3 |
| 420 | 3:1 | 28.8 | 79.5 | 35 | 10 | 83.8 |
| 420 | 15:1 | 30 | 80 | 42.5 | 10 | 88 |
| 420 | 30:1 | 31.3 | 84.3 | 41.3 | 10 | 82 |
| 683 | — | 36.3 | 87.3 | 45 | 10 | 90.5 |
| 683 | 3:1 | 36.3 | 84.8 | 37.5 | 10 | 92.8 |
| 683 | 15:1 | 26.3 | 87.5 | 46.3 | 10 | 92 |
| 683 | 30:1 | 36.3 | 96 | 46.3 | 10 | 95.8 |
| 946 | — | 36.3 | 93.5 | 45 | 10 | 93.8 |
| 946 | 3:1 | 37.5 | 88.5 | 46.3 | 10 | 95.8 |
| 946 | 15:1 | 35 | 93.3 | 48.8 | 10 | 96.8 |
| 946 | 30:1 | 35 | 90.3 | 46.3 | 10 | 94.8 |
| 1366 | — | 40 | 97 | 51.3 | 10 | 97 |
| 1366 | 3:1 | 38.8 | 94.5 | 50 | 10 | 93.5 |
| 1366 | 15:1 | 41.3 | 95.8 | 56.3 | 10 | 96.8 |
| 1366 | 30:1 | 42.5 | 95.3 | 62.5 | 12.5 | 95.8 |

TABLE 63c

% Control after treatment with TD IQ and oxalic acid

| App. Rate (g a.e./ha) | g a.e.:g oxalic | CASOB | DEDTO | IPOLA | SEBEX | ABUTH |
|---|---|---|---|---|---|---|
| 420 | — | 82 | 96 | 48.8 | 77 | 89.3 |
| 420 | 3:1 | 82.3 | 96 | 55 | 75.5 | 91.8 |
| 420 | 15:1 | 80.5 | 96 | 56.3 | 76.8 | 86.8 |
| 420 | 30:1 | 85.8 | 96 | 52.5 | 79.8 | 93.5 |
| 683 | — | 80.8 | 98 | 60.8 | 85 | 98 |
| 683 | 3:1 | 85.5 | 96.3 | 67.5 | 86.8 | 99 |
| 683 | 15:1 | 86.5 | 98 | 69.5 | 86.3 | 99 |
| 683 | 30:1 | 84 | 99 | 65 | 88 | 99 |
| 946 | — | 84.3 | 99 | 66.3 | 85 | 99 |
| 946 | 3:1 | 86.3 | 97 | 76.5 | 96.8 | 99 |
| 946 | 15:1 | 84.8 | 99 | 74.5 | 89.5 | 99 |
| 946 | 30:1 | 85.3 | 99 | 72 | 90.5 | 99 |
| 1366 | — | 89.8 | 98 | 69.5 | 98 | 99 |
| 1366 | 3:1 | 86.5 | 99 | 77.5 | 99 | 98 |
| 1366 | 15:1 | 87.5 | 99 | 81.3 | 99 | 99 |
| 1366 | 30:1 | 86.8 | 98 | 81 | 98 | 98 |

TABLE 63d

% Control after treatment with Roundup UltraMax without added oxalic acid

| App. Rate (g a.e./ha) | CASOB | DEDTO | IPOLA | SEBEX | ABUTH |
|---|---|---|---|---|---|
| 420 | 82.5 | 97 | 56.3 | 79 | 90 |
| 683 | 85.5 | 97 | 63.8 | 84 | 98 |
| 946 | 90.5 | 99 | 72.5 | 89 | 99 |
| 1366 | 90.3 | 99 | 80 | 99 | 99 |

TD IQ formulations including oxalic acid performed significantly better than TD IQ in IPOLA and SEBEX, and in CASOB and ABUTH at the 30:1 glyphosate to oxalic acid ratio.

Composition 725K formulations including oxalic acid performed significantly better than Composition 725K in IPOLA and ABUTH at 15:1 and 30:1 glyphosate to oxalic acid ratios.

Example 64

The efficacy of oxalic acid formulated with Composition 480I, Composition 725K and TD IQ at varying application rates and ratios of active to oxalic acid were evaluated on pitted morningglory (IPOLA), velvetleaf (ABUTH), sicklepod (CASOB) and hemp sesbania (SEBEX). Composition 480I, Composition 725K and TD IQ formulated with no oxalic acid, and ratios of 3:1, 15:1 and 30:1 glyphosate a.e. to oxalic acid were each tested at active application rates of 455, 650, 845 and 1040 g active (a.e.) per hectare. Comparative compositions of Roundup UltraMax with no added oxalic acid were tested at active application rates of 455, 650, 845 and 1040 g active (a.e.) per hectare. Results are given in tables 64a, b, c and d.

TABLE 64a

% Control after treatment with Composition 480I and oxalic acid

| App. Rate (g a.e./ha) | g a.e.:g oxalic | IPOLA | ABUTH | CASOB | SEBEX |
|---|---|---|---|---|---|
| 455 | — | 53.8 | 53.8 | 90 | 70 |
| 455 | 3:1 | 57.5 | 52.5 | 86.3 | 65 |
| 455 | 15:1 | 58.8 | 61.3 | 86.3 | 67.5 |
| 455 | 30:1 | 61.3 | 62.5 | 88.8 | 61.3 |
| 650 | — | 58.8 | 62.5 | 88.8 | 90 |
| 650 | 3:1 | 60 | 58.8 | 92.5 | 82.5 |
| 650 | 15:1 | 62.5 | 63.8 | 88.8 | 87.5 |
| 650 | 30:1 | 58.8 | 60 | 86.3 | 62.5 |
| 845 | — | 80 | 71.3 | 92.5 | 88.8 |
| 845 | 3:1 | 67.5 | 68.8 | 90 | 83.8 |
| 845 | 15:1 | 70 | 68.8 | 90 | 82.5 |
| 845 | 30:1 | 72.5 | 70 | 88.8 | 82.5 |
| 1040 | — | 87.5 | 83.8 | 93.8 | 90 |
| 1040 | 3:1 | 81.3 | 83.8 | 95 | 95 |
| 1040 | 15:1 | 85 | 72.5 | 97.5 | 90 |
| 1040 | 30:1 | 81.3 | 73.8 | 90 | 86.3 |

TABLE 64b

% Control after treatment with Composition 725K and oxalic acid

| App. Rate (g a.e./ha) | g a.e.:g oxalic | IPOLA | ABUTH | CASOB | SEBEX |
|---|---|---|---|---|---|
| 455 | — | 60 | 56.3 | 70 | 41.3 |
| 455 | 3:1 | 57.5 | 56.3 | 66.3 | 45 |
| 455 | 15:1 | 57.5 | 57.5 | 66.3 | 40 |
| 455 | 30:1 | 58.8 | 56.3 | 63.8 | 43.8 |
| 650 | — | 57.5 | 56.3 | 72.5 | 47.5 |
| 650 | 3:1 | 62.5 | 65 | 68.8 | 56.3 |
| 650 | 15:1 | 61.3 | 58.8 | 71.3 | 45 |
| 650 | 30:1 | 65 | 63.8 | 75 | 46.3 |
| 845 | — | 71.3 | 70 | 68.8 | 42.5 |
| 845 | 3:1 | 66.3 | 72.5 | 75 | 57.5 |
| 845 | 15:1 | 62.5 | 66.3 | 73.8 | 57.5 |
| 845 | 30:1 | 61.3 | 61.3 | 80 | 50 |
| 1040 | — | 76.3 | 76.3 | 82.5 | 63.8 |
| 1040 | 3:1 | 71.3 | 75 | 77.5 | 48.8 |
| 1040 | 15:1 | 78.8 | 73.8 | 76.3 | 48.8 |
| 1040 | 30:1 | 68.8 | 80 | 76.3 | 48.8 |

TABLE 64c

% Control after treatment with TD IQ and oxalic acid

| App. Rate (g a.e./ha) | g a.e.:g oxalic | IPOLA | ABUTH | CASOB | SEBEX |
|---|---|---|---|---|---|
| 455 | — | 62.5 | 58.8 | 91.3 | 76.3 |
| 455 | 3:1 | 62.5 | 63.8 | 91.3 | 73.8 |
| 455 | 15:1 | 65 | 65 | 87.5 | 72.5 |
| 455 | 30:1 | 61.3 | 58.8 | 86.3 | 81.3 |
| 650 | — | 62.5 | 65 | 91.3 | 91.3 |
| 650 | 3:1 | 67.5 | 73.8 | 91.3 | 87.5 |
| 650 | 15:1 | 63.8 | 71.3 | 88.8 | 91.3 |
| 650 | 30:1 | 63.8 | 68.8 | 90 | 81.3 |
| 845 | — | 75 | 68.8 | 92.5 | 92.5 |

TABLE 64c-continued

% Control after treatment with TD IQ and oxalic acid

| App. Rate (g a.e./ha) | g a.e.:g oxalic | IPOLA | ABUTH | CASOB | SEBEX |
|---|---|---|---|---|---|
| 845 | 3:1 | 67.5 | 68.8 | 92.5 | 87.5 |
| 845 | 15:1 | 68.8 | 73.8 | 95 | 93.8 |
| 845 | 30:1 | 72.5 | 71.3 | 91.3 | 90 |
| 1040 | — | 86.3 | 76.3 | 91.3 | 90 |
| 1040 | 3:1 | 82.5 | 77.5 | 92.5 | 83.8 |
| 1040 | 15:1 | 83.8 | 75 | 93.8 | 86.3 |
| 1040 | 30:1 | 85 | 72.5 | 96.3 | 93.8 |

TABLE 64d

% Control after treatment with Roundup UltraMax without added oxalic acid

| App. Rate (g a.e./ha) | IPOLA | ABUTH | CASOB | SEBEX |
|---|---|---|---|---|
| 455 | 66.3 | 61.3 | 93.8 | 70 |
| 650 | 66.3 | 68.8 | 91.3 | 90 |
| 845 | 81.3 | 68.8 | 95 | 88.8 |
| 1040 | 82.5 | 75 | 91.3 | 93.8 |

Composition 725K formulations including oxalic acid performed significantly better or the same as Composition 725K in ABUTH and SEBEX at 3:1 and 15:1 glyphosate to oxalic acid ratios.

TD IQ formulations including oxalic acid performed significantly better than TD IQ in ABUTH at 3:1 and 15:1 glyphosate to oxalic acid ratios.

Example 65

The efficacy of oxalic acid formulated with Composition 360I, composition 450IS and composition 450I at varying application rates and ratios of active to oxalic acid were evaluated on pitted morningglory (IPOLA), velvetleaf (ABUTH), sicklepod (CASOB) and hemp sesbania (SEBEX). Composition 360I, composition 450IS and composition 450I formulated with no oxalic acid, and weight ratios of 3:1, 15:1 and 30:1 glyphosate a.e. to oxalic acid were each tested at active application rates of 455, 650, 845 and 1040 g active (a.e.) per hectare. Comparative compositions of Roundup UltraMax with no added oxalic acid were tested at active application rates of 455, 650, 845 and 1040 g active (a.e.) per hectare. Results are given in tables 65a, b, c and d.

TABLE 65a

% Control after treatment with Composition 360I and oxalic acid

| App. Rate (g a.e./ha) | Gly:OA | IPOLA | ABUTH | CASOB | SEBEX |
|---|---|---|---|---|---|
| 455 | — | 51.3 | 60 | 83.8 | 63.8 |
| 455 | 3:1 | 61.3 | 63.8 | 77.5 | 72.5 |
| 455 | 15:1 | 58.8 | 58.8 | 76.3 | 61.3 |
| 455 | 30:1 | 58.8 | 57.5 | 75 | 71.3 |
| 650 | — | 61.3 | 70 | 85 | 77.5 |
| 650 | 3:1 | 61.3 | 66.3 | 88.8 | 78.8 |
| 650 | 15:1 | 63.8 | 66.3 | 85 | 78.8 |
| 650 | 30:1 | 62.5 | 72.5 | 81.3 | 70 |
| 845 | — | 67.5 | 80 | 90 | 81.3 |
| 845 | 3:1 | 68.8 | 76.3 | 91.3 | 77.5 |
| 845 | 15:1 | 62.5 | 70 | 85 | 72.5 |
| 845 | 30:1 | 68.8 | 78.8 | 91.3 | 76.3 |
| 1040 | — | 73.8 | 81.3 | 96.3 | 91.3 |
| 1040 | 3:1 | 76.3 | 78.8 | 96.3 | 91.3 |
| 1040 | 15:1 | 76.3 | 88.8 | 95 | 86.3 |
| 1040 | 30:1 | 78.8 | 81.3 | 95 | 91.3 |

TABLE 65b

% Control after treatment with composition 450IS and oxalic acid

| App. Rate (g a.e./ha) | g a.e.:g oxalic | IPOLA | ABUTH | CASOB | SEBEX |
|---|---|---|---|---|---|
| 455 | — | 58.8 | 73.8 | 85 | 68.8 |
| 455 | 3:1 | 63.8 | 70 | 82.5 | 60 |
| 455 | 15:1 | 61.3 | 70 | 81.3 | 67.5 |
| 455 | 30:1 | 57.5 | 63.8 | 77.5 | 62.5 |
| 650 | — | 60 | 73.8 | 86.3 | 82.5 |
| 650 | 3:1 | 63.8 | 73.8 | 81.3 | 76.3 |
| 650 | 15:1 | 66.3 | 76.3 | 88.8 | 83.8 |
| 650 | 30:1 | 63.8 | 76.3 | 87.5 | 76.3 |
| 845 | — | 77.5 | 75 | 92.5 | 82.5 |
| 845 | 3:1 | 78.8 | 80 | 95 | 83.8 |
| 845 | 15:1 | 75 | 82.5 | 91.3 | 82.5 |
| 845 | 30:1 | 75 | 73.8 | 91.3 | 82.5 |
| 1040 | — | 88.8 | 85 | 93.8 | 85 |
| 1040 | 3:1 | 83.8 | 81.3 | 95 | 85 |
| 1040 | 15:1 | 81.3 | 88.8 | 93.8 | 87.5 |
| 1040 | 30:1 | 76.3 | 80 | 88.8 | 83.8 |

TABLE 65c

% Control after treatment with composition 450I and oxalic acid

| App. Rate (g a.e./ha) | g a.e.:g oxalic | IPOLA | ABUTH | CASOB | SEBEX |
|---|---|---|---|---|---|
| 455 | — | 53.8 | 56.3 | 60 | 43.8 |
| 455 | 3:1 | 61.3 | 68.8 | 72.5 | 47.5 |
| 455 | 15:1 | 56.3 | 56.3 | 63.8 | 48.8 |
| 455 | 30:1 | 56.3 | 58.8 | 63.8 | 48.8 |
| 650 | — | 57.5 | 70 | 71.3 | 46.3 |
| 650 | 3:1 | 60 | 72.5 | 76.3 | 70 |
| 650 | 15:1 | 66.3 | 71.3 | 78.8 | 62.5 |
| 650 | 30:1 | 60 | 83.8 | 72.5 | 58.8 |
| 845 | — | 65 | 76.7 | 81.7 | 78.3 |
| 845 | 3:1 | 73.8 | 76.3 | 86.3 | 77.5 |
| 845 | 15:1 | 70 | 75 | 82.5 | 76.3 |
| 845 | 30:1 | 75 | 80 | 83.8 | 71.3 |
| 1040 | — | 76.3 | 76.3 | 85 | 81.3 |
| 1040 | 3:1 | 82.5 | 82.5 | 93.8 | 86.3 |
| 1040 | 15:1 | 81.3 | 82.5 | 86.3 | 80 |
| 1040 | 30:1 | 78.8 | 85 | 85 | 85 |

TABLE 65d

% Control after treatment with Roundup UltraMax without added oxalic acid

| App. Rate (g a.e./ha) | IPOLA | ABUTH | CASOB | SEBEX |
|---|---|---|---|---|
| 455 | 60 | 61.3 | 83.8 | 58.8 |
| 650 | 61.3 | 73.8 | 85 | 70 |
| 845 | 77.5 | 77.5 | 87.5 | 75 |
| 1040 | 78.8 | 90 | 93.8 | 81.3 |

Composition 450I formulations including oxalic acid performed significantly better than composition 450I in all species tested, with the formulation including a 3:1 ratio of glyphosate to oxalic acid outperforming the other oxalic acid containing formulations.

In IPOLA, composition 360I formulations including oxalic acid performed significantly better than Composition 360I, with the formulation including a 3:1 ratio of glyphosate to oxalic acid outperforming the other oxalic acid containing formulations. Composition 360I results in other weed species generally did not show significantly improved performance for the oxalic acid containing formulations.

In all species, the composition 450IS formulations containing 3:1 and 15:1 ratios of glyphosate to oxalic acid generally performed as well or better than composition 450IS. In all species, the performance of composition 450IS formulations containing 30:1 ratios of glyphosate to oxalic acid was below that of composition 450IS.

Example 66

The effect of organic bases in combination with oxalic acid in tank mixes comprising potassium glyphosate and alkyl etheramine surfactant M-1415E13-2 (from Tomah) was evaluated. Glyphosate concentrations for each composition were 62.7 g a.e. per liter.

TABLE 66a

| Composition | Component 1 | wt % | Component 2 | wt % |
|---|---|---|---|---|
| 630A2L | S1 | 2 | — | — |
| 630B6N | S1 | 2 | Oxalic acid | 0.3 |

The compositions of Table 66a and a comparative composition Roundup UltraMax were applied to Yellow nutsedge (*Cyperus esculentus*, CYPES) plants. Results, averaged for all replicates of each treatment, are shown in Table 66b.

TABLE 66b

| | CTPES % Control | | | |
|---|---|---|---|---|
| Composition | 200 g a.e./ha | 400 g a.e./ha | 600 g a.e./ha | 800 g a.e./ha |
| 630A2L | 72.8 | 80.4 | 80.4 | 86 |
| 630B6N | 63.7 | 81.8 | 76 | 84.7 |
| Roundup UltraMax | 75.8 | 70.6 | 79.7 | 91.7 |

Addition of 0.03% oxalic acid to the alkoxylated amine surfactant and potassium glyphosate tank mixes did not provide synergy on yellow nutsedge.

Example 67

The rainfastedness of a Roundup UltraMax and oxalic acid, at a weight ratio of glyphosate a.e. to oxalic acid of 15:1, was evaluated. The Roundup UltraMax formulations were applied at rates of 300 and 500 g a.e./ha and evaluated with no rain, 0.25 inches of rain at one hour after treatment, and 0.25 inches of rain at two hours after treatment. The results are given in table 68a below.

TABLE 67a

| | ABUTH % Control 15 days after treatment | | |
|---|---|---|---|
| Roundup UltraMax Formulations | No Rain | 0.25" rain @ 1 hour | 0.25" rain @ 2 hours |
| 300 g a.e./ha | 84.6 | 32.5 | 49.1 |
| 500 g a.e./ha | 94.8 | 55.7 | 72.5 |
| 300 g a.e./ha + 20 g/ha oxalic acid | 90.8 | 24.2 | 40.8 |
| 300 g a.e./ha + 30 g/ha oxalic acid | 95.5 | 15 | 50.8 |
| 500 g a.e./ha + 33 g/ha oxalic acid | 96.2 | 42.5 | 63.3 |
| 500 g a.e./ha + 50 g/ha oxalic acid | 99.3 | 48.3 | 61.7 |

Slight efficacy advantages were obtained for formulations containing oxalic acid when no rain was applied. Oxalic acid did not provide any rainfastness properties for Roundup UltraMax on velvetleaf at the one hour and two hour rain events.

The present invention is not limited to the above embodiments and can be variously modified. The above description of the preferred embodiment is intended only to acquaint others skilled in the art with the invention, its principles, and its practical application so that others skilled in the art may adapt and apply the invention in its numerous forms, as may be best suited to the requirements of a particular use.

With reference to the use of the word(s) "comprise" or "comprises" or "comprising" in this entire specification (including the claims below), Applicants note that unless the context requires otherwise, those words are used on the basis and clear understanding that they are to be interpreted inclusively, rather than exclusively, and the Applicants intend each of those words to be so interpreted in construing this entire specification.

What is claimed is:

1. An aqueous herbicidal concentrate composition comprising:
   glyphosate predominantly in the form of the potassium, monoammonium, diammonium, sodium, monoethanolamine, isopropylamine, n-propylamine, ethylamine, ethylenediamine, hexamethylenediamine or trimethylsulfonium salt thereof, in solution in an aqueous medium in a concentration of at least 420 grams glyphosate a.e. per liter; and
   oxalic acid or a salt thereof in a concentration such that, when the composition is diluted in a suitable volume of water to form an enhanced application mixture and applied to the foliage of a susceptible plant, growth of the plant is controlled to a greater extent than in a plant treated with a reference application mixture devoid of oxalic acid and said salt but otherwise having the same composition as said enhanced application mixture.

2. A composition of claim 1 further including a surfactant component in solution or stable suspension, emulsion, or dispersion in said medium, comprising one or more surfactants, the surfactant component being present in a concentration sufficient to provide acceptable temperature stability of the composition such that the composition has a cloud point of at least 50° C. and a crystallization point not greater than 0° C.

3. A composition of claim 2 wherein the surfactant component comprises one or more surfactant(s) in a total amount of about 20 to about 300 grams per liter of composition.

4. A composition of claim 2 wherein the surfactant component comprises one or more cationic, nonionic or anionic surfactants.

5. A composition of claim 4 wherein the cationic surfactant component comprises at least one surfactant selected from the group consisting of:

(a) aminated alkoxylated alcohols having the formula:

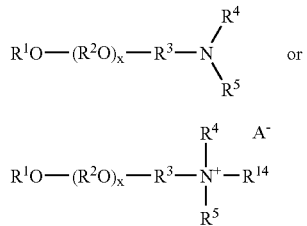

(5)

(6)

wherein $R^1$ is hydrogen or hydrocarbyl or substituted hydrocarbyl having from 1 to about 30 carbon atoms; $R^2$ in each of the x $(R^2O)$ and y $(R^2O)$ groups is independently $C_2$-$C_4$ alkylene; $R^3$ and $R^6$ are each independently hydrocarbylene or substituted hydrocarbylene having from 1 to about 6 carbon atoms; $R^4$ is hydrogen, Hydrocarbyl or substituted hydrocarbyl having from 1 to about 30 carbon atoms, hydroxy substituted hydrocarbyl, $—(R^6)_n—(R^2O)_yR^7$, $—C(=NR^{11})NR^{12}R^{13}$, $—C(=O)NR^{12}R^{13}$, $—(R^6)_n—C(O)OR^7$, $—C(=S)NR^{12}R^{13}$ or together with $R^5$ and the nitrogen atom to which they are attached, form a heterocyclic ring; $R^5$ is hydrogen, hydrocarbyl or substituted hydrocarbyl having from 1 to about 30 carbon atoms, hydroxy substituted hydrocarbyl, $—(R^6)_n—(R^2O)_yR^7$, $—C(=NR^{11})NR^{12}R^{13}$, $—C(=O)NR^{12}R^{13}$, $—(R^6)_n—C(O)OR^7$, $—C(=S)NR^{12}R^{13}$, or together with $R^4$ and the nitrogen atom to which they are attached, form a cyclic or heterocyclic ring; $R^7$ is hydrogen or a linear or branched alkyl group having 1 to about 4 carbon atoms; $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, $—(R^6)_n—(R^2O)_yR^7$, $—C(=NR^{11})NR^{12}R^{13}$, $—C(=O)NR^{12}R^{13}$, or $—C(=S)NR^{12}R^{13}$, n is 0 or 1, x and y are independently an average number from 1 to about 60, and A- is an agriculturally acceptable anion;

(b) secondary or tertiary amines having the formula:

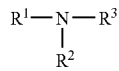

(27)

wherein $R^1$ and $R^2$ are hydrocarbyl having from 1 to about 30 carbon atoms, and $R^3$ is hydrogen or hydrocarbyl having from 1 to about 30 carbon atoms;

(c) monoalkylated amines having the formula:

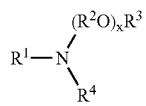

(28)

wherein $R^1$ and $R^4$ are independently hydrocarbyl or substituted hydrocarbyl groups having from 1 to about 30 carbon atoms or $—R^5SR^6$, $R^2$ in each of the x $(R^2O)$ groups is independently $C_2$-$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60;

(d) dialkoxylated quaternary ammonium salts having the formula:

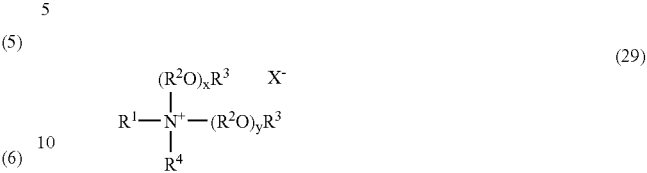

(29)

wherein $R^1$ is hydrocarbyl or substituted hydrocarbyl having from 1 to about 30 carbon atoms, $R^2$ in each of the x $(R^2O)$ and y $(R^2O)$ groups is independently $C_2$-$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X- is an agriculturally acceptable anion, provided, however, that either $R^1$ or $R^4$ is other than alkyl;

(e) monoalkoxylated quaternary ammonium salts having the formula:

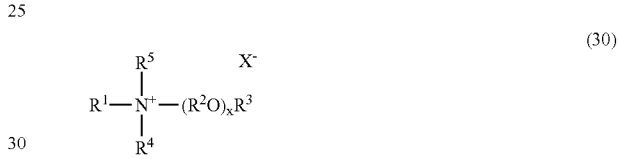

(30)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x $(R^2O)$ groups is independently $C_2$-$C_4$ alkylene, $R^3$ is hydrogen, or a linear or branched alkyl group having from 1 to about 30 carbon atoms, x is an average number from 1 to about 60, and X- is an agriculturally acceptable anion;

(f) quaternary ammonium salts having the formula:

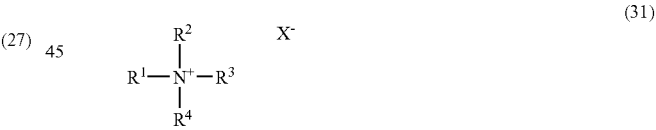

(31)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X- is an agriculturally acceptable anion, provided, however that $R^1$ is not alkyl when $R^2$, $R^3$ and $R^4$ are lower alkyl;

(g) etheramines having the formula:

(32)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —$(R^5O)_xR^6$, $R^5$ in each of the x ($R^5$-O) groups is independently $C_2$-$C_4$ alkylene, $R^6$ is hydrogen, or a linear or branched alkyl group having from 1 to about 4 carbon atoms, and x is an average number from 1 to about 50;

(h) amine oxides having the formula:

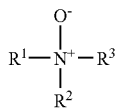 (34)

wherein $R^1$, $R^2$ and $R^3$ are independently hydrogen, hydrocarbyl or substituted hydrocarbyl having from 1 to about 30 carbon atoms, —$(R^4O)_xR^5$, or —$R^6(OR^4)_xOR^5$; $R^4$ in each of the x ($R^4O$) groups is independently $C_2$-$C_4$ alkylene, $R^5$ is hydrogen, or a hydrocarbyl or substituted hydrocarbyl having from 1 to about 30 carbon atoms, $R^6$ is a hydrocarbylene or substituted hydrocarbylene having from 1 to about 6 carbon atoms, x is an average number from 1 to about 50, and the total number of carbon atoms in $R^1$, $R^2$ and $R^3$ is at least 8;

(i) alkoxylated amine oxides having the formula:

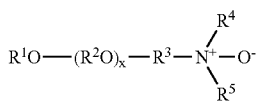 (35)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —$(R^6)_n$—$(R^2O)_xR^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60; and (j) dialkoxylated amines having the formula:

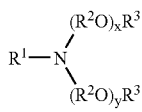 (36)

wherein $R^1$ is hydrogen or hydrocarbyl or substituted hydrocarbyl having from 1 to about 30 carbon atoms, —$R^4SR^5$, or —$(R^2O)_zR^3$, $R^2$ in each of the x ($R^2O$), y ($R^2O$) and z ($R^2O$) groups is independently $C_2$-$C_4$ alkylene, $R^3$ is hydrogen, or a linear or branched alkyl group having from 1 to about 22 carbon atoms, $R^4$ is a linear or branched alkyl group having from about 6 to about 30 carbon atoms, $R^5$ is a linear or branched alkyl group having from about 4 to about 15 carbon atoms, and x, y and z are independently an average number from 1 to about 40, provided, however, that when $R^1$ is alkyl, either the sum of x and y is greater than 20 or $R^3$ is other than hydrogen.

6. A composition of claim 4 wherein the nonionic surfactant component comprises at least one surfactant selected from the group consisting of:

(a) alkoxylated alcohols having the formula:

 (45)

wherein $R^1$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 4 carbon atoms, and x is an average number from 1 to about 60, provided, however, that when $R^1$ is alkyl, either $R^3$ is other than hydrogen or x is at least 10;

(b) dialkoxylated alcohols having the formula:

 (46)

wherein $R^1$ is independently hydrogen, or a linear or branched alkyl group having from 1 to about 4 carbon atoms, $R^2$ in each of the x ($R^2O$) and the y ($R^2O$) groups is independently $C_2$-$C_4$ alkylene, $R^3$ is hydrocarbylene or substituted hydrocarbylene having from 2 to about 30 carbon atoms, and x and y are independently an average number from 1 to about 60; and (c) glycosides having the formula:

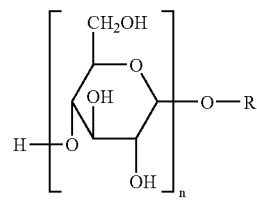 (62)

wherein n is the degree of polymerization, or number of glycose groups, and R is a branched or straight chain alkyl group wherein n is between 1 and about 5 having from 4 to 18 carbon atoms, or a mixture of alkyl groups having an average value within the given range.

7. A composition of claim 4 wherein the anionic surfactant component comprises at least one surfactant selected from the group consisting of:

(a) compounds having the formula:

 (47A)

wherein $R_1$ is a hydrocarbyl group having from about 8 to about 22 carbon atoms, each of the n ($R_2O$) groups is independently $C_2$-$C_4$ alkylene, n is a number from 0 to about 60, and $X_1$ is a carboxylate, sulfate or phosphate;

(b) phosphate diesters having the formula:

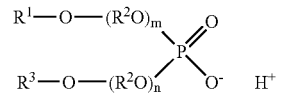 (56)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2O$) and the n ($R^2O$) groups is independently $C_2$-$C_4$ alkylene; and m and n are independently from 1 to about 30; and (c) phosphate esters having the formula:

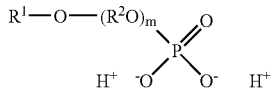

(57)

wherein $R^1$ is a linear or branched alkyl, linear or branched alkenyl, linear or branched alkynyl, aryl, or aralkyl group having from about 4 to about 30 carbon atoms; $R^2$ in each of the m ($R^2O$) groups is independently $C_2$-$C_4$ alkylene; and m is from 1 to about 30.

8. A composition of claim 2 wherein said surfactant component and said oxalic acid or a salt thereof are present in a weight ratio between about 5:1 and about 40:1.

9. A composition of claim 1 wherein the glyphosate concentration is at least 450 grams glyphosate a.e. per liter.

10. A composition of claim 9 wherein the glyphosate concentration is at least 500 grams glyphosate a.e. per liter.

11. A composition of claim 10 wherein the glyphosate concentration is at least 540 grams glyphosate a.e. per liter.

12. An aqueous herbicidal concentrate composition comprising:
glyphosate predominantly in the form of the monoammonium salt thereof in a concentration of at least 420 grams glyphosate a.e. per liter, in solution in an aqueous medium in a concentration that is biologically effective when the composition is diluted in a suitable volume of water to form an enhanced application mixture and applied to the foliage of a susceptible broadleaf plant; and
oxalic acid or a salt thereof in a concentration such that growth of the plant is controlled to a greater extent as compared to a plant treated with a reference application mixture devoid of oxalic acid and said salt but otherwise having the same composition as said enhanced application mixture.

13. A composition of claim 12 further including a surfactant component in solution or stable suspension, emulsion, or dispersion in said medium, comprising one or more surfactants.

14. A composition of claim 13 wherein the surfactant component is present in a concentration sufficient to provide acceptable temperature stability of the composition such that the composition has a cloud point of at least 50° C. and a crystallization point not greater than 0° C.

15. A composition of claim 13 wherein the surfactant component comprises one or more surfactant(s) in a total amount of about 20 to about 300 grams per liter of composition.

16. A composition of claim 13 wherein the surfactant component comprises one or more cationic, nonionic or anionic surfactants.

17. A composition of claim 16 wherein the cationic surfactant component comprises at least one surfactant selected from the group consisting of:

(a) aminated alkoxylated alcohols having the formula:

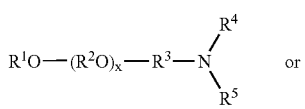 or (5)

-continued

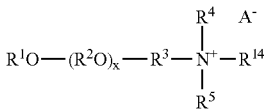

(6)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ and $R^6$ are each independently hydrocarbylene or substituted hydrocarbylene having from 1 to about 6 carbon atoms; $R^4$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-(R^6)_n-C(O)OR^7$, $-C(=S)NR^{12}R^{13}$ or together with $R^5$ and the nitrogen atom to which they are attached, form a heterocyclic ring; $R^5$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-(R^6)_n-C(O)OR^7$, $-C(=S)NR^{12}R^{13}$, or together with $R^4$ and the nitrogen atom to which they are attached, form a cyclic or heterocyclic ring; $R^7$ is hydrogen or a linear or branched alkyl group having 1 to about 4 carbon atoms; $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, or $-C(=S)NR^{12}R^{13}$, n is 0 or 1, x and y are independently an average number from 1 to about 60, and A- is an agriculturally acceptable anion;

(b) secondary or tertiary amines having the formula:

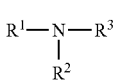

(27)

wherein $R^1$ and $R^2$ are hydrocarbyl having from 1 to about 30 carbon atoms, and $R^3$ is hydrogen or hydrocarbyl having from 1 to about 30 carbon atoms;

(c) monoalkylated amines having the formula:

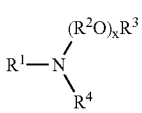

(28)

wherein $R^1$ and $R^4$ are independently hydrocarbyl or substituted hydrocarbyl groups having from 1 to about 30 carbon atoms or $-R^5SR^6$, $R^2$ in each of the x ($R^2O$) groups is independently $C_2$-$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60;

(d) dialkoxylated quaternary ammonium salts having the formula:

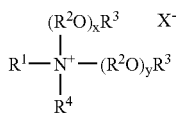

(29)

wherein $R^1$ is hydrocarbyl or substituted hydrocarbyl having from 1 to about 30 carbon atoms, $R^2$ in each of the x ($R^2O$) and y ($R^2O$) groups is independently $C_2$-$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X- is an agriculturally acceptable anion, provided, however, that either $R^1$ or $R^4$ is other than alkyl;

(e) monoalkoxylated quaternary ammonium salts having the formula:

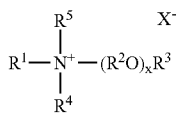

(30)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 30 carbon atoms, x is an average number from 1 to about 60, and X- is an agriculturally acceptable anion;

(f) quaternary ammonium salts having the formula:

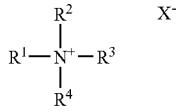

(31)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X- is an agriculturally acceptable anion, provided, however that $R^1$ is not alkyl when $R^2$, $R^3$ and $R^4$ are lower alkyl;

(g) etheramines having the formula:

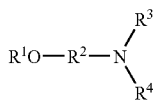

(32)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —($R^5O$)$_x$$R^6$, $R^5$ in each of the x ($R^5$-O) groups is independently $C_2$-$C_4$ alkylene, $R^6$ is hydrogen, or a linear or branched alkyl group having from 1 to about 4 carbon atoms, and x is an average number from 1 to about 50;

(h) amine oxides having the formula:

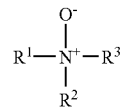

(34)

wherein $R^1$, $R^2$ and $R^3$ are independently hydrogen, hydrocarbyl or substituted hydrocarbyl having from 1 to about 30 carbon atoms, —($R^4O$)$_x$$R^5$, or —$R^6$($OR^4$)$_x$$OR^5$; $R^4$ in each of the x ($R^4O$) groups is independently $C_2$-$C_4$ alkylene, $R^5$ is hydrogen, or a hydrocarbyl or substituted hydrocarbyl having from 1 to about 30 carbon atoms, $R^6$ is a hydrocarbylene or substituted hydrocarbylene having from 1 to about 6 carbon atoms, x is an average number from 1 to about 50, and the total number of carbon atoms in $R^1$, $R^2$ and $R^3$ is at least 8;

(i) alkoxylated amine oxides having the formula:

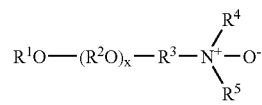

(35)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —($R^6$)$_n$—($R^2O$)$_y$$R^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60; and (j) dialkoxylated amines having the formula:

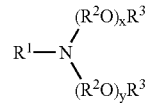

(36)

wherein $R^1$ is hydrogen or hydrocarbyl or substituted hydrocarbyl having from 1 to about 30 carbon atoms, —$R^4SR^5$, or —($R^2O$)$_z$$R^3$, $R^2$ in each of the x ($R^2O$), y ($R^2O$) and z ($R^2O$) groups is independently $C_2$-$C_4$ alkylene, $R^3$ is hydrogen, or a linear or branched alkyl group having from 1 to about 22 carbon atoms, $R^4$ is a linear or branched alkyl group having from about 6 to about 30 carbon atoms, $R^5$ is a linear or branched alkyl group having from about 4 to about 15 carbon atoms, and x, y and z are independently an average number from 1 to about 40, provided, however, that when $R^1$ is alkyl, either the sum of x and y is greater than 20 or $R^3$ is other than hydrogen.

18. A composition of claim 16 wherein the nonionic surfactant component comprises at least one surfactant selected from the group consisting of:

(a) alkoxylated alcohols having the formula:

$$R^1O—(R^2O)_xR^3 \quad (45)$$

wherein $R^1$ is hydrocarbyl or substituted hydrocarbyl having from 1 to about 30 carbon atoms, $R^2$ in each of the x $(R^2O)$ groups is independently $C_2$-$C_4$ alkylene, $R^3$ is hydrogen, or a linear or branched alkyl group having from 1 to about 4 carbon atoms, and x is an average number from 1 to about 60, provided, however, that when $R^1$ is alkyl, either $R^3$ is other than hydrogen or x is at least 10;

(b) dialkoxylated alcohols having the formula:

$$R^1(OR^2)_xO—R^3—O—(R^2O)_yR^1 \quad (46)$$

wherein $R^1$ is independently hydrogen, or a linear or branched alkyl group having from 1 to about 4 carbon atoms, $R^2$ in each of the x $(R^2O)$ and the y $(R^2O)$ groups is independently $C_2$-$C_4$ alkylene, $R^3$ is hydrocarbylene or substituted hydrocarbylene having from 2 to about 30 carbon atoms, and x and y are independently an average number from 1 to about 60; and (c) glycosides having the formula:

(62)

wherein n is the degree of polymerization, or number of glycose groups, and R is a branched or straight chain alkyl group preferably having from 4 to 18 carbon atoms, or a mixture of alkyl groups having an average value within the given range.

19. A composition of claim 16 wherein the anionic surfactant component comprises at least one surfactant selected from the group consisting of:

(a) compounds having the formula:

$$R_1O(R_2O)_nX_1 \quad (47A)$$

wherein $R_1$ is a hydrocarbyl group having from about 8 to about 22 carbon atoms, each of the n $(R_2O)$ groups is independently $C_2$-$C_4$ alkylene, n is a number from 0 to about 60, and $X_1$ is a carboxylate, sulfate or phosphate;

(b) phosphate diesters having the formula:

(56)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m $(R^2O)$ and the n $(R^2O)$ groups is independently $C_2$-$C_4$ alkylene; and m and n are independently from 1 to about 30; and (c) phosphate esters having the formula:

(57)

wherein $R^1$ is a linear or branched alkyl, linear or branched alkenyl, linear or branched alkynyl, aryl, or aralkyl group having from about 4 to about 30 carbon atoms; $R^2$ in each of the m $(R^2O)$ groups is independently $C_2$-$C_4$ alkylene; and m is from 1 to about 30.

20. A composition of claim 12 wherein a weight ratio of glyphosate a.e. to said oxalic acid or salt thereof is between about 1:1 and about 10:1.

21. A composition of claim 20 wherein a weight ratio of glyphosate a.e. to said oxalic acid or salt thereof is about 3:1.

22. A composition of claim 13 wherein said surfactant component and said oxalic acid or a salt thereof are present in a weight ratio between about 5:1 and about 40:1.

23. A composition of claim 12 wherein the glyphosate concentration is at least 450 grams glyphosate a.e. per liter.

24. A composition of claim 23 wherein the glyphosate concentration is at least 500 grams glyphosate a.e. per liter.

25. A composition of claim 24 wherein the glyphosate concentration is at least 540 grams glyphosate a.e. per liter.

\* \* \* \* \*

UNITED STATES PATENT AND TRADEMARK OFFICE
CERTIFICATE OF CORRECTION

PATENT NO.        : 7,723,265 B2
APPLICATION NO.   : 11/205978
DATED             : May 25, 2010
INVENTOR(S)       : Xu et al.

It is certified that error appears in the above-identified patent and that said Letters Patent is hereby corrected as shown below:

On the front cover of the patent, Section 73, Assignee:

"Monsanto Technology, St. Louis, MO (US)"
should read
--Monsanto Technology LLC, St. Louis, MO (US)--.

Column 140, Claim 17, Line 27: "cyclic or" should be deleted.

Signed and Sealed this
Sixteenth Day of August, 2011

David J. Kappos
*Director of the United States Patent and Trademark Office*